(12) United States Patent
Brugliera et al.

(10) Patent No.: US 7,612,257 B2
(45) Date of Patent: Nov. 3, 2009

(54) FLAVONOID 3',5' HYDROXYLASE GENE SEQUENCES AND USES THEREFOR

(75) Inventors: Filippa Brugliera, Preston (AU); Yoshikazu Tanaka, Shiga (JP); John Mason, Carlton North (AU)

(73) Assignee: International Flower Developments Pty. Ltd., Bundoora, Victoria (AU)

( * ) Notice: Subject to any disclaimer, the term of this patent is extended or adjusted under 35 U.S.C. 154(b) by 115 days.

(21) Appl. No.: 10/526,133

(22) PCT Filed: Aug. 29, 2003

(86) PCT No.: PCT/AU03/01111

§ 371 (c)(1), (2), (4) Date: Mar. 29, 2006

(87) PCT Pub. No.: WO2004/020637

PCT Pub. Date: Mar. 11, 2004

(65) Prior Publication Data

US 2007/0033674 A1    Feb. 8, 2007

(30) Foreign Application Priority Data

Aug. 30, 2002    (AU)    ............... 2002951088
Sep. 16, 2002    (AU)    ............... 2002952835

(51) Int. Cl.
    *A01H 5/00*      (2006.01)
    *C12N 15/63*     (2006.01)
    *C12N 5/14*      (2006.01)
    *C07H 21/00*     (2006.01)

(52) U.S. Cl. .................. 800/295; 800/323; 435/320.1; 435/419; 536/23.2; 536/23.6

(58) Field of Classification Search .............. None
See application file for complete search history.

(56) References Cited

FOREIGN PATENT DOCUMENTS

JP    11-178572    7/1999

WO    WO 94/28140    * 12/1994
WO    WO 9428140 A1 * 12/1994

OTHER PUBLICATIONS

Wells (Biochemistry 29:8509-8517, 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Maniatis et al. (Molecular Cloning: A Laboratory Manual, Cold Spring Harbor Laboratory, 1982).*
Van der Krol A.R. et al., "An Anti-Sense Chalcone Synthase Gene in Transgenic Plants Inhibits Flower Pigmentation", *Nature*, 333:866-869 (1988). XP-002907995.

* cited by examiner

*Primary Examiner*—Vinod Kumar
(74) *Attorney, Agent, or Firm*—Scully, Scott, Murphy & Presser, P.C.

(57) ABSTRACT

The present invention relates generally to a genetic sequence encoding a polypeptide having flavonoid 3',5'-hydroxylase (F3'5'H) activity and to the use of the genetic sequence and/or its corresponding polypeptide thereof inter alia to manipulate color in flowers or parts thereof or in other plant tissue. More particularly, the F3'5'H has the ability to modulate dihydrokaempferol (DHK) metabolism as well as the metabolism of other substrates such as dihydroquercetin (DHQ), naringenin and eriodictyol. Even more particularly, the present invention provides a genetic sequence encoding a polypeptide having F3'5'H activity when expressed in rose or gerbera or botanically related plants. The instant invention further relates to antisense and sense molecules or RNAi-inducing molecules corresponding to all or part of the subject genetic sequence or a transcript thereof. The present invention further relates to promoters which operate efficiently in plants such as rose, gerbera or botanically related plants.

7 Claims, 53 Drawing Sheets

Replicon: pBluescript SK (+) vector 2.95kb

Insert: ~1.8kb petunia F3'5'H *petHf1* cDNA homologs from *P. hybrida* cv. OGB

Replicon: pBluescript SK (+) vector 2.95kb

Insert: ~1.8kb petunia F3'5'H *petHf2* cDNA from *P. hybrida* cv. OGB

Replicon: ~2.7kb EcoRI (blunted) pUC19 vector

Insert: ~1.6kb BspHI (blunted)/FspI fragment containing petunia F3'5'H *petHf1* cDNA from pCGP601

Replicon: ~18.7kb SmaI pWTT2132 vector

Insert: ~3.5kb PstI (blunted) fragment containing *AmCHS 5': petHf1: petD8 3'* gene from pCGP485

Replicon: 2.95kb (BamHI/XbaI) blunted vector fragment of pBluescript II KS (+)

Insert: ~3.5kb PstI (blunted) fragment containing *AmCHS 5': petHf1: petD8 3'* gene from pCGP483

Replicon: ~18.7kb SmaI pWTT2132 vector

Insert: ~3.9kb PstI (blunted) fragment containing *Mac: petHf1: mas 3'* gene from pCGP628

Replicon: ~18.7kb SmaI/PstI pWTT2132 vector

Insert: ~5.3kb XbaI (blunted)/PstI fragment containing *petD8 5': petHf1: petD8 3'* gene from pCGP1107

Replicon: ~18.7kb PstI (blunted)/KpnI pWTT2132 vector

Insert: ~4.35kb SacI (blunted)/KpnI fragment containing *shortFLS 5': petHf1: petFLS 3'* gene from pCGP497

Replicon: ~18.7kb PstI/BamHI pWTT2132 vector

Insert: ~3kb PstI/BamHI fragment containing petRT5': petHf1: nos 3' gene from pCGP846

Replicon: ~18.7kb SalI pWTT2132 vector

Insert: ~4.9kb XhoI fragment containing *mas/35S: petHf1: ocs 3'* gene from pCGP1619

Replicon: ~18.7kb SmaI pWTT2132 vector

Insert: ~2.6kb (PstI/EcoRI) blunted fragment containing *CaMV 35S: petHf1: ocs 3'* gene from pCGP1636

Replicon: ~18.7kb BamHI pWTT2132 vector

Insert: ~4.9kb BglII fragment from containing *RoseCHS 5';petHf1: nos 3'* gene from pCGP200

Replicon: ~18.4kb Asp718 (blunted) pCGP1988 vector

Insert: ~3.7kb (Asp718/XbaI) blunted fragment containing *CaMV 35S: petHf2: ocs 3'* gene from pCGP2109

Replicon: ~18.4kb SalI (blunted)/PstI vector fragment from pWTT2132

Insert: ~66bp EcoRI (blunted)/ PstI fragment containing multi-cloning site from pNEB193

Replicon: ~3.3 kb HincII/XhoI vector fragment from pCGP2000 (containing CaMV 35S promoter fragment in pBluescript SK)

Insert: ~1.6kb EcoRI (blunted)/ XhoI ocs 3' fragment from pKIWI101

Replicon: ~15kb HindIII/PstI pCGN1548 vector

Insert: ~5.3kb HindIII/PstI fragment containing *petD8 5': GUS: petD8 3'* gene from pCGP1106

Replicon:~11.8kb BamHI (GA-filled)/SacI pBIN19 vector

Insert: ~6.7kb XhoI (TC-filled)/SacI fragment containing *longpetFLS 5': GUS: petFLS 3'* gene from pCGP496

Replicon: ~18.7kb PstI/BamHI pWTT2132 vector

Insert: ~4.6kb PstI/BglII fragment containing *ChrysCHS 5'*: *GUS*: *nos 3'* gene from pCGP1622

Replicon: ~18.7kb PstI pWTT2132 vector

Insert: ~5.4kb PstI fragment containing *petRT 5': GUS: petRT 3'* gene from pCGP1628

Replicon: ~18.7kb BamHI pWTT2132 vector

Insert: ~5kb BglII fragment containing RoseCHS 5': GUS: nos 3' gene from pCGP197

Replicon: ~18.7kb Asp718 (blunted) pWTT2132 vector

Insert: ~3.8kb (EagI/PstI) blunted fragment containing *AmCHS 5': GUS: petD8 3'* gene from pCGP1952

Replicon: pBluescript SK II (+) vector 2.95kb

Insert: ~1.6kb *pansy F3'5'H BP#18* cDNA from *Viola spp.* cv. Black Pansy

Replicon: pBluescript SK II (+) vector 2.95kb

Insert: ~1.6kb *pansy F3'5'H BP#40* cDNA from *Viola spp.* cv. Black Pansy

Replicon: ~18.7kb Asp718 (blunted) pWTT2132 vector

Insert: ~3.8kb NotI (blunted)/ EcoRV fragment containing *AmCHS 5': BP#18: petD8 3'* gene from pCGP1970

Replicon: ~18.7kb Asp718 (blunted) pWTT2132 vector

Insert: ~3.8kb NotI (blunted)/ EcoRV fragment containing *AmCHS 5': BP#40: petD8 3'* gene from pCGP1971

Replicon: ~18.7kb Asp718 (blunted) pWTT2132 vector

Insert: ~3.6kb (XhoI /XbaI) blunted fragment containing CaMV 35S: BP#18: ocs 3' gene from pCGP1965

Replicon: ~18.7kb Asp718 (blunted) pWTT2132 vector

Insert: ~3.6kb (XhoI/XbaI) blunted fragment containing *CaMV 35S: BP#40: ocs 3'* gene from pCGP1966

Replicon: pBluescript SK II (+) vector 2.95kb

Insert: ~1.6kb *F3'5'H Sal#2* cDNA from *Salvia spp.*

Replicon: pBluescript SK II (+) vector 2.95kb

Insert: ~1.6kb *F3'5'H Sal#47* cDNA from *Salvia spp.*

Replicon: ~18.4kb Asp718 (blunted) pCGP1988 vector

Insert: ~3.6kb NotI (blunted)/ EcoRV fragment containing *AmCHS 5': Sal#2: petD8 3'* gene from pCGP2116

Replicon: ~18.4kb Asp718 (blunted) pCGP1988 vector

Insert: ~3.6kb NotI (blunted)/ EcoRV fragment containing AmCHS 5': Sal#47: petD8 3' gene from pCGP2117

Replicon: ~18.4kb Asp718 (blunted) pCGP1988 vector

Insert: ~3.6kb (XhoI/XbaI) blunted fragment containing CaMV 35S: Sal#2: ocs 3' gene from pCGP2112

Replicon: ~18.4kb Asp718 (blunted) pCGP1988 vector

Insert: ~3.6kb (XhoI/XbaI) blunted fragment containing *CaMV 35S: Sal#47: ocs 3'* gene from pCGP2111

Replicon: pBluescript SK II (+) vector 2.95kb

Insert: ~1.7kb *F3'5'H Sol/#5* cDNA from *Sollya spp.*

Replicon: ~18.4kb Asp718 (blunted) pCGP1988 vector

Insert: ~3.5kb NotI (blunted)/ EcoRV fragment containing *AmCHS 5': SoII#5: petD8 3'* gene from pCGP2128

Replicon: ~18.4kb Asp718 (blunted)
pCGP1988 vector

Insert: ~3.6kb (Asp718/XbaI) blunted fragment containing *CaMV 35S: SoI1#5: ocs 3'* gene from pCGP2129

Replicon: pBluescript SK II (+) vector 2.95kb

Insert: ~1.8kb *F3'5'H Kenn#31* cDNA from *Kennedia spp.*

Replicon: ~18.4kb Asp718 (blunted) pCGP1988 vector

Insert: ~3.7kb (NotI/ EcoRI) blunted fragment containing *AmCHS 5': Kenn#31: petD8 3'* gene from pCGP2242

Replicon: ~18.4kb Asp718 (blunted) pCGP1988 vector

Insert: ~3.6kb (XhoI/NotI) blunted fragment containing *CaMV 35S: Kenn#31: ocs 3'* gene from pCGP2236

Replicon: pBHF2 BamHI/PstI 4.5kb vector + partial *BpeaHF2* insert (backbone = pBluescript SK II (+) vector)

Insert: ~200bp BamHI/PstI fragment from PCR using pBHF2 as template (5' fragment of butterfly pea *F3'5'H* cDNA (*BpeaHF2*) from *Clitoria ternatea* including putative initiating codon (ATG))

Replicon: ~18.4kb Asp718 (blunted) pCGP1988 vector

Insert: ~3.6kb NotI (blunted)/ EcoRV fragment containing *AmCHS 5': BpeaHF2: petD8 3'* gene from pCGP2133

Replicon: ~12.8kb pBE2113-GUSs BamHI/SalI (pBI121 backbone)

Insert: ~1.7kb BamHI/XhoI fragment containing *Clitoria F3'5'H BpeaHF2* cDNA clone from pBHF2F Replicon: ~18.4kb Asp718 (blunted) pCGP1988 vector Insert: ~3.6kb (XhoI/XbaI) blunted fragment containing CaMV 35S: BpeaHF2: ocs 3' gene from pCGP2132

Replicon: pBluescript SK II (+) vector 2.95kb

Insert: ~1.7kb *F3'5'H Gen#48* cDNA from *Gentiana triflora*

Replicon: ~18.7kb Asp718 (blunted)
pWTT2132 vector

Insert: ~3.6kb NotI (blunted)/ EcoRV fragment containing *AmCHS 5': Gen#48: petD8 3'* gene from pCGP1496

Replicon: ~12.8kb pBE2113-GUSs BamHI/SalI (pBI121 backbone)

Insert: ~1.8kb BamHI/XhoI fragment containing gentian F3'5'H (Genn#48) cDNA clone from pG48

Replicon: ~18.7kb Asp718 (blunted) pWTT2132 vector

Insert: ~3.6kb (XhoI/XbaI) blunted fragment containing *CaMV 35S: Gen#48: ocs 3'* gene from pCGP1981

Replicon: pBluescript SK II (+) vector 2.95kb

Insert: ~1.8kb *lavender F3'5'H LBG* cDNA from *Lavendula nil*

Replicon: ~12.8kb pBE2113-GUSs BamHI/SalI (pBI121 backbone)

Insert: ~1.8kb BamHI/XhoI fragment containing lavender F3'5'H (LBG) cDNA clone from pLHF8

FLAVONOID 3',5' HYDROXYLASE GENE SEQUENCES AND USES THEREFOR

This is a national stage application filed under 35 U.S.C. 371 from PCT/AU03/01111, filed Aug. 29, 2003, which claims priority to AUSTRALIA 2002951088 filed Aug. 30, 2002, and AUSTRALIA 2002952835 filed Sep. 16, 2002.

BACKGROUND OF THE INVENTION

1. Field of the Invention

The present invention relates generally to a genetic sequence encoding a polypeptide having flavonoid 3',5'-hydroxylase (F3'5'H) activity and to the use of the genetic sequence and/or its corresponding polypeptide thereof inter alia to manipulate color in flowers or parts thereof or in other plant tissue. More particularly, the F3'5'H has the ability to modulate dihydrokaempferol (DHK) metabolism as well as the metabolism of other substrates such as dihydroquercetin (DHQ), naringenin and eriodictyol. Even more particularly, the present invention provides a genetic sequence encoding a polypeptide having F3'5'H activity when expressed in rose or gerbera or botanically related plants. The instant invention further relates to antisense and sense molecules or RNAi-inducing molecules corresponding to all or part of the subject genetic sequence or a transcript thereof as well as to genetically modified plants as well as cut flowers, parts and reproductive tissue from such plants. The present invention further relates to promoters which operate efficiently in plants such as rose, gerbera or botanically related plants.

2. Description of Prior Art

Reference to any prior art in this specification is not, and should not be taken as an acknowledgment or any form of suggestion that this prior art forms part of the common general knowledge in any country.

Bibliographic details of references provided in the subject specification are listed at the end of the specification.

The flower or ornamental plant industry strives to develop new and different varieties of flowers and/or plants. An effective way to create such novel varieties is through the manipulation of flower color. Classical breeding techniques have been used with some success to produce a wide range of colors for almost all of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such is flowers, foliage and stems would offer a significant opportunity in both the cut flower and ornamental markets. In the flower or ornamental plant industry, the development of novel colored varieties of major flowering species such as rose, chrysanthemum, tulip, lily, carnation, gerbera, orchid, lisianthus, begonia, torenia, geranium, petunia, meremubergia, pelargonium, iris, impatiens and cyclamen would be of great interest. A more specific example would be the development of a blue rose or gerbera for the cut flower market.

In addition, the development of novel colored varieties of plant parts such as vegetables, fruits and seeds would offer significant opportunities in agriculture. For example, novel colored seeds would be useful as proprietary tags for plants. Furthermore modifications to flavonoids common to berries or fruits including grapes and apples and their juices including wine have the potential to impart altered style characteristics of value to such fruit and byproduct industries.

Flower color is predominantly due to three types of pigment: flavonoids, carotenoids and betalains. Of the three, the flavonoids are the most common and contribute a range of colors from yellow to red to blue. The flavonoid molecules that make the major contribution to flower color are the anthocyanins, which are glycosylated derivatives of cyanidin and its methylated derivative peonidin, delphinidin or delphinidin-based molecules and its methylated derivatives petunidin and malvidin and pelargonidin. Anthocyanins are localised in the vacuole of the epidermal cells of petals or the vacuole of the sub epidermal cells of leaves.

The flavonoid pigments are secondary metabolites of the phenylpropanoid pathway. The biosynthetic pathway for the flavonoid pigments (flavonoid pathway) is well established, (Holton and Cornish, *Plant Cell* 7: 1071-1083, 1995; Mol et al., *Trends Plant Sci.* 3: 212-217, 1998; Winkel-Shirley, *Plant Physiol.* 126: 485-493, 2001a; and Winkel-Shirley, *Plant Physiol,* 127: 1399-1404, 2001b) and is shown in FIGS. 1A and B. Three reactions and enzymes are involved in the conversion of phenylalanine to p-coumaroyl-CoA, one of the first key substrates in the flavonoid pathway. The enzymes are phenylalanine ammonia-lyase (PAL), cinnamate 4-hydroxylase (C4H) and 4-coumarate: CoA ligase (4CL). The first committed step in the pathway involves the condensation of three molecules of malonyl-CoA provided by the action of acetyl CoA carboxylase (ACC) on acetyl CoA and $CO_2$) with one molecule of p-coumaroyl-CoA. This reaction is catalysed by the enzyme chalcone synthase (CHS). The product of this reaction, 2',4,4,6', tetrahydroxy-chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The pattern of hydroxylation of the B-ring of dihydrokaempferol (DHK) plays a key role in determining petal color. The B-ring can be hydroxylated at either the 3', or both the 3' and 5' positions, to produce dihydroquercetin (DHQ) or dihydromyricetin (DHM), respectively. Two key enzymes involved in this part of the pathway are flavonoid 3'-hydroxylase and flavonoid 3,5'-hydroxylase, both of the cytochrome P450 class of enzymes. Cytochrome P450 enzymes are widespread in nature and genes have been isolated and sequenced from vertebrates, insects, yeasts, fungi, bacteria and plants.

Flavonoid 3'-hydroxylase (F3H) is a key enzyme in the flavonoid pathway leading to the cyanidin-based pigments which, in many plant species (for example *Rosa* spp., *Dianthus* spp., *Petunia* spp., begonia, *cyclamen*, impatiens, morning glory and chrysanthemum), contribute to red and pink flower color.

Flavonoid 3',5'-hydroxylase (F3'5'H) is a key enzyme in the flavonoid pathway leading to the delphinidin-based pigments which, in many plant species (for example, *Petunia* spp., *Viola* spp., *Lisianthus* spp., *Gentiana* spp., *Sollya* spp., *Salvia* spp., *Clitoria* spp., *Kennedia* spp., *Campanula* spp., *Lavandula* spp., *Verbena* spp., *Torenia* spp., *Delphinium* spp., *Solanum* spp., *Cineraria* spp., *Vitis* spp., *Babiana stricta,* *Pinus* spp., *Picea* spp., *Larix* spp., *Phaseolus* spp., *Vaccinium* spp., *Cyclamen* spp., *Iris* spp., *Pelargonium* spp., Liparieae, *Geranium* spp., *Pisum* spp., *Lathyrus* spp., *Catharanthus* spp., *Malvia* spp., *Mucuna* spp., *Vicia* spp., *Saintpaulia* spp., *Lagerstroemia* spp., *bouchina* sp., *Plumbago* spp., *Hypocalyptus* spp., *Rhododedron* spp., *Linum* spp., *Macroptiltium* spp., *Hibiscus* spp., *Hydrangea* spp., *Cymbidium* spp., *Millettia* spp., *Hedysarum* spp., *Lespedeza* spp., *Asparagus* spp. *Antigonon* spp., *Pisum* spp., *Freesia* sap. *Brunella* spp., *Clarkia* spp., etc.), contribute to purple and blue flower color. Many plant species such as roses, gerberas, chrysanthemums and carnations, do not produce delphinidin-based pigments because they lack a F3'5'H activity.

The next step in the pathway, leading to the production of the colored anthocyanins from the dihydroflavonols (DHK, DHQ, DHM), involves dihydroflavonol-4-reductase (DFR) leading to the production of the leucoanthocyanidins. The leucoanthocyanidins are subsequently converted to the anthocyanidins, pelargonidin, cyanidin and delphinidin or delphinidin-based molecules. These flavonoid molecules are unstable under normal physiological conditions and glycosylation at the 3-position, through the action of glycosyltransferases, stabilizes the anthocyanidin molecule thus allowing accumulation of the anthocyanins. In general, the glycosyltransferases transfer the sugar moieties from UDP sugars to the flavonoid molecules and show high specificities for the position of glycosylation and relatively low specificities for the acceptor substrates (Seitz and Hinderer, Anthocyanins. In: *Cell Culture and Somatic Cell Genetics of Plants*. Constabel, F. and Vasil, I. K. (eds.), Academic Press, New York, USA, 5: 49-76, 1988). Anthorcyanins can occur as 3-monosides, 3-biosides and 3-triosides as well as 3,5-diglycosides and 3,7-diglycosides associated with the sugars glucose, galactose, rhamnose, arabinose and xylose (Strack and Wray, In; *The Flavonoids—Advances in Research since* 1986. Harborne, J. B. (ed), Chapman and Hall, London, UK, 1-22, 1993).

Glycosyltransferases involved in the stabilisation of the anthocyanidin molecule include UDP glucose: flavonoid 3-glucosyltransferase (3GT), which transfers a glucose moiety from UDP glucose to the 3-O-position of the anthocyanidin molecule to produce anthocyanidin 3-O-glucoside.

In *petunia* and pansy (amongst others), anthocyanidin 3-O-glucoside are generally glycosylated by another glycosyltransferase, UDP rhamnose: anthocyanidin 3-glucoside rhamnosyltransferase (3RT), which adds a rhamnose group to the 3-O-bound glucose of the anthocyanin molecule to produce the anthocyanidin 3-rutinosides, and once acylated, can be further modified by UDP: glucose anthocyanin 5 glucosyltansferase (5GT). However, in roses (amongst others), the anthocyanidin 3-O-glucosides are generally glycosylated by another glycosyltrasferase, UDP: glucose anthocyanin 5 glucosyltransferase (5GT) to produce anthocyanidin 3,5 diglucosides.

Many anthocyanidin glycosides exist in the form of acylated derivatives. The acyl groups that modify the anthocyanidin glycosides can be divided into two major classes based upon their structure. The aliphatic acyl groups include malonic acid or succinic acid and the aromatic class include the hydroxy cinnamic acids such as p-coumaric acid, caffeic acid and ferulic acid and the benzoic acids such as p-hydroxybenzoic acid.

Methylation at the 3' and 5' positions of the B-ring of anthocyanidin glycosides can also occur. Methylation of cyanidin-based pigments leads to the production of peonidin. Methylation of the 3' position of delphinidin-based pigments results in the production of petunidin, whilst methylation of the 3' and 5' positions results in malvidin production. Methylation of malvidin can also occur at the 5-O and 7-O positions to produce capensinin (5-O-methyl malvidin) and 5,7-di-O-methyl malvidin.

In addition to the above modifications, pH of the vacuole or compartment where pigments are localised and copigmentation with other flavonoids such as flavonols and flavones can affect petal color. Flavonols and flavones can also be aromatically acylated (Brouillard and Dangles, In: *The Flavonoids—Advances in Research since* 1986. Harborne, J. B. (ed), Chapman and Hall, London, UK, 1-22, 1993).

The ability to control F3'5'H activity, or other enzymes involved in the flavonoid pathway, in flowering plants would provide a means of manipulating the color of plant parts such as petals, fruit, leaves, sepals, seeds etc. Different colored versions of a single cultivar could thereby be generated and in some instances a single species would be able to produce a broader spectrum of colors.

Two nucleotide sequences (referred to herein as SEQ ID NO:1 and SEQ ID NO:3) encoding *petunia* F3'5'Hs have been cloned (see International Patent Application No. PCT/AU92/00334 and Holton et al, *Nature*, 366: 276-279, 1993a). These sequences were efficient in modulating 3',5' hydroxylation of flavonoids in *petunia* (see International Patent Application No. PCT/AU92/00334 incorporated herein by reference and Holton et al., 1993a, supra), tobacco (see International Patent Application No. PCT/AU92/00334 incorporated herein by reference) and carnations (see International Patent Application No. PCT/AU96/00296 incorporated herein by reference). Surprisingly, however, inclusion of these sequences in standard expression cassettes, did not lead to the production of intact or full-length transcripts as detectable by RNA or Northern blot analysis and consequently 3',5'-hydroxylated flavonoids were not produced in roses. There is a need, therefore, to identify further genetic sequences encoding F3'5'Hs which efficiently accumulate and are then able to modulate 3',5' hydroxylation of flavonoids such as anthocyanins in roses and other key commercial plant species.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and ado acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc.

Genetic sequences encoding a F3'5'H have been identified and cloned from a number of plant species. The F3'5'H genetic sequences when expressed in rose petal tissue results in detectable level of delphinidin or delphinidin-based molecules as determined by a chromatographic technique such as thin layer chromatography (TLC) or high performance liquid chromatography (HPLC). Alternatively, or in addition, expression of the genetic sequences in rose petal tissue results in a sufficient level and length of transcript which is capable of being translated to F3'5'H. This is conveniently measured as delphinidin or delphinidin-based molecules, detectable using a chromatographic technique such as TLC or HPLC. The genetic sequences of the present invention permit the modulation of expression of genes encoding this enzyme by, for example, de novo expression, over-expression, suppression, antisense inhibition, ribozyme activin, RNAi-induction or methylation-induction. The ability to control F3'5'H synthesis in plants and more specifically in roses or gerberas permits modulation of the composition of individual anthocyanins as well as alteration of relative levels of flavonols and anthocyanins, thereby enabling the manipulation of color of tissues and/or organs of plants such as petals, leaves, seeds, sepals, fruits etc.

Accordingly, one aspect of the present invention provides an isolated nucleic acid molecule comprising a sequence of nucleotides encoding or complementary to a sequence encoding a flavonoid 3',5' hydroxylase (F3'5'H) or a polypeptide having F3'5'H activity wherein expression of said nucleic acid molecule in a rose petal tissue results in detectable levels of delphinidin or delphinidin-based molecules as measured by a chromatographic technique.

Another aspect of the present invention is directed to an isolated nucleic acid molecule comprising a sequence of nucleotides encoding or complementary to a sequence encoding a F3'5'H or a polypeptide having F3'5'H activity wherein expression of said nucleic acid molecule in a rose petal tissue results in a sufficient level and length of transcript which is translated to said F3'5'H as determined by detectable levels of delphinidin or delphinidin-based molecules as measured by a chromatographic technique.

The isolated nucleic acid molecule of the present invention, therefore, encodes a F3'5'H which is capable of more efficient conversion of DHK to DHM in roses than is the F3'5'H encoded by the nucleotide sequence set forth in SEQ ID NO:1 and SEQ ID NO:3 as measured by delphinidin production in rose petals.

Efficiency as used herein relates to the capability of the F3'5'H enzyme to convert its substrate DHK or DHQ into DHM in a rose cell (or any cell of a commercially important plant such as gerber). This conversion provides the plant with a substrate (DHM) for other enzymes of the flavonoid pathway which are present in the paint to further modify the substrate. This modification may include for example, glycosylation, acylation, rhamnosylation and/or methylation, to produce various anthocyanins which contribute to the production of a range of colors. The modulation of 3',5'-hydroxylated anthocyanins in rose is thereby enabled. Efficiency is conveniently assessed by one or more parameters selected from: extent of F3'5'H transcription, as determined by the amount of intact F3'5'H mRNA produced (as detected by Northern blot analysis); extent of translation of the F3'5'H mRNA, as determined by the amount of translation product produced; extent of F3'5'H enzyme activity as determined by the production of anthocyanin derivatives of DHQ or DHM including delphinidin or delphinidin-based pigments (as detected by TLC or HPLC); the extent of effect on flower color.

It has also been surprisingly determined that certain combinations of promoter and F3'5'H gene sequences that were functional in carnation and *petunia* were not functional in rose. Surprisingly, only a particular subset of promoter and F3'5'H gene sequence combinations resulted in 3',5'-hydroxylated flavonoids in rose flowers. These included F3'5'H sequences isolated from *Viola* spp., *Salvia* spp. *Lavandula* spp. and *Sollya* spp. Furthermore, the *Viola* F3'5'H (or pansy F3'5'H) sequences were found to result in the highest accumulation of 3',5'-hydroxylated flavonoids in rose. The novel promoter and F3'5'H gene sequence combinations can be employed inter alia to modulate the color or flavour or other characteristics of plants or plant parts such as but not limited to flowers, fruits, nuts, roots, stems, leaves or seeds. Thus, the present invention represents a new approach to developing plant varieties having altered color characteristics. Other uses include, for example, the production of novel extracts of F3'5'H transformed plants wherein the extract has use, for example, as a flavouring or food additive or health product or beverage or juice or coloring. Beverages may include but are not limited to wines, spirits, teas, coffee, milk and dairy products.

In a preferred embodiment, therefore, the present invention provides an isolated nucleic acid molecule comprising a sequence of nucleotides encoding, or complementary to a sequence encoding pansy F3'5'R, *salvia* F3'5'H, lavender F3'5'H, *kennedia* F3'5'H or *sollya* F3'5'H or a functional derivative of the enzyme.

The nucleotide sequences encoding the pansy F3'5'H (SEQ ID NOs:9 and 11), *salvia* F3'5'H (SEQ ID NOs:13 and 15), *sollya* F3'5'H (SEQ ID NO:17), lavender F3'5'H (SEQ ID NO:31) and *kennedia* F3'5'H (SEQ ID NO:26) are defined by sequence identifiers indicated in parentheses. A summary of the sequence identifiers is shown in Table 1.

Accordingly, another aspect of the present invention provides a nucleic acid molecule comprising a nucleotide sequence or complementary nucleotide sequence substantially as set forth in SEQ ID NO:9 (pansy) or SEQ ID NO:11 (pansy) or SEQ ID NO:13 (*salvia*) or SEQ ID NO:15 (*salvia*) or SEQ ID NO:17 (*sollya*) or SEQ ID NO:31 (lavender) or SEQ ID NO:26 (*kennedia*) or having at least about 50% similarity thereto or capable of hybridizing to the sequence set forth in SEQ ID NO:9 or SEQ ID NO:11 or SEQ ID NO:13 or SEQ ID NO:15 or SEQ ID NO:17 or SEQ ID NO:31 or SEQ ID NO:26 under low stringency conditions.

The amino acid sequences of the preferred F3'5'H enzymes are set forth in SEQ ID NO:10 (pansy) or SEQ ID NO:12 (pansy) or SEQ ID NO:14 (*salvia*) or SEQ ID NO:16 (*salvia*) or SEQ ID NO:18 (*sollya*) or SEQ ID NO:32 (lavender) or SEQ ID NO:27 (*kennedia*).

A further aspect of the present invention provides a method for producing a transgenic flowering plant capable of synthesizing a F3'5'H said method comprising stably transforming a cell of a suitable plant with a nucleic acid sequence which comprises a sequence of nucleotides encoding said F3'5'H under conditions permitting the eventual expression of said nucleic acid sequence, regenerating a transgenic plant from the cell and growing said transgenic plant, for a time and under conditions sufficient to permit the expression of the nucleic acid sequence. The expression of the nucleic acid sequence generally results in a transcription of sufficient level and length to encode a F3'5'H. This is conveniently determined by detectable levels of delphinidin or delphinidin-based molecules as measured by chromatographic techniques such as TLC or HPLC. The transgenic plant may thereby produce a non-indigenous F3'5'H at elevated levels relative to the amount expressed in a comparable non-transgenic plant. This generally results in a visually detectable color change in the plant or plant part or preferably in the inflorescence or flowers of said plant.

Another aspect of the present invention contemplates a method for producing a transgenic plant with reduced F3'5'H activity, said method comprising stably transforming a cell of a suitable plant with a nucleic acid molecule which comprises a sequence of nucleotides encoding or complementary to a sequence encoding a F3'5' activity, regenerating a transgenic plant from the cell and where necessary growing said transgenic plant under conditions sufficient to permit the expression of the nucleic acid.

Yet another aspect of the present invention contemplates a method for producing a genetically modified plant with reduced F3'5'H activity, said method comprising altering the F3'5'H gene through modification of the indigenous sequences via homologous recombination from an appropriately altered F3'5'H gene or derivative or part thereof introduced into the plant cell, and regenerating the genetically modified plant from the cell.

Still another aspect of the present invention contemplates a method for producing a transgenic flowering plant exhibiting altered floral or inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence.

Still a further aspect of the present invention contemplates a method for producing a transgenic flowering plant exhibiting altered floral or inflorescence properties, said method comprising alteration of the F3'5'H gene through modification of nucleotide sequences via homologous recombination from an appropriately altered F3'5'H gene or derivative or part thereof introduced into the plant cell, and regenerating the genetically modified plant from the cell.

Even yet another aspect of the present invention extends to a method for producing a transgenic plant capable of expressing a recombinant gene encoding a F3'5'H or part thereof or which carries a nucleic acid sequence which is substantially complementary to all or a part of a mRNA molecule encoding said F3'5'H, said method comprising stably transforming a cell of a suitable plant within the isolated nucleic acid molecule comprising a sequence of nucleotides encoding, or complementary to a sequence encoding, a F3'5'H where necessary under conditions permitting the eventual expression of said isolated nucleic acid molecule, and regenerating a transgenic plant from the cell.

Even still another aspect of the present invention extends to all transgenic plants or parts of transgenic plants or progeny of the transgenic plants containing all or part of the nucleic acid sequences of the present invention, or antisense forms thereof and/or any homologs or related forms thereof and, in particular, those transgenic plants which exhibit altered floral or inflorescence properties.

Even still another aspect of the present invention extends to all transgenic plants or parts of transgenic plants or progeny of the transgenic plants containing all or part of the nucleic acid sequences of the present invention, or antisense forms thereof and/or any homologs or related forms thereof and, in particular, those transgenic plants which exhibit altered aerial parts of the plant such as fruit, berries, sepal, bract, petiole, peduncle, ovaries, anthers or stem properties.

Another aspect of the present invention contemplates the use of the extracts from transgenic plants or plant parts transgenic plants or progeny of the transgenic plants containing all or part of the nucleic acid sequences of the present invention and, in particular, the extracts from those transgenic plants when used as a flavouring or food additive or health product or beverage or juice or coloring.

A further aspect of the present invention is directed to recombinant forms of F3'5'H.

Another aspect of the present invention contemplates the use of the genetic sequences described herein in the manufacture of a genetic construct capable of expressing a F3'5'H or down-regulating an indigenous F3'5'H enzyme in a plant.

Yet another aspect of the present invention is directed to a prokaryotic or eukaryotic organism carrying a genetic sequence encoding a F3'5'H extrachromasomally in plasmid form.

Still another aspect of the present invention extends to a recombinant polypeptide comprising a sequence of amino acids substantially as set forth in SEQ ID NO:10 or SEQ ID NO:12 or SEQ ID NO:14 or SEQ ID NO:16 or SEQ ID NO:18 or SEQ ID NO:32 or SEQ ID NO:27 or an amino acid sequence having at least about 50% similarity to SEQ ID NO:10 or SEQ ID NO:12 or SEQ ID NO:14 or SEQ ID NO:16 or SEQ ID NO:18 or SEQ ID NO:32 or SEQ ID NO:27 or a derivative of said polypeptide.

The present invention further provides promoters which operate efficiently in plants such as rose and gerbera or botanically related plants. Such promoters include a rose CHS promoter, chrysanthemum CHS promoter and a CaMV 35S promoter.

A summary of sequence identifiers used throughout the subject specification is provided in Table 1:

TABLE 1

Summary of sequence identifiers

| SEQ ID NO: | NAME | SPECIES | TYPE OF SEQ | DESCRIPTION |
|---|---|---|---|---|
| 1 | petHf1.nt | *Petunia hybrida* | nucleotide | F3'5'H cDNA |
| 2 | petHf1.aa | *Petunia hybrida* | amino acid | translation of F3'5'H cDNA |
| 3 | petHf2.nt | *Petunia hybrida* | nucleotide | F3'5'H cDNA |
| 4 | petHf2.aa | *Petunia hybrida* | amino acid | translation of F3'5'H cDNA |
| 5 | RoseCHS promoter | *Rosa hybrida* | nucleotide | promoter fragment |
| 6 | D8 oligo#2 | *Petunia hybrida* | nucleotide | oligonucleotide |
| 7 | D8 oligo #4 | *Petunia hybrida* | nucleotide | oligonucleotide |
| 8 | chrysanCHSATG | chrysanthemum | nucleotide | oligonucleotide |
| 9 | BP#18.nt | *Viola* spp. | nucleotide | F3'5'H cDNA |
| 10 | BP#18.aa | *Viola* spp. | amino acid | translation of F3'5'H cDNA |
| 11 | BP#40.nt | *Viola* spp. | nucleotide | F3'5'H cDNA |
| 12 | BP#40.aa | *Viola* spp. | amino acid | translation of F3'5'H cDNA |
| 13 | Sal#2.nt | *Salvia* spp. | nucleotide | F3'5'H cDNA |
| 14 | Sal#2.aa | *Salvia* spp. | amino acid | translation of F3'5'H cDNA |
| 15 | Sal#47.nt | *Salvia* spp. | nucleotide | F3'5'H cDNA |
| 16 | Sal#47.aa | *Salvia* spp. | amino acid | translation of F3'5'H cDNA |
| 17 | Soll#5.nt | *Sollya* spp. | nucleotide | F3'5'H cDNA |
| 18 | Soll#5.aa | *Sollya* spp. | amino acid | translation of F3'5'H cDNA |
| 19 | FLS-Nco | *Petunia hybrida* | nucleotide | oligonucleotide |
| 20 | BpeaHF2.nt | *Clitoria ternatea* | nucleotide | F3'5'H cDNA |
| 21 | BpeaHF2.aa | *Clitoria ternatea* | amino acid | translation of F3'5'H cDNA |
| 22 | Gen#48.nt | *Gentiana triflora* | nucleotide | F3'5'H cDNA |
| 23 | Gen#48.aa | *Gentiana triflora* | amino acid | translation of F3'5'H cDNA |
| 24 | PetD8 5' | *Petunia hybrida* | nucleotide | oligonucleotide |
| 25 | Bpea primer | *Clitoria ternatea* | nucleotide | oligonucleotide |
| 26 | Kenn#31.nt | *Kennedia* spp. | nucleotide | F3'5'H cDNA |
| 27 | Kenn#31.aa | *Kennedia* spp. | amino acid | translation of F3'5'H cDNA |

TABLE 1-continued

Summary of sequence identifiers

| SEQ ID NO: | NAME | SPECIES | TYPE OF SEQ | DESCRIPTION |
|---|---|---|---|---|
| 28 | chrysCHS.nt | chrysanthemum | nucleotide | CHS cDNA |
| 29 | chrysCHS.aa | chrysanthemum | amino acid | translation of CHS cDNA |
| 30 | chrysCHS promoter | chrysanthemum | nucleotide | promoter fragment |
| 31 | LBG.nt | Lavandula nil | nucleotide | F3'5'H cDNA |
| 32 | LBG.aa | Lavandula nil | amino acid | translation of F3'5'H cDNA |

BRIEF DESCRIPTION OF THE FIGURES

FIG. 1A illustrates the general production of the anthocyanidin 3-glucosides that occur in most plants that produce anthocyanins. FIG. 1B represents further modifications of anthocyanins that occur in petunia. Enzymes involved in the pathway have been indicated as follows: PAL=Phenylalanine ammonia-lyase; C4H=Cinnamate 4-hydroxylase; 4CL=4-coumarate: CoA ligase; CHS=Chalcone synthase; CHI=Chalcone flavanone isomerase; F3H=Flavanone 3-hydroxylase; DFR=Dihydroflavonol-4-reductase; ANS=Anthocyanidin synthase, 3GT=UDP-glucose: flavonoid 3-O-glucosyltransferase; 3RT=UDP rhamnose: anthocyanidin 3-glucoside rhamnosyltransferase, AR-AT=Anthocyanidin-rutinoside acyltransferase, 5GT=Anthocyanin 5-glucosyltransferase; 3'OMT=Anthocyanin 3' O-methyltransferase, 3'5' OMT=Anthocyanin 3',5' O-methyltransferase. Other abbreviations include: DHK=dihydrokaempferol, DHQ=dihydroquercetin, DHM=dihydromyricetin, were used to probe petal cDNA libraries. Selected restriction endonuclease sites are marked. Refer to Table 2 and Table 4 for a description of the abbreviations.

TABLE 2

Descriptions of the abbreviations used in FIGS. 2 to 52

| ABBREVIATION | DESCRIPTION |
|---|---|
| Amp | ampicillin resistance gene which confers resistance to the antibiotic ampicillin |
| ColE1ori | plasmid origin of replication |
| f1 ori (+) | f1 filamentous phage origin of replication |
| GentR | gentamycin resistance gene which confers resistance to the antibiotic gentamycin |
| LB | left border of the T-DNA |
| nptIII | the neomycin phosphotransferase III gene which confers resistance to the antibiotic kanamycin |
| ori pRi | plasmid origin of replication |
| ori 322 | plasmid origin of replication |
| pACYC ori | modified replicon from pACYC184 from *E. coli* |
| pVS1 | a broad host range origin of replication from a plasmid from *Pseuodomonas aeruginosa* |
| rev | approximate location of the M13 reverse primer site used in sequence analysis |
| RB | right border of the T-DNA |
| TetR | tetracycline resistance gene which confers resistance to the antibiotic tetracycline |
| −20 | approximate location of the M13 −20 primer site used in sequence analysis |
| RK2 | broad host range Gram-negative plasmid RK2 origin |

Figure 2:
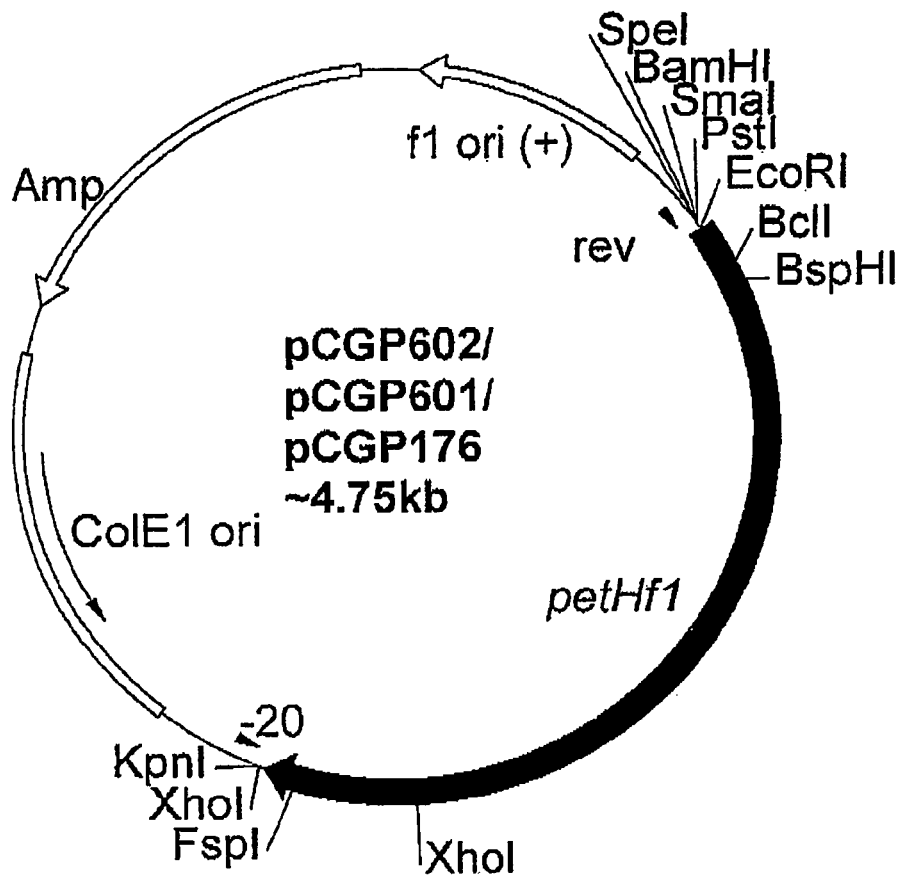
Figure 3:
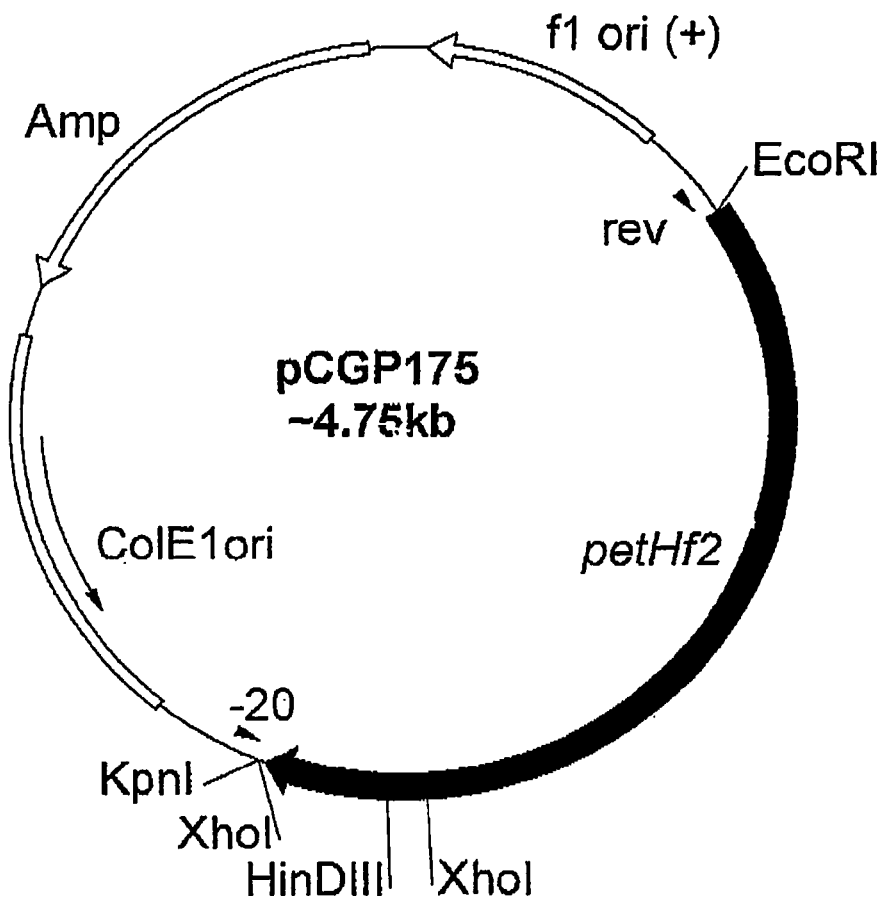
FIG. 3 is a diagrammatic representation of the plasmid pCGP175 containing the petunia F3'5'H petHf2 cDNA clone from *P. hybrida* cv. OGB. Selected restriction endonuclease sites are marked. Refer to Table 2 and Table 4 for a description of the abbreviations.
Figure 6:
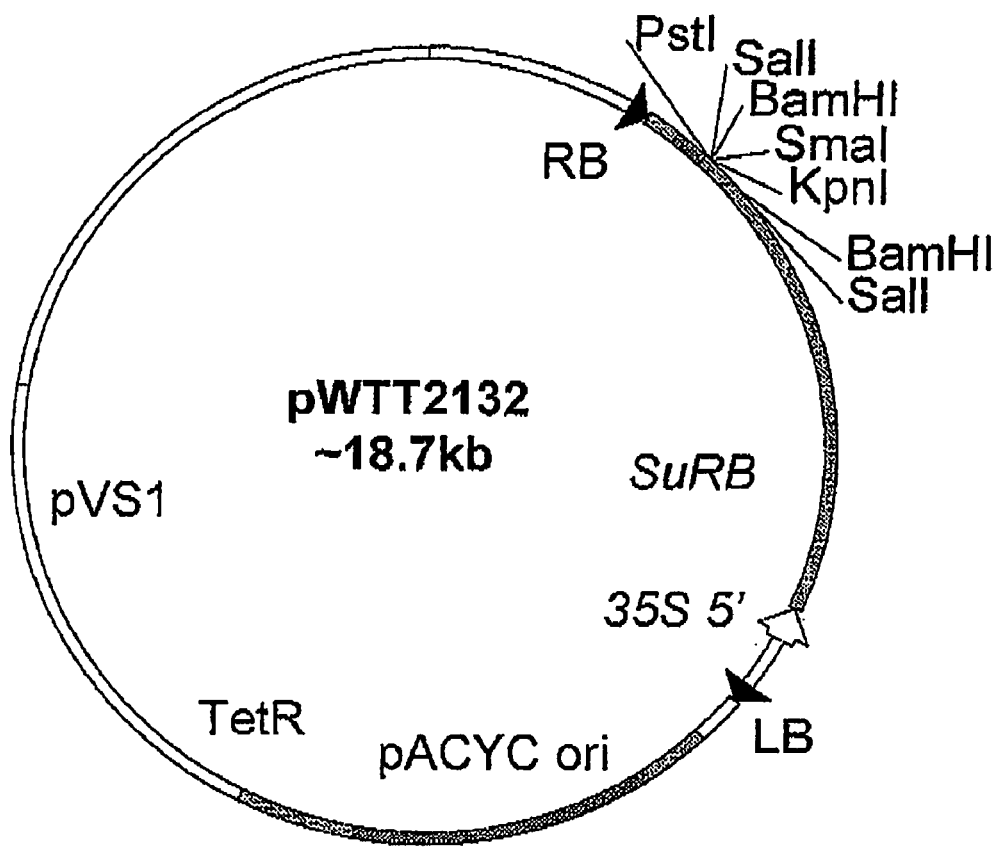

FIG. 2 is a diagrammatic representation of the plasmid pCGP602, pCGP601 and pCGP176 containing *petunia* F3'5'H petHf1 cDNA clones from *P. hybrida* cv. OGB. The *petunia* F3'5'H petHf1 fragment was used in the preparation of constructs containing the *petunia* F3'5'H cDNA clone, $^{32}$P-labelled fragments of the 1.6 kb BspHI/FspI fragment FIG. 6 is a diagrammatic representation of the binary plasmid pWTT2132 (DNAP) containing the 35S 5': SuRB selectable marker gene and a multi-cloning site. A description of pWTT2132 is given in Example 4. Selected restriction endonuclease sites are marked. Refer to Table 2 and Table 4 for a description of the abbreviations.

Figure 7:
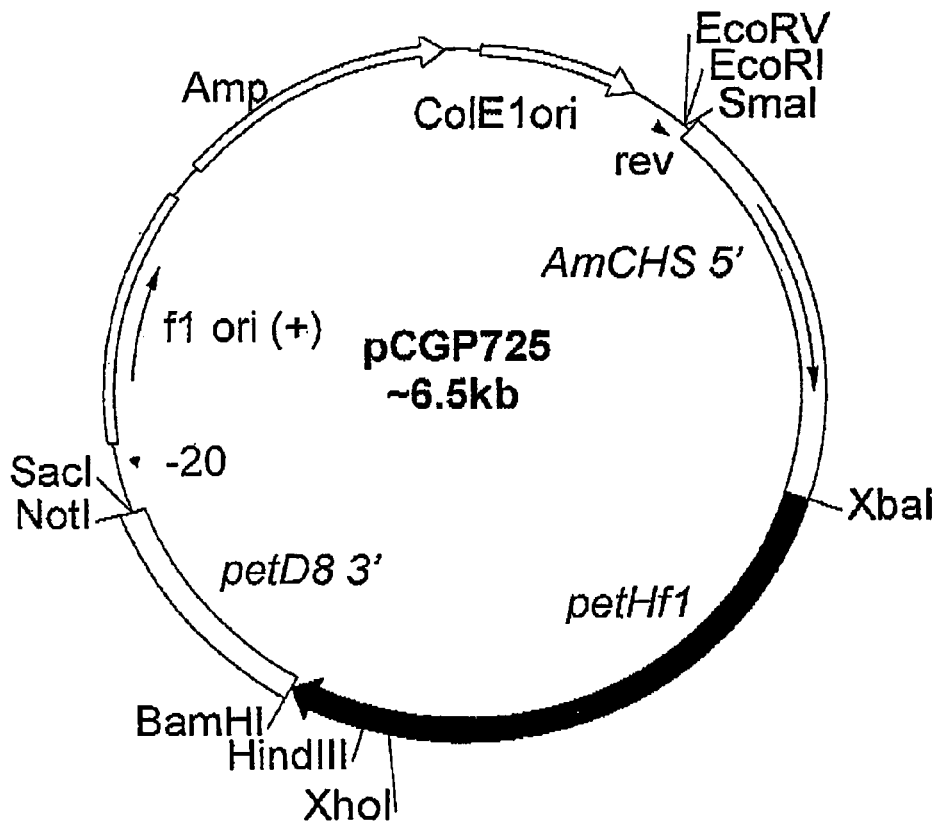

FIG. 7 is a diagrammatic representation of the plasmid pCGP725. The AmCHS 5': petHf1: petD8 3' gene from pCGP485 was cloned into pBluescript II (KS (+) vector. The construction of pCGP725 is described in Example 4. Selected restriction endonuclease sites are marked. Refer to Table 2 and Table 4 for a description of the abbreviations.

Figure 8:
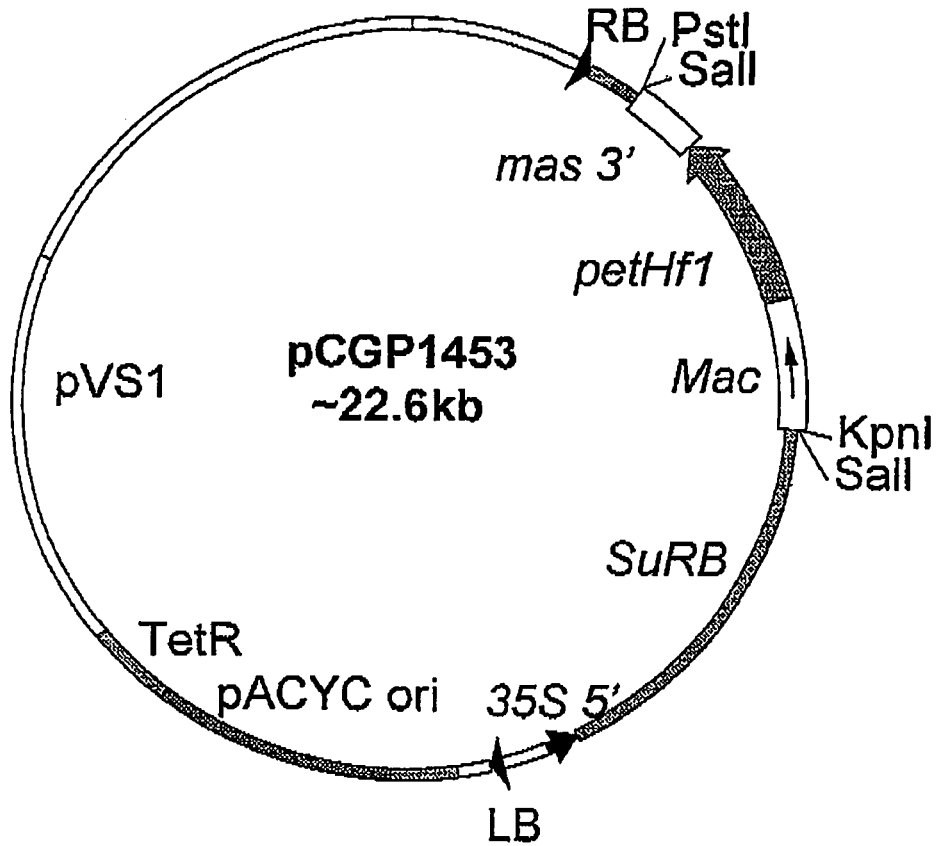

FIG. 8 is a diagrammatic representation of the binary plasmid pCGP1453. The Mac: petHf1: mas 3' gene from pCGP628 was cloned into the binary vector pWTT2132 (DNAP) in a tandem orientation with the chimaeric SuRB gene. The construction of pCGP1453 is described in Example 4. Selected restriction endonuclease sites are marked. Refer to Table 2 and Table 4 for a description of the abbreviations.

Figure 9:
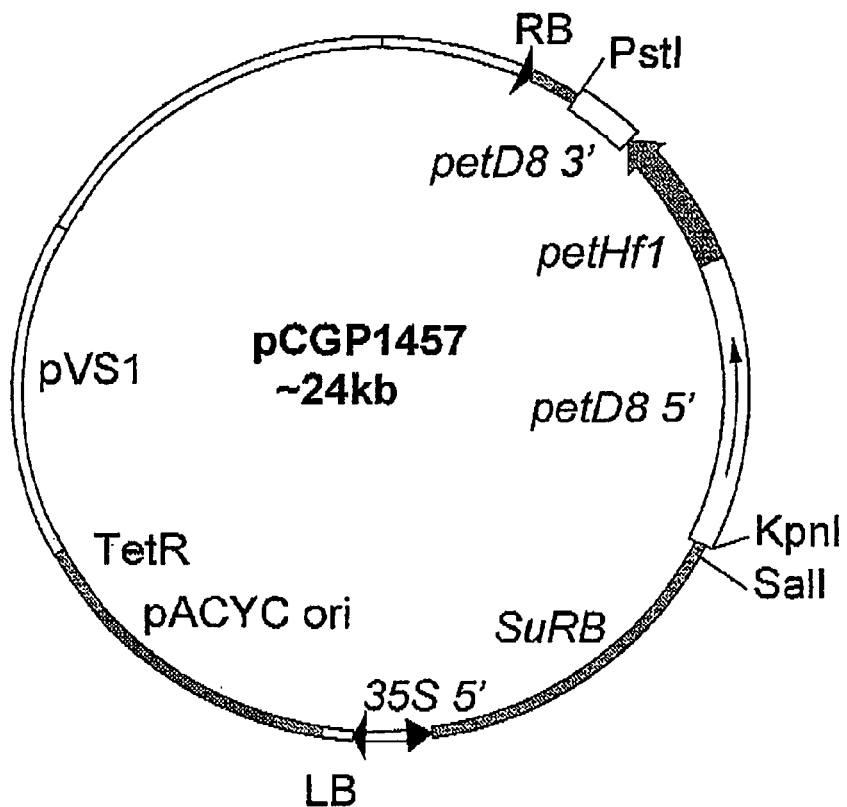

FIG. 9 is a diagrammatic representation of the binary plasmid pCGP1457. The petD8 5': petHf1: petD8 3' gene from pCGP1107 was cloned into the binary vector pWTT2132 (DNAP) in a tandem orientation with the chimaeric SuRB gene. The construction of pCGP1457 is described in Example 4. Selected restriction endonuclease sites are marked. Refer to Table 2 and Table 4 for a description of the abbreviations.

Figure 10:
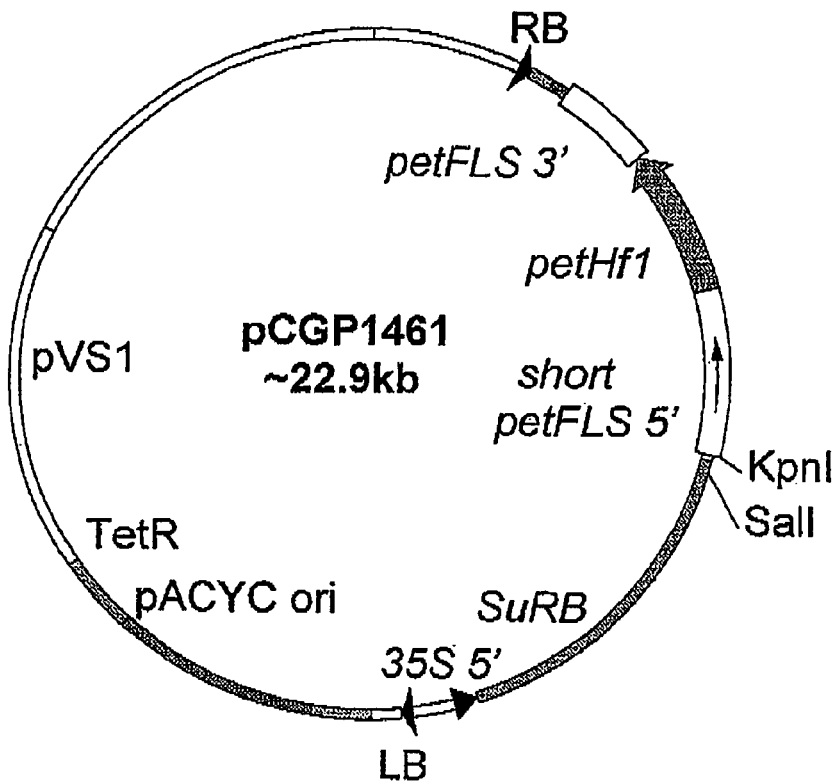

FIG. 10 is a diagrammatic representation of the binary plasmid pCGP1461. The shortpetFLS 5': petHf1: petFLS 3' gene from pCGP497 was cloned into the binary vector pWTT2132 (DNAP) in a tandem orientation with the chimeric SuRB gene. The construction of pCGP1461 is described in Example 4. Selected restriction endonuclease sites are marked. Refer to Table 2 and Table 4 for a description of the abbreviations.

Figure 11:
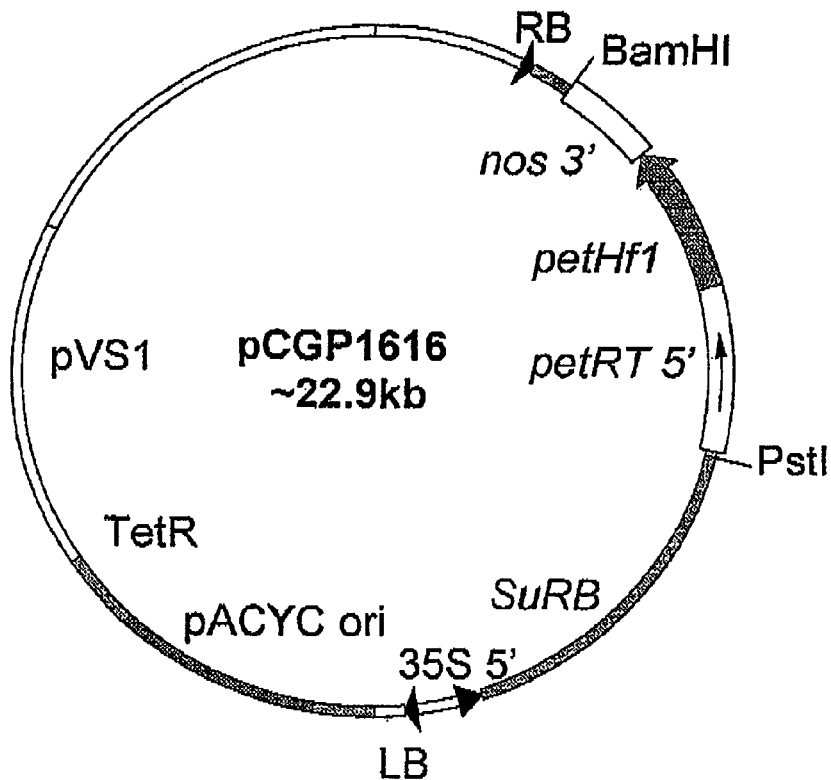

FIG. 11 is a diagrammatic representation of the binary plasmid pCGP1616. The petRT 5': petHf1: nos 3' gene from pCGP846 was cloned into the binary vector pWTT2132 (DNAP) in a tandem orientation with the chimaeric SuRB gene. The construction of pCGP1616 is described in Example 4. Selected restriction endonuclease sites are marked. Refer to Table 2 and Table 4 for a description of the abbreviations.

Figure 12:
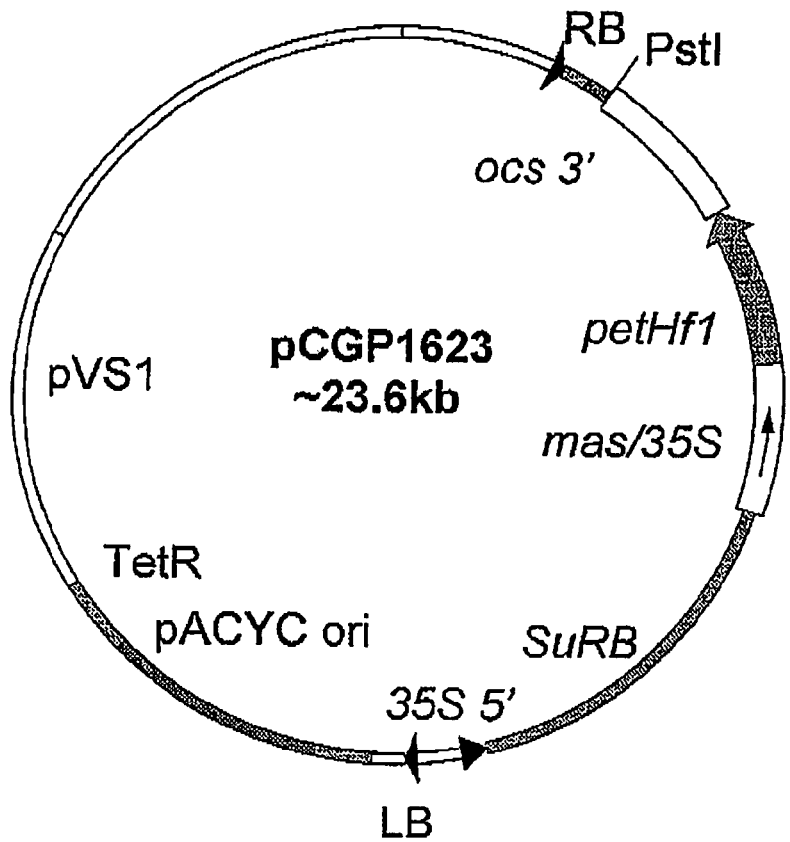

FIG. 12 is a diagrammatic representation of the binary plasmid pCGP1623. The mas/35S: petHf1: ocs 3' gene from pCGP1619 was cloned into the binary vector pWTT2132 (DNAP) in a tandem orientation with the chimaeric SuRB gene. The construction of pCGP1623 is described in Example 4. Selected restriction endonuclease sites are marked. Refer to Table 2 and Table 4 for a description of the abbreviations.

Figure 13:
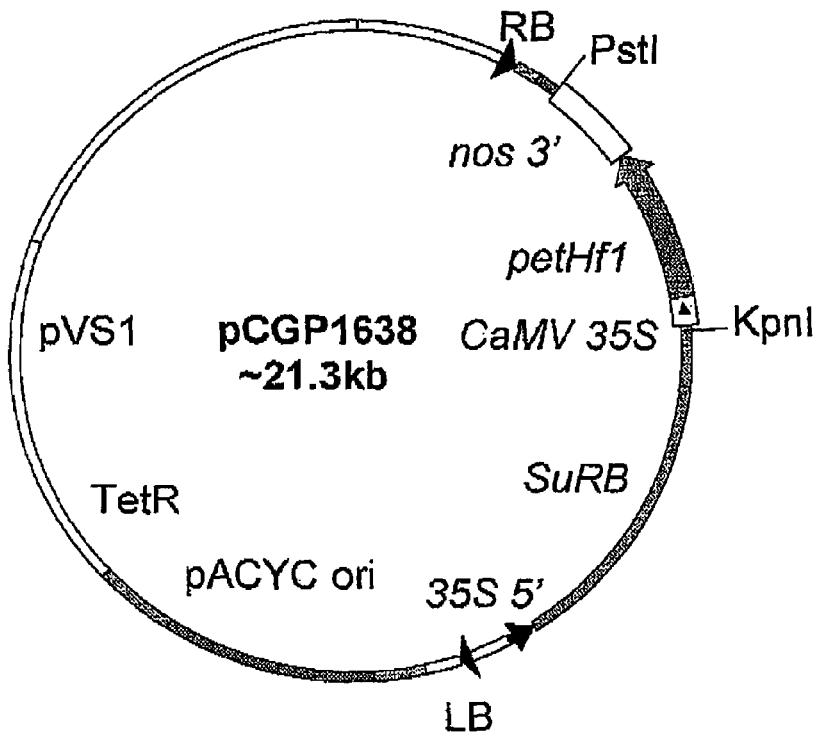

FIG. 13 is a diagrammatic representation of the binary plasmid pCGP1638. The CaMV 35S: petHf1: nos 3' gene from pCGP1636 was cloned into the binary vector pWTT2132 (DNAP) in a tandem orientation with the chimaeric SuRB gene. The construction of pCGP1636 is described in Example 4. Selected restriction endonuclease sites are marked. Refer to Table 2 and Table 4 for a description of the abbreviations.

Figure 14:
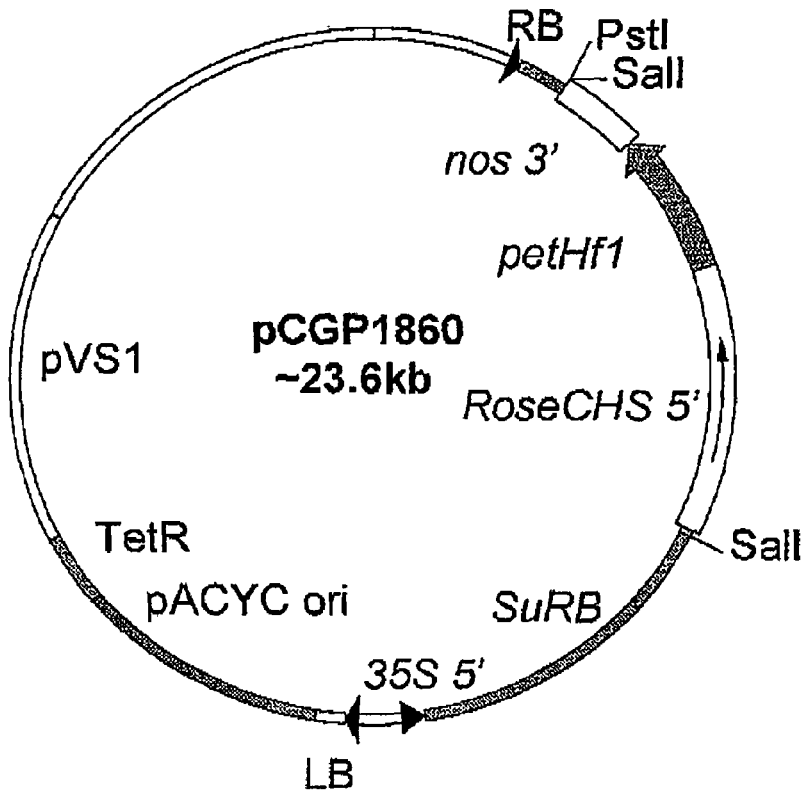

FIG. 14 is a diagrammatic representation of the binary plasmid pCGP1860. The RoseCHS 5': petHf1: nos 3' gene from pCGP200 was cloned into the binary vector pWTT2132 (DNAP) in a tandem orientation with the chimaeric SuRB gene. The construction of pCGP1860 is described in Example 4. Selected restriction endonuclease sites are marked. Refer to Table 2 and Table 4 for a description of the abbreviations.

Figure 15:
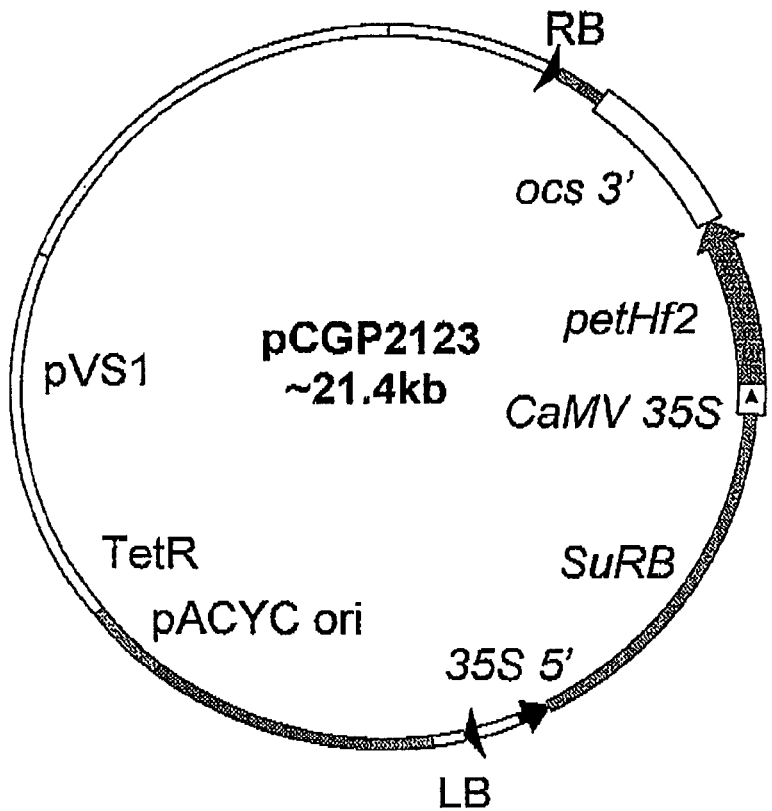

FIG. 15 is a diagrammatic representation of the binary plasmid pCGP2123. The CaMV35S: petHf2: ocs 3' gene from pCGP2109 was cloned into the binary vector pCGP1988 in a tandem orientation with the chimaeric SuRB gene. The construction of pCGP2123 is described in Example 4. Selected restriction endonuclease sites are marked. Refer to Table 2 and Table 4 for a description of the abbreviations.

Figure 16:
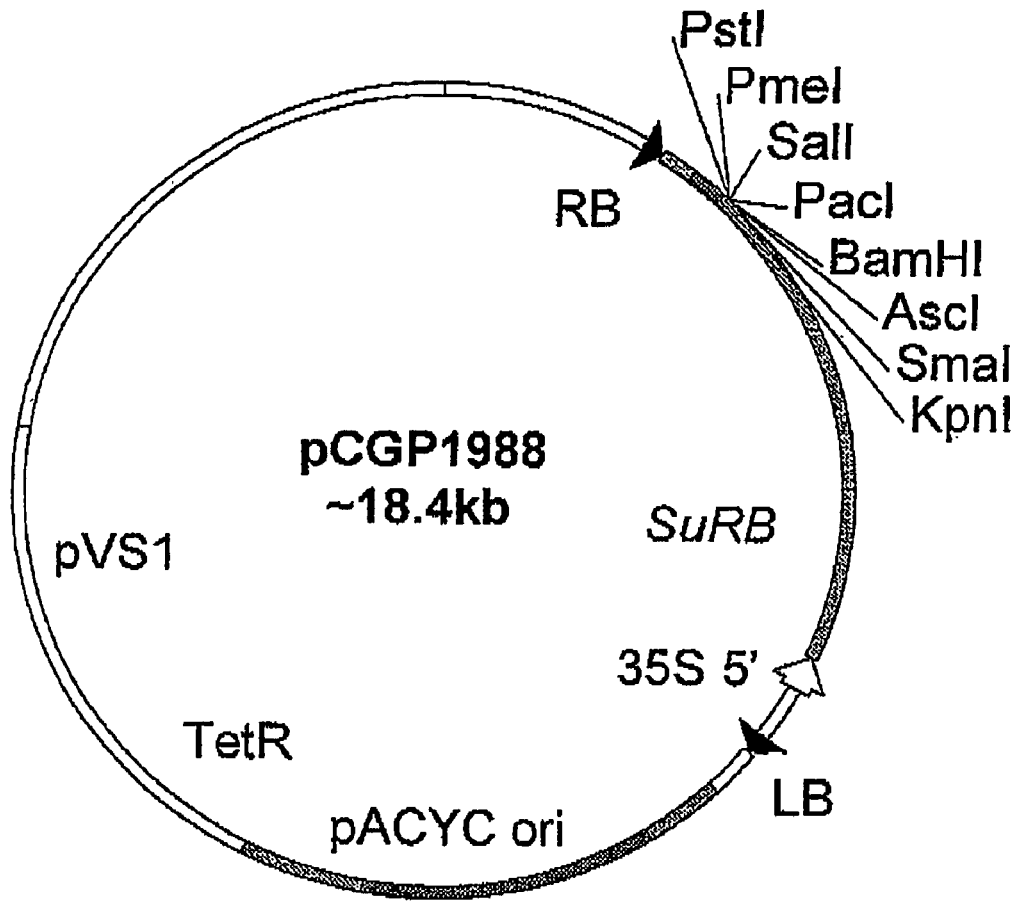

FIG. 16 is a diagrammatic representation of the binary plasmid pCGP1988. The multi-cloning site of the binary vector pWTT1132 (DNAP) was replaced with the multi-cloning site from pNEB193 (New England Biolabs). The construction of pCGP1988 is described in Example 4. Selected restriction endonuclease sites are marked. Refer to Table 2 and Table 4 for a description of the abbreviations.

Figure 17:
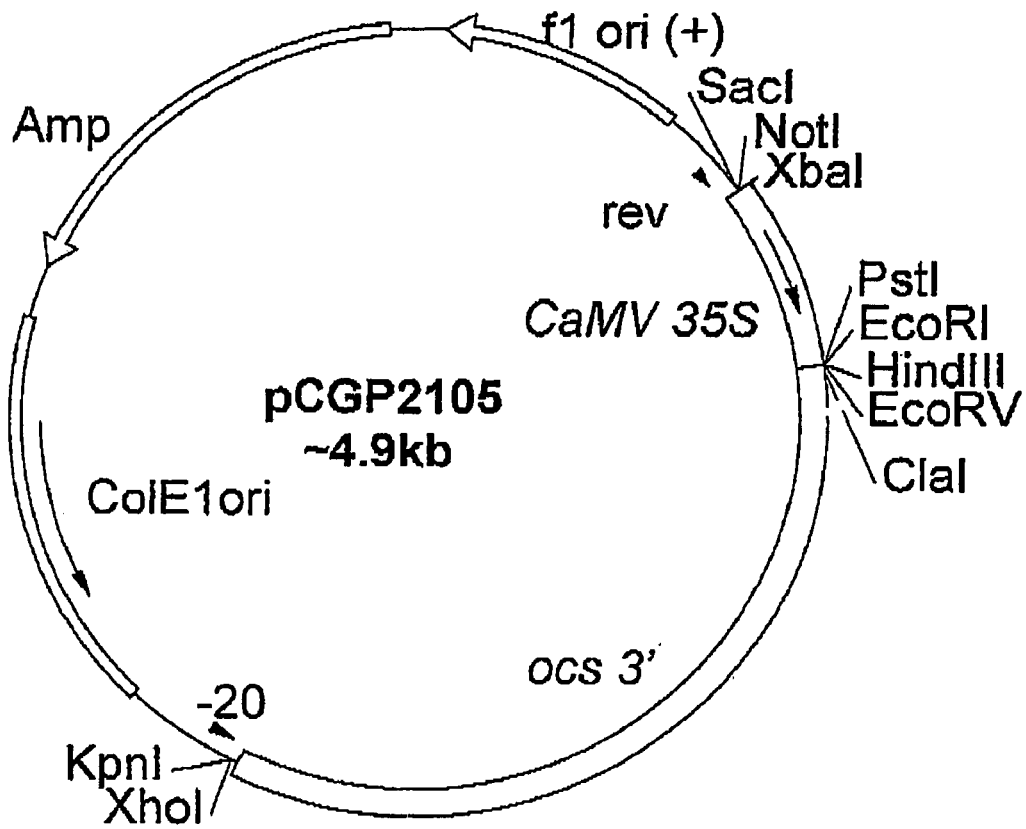

FIG. 17 is a diagrammatic representation of the plasmid pCGP2105. The 35S 5': ocs 3' expression cassette with multiple restriction endonuclease sites between the promoter and terminator fragments is in a pBluescript SK (+) vector backbone. The construction of pCGP2105 is described in Example 4. Selected restriction endonuclease sites are marked. Refer to Table 2 and Table 4 for a description of the abbreviations.

Figure 18:
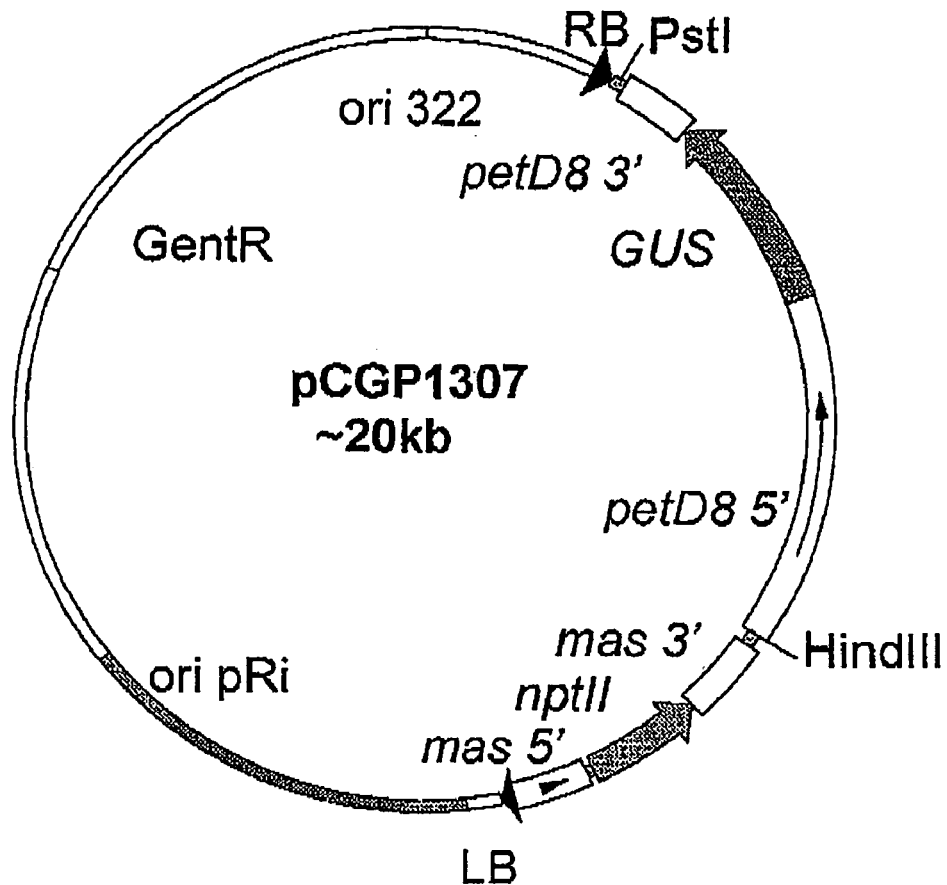

FIG. 18 is a diagrammatic representation of the binary plasmid pCGP1307. The petD8 5': GUS: petD8 3' gene from pCGP1106 was cloned into the binary vector pCGP1548 in a tandem orientation to the chimaeric nptII selectable marker gene. The construction of pCGP1307 is described in Example 6. Selected restriction endonuclease sites are marked. Refer to Table 2 and Table 4 for a description of the abbreviations.

Figure 19:
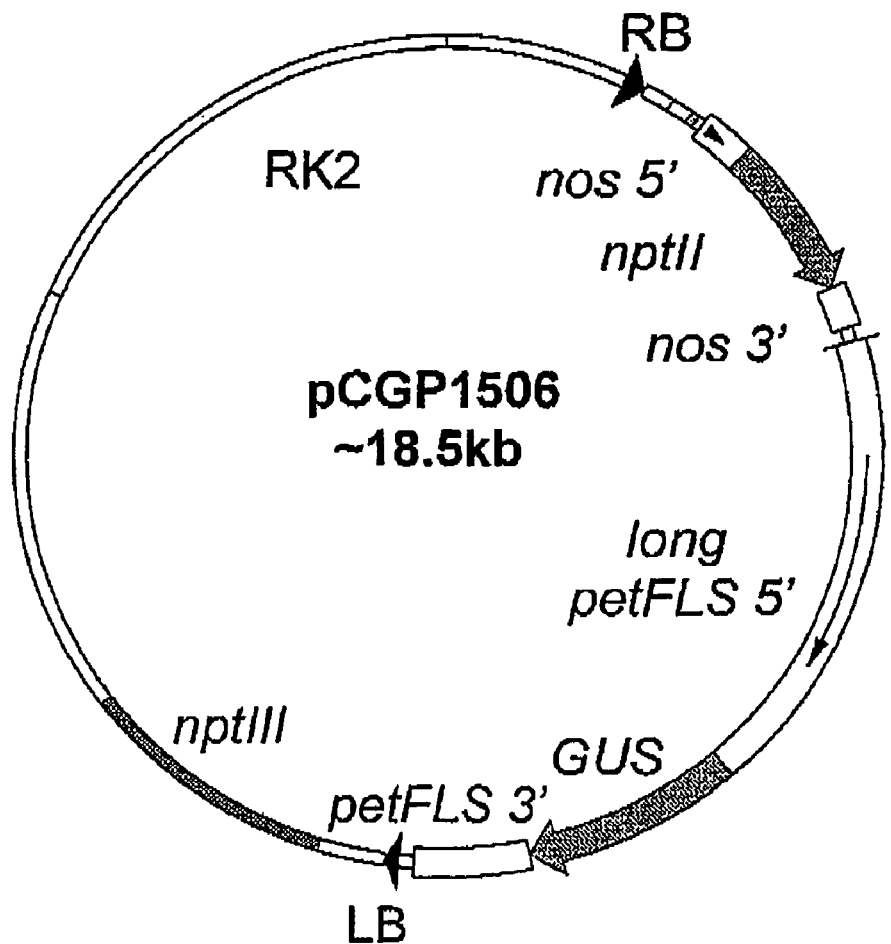

FIG. 19 is a diagrammatic representation of the binary plasmid pCGP1506. The longpetFLS 5': GUS: petFLS 3' gene from pCGP496 was cloned into the binary vector pBIN19 in a tandem orientation to the chimaeric nptII selectable marker gene. The construction of pCGP1506 is described in Example 6. Refer to Table 2 and Table 4 for a description of the abbreviations.

Figure 20:
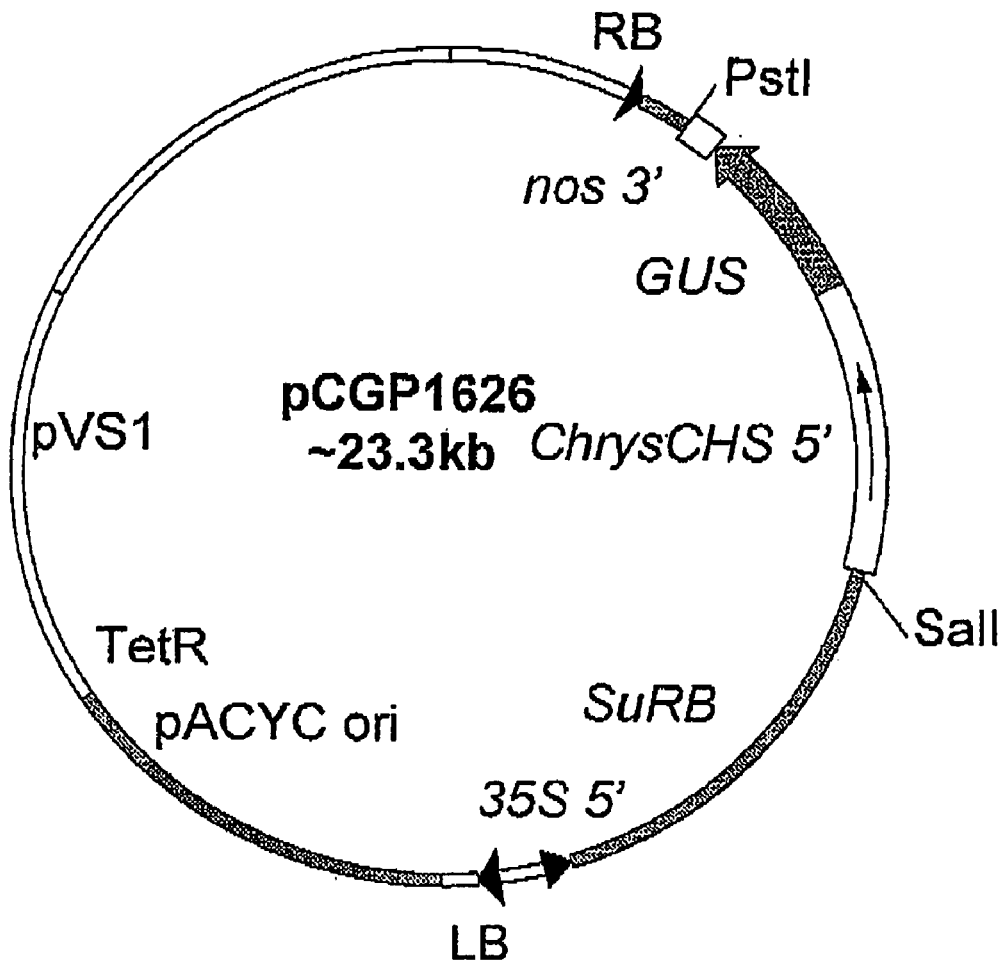

FIG. 20 is a diagrammatic representation of the binary plasmid pCGP1626. The ChyrsCHS 5': GUS: nos 3' gene from pCGP1622 was cloned into the binary vector pWTT2132 in a tandem orientation with the chimaeric SuRB gene. The construction of pCGP1626 is described in Example 6. Selected restriction endonuclease sites are marked. Refer to Table 2 and Table 4 for a description of the abbreviations.

Figure 21:
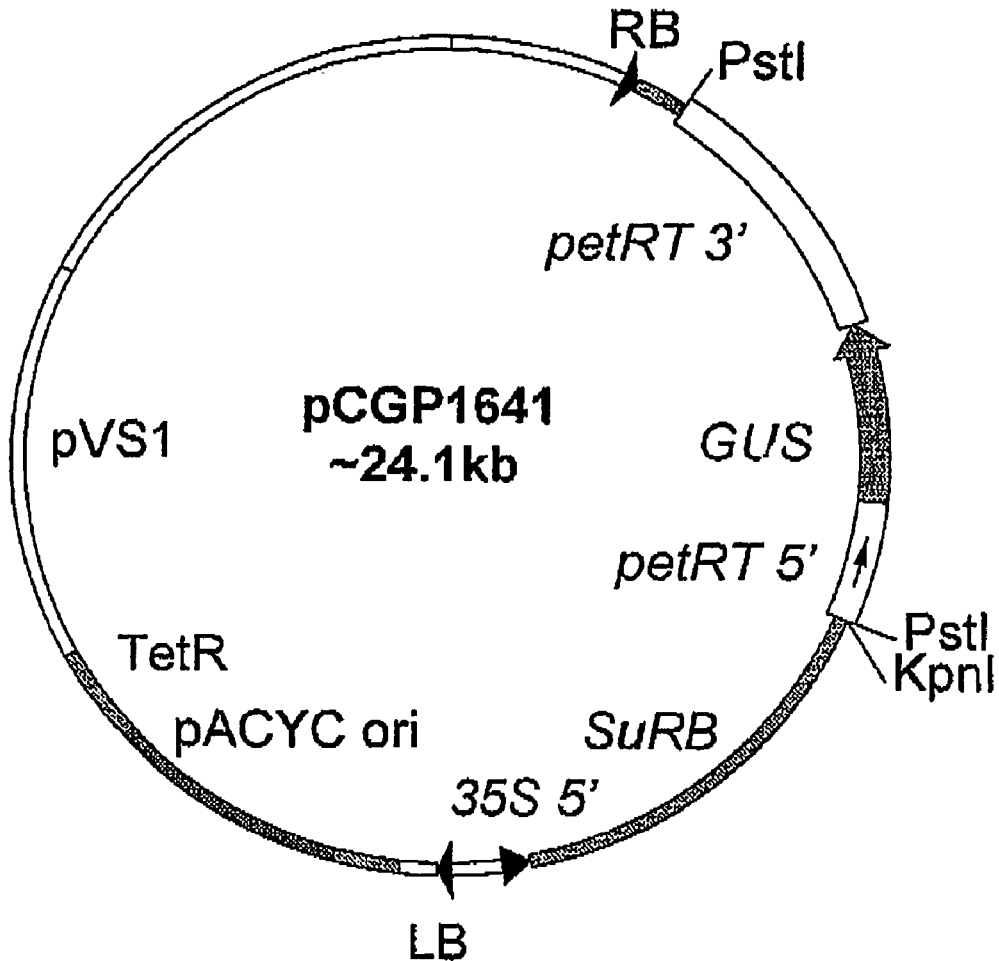

FIG. 21 is a diagrammatic representation of the binary plasmid pCGP1641. The petRT 5': GUS: petRT 3' gene from pCGP1628 was cloned into the binary vector pWTT2132 in a tandem orientation with the chimaeric SuRB gene. The construction of pCGP1641 is described in Example 6. Selected restriction endonuclease sites are marked. Refer to Table 2 and Table 4 for a description of the abbreviations.

Figure 22:
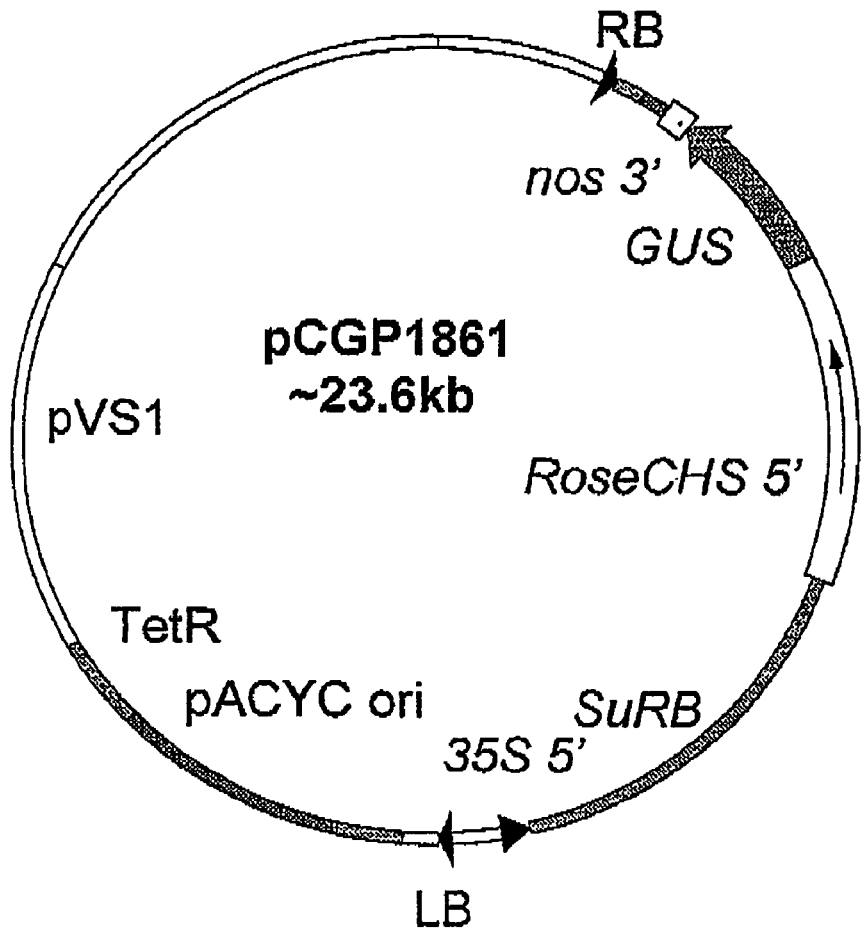

FIG. 22 is a diagrammatic representation of the binary plasmid pCGP1861. The RoseCHS 5': GUS: nos 3' gene from pCGP197 was cloned into the binary vector pWTT2132 in a tandem orientation with the chimaeric SuRB gene. The construction of pCGP1861 is described in Example 6. Refer to Table 2 and Table 4 for a description of the abbreviations.

Figure 23:
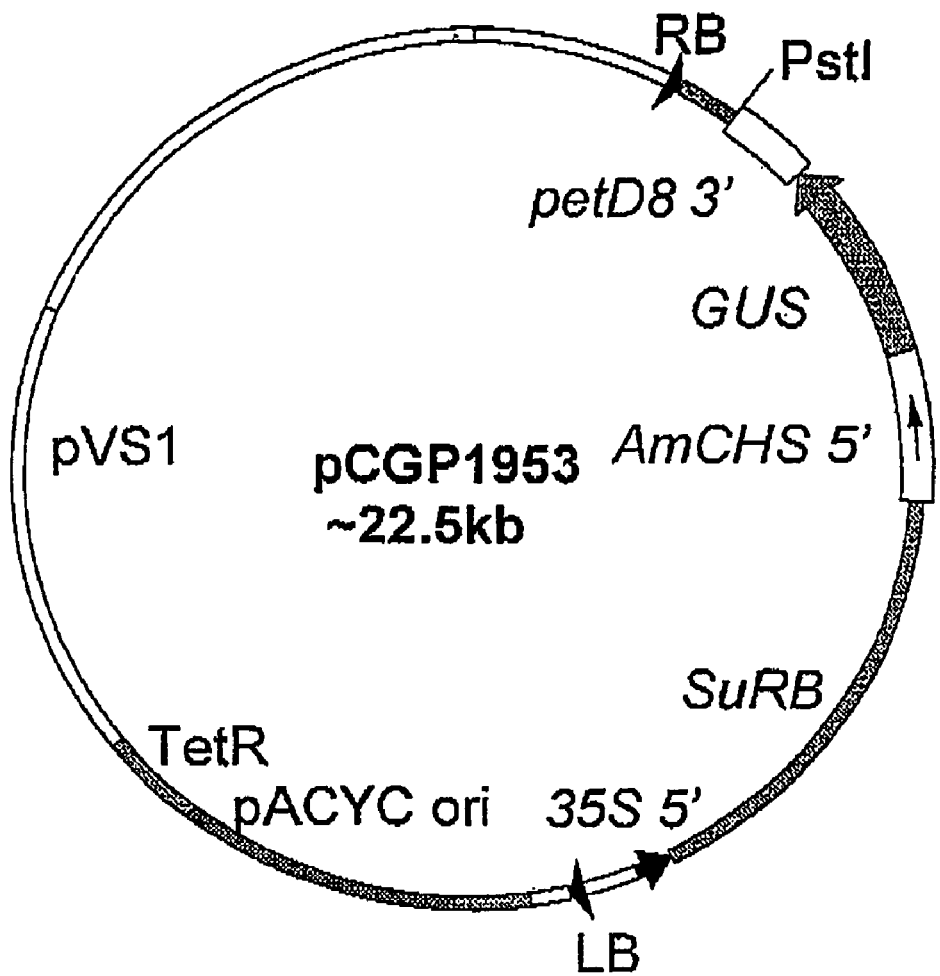

FIG. 23 is a diagrammatic representation of the binary plasmid pCGP1953. The AmCHS 5': GUS: petD8 3' gene from pCGP1952 was cloned into the binary vector pWTT2132 in a tandem orientation with the chimaeric SuRB gene. The construction of pCGP1953 is described in Example 6. Refer, to Table 2 and Table 4 for a description of the abbreviations.

Figure 24:
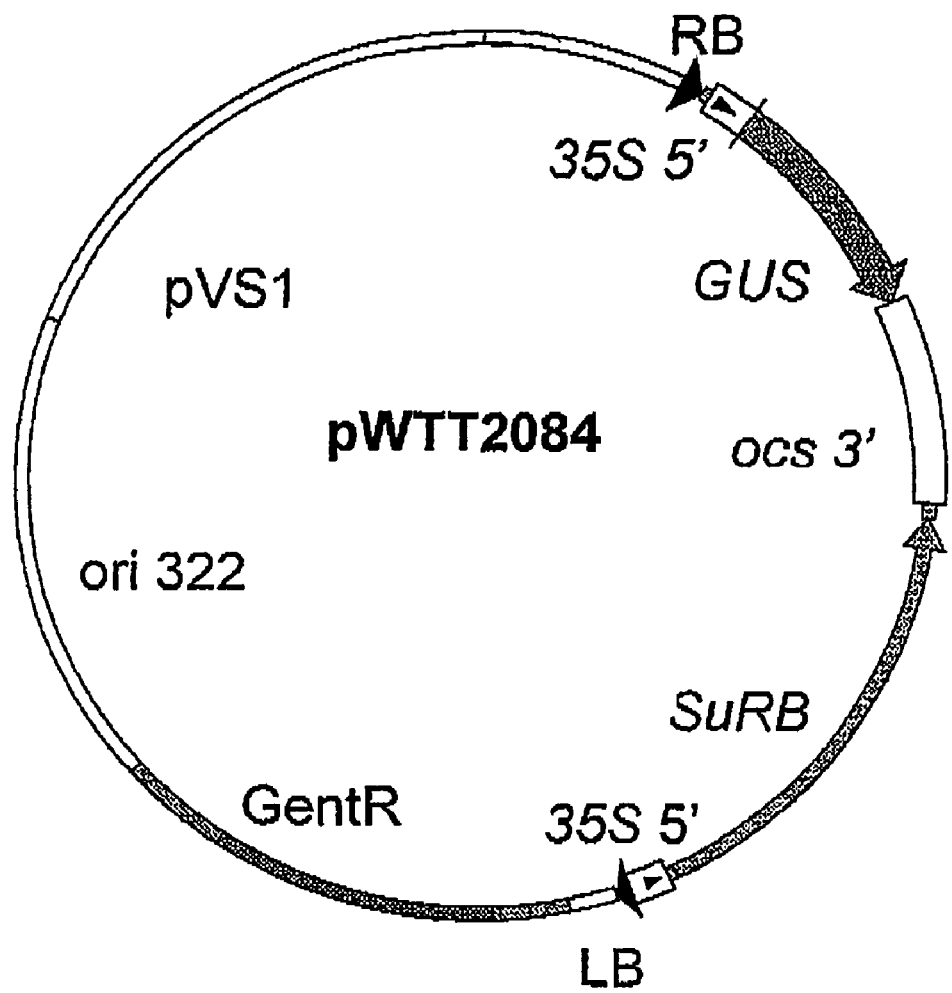

FIG. 24 is a diagrammatic representation of the binary plasmid pWTT2084 (DNAP) containing a 35S 5': GUS: ocs 3' gene in a convergent orientation to the chimaeric SuRB selectable marker gene. A description of pWTT2084 is given in Example 6. Refer to Table 2 and Table 4 for a description of the abbreviations.

Figure 25:
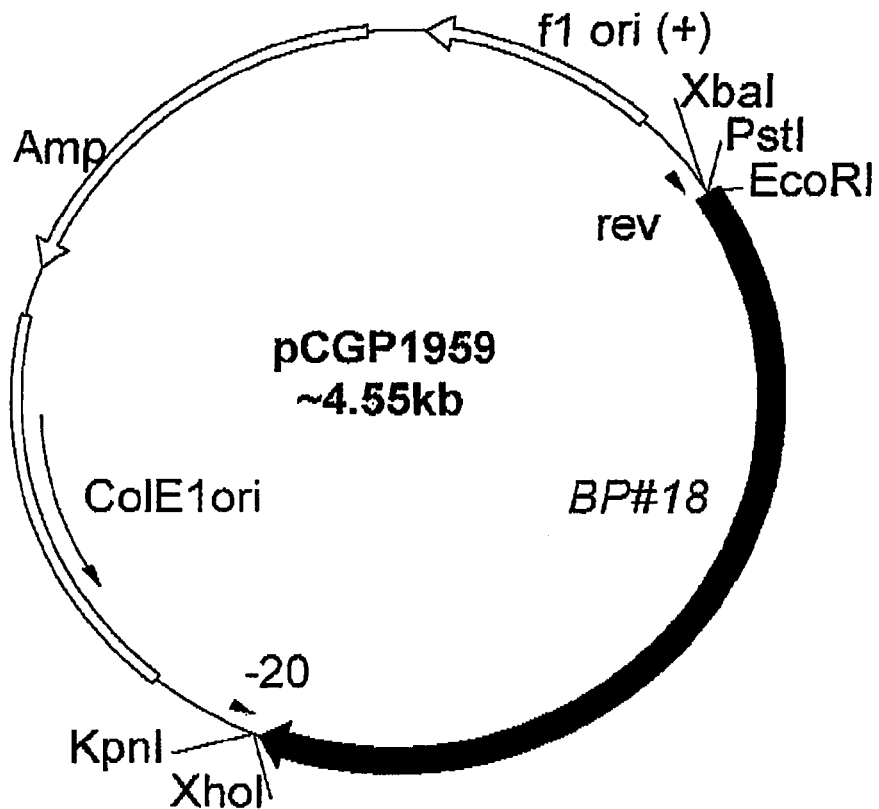

FIG. 25 is a diagrammatic representation of the plasmid pCGP1959 containing the F3'5'H BP#18 cDNA clone from *Viola* spp. cv Black Pansy in a pBluescript SK II (+) backbone. A description of pCGP1959 is given in Example 7. Selected restriction endonuclease sites are marked. Refer to Table 2 and Table 4 for a description of the abbreviations.

Figure 26:
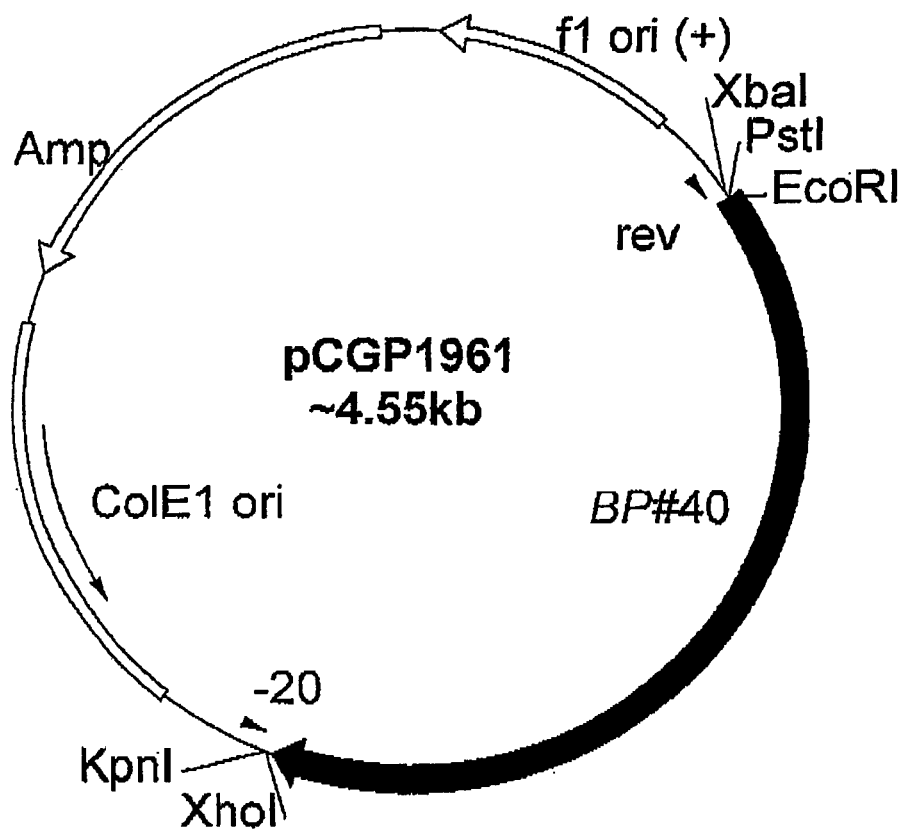

FIG. 26 is a diagrammatic representation of the plasmid pCGP1961 containing the F3'5'H BP#40 cDNA clone from *Viola* spp. cv Black Pansy in a pBluescript SK II (+) backbone. A description of pCGP1961 is given in Example 7. Selected restriction endonuclease sites are marked. Refer to Table 2 and Table 4 for a description of the abbreviations.

Figure 27:
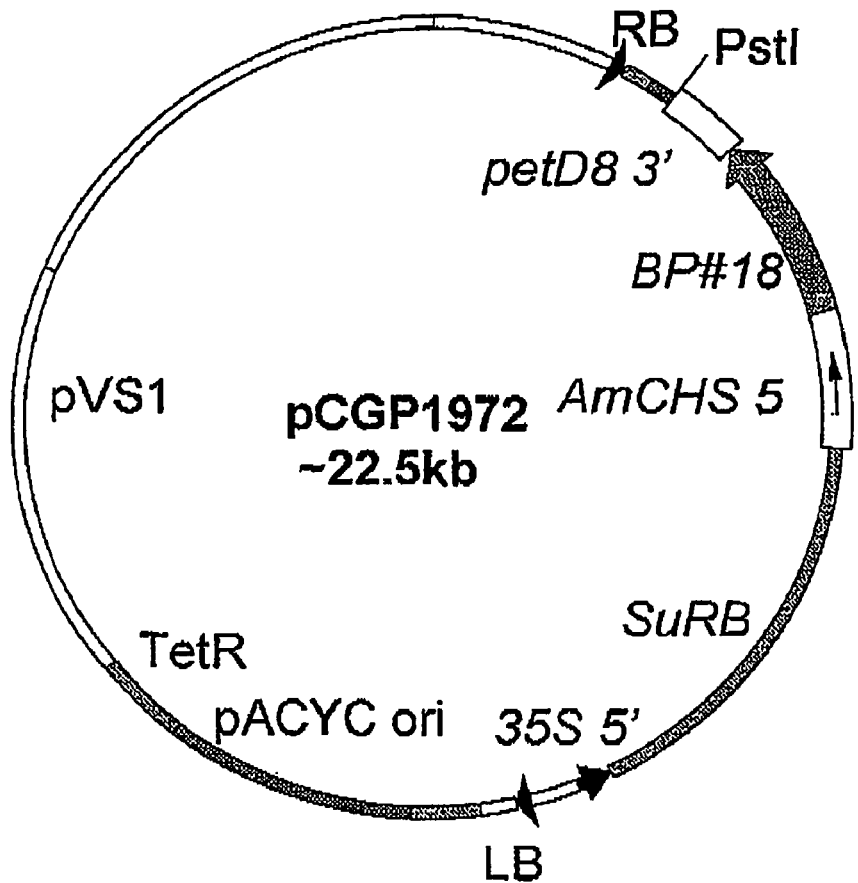

FIG. 27 is a diagrammatic representation of the binary plasmid pCGP1972. The AmCHS 5': BP#18: petD8 3' gene from pCGP1970 was cloned into the binary vector pWTT2132 (DNAP) in a tandem orientation with the chimaeric SuRB gene. The construction of pCGP1972 is described in Example 7. Selected restriction endonuclease sites are marked. Refer to Table 2 and Table 4 for a description of the abbreviations.

Figure 28:
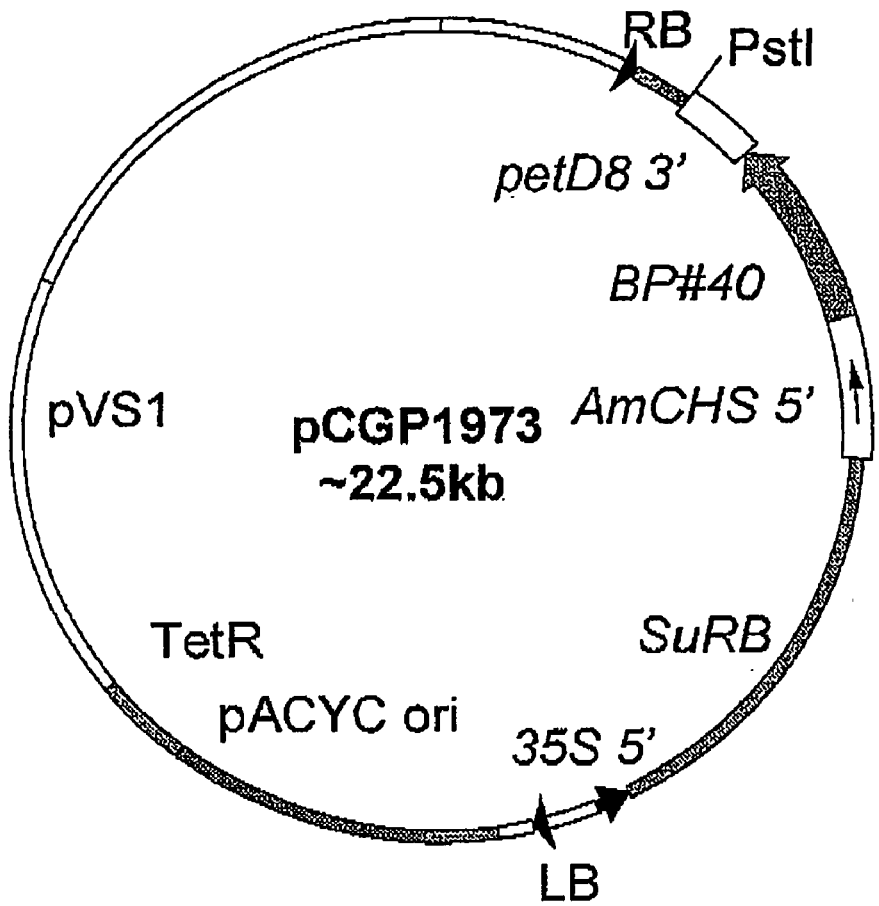

FIG. 28 is a diagrammatic representation of the binary plasmid pCGP1973. The AmCHS 5': BP#40: petD8 3' gene from pCGP1971 was cloned into the binary vector pWTT2132 (DNAP) in a tandem orientation with the chimaeric SuRB gene. The construction of pCGP1973 is described in Example 7. Selected restriction endonuclease sites are marked. Refer to Table 2 and Table 4 for a description of the abbreviations.

Figure 29:
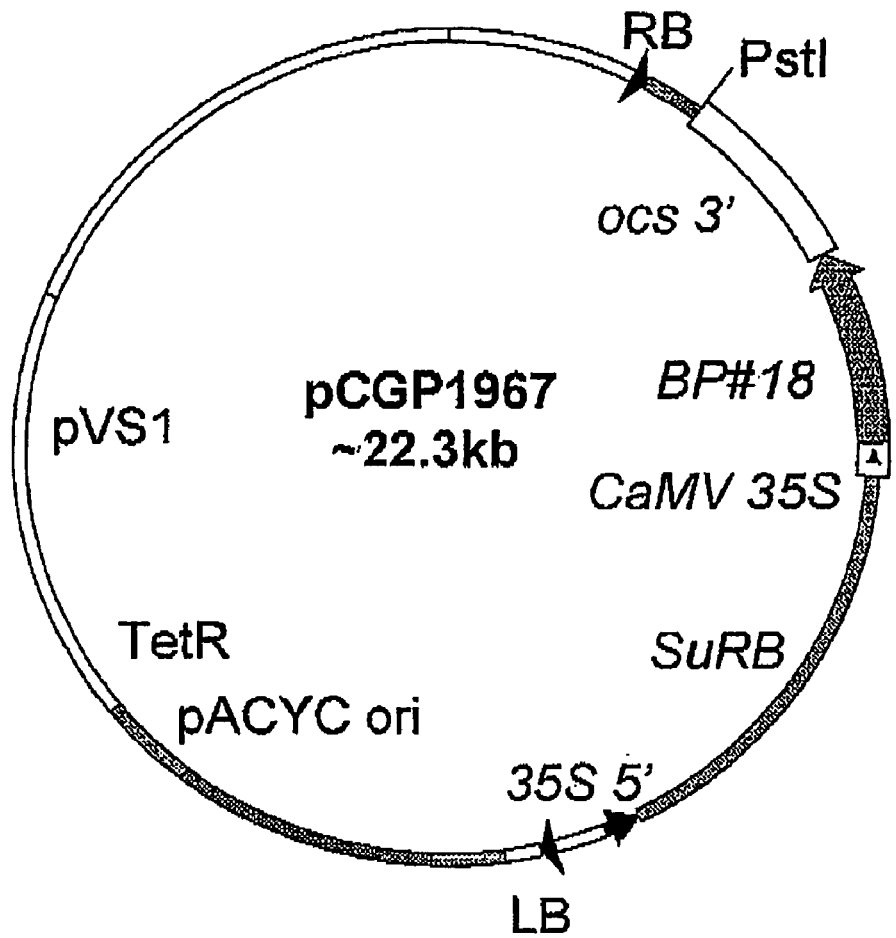

FIG. 29 is a diagrammatic representation of the binary plasmid pCGP1967. The CaMV 35S: BP#18:ocs 3' gene from pCGP1965 was cloned into the binary vector pWTT2132 (DNAP) in a tandem orientation with the chimaeric SuRB gene. The construction of pCGP1967 is described in Example 7. Selected restriction endonuclease sites are marked. Refer to Table 2 and Table 4 for a description of the abbreviations.

Figure 30:
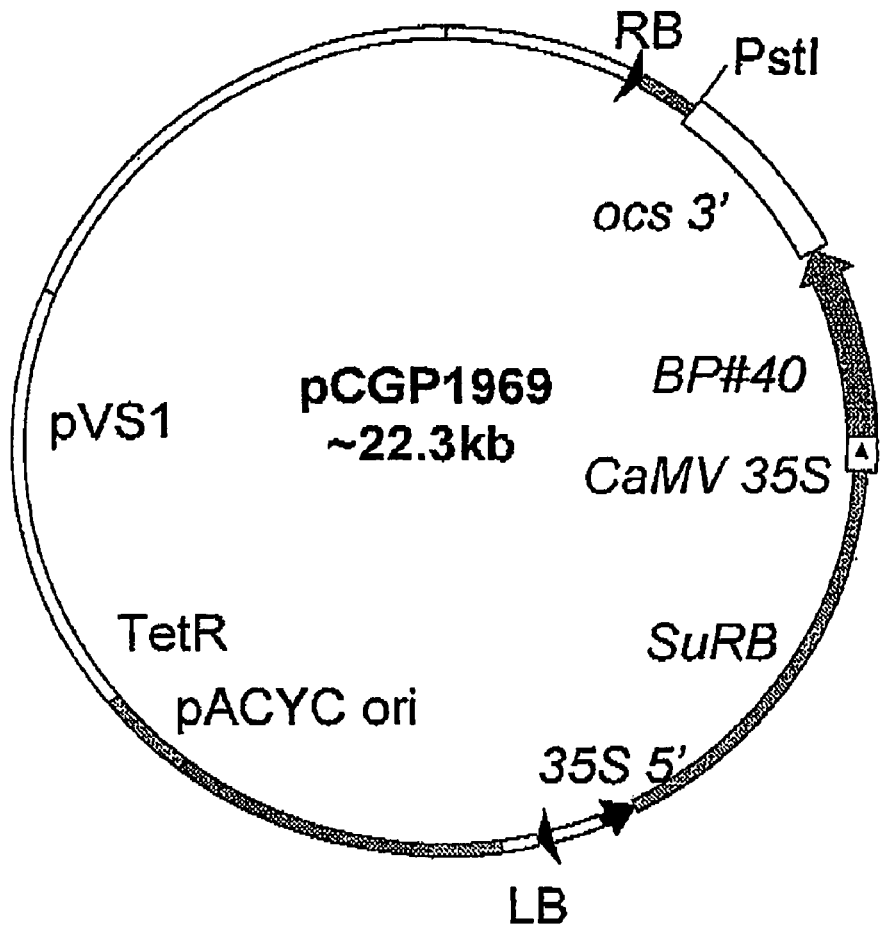

FIG. 30 is a diagrammatic representation of the binary plasmid pCGP1969. The CaMV 35S: BP#40:ocs 3' gene from pCGP1966 was cloned into the binary vector pWTT2132 (DNAP) in a tandem orientation with the chimaeric SuRB gene. The construction of pCGP1969 is described in Example 7. Selected restriction endonuclease sites are marked. Refer to Table 2 and Table 4 for a description of the abbreviations.

Figure 31:
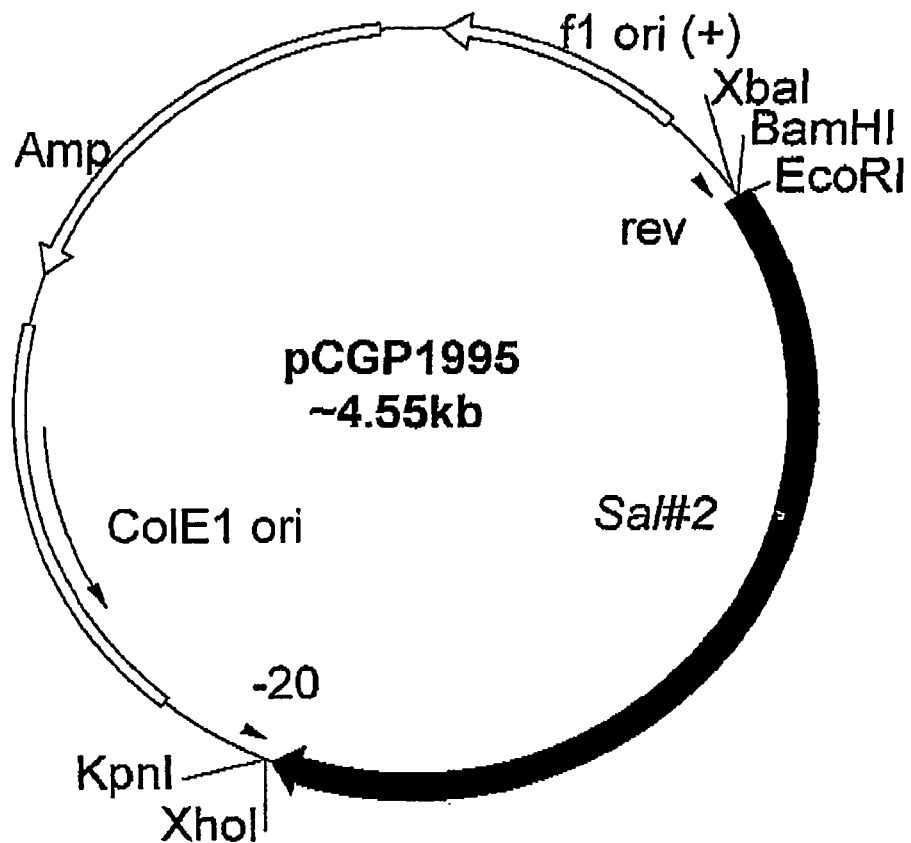

FIG. 31 is a diagrammatic representation of the plasmid pCGP1995 containing the F3'5'H Sal#2 cDNA clone from *Salvia* spp, in a pBluescript SK II (+) backbone. A description of pCGP1995 is given in Example 7. Selected restriction endonuclease sites are marked. Refer to Table 2 and Table 4 for a description of the abbreviations.

Figure 32:
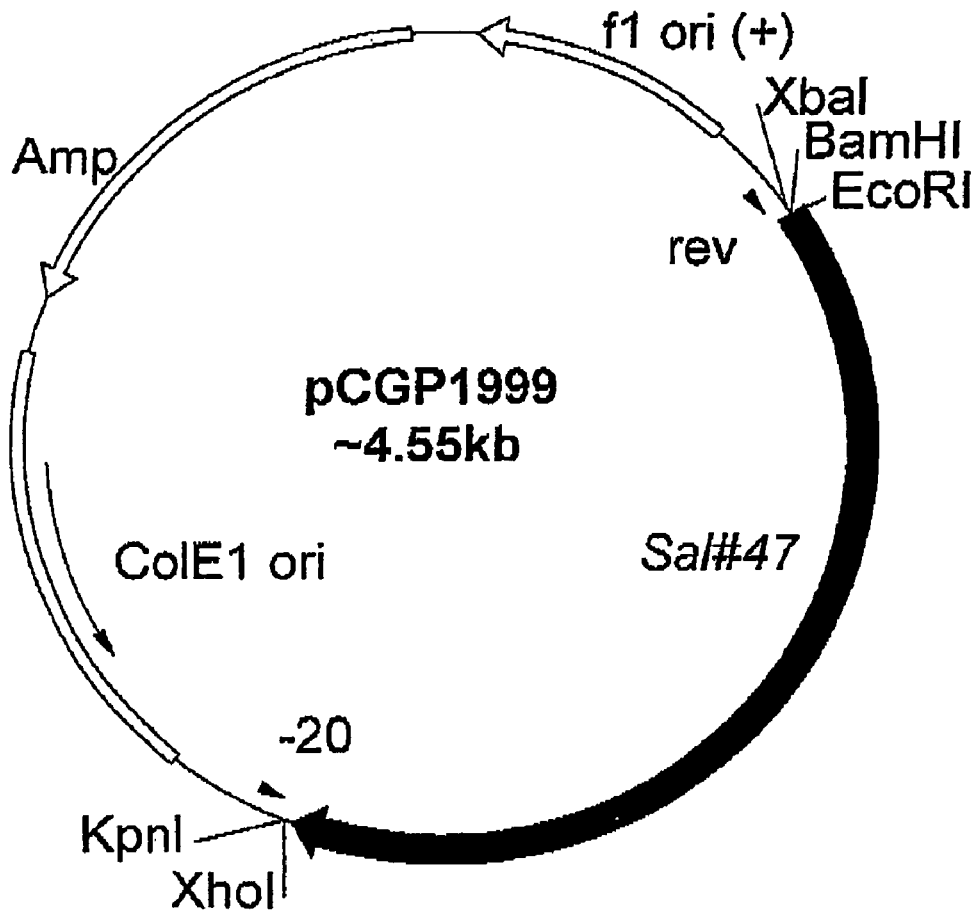

FIG. 32 is a diagrammatic representation of the plasmid pCGP1999 containing the F3'5'H Sal#47 cDNA clone from *Salvia* spp in a pBluescript SK II (+) backbone. A description of pCGP1999 is given in Example 7. Selected restriction endonuclease sites are marked. Refer to Table 2 and Table 4 for a description of the abbreviations.

Figure 33:
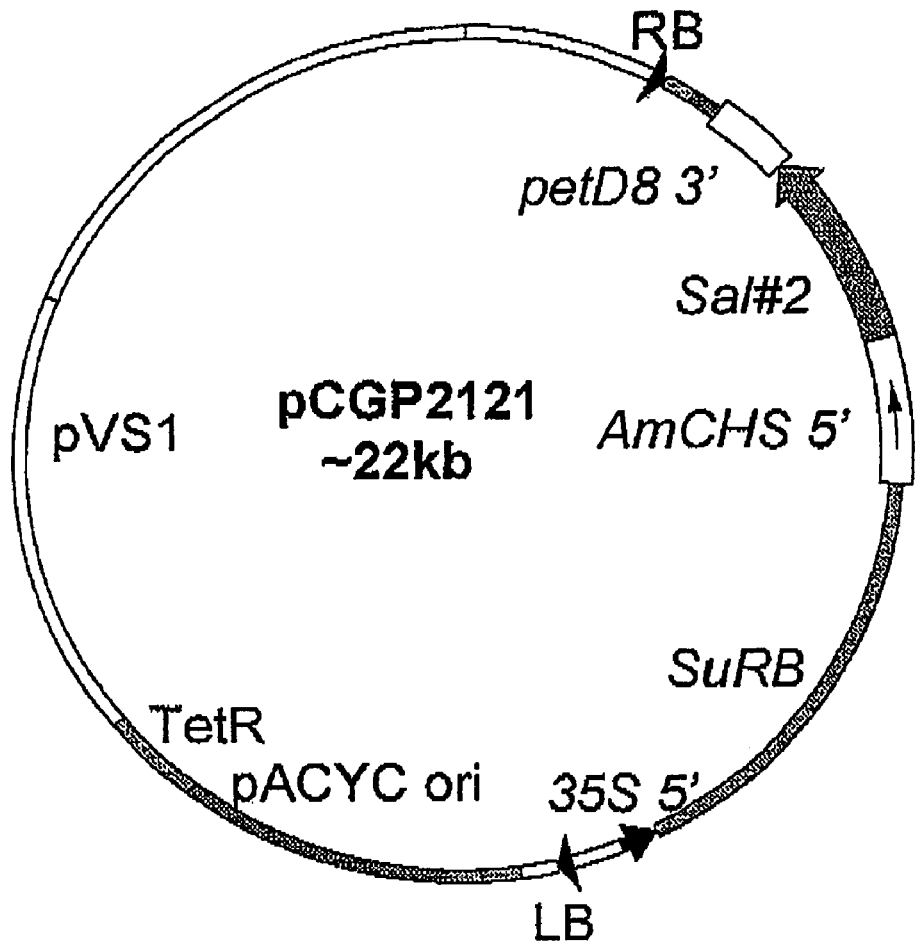

FIG. 33 is a diagrammatic representation of the binary plasmid pCGP2121. The AmCHS 5': Sal#2: petD8 3' gene from pCGP2116 was cloned into the binary vector pCGP1988 in a tandem orientation with the chimaeric SuRB gene. The construction of pCGP2121 is described in Example 7. Selected restriction endonuclease sites are marked. Refer to Table 2 and Table 4 for a description of the abbreviations.

Figure 34:
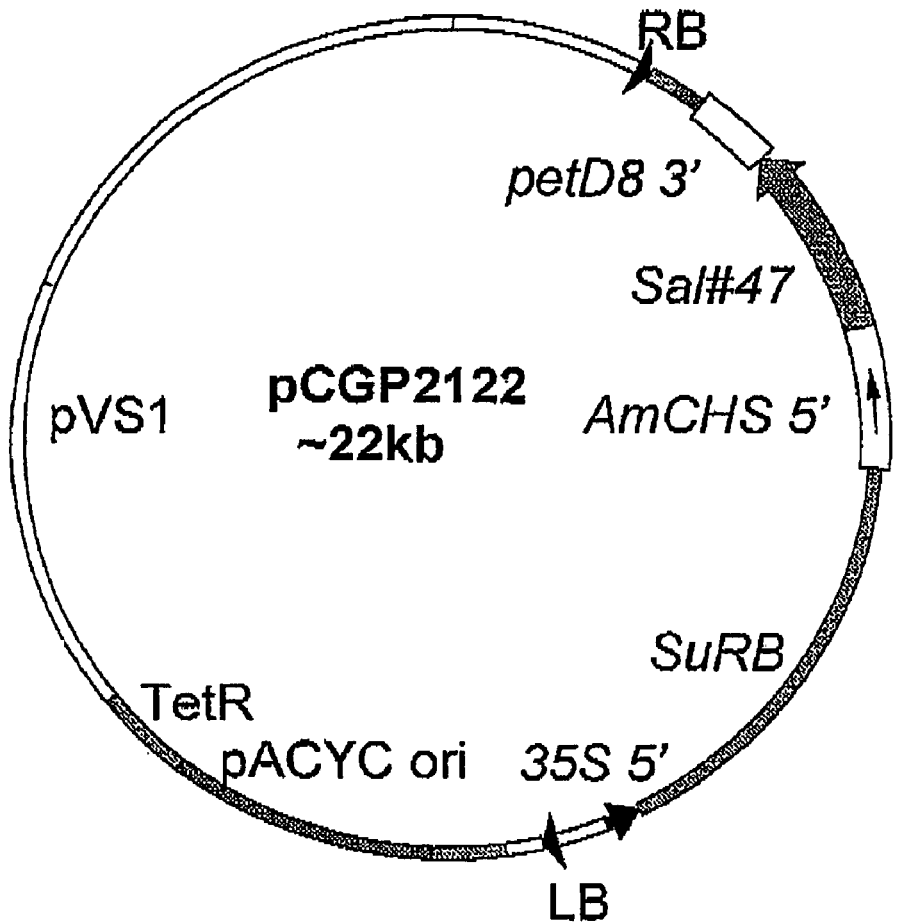

FIG. 34 is a diagrammatic representation of the binary plasmid pCGP2122. The AmCHS 5': Sal#47: petD8 3' gene from pCGP2117 was cloned into the binary vector pCGP1988 in a tandem orientation with the chimaeric SuRB gene. The construction of pCGP2122 is described in Example 7. Selected restriction endonuclease sites are marked. Refer to Table 2 and Table 4 for a description of the abbreviations.

Figure 35:
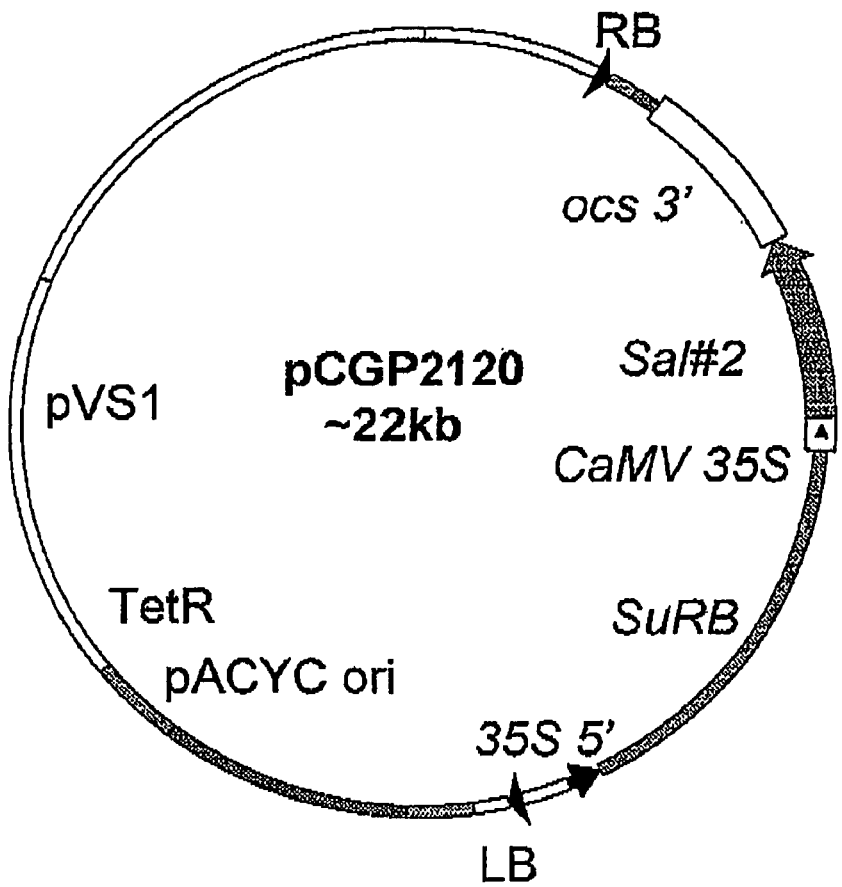

FIG. 35 is a diagrammatic representation of the binary plasmid pCGP2120. The CaMV 35S:Sal#2:ocs 3' gene from pCGP2112 was cloned into the binary vector pCGP1988 in a tandem orientation with the chimaeric SuRB gene. The construction of pCGP2120 is described in Example 7. Selected restriction endonuclease sites are marked. Refer to Table 2 and Table 4 for a description of the abbreviations.

Figure 36:
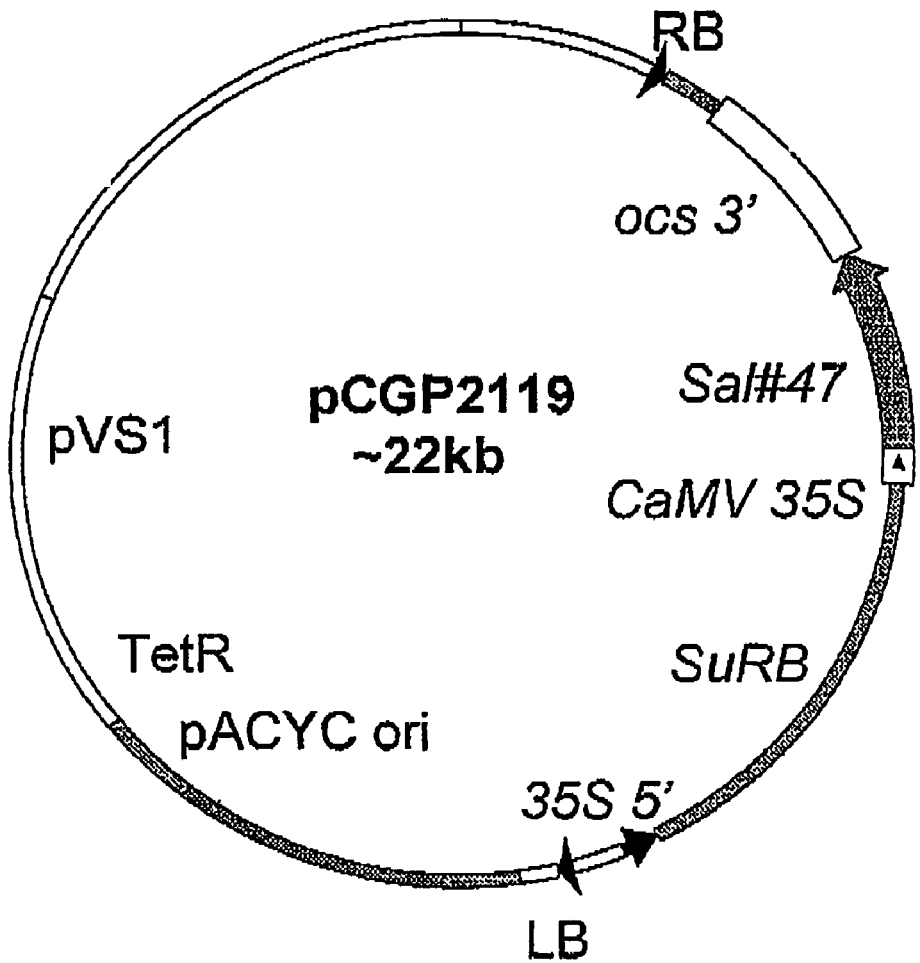

FIG. 36 is a diagrammatic representation of the binary plasmid pCGP2119. The CaMV 35S:Sal#47:ocs 3' gene from pCGP2111 was cloned into the binary vector pCGP1988 in a tandem orientation with the chimaeric SuRB gene. The construction of pCGP2119 is described in Example 7. Selected restriction endonuclease sites are marked. Refer to Table 2 and Table 4 for a description of the abbreviations.

Figure 37:
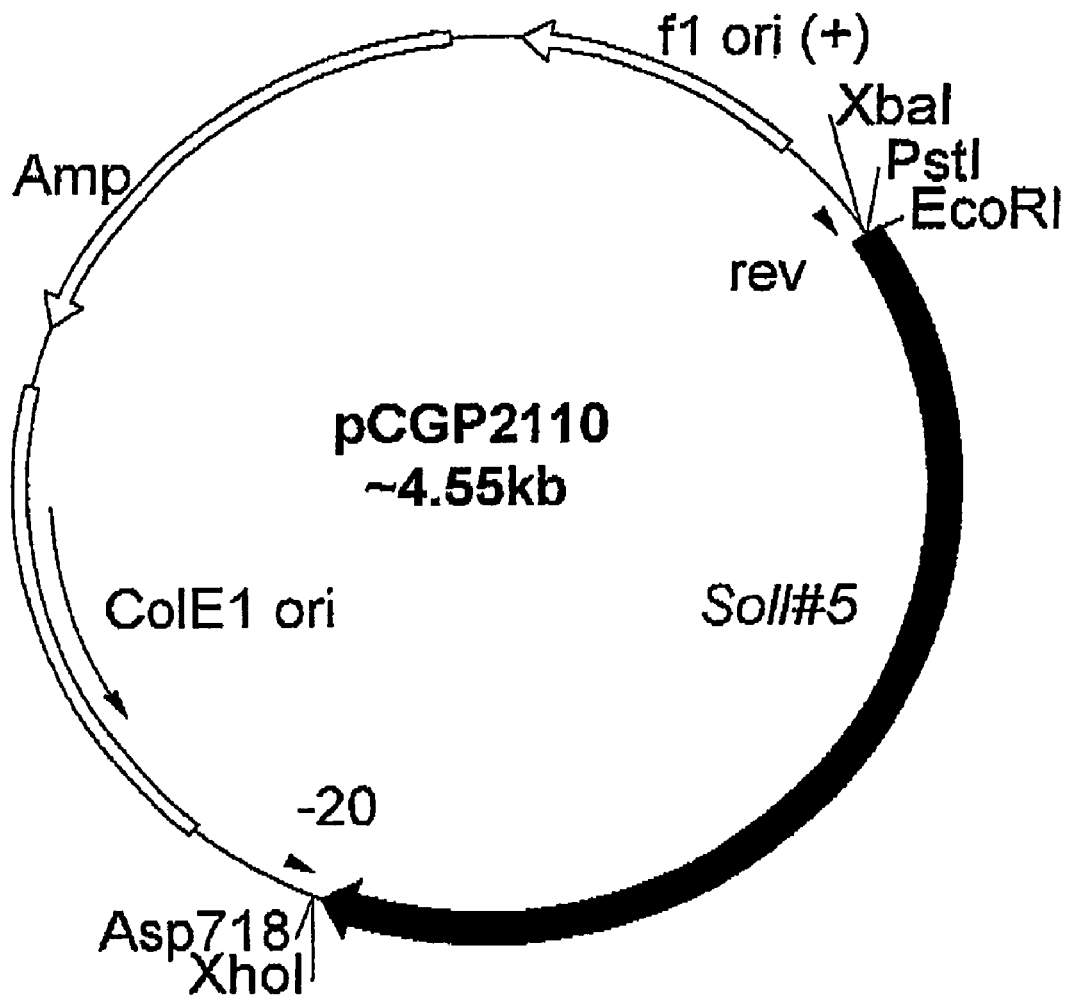

FIG. 37 is a diagrammatic representation of the plasmid pCGP2110 containing the F3'5'H Soll#5 cDNA clone from *Sollya* spp. in a pBluescript SK II (+) backbone. A description of pCGP2110 is given in Example 7. Selected restriction endonuclease sites are marked. Refer to Table 2 and Table 4 for a description of the abbreviations.

Figure 38:
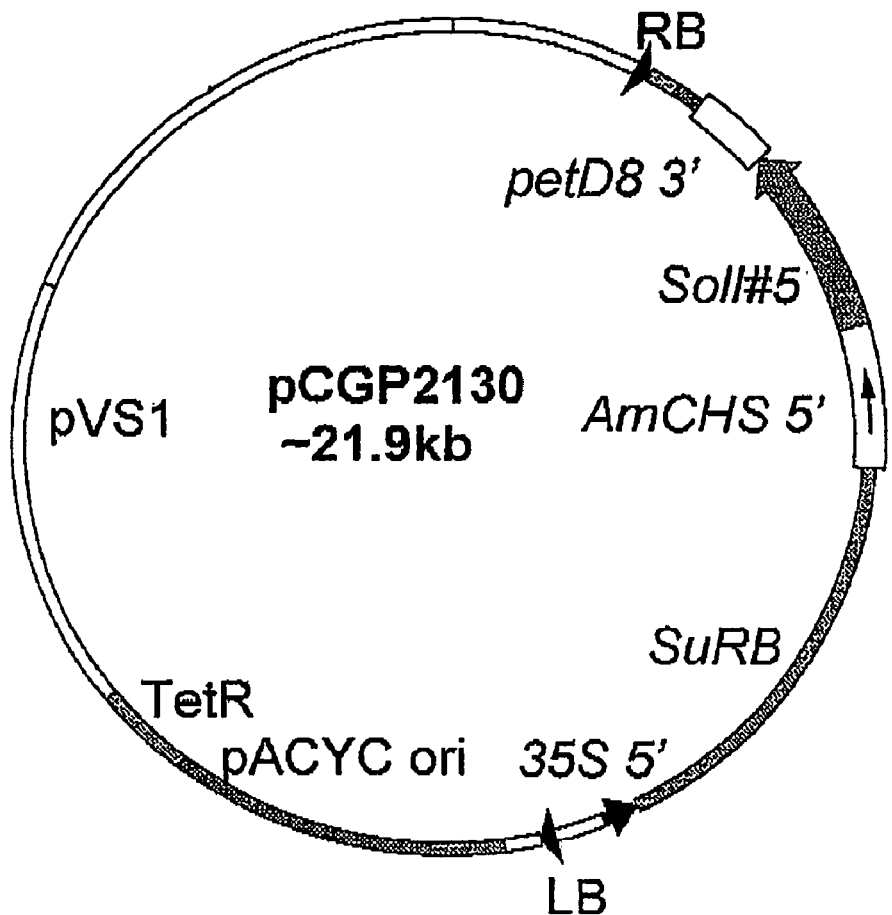

FIG. 38 is a diagrammatic representation of the binary plasmid pCGP2130. The AmCHS 5': Soll#5: petD8 3' gene from pCGP2128 was cloned into the binary vector pCGP1988 in a tandem orientation with the chimaeric SuRB gene. The construction of pCGP2130 is described in Example 7. Refer to Table 2 and Table 4 for a description of the abbreviations.

Figure 39:
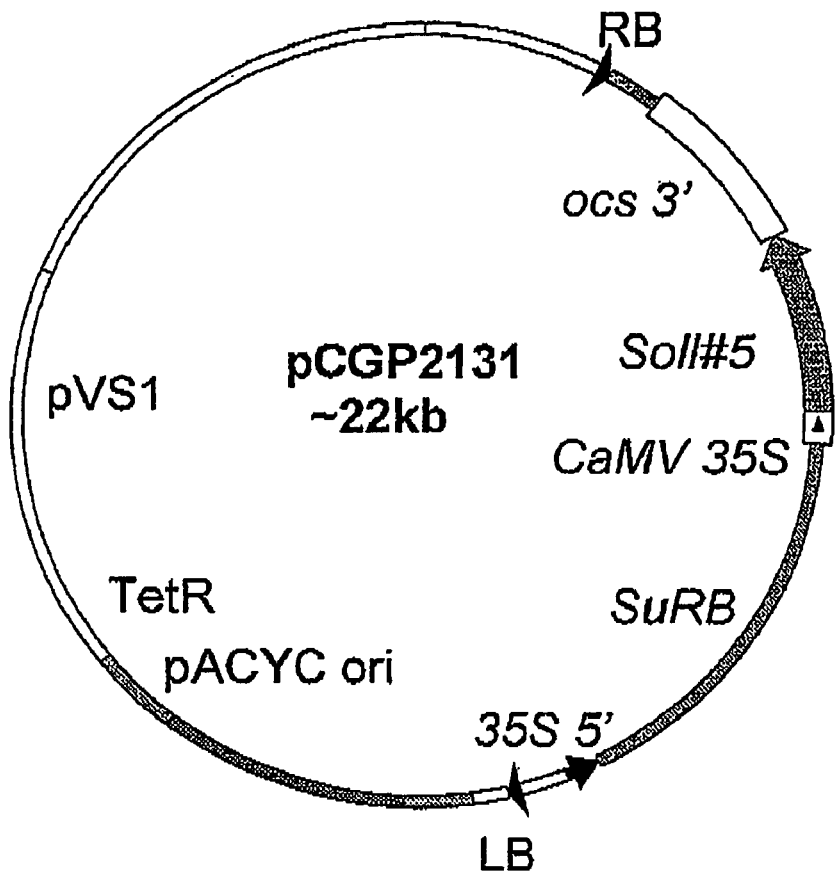

FIG. 39 is a diagrammatic representation of the binary plasmid pCGP2131. The CaMV 35S: Soll#5:ocs 3' gene from pCGP2129 was cloned into the binary vector pCGP1988 in a tandem orientation with the chimaeric SuRB gene. The construction of pCGP2131 is described in Example 7. Refer to Table 2 and Table 4 for a description of the abbreviations.

Figure 40:
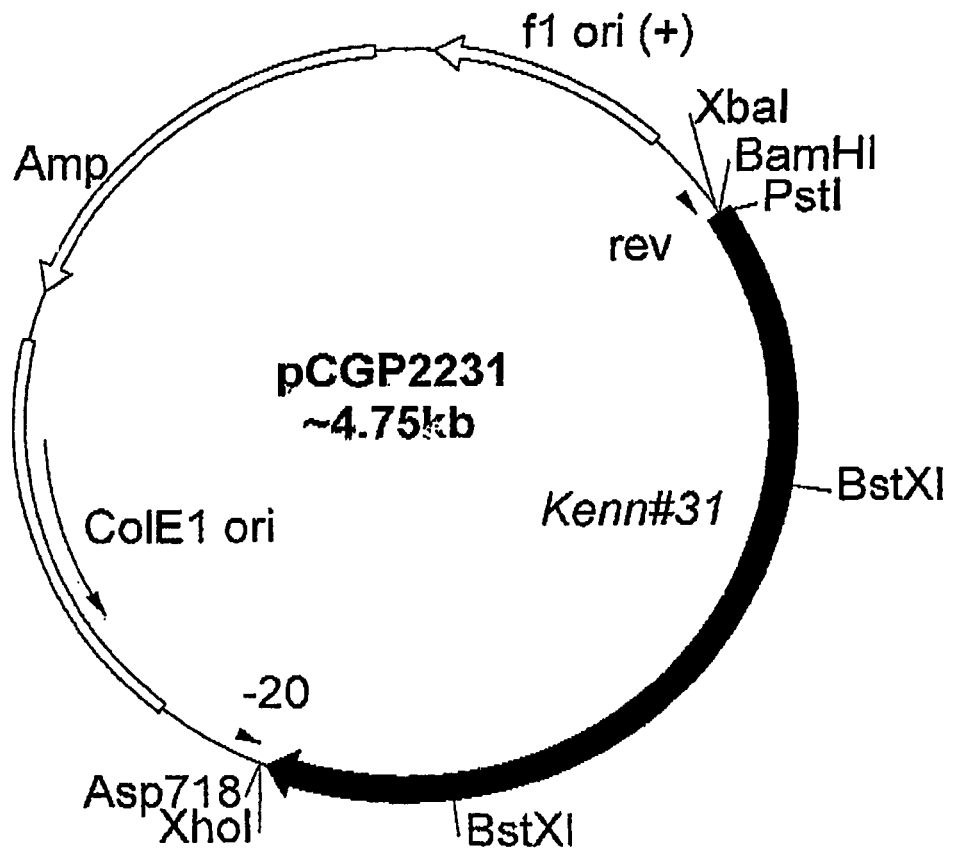

FIG. 40 is a diagrammatic representation of the plasmid pCGP2231 containing the F3'5'H Kenn#31 cDNA clone from *Kennedia* spp. in a pBluescript SK II (+) backbone. A description of pCGP2231 is given in Example 7. Selected restriction endonuclease sites are marked. Refer to Table 2 and Table 4 for a description of the abbreviations.

Figure 41:
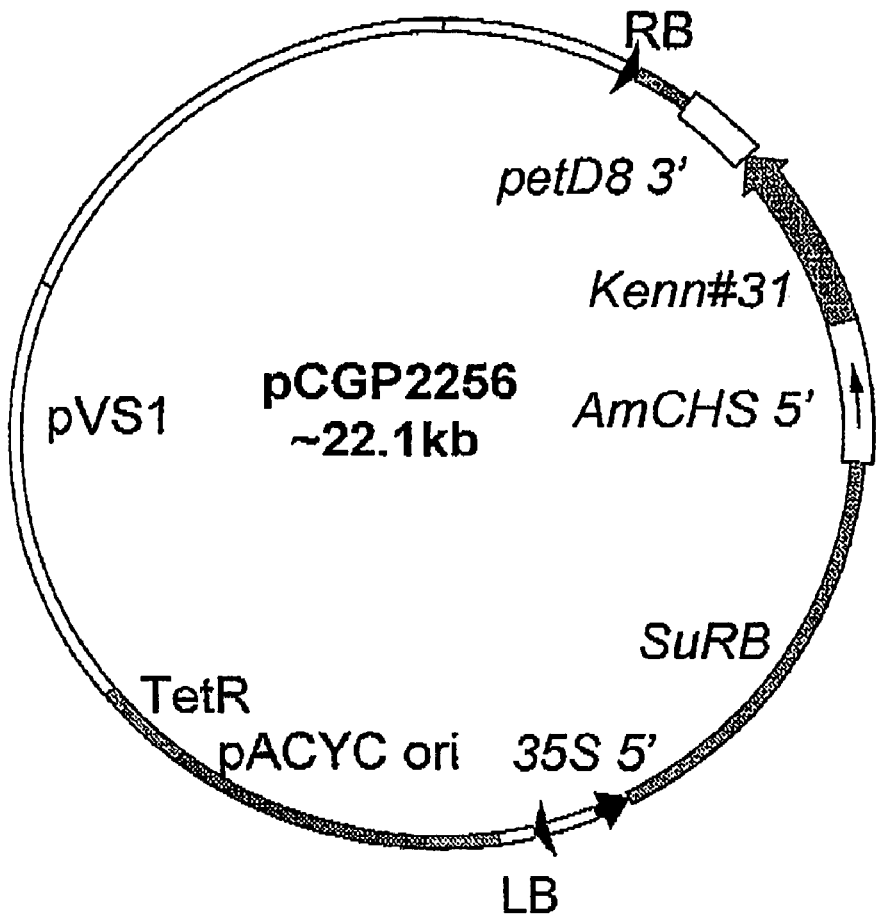

FIG. 41 is a diagrammatic representation of the binary plasmid pCGP2256. The AmCHS 5': Kenn#31: petD8 3' gene from pCGP2242 was cloned into the binary vector pCGP1988 in a tandem orientation with the chimaeric SuRB gene. The construction of pCGP2256 is described in Example 7. Refer to Table 2 and Table 4 for a description of the abbreviations.

Figure 42:
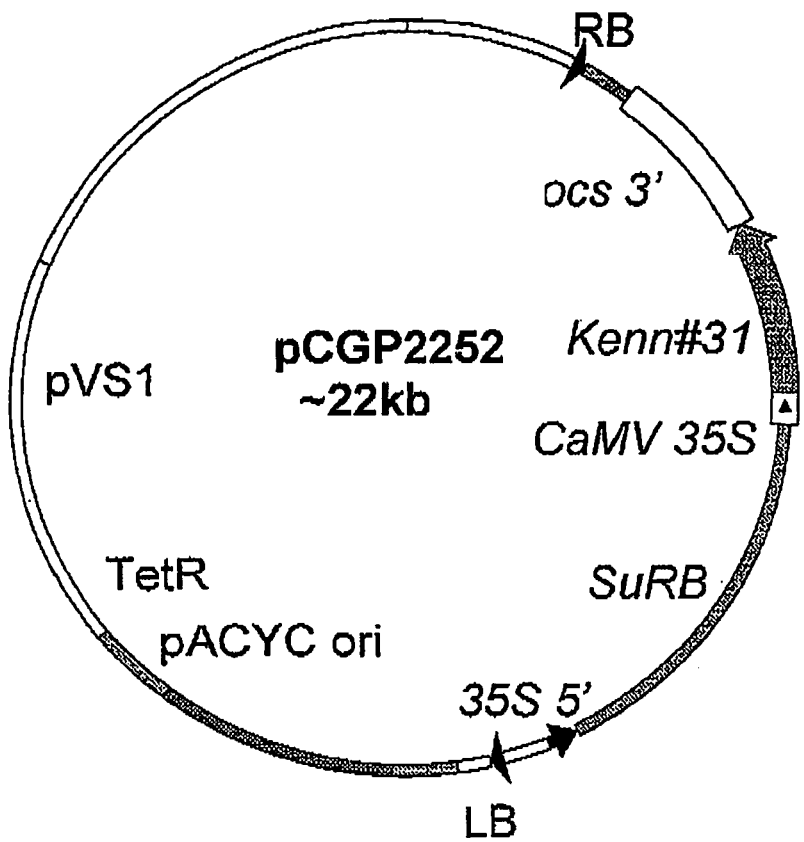

FIG. 42 is a diagrammatic representation of the binary plasmid pCGP2252. The CaMV 35S: Kenn#31:ocs 3' gene from pCGP2236 was cloned into the binary vector pCGP1988 in a tandem orientation with the chimaeric SuRB gene. The construction of pCGP2252 is described in Example 7. Refer to Table 2 and Table 4 for a description of the abbreviations.

Figure 43:
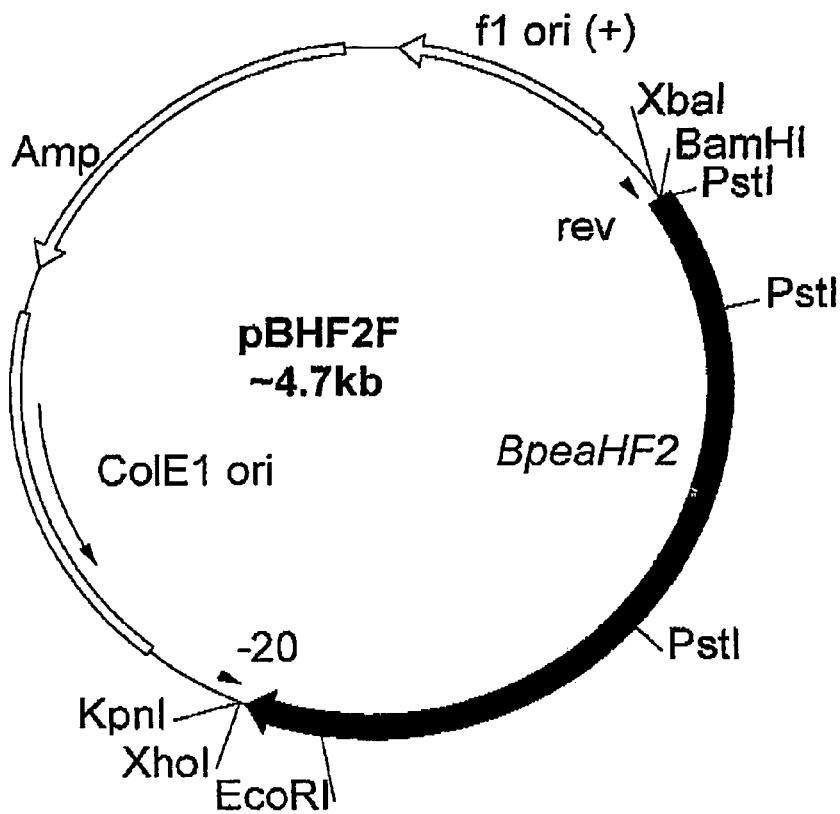

FIG. 43 is a diagrammatic representation of the plasmid pBHF2F containing the full-length F3'5'H BpeaHF2 cDNA clone tom *Clitoria ternatea* in a pBluescript SK II (+) backbone. A description of pBHF2F is given in Example 7. Selected restriction endonuclease sites are marked. Refer to Table 2 and Table 4 for a description of the abbreviations.

Figure 44:
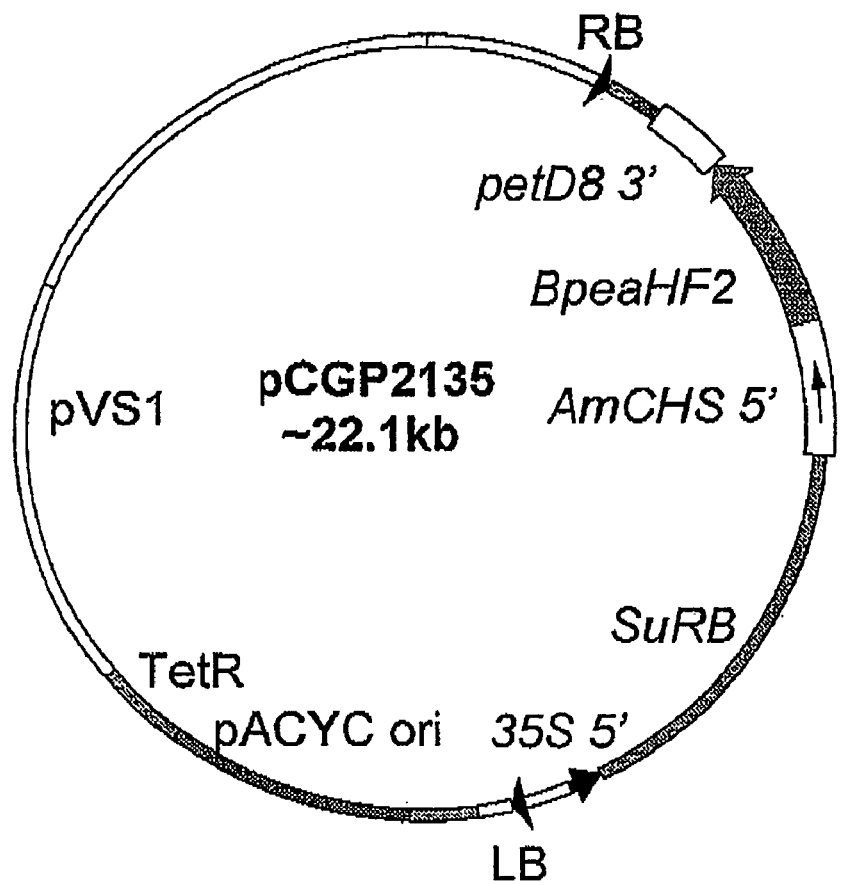

FIG. 44 is a diagrammatic representation of the binary plasmid pCGP2135. The AmCHS 5': BpeaHF2: petD8 3' gene from pCGP2133 was cloned into the binary vector pCGP1988 in a tandem orientation with the chimaeric SuRB gene. The construction of pCGP2135 is described in Example 7. Selected restriction endonuclease sites are marked. Refer to Table 2 and Table 4 for a description of the abbreviations.

Figure 45:
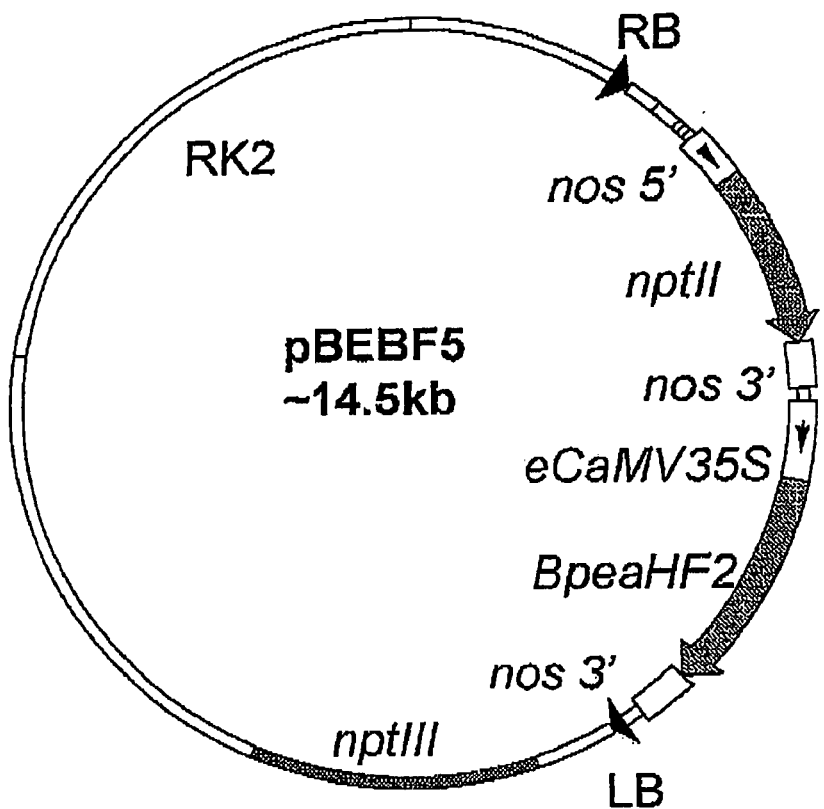

FIG. 45 is a diagrammatic representation of the binary plasmid pBEBF5. The eCaMV 35S: BpeaHF2: nos 3' gene was constructed by replacing the GUS fragment from pBE2113-GUSs with the *Clitoria* F3'5'H peaHF2 cDNA clone from pBHF2F. The construction of pBEBF5 is described in Example 7. Refer to Table 2 and Table 4 for a description of the abbreviations.

Figure 46:
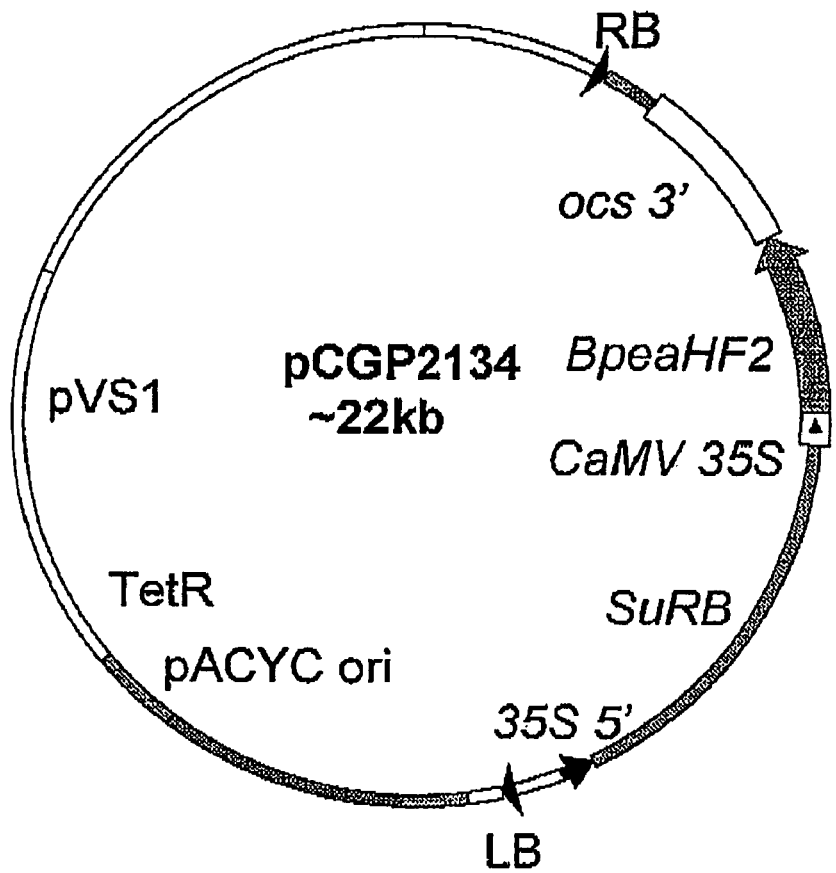

FIG. 46 is a diagrammatic representation of the binary plasmid pCGP2134. The CaMV 35S: BpeaHF2: ocs 3' gene from pCGP2132 was cloned into the binary vector pCGP1988 in a tandem orientation with the chimaeric SuRB gene. The construction of pCGP2134 is described in Example 7. Refer to Table 2 and Table 4 for a description of the abbreviations.

Figure 47:
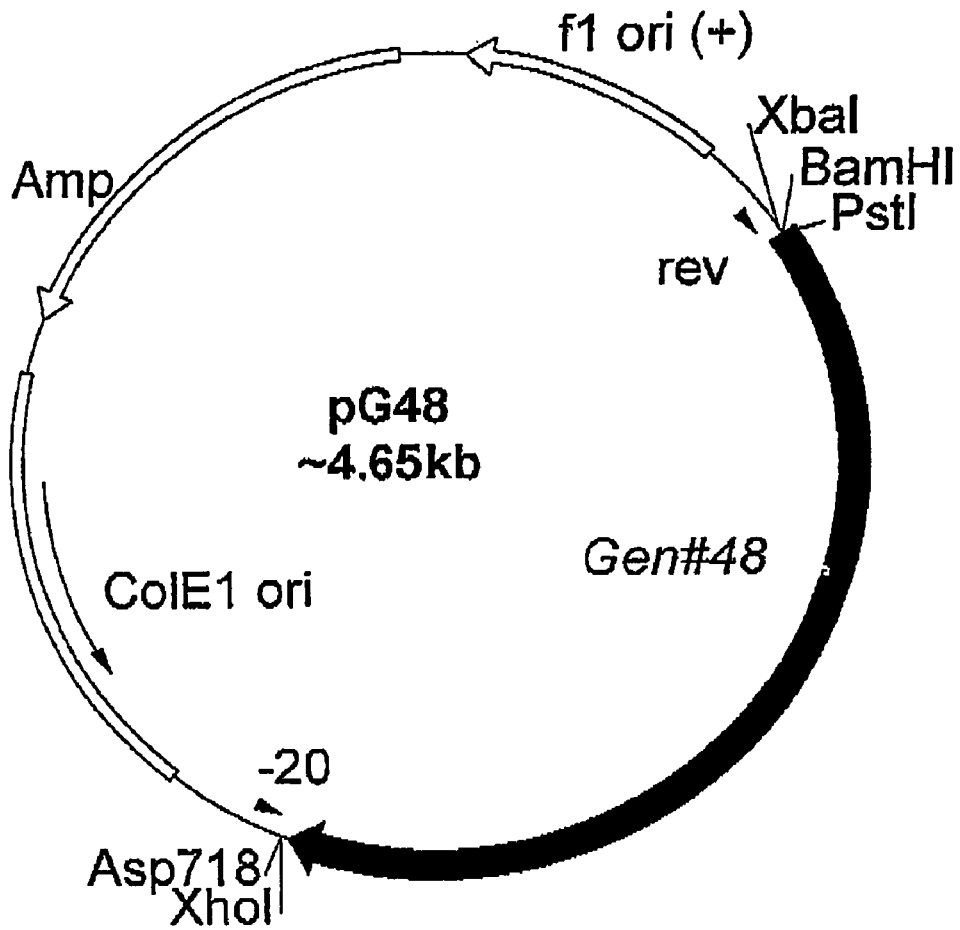

FIG. 47 is a diagrammatic representation of the plasmid pG48 containing the F3'5'H Gen#48 cDNA clone from *Gentiana triflora* in a pBluescript SK II (+) backbone. A description of pG48 is given in Example 7. Selected restriction endonuclease sites are marked. Refer to Table 2 and Table 4 for a description of the abbreviations.

Figure 48:
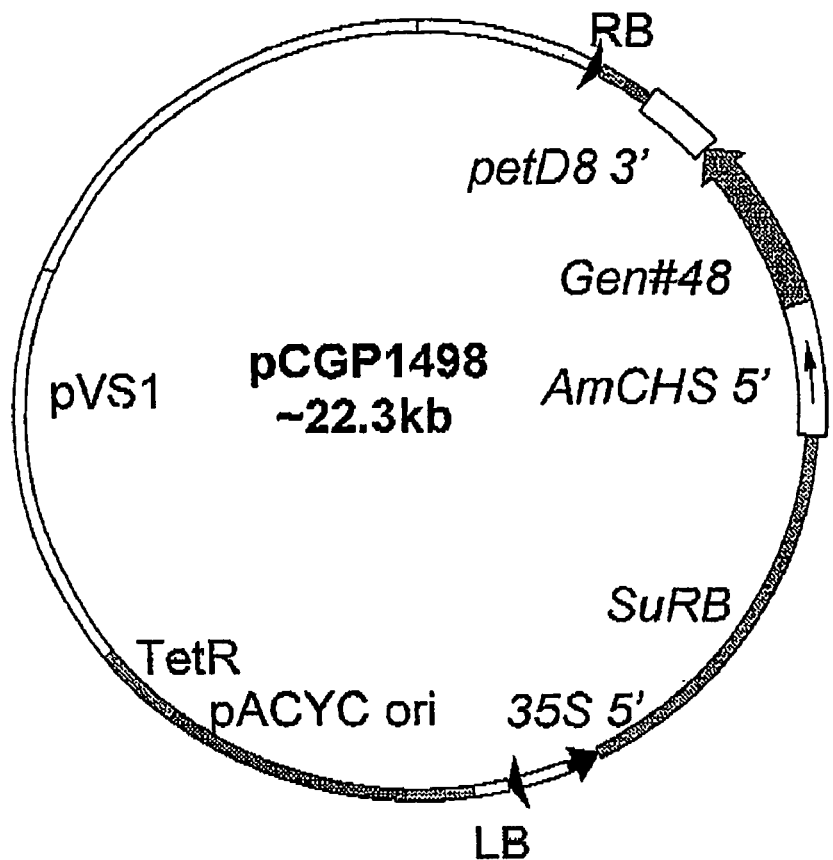

FIG. 48 is a diagrammatic representation of the binary plasmid pCGP1498. The AmCHS 5': Gen#48: petD8 3' gene from pCGP1496 was cloned into the binary vector pCGP1988 in a tandem orientation with the chimaeric SuRB gene. The construction of pCGP1498 is described in Example 7. Selected restriction endonuclease sites are marked. Refer to Table 2 and Table 4 for a description of the abbreviations.

Figure 49:
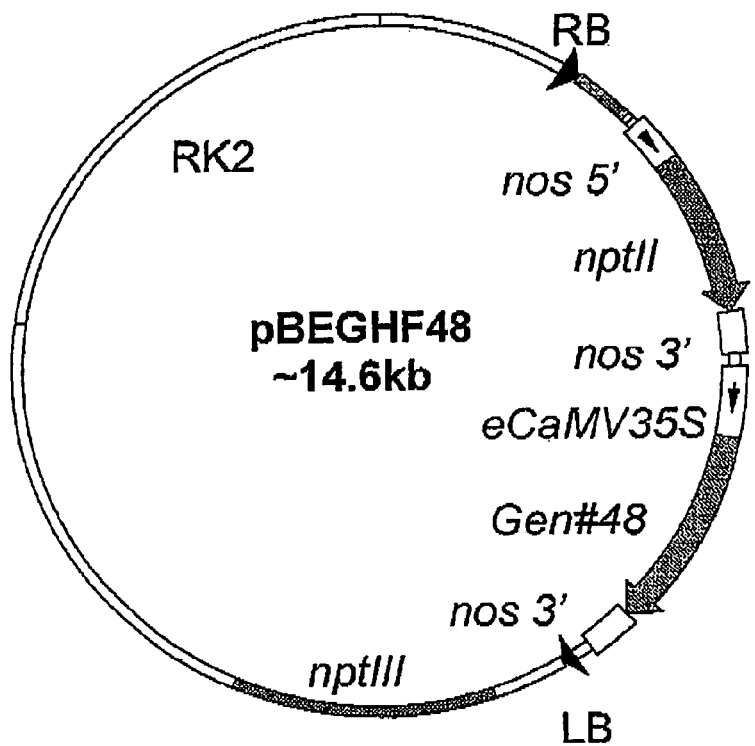

FIG. 49 is a diagrammatic representation of the binary plasmid pBEGHF48. The eCaMV 35S: Gen#48: nos 3' gene was constructed by replacing the GUS fragment from a pBE2113-GUSs with the *Gentiana* F3'5'H Gen#48 cDNA clone from pG48. The construction of pBEGHF48 is described in Example 7. Selected restriction endonuclease sites are marked. Refer to Table 2 and Table 4 for a description of the abbreviations.

Figure 50:
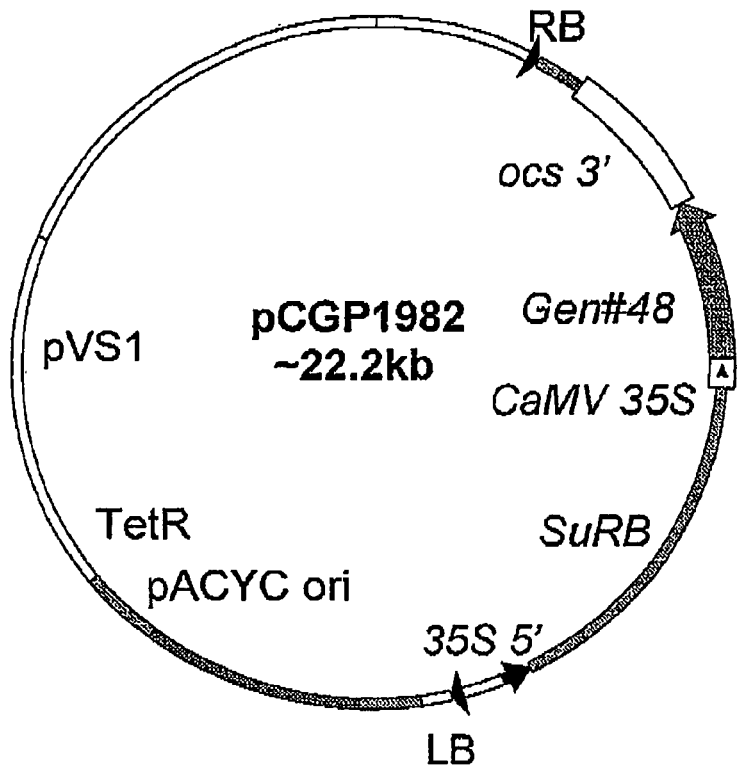

FIG. 50 is a diagrammatic representation of the binary plasmid pCGP1982. The CaMV 35S:Gen#48:ocs 3' gone from pCGP1981 was cloned into the binary vector pWTT2132 (DNAP) in a tandem orientation with the chimaeric SuRB gene. The construction of pCGP1982 is described in Example 7. Refer to Table 2 and Table 4 for a description of the abbreviations.

Figure 51:
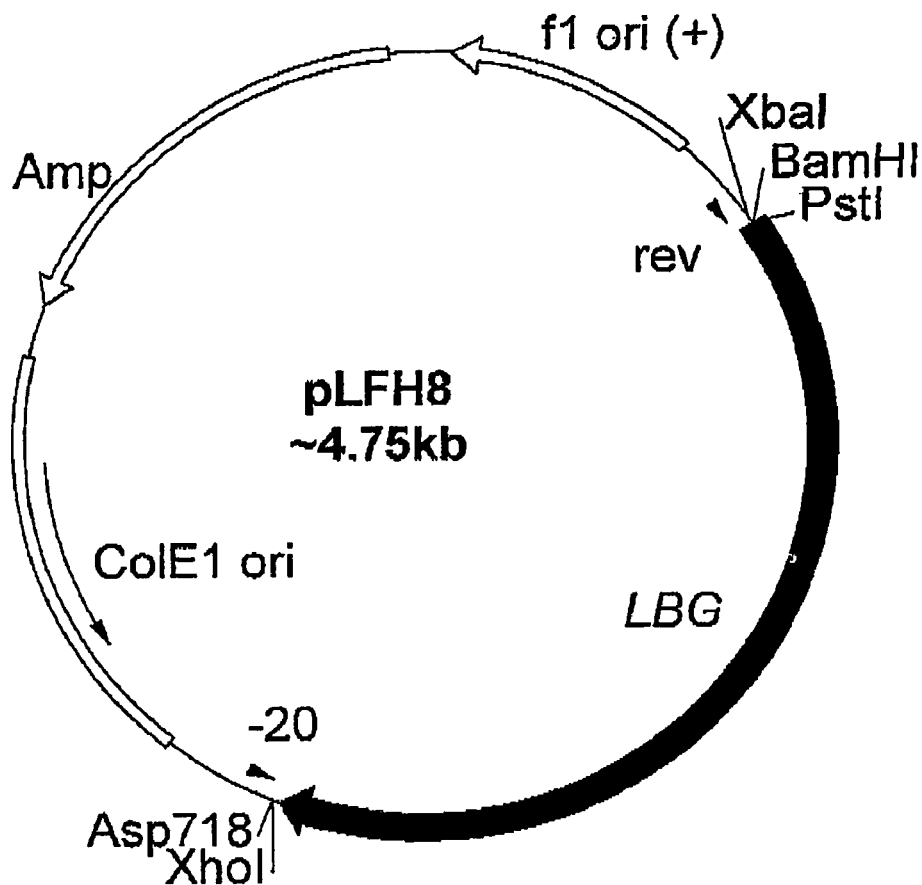

FIG. 51 is a diagrammatic representation of the plasmid pLFH8 containing the F3'5'H LBG cDNA clone from *Lavandula nil* in a pBluescript SK II (+) backbone. A description of pLFH8 is given in Example 7. Selected restriction endonuclease sites are marked. Refer to Table 2 and Table 4 for a description of the abbreviations.

Figure 52:
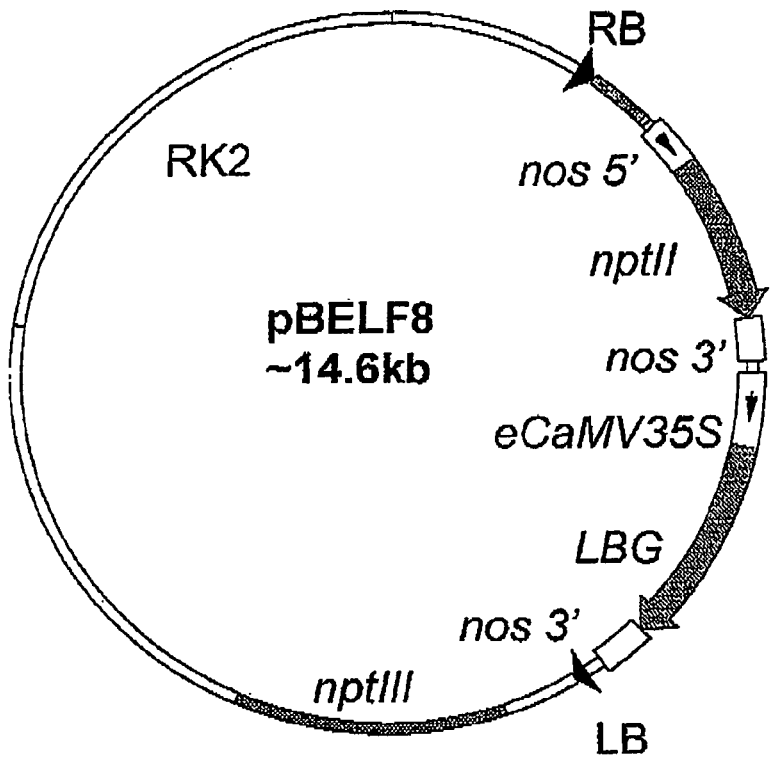

FIG. 52 is a diagrammatic representation of the binary plasmid pBELF8. The eCaMV 35S: LBG: nos 3' gene was constructed by replacing the GUS fragment from pBE2113-GUSs with the *Lavandula* F3'5'H LBG cDNA clone from pLHF8. The construction of pBELF8 is described in Example 7. Refer to Table 2 and Table 4 for a description of the abbreviations.

DETAILED DESCRIPTION OF THE PREFERRED EMBODIMENTS

In accordance with the present invention, genetic sequences encoding polypeptides having F3'5'H activity have been identified, cloned and assessed. The recombinant genetic sequences of the present invention permit the modulation of expression of genes encoding this enzyme by, for example, de novo expression, over-expression, sense suppression, antisense inhibition, ribozyme, minizyme and DNAzyme activity, RNAi-induction or methylation-induction or other transcriptional or post-transcriptional silencing activities. RNAi-induction includes genetic molecules such as hairpin, short double stranded DNA or RNA, and partially double stranded DNAs or RNAs with one or two single stranded nucleotide over hangs. The ability to control F3'5'H synthesis in plants permits modulation of the composition of individual anthocyanins as well as alteration of relative levels of flavonols and anthocyanins, thereby enabling the manipulation of petal color. Moreover, the present invention extends to plants and reproductive or vegetative parts thereof including flowers, fruits, seeds, vegetables, leaves, stems and the like. The present invention farther extends to ornamental transgenic or genetically modified plants. The term "transgenic" also includes progeny plants and plants from subsequent genetics and/or crosses thereof from the primary transgenic plants.

Accordingly, one aspect of the present invention provides an isolated nucleic acid molecule comprising a sequence of nucleotides encoding or complementary to a sequence encoding a F3'5'H or a polypeptide having F3'5'H activity wherein expression of said nucleic acid molecule in a rose petal tissue results in detectable levels of delphinidin or delphinidin-based molecules as measured by a chromatographic technique.

Another aspect of the present invention is directed to an isolated nucleic acid molecule comprising a sequence of nucleotides encoding or complementary to a sequence encoding a F3'5'H or a polypeptide having F3'5'H activity wherein expression of said nucleic acid molecule in a rose petal tissue results in a sufficient level and length of transcript which is translated to said F3'5'H as determined by detectable levels of delphinidin or delphinidin-based molecules as measured by a chromatographic technique.

A further aspect of the present invention is directed to an isolated nucleic acid molecule comprising a sequence of nucleotides encoding or complementary to a sequence encoding a F3'5'H or a polypeptide having F3'5'H activity wherein expression of said nucleic acid molecule in a rose petal tissue results a full-length transcript which is detectable by Northern blot analysis of total RNA isolated from rose petals.

The present invention is described and exemplified herein by reference to the identification, cloning and manipulation of genetic sequences encoding a F3'5'H which acts on DHK as well as DHQ. Preferably, the F3'5'H enzyme is a pansy; *salvia, sollya* lavender or *kennedia* F3'5'H. The F3'5'H enzyme may also be considered to include a polypeptide or protein having a F3'5'H activity or F3'5'H-like activity. The latter encompasses derivatives having altered F3'5'H activities.

A preferred aspect of the present invention, therefore, is directed to an isolated nucleic acid molecule comprising a sequence of nucleotides encoding, or complementary to a sequence encoding a F3'5'H or a functional mutant, derivative, part, fragment, homolog or analog thereof wherein the nucleic acid molecule is characterized by the following:

(i) the F3'5'H transcript in rose petal tissue is of sufficient level and size to encode a F3'5'H resulting in detectable delphinidin or delphinidin-based molecules in the rose petal tissue as measured by a chromatographic procedure (eg. TLC or HPLC);

(ii) the F3'5'H transcript in rose petal tissue is full-length and detected by Northern blot analysis of total RNA isolated from rose petal tissue (iii) the F3'5'H in rose petal tissue results in detectable delphinidin or delphinidin-based molecules as measured by a chromatographic procedure (eg. TLC or HOPLC); and/or (iv) the F3'5'H results in a visual color change in rose petal tissue.

The term delphinidin-based pigments includes the anthocyanidin, delphinidin or any derivatives thereof including but not limited to glycosylated, acylated, methylated or other modified forms. Methylated forms of delphinidin include but are not limited to the anthocyanidin petunidin (methylated at the 3'-position), malvidin (methylated at the 3' and 5' position), 5-O-methyl malvidin (methylated at the 5,7,3' and 5' positions), 5,7-O dimethyl malvidin (methylated at the 5,7,3' and 5' positions). The methylated anthocyanidins can also be modified by glycosylation and acylation. The term anthocyanins defines glycosylated forms of the respective anthocyanidins.

By the term "nucleic acid molecule" is meant a genetic sequence in a non-naturally occurring condition. Generally, this means isolated away from its natural state or synthesized or derived in a non-naturally-occurring environment. More specifically, it includes nucleic acid molecules formed or maintained in vitro, including genomic DNA fragments recombinant or synthetic molecules and nucleic acids in combination with heterologous nucleic acids. It also extends to the genomic DNA or cDNA or part thereof encoding F3'5'H or a part thereof in reverse orientation relative to its own or another promoter. It further extends to naturally occurring sequences following at least a partial purification relative to other nucleic acid sequences.

The term "genetic sequences" is used herein in its most general sense and encompasses any contiguous series of nucleotide bases specifying directly, or via a complementary series of bases, a sequence of amino acids in a F3'5'H enzyme. Such a sequence of amino acids may constitute a full-length F3'5'H such as is set forth in SEQ ID NO: 10 (pansy) or SEQ ID NO:12 (pansy) or SEQ ID NO:14 (*salvia*) or SEQ ID NO:16 (*salvia*) or SEQ ID NO:18 (*sollya*) or SEQ ID NO:32 (lavender) or SEQ ID NO:27 (*kennedia*) or an active truncated form thereof or may correspond to a particular region such as an N-terminal, C-terminal or internal portion of the enzyme. A genetic sequence may also be referred to as a sequence of nucleotides or a nucleotide sequence and includes a recombinant fusion of two or more sequences.

In accordance with the above aspects of the present invention there is provided a nucleic acid molecule comprising a nucleotide sequence or complementary nucleotide sequence substantially as set forth in SEQ ID NO:9 (pansy) or SEQ ID NO:11 (pansy) or SEQ ID NO:13 (*salvia*) or SEQ ID NO:15 (*salvia*) or SEQ ID NO:17 (*sollya*) or SEQ ID NO:31 (lavender) or SEQ ID NO:26 (*kennedia*) or having at least about 50% similarity thereto or capable of hybridizing to the sequence set forth in SEQ ID NO:9 or SEQ ID NO:11 or SEQ ID NO:13 or SEQ ID NO:15 or SEQ ID NO:17 or SEQ ID NO:31 or SEQ ID NO:26 under low stringency conditions.

Table 1 provides a summary of the sequence identifiers.

Alternative percentage similarities and identities (at the nucleotide or amino acid level) encompassed by the present invention include at least about 60% or at least about 65% or at least about 70% or at least about 75% or at least about 80% or at least about 85% or at least about 90% or above, such as about 95% or about 96% or about 97% or about 98% or about 99%, such as at least about 60%, 61%, 62%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%.

In a particularly preferred embodiment, there is provided an isolated nucleic acid molecule comprising a nucleotide sequence or complementary nucleotide sequence substantially as set forth in SEQ ID NO:9 (pansy) or SEQ ID NO:11 (pansy) or SEQ ID NO:13 (*salvia*) or SEQ ID NO:15 (*salvia*) or SEQ ID NO:17 (*sollya*) or SEQ ID NO:31 (lavender) or SEQ ID NO:26 (*kennedia*) or having at least about 50% similarity thereto or capable of hybridizing to the sequence set forth in SEQ ID NO:1 (*petunia*) or SEQ ID NO:3 (*petunia*) or complementary strands of either under low stringency conditions, wherein said nucleotide sequence encodes a polypeptide having a F3'5'H activity.

For the purposes of determining the level of stringency to define nucleic acid molecules capable of hybridizing to SEQ ID NO:1, SEQ ID NO:3, SEQ ID NO:9 or SEQ ID NO:11 or SEQ ID NO:13 or SEQ ID NO:15 or SEQ ID NO:17 or SEQ ID NO:31 or SEQ ID NO:26 reference herein to a low stringency includes and encompasses from at least about 0% to at least about 15%, v/v formamide and from at least about 1M to at least about 2 M salt for hybridization, and at least about 1 M to at least about 2 M salt for washing conditions. Generally, low stringency is from about 25-30° C. to about 42° C. The temperature may be altered and higher temperatures used to replace the inclusion of formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+041$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 1.0% w/v SDS at 25-42° C.; a moderate stringency is 2×SSC buffer, 1.0% w/v SDS at a temperature in the range 20° C. to 65° C.; high stringency is 0.1×SSC buffer, 0.1% w/v SDS at a temperature of at least 65° C.

Another aspect of the present invention provides a nucleic acid molecule comprising a sequence of nucleotides encoding or complementary to a sequence encoding an amino acid sequence substantially as set forth in SEQ ID NO:10 or SEQ ID NO:12 or SEQ ID NO:14 or SEQ ID NO:16 or SEQ ID NO:18 or SEQ ID NO:32 or SEQ ID NO:27 or an amino acid sequence having at least about 50% similarity thereto.

The term similarity as used herein includes exact identity between compared sequences at the nucleotide or amino acid level. Where there is non-identity at the nucleotide level, similarity includes differences between sequences which result in different amino acids that are nevertheless related to each other at the structural, functional, biochemical and/or conformational levels. Where there is non-identity at the amino acid level, similarity includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

The terms "sequence similarity" and "sequence identity" as used herein refers to the extent that sequences are identical or fictionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Lou, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd, South San Francisco, Calif., USA) using standard defaults as used in the reference manual accompanying the software. Similar comments apply in relation to sequence similarity.

The nucleic acid molecules of the present invention may be flier characterized by having, or previously having, prior to derivatization on overall lower AT content (or higher GC content) compared to a nucleic acid molecule which encodes a F3'5'H but which does not result in detectable intact transcript in rose petal tissue or, when expressed, does not result in detectable delphinidin or delphinidin-based molecules, as measured by a chromatographic procedure such as TLC or HPLC. Furthermore, the % of A's or T's in the third position of a codon is also lower than other F4'5'H enzymes. Reference herein to a chromatographic procedure includes a related procedure. By "related" means a technically related procedure or a procedure which provides a similar result. Examples of related procedures include other forms of chromatography (eg. gas chromatography).

In addition, nucleotide sequences which do not express well in rose tissue may be modified such as in reducing overall % AT or at least reduce the levels of % AT in the third position of a codon. Such time expression in rose tissue is elevated.

The nucleic acid sequences contemplated herein also encompass oligonucleotides useful as genetic probes for amplification reactions or as antisense or sense molecules capable of regulating expression of the corresponding gene in a plant. Sense molecules include hairpin constructs, short double stranded DNAs and RNAs and partially double stranded DNAs and RNAs which one or more single stranded nucleotide over hangs. An antisense molecule as used herein may also encompass a genetic construct comprising the structural genomic or cDNA gene or part thereof in reverse orientation relative to its or another promoter. It may also encompass a homologous genetic sequence. An antisense or sense molecule may also be directed to terminal or internal portions of the gene encoding a polypeptide having a F3'5'H activity or to combinations of the above such that the expression of the gene is reduced or eliminated.

With respect to this aspect of the invention, there is provided an oligonucleotide of 5-50 nucleotides such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 having substantial similarity to a part or region of a molecule with a nucleotide sequence set forth in SEQ ID NO:9 or SEQ ID NO:11 or SEQ ID NO:13 or SEQ ID NO:15 or SEQ ID NO:17 or SEQ ID NO:31 or SEQ ID NO:26. By substantial similarity or complementarity in this context is meant a hybridizable similarity under low, alternatively and preferably medium and alternatively and most preferably high stringency conditions specific for oligonucleotide hybridization (Sambrook et al., *Molecular Cloning: A Laboratory Manual*, $2^{nd}$ edition, Cold Spring Harbor Laboratories, Cold Spring Harbor, N.Y., USA, 1989). Such an oligonucleotide is useful, for example, in screening for F3'5'H genetic sequences from various sources or for monitoring an introduced genetic sequence in a transgenic plant. The preferred oligonucleotide is directed to a conserved F3'5'H genetic sequence or a sequence conserved within a plant genus, plant species and/or plant variety.

In one aspect of the present invention, the oligonucleotide corresponds to the 5' or the 3' end of the F3'5'H genetic sequences. For convenience, the 5' end is considered herein to define a region substantially between the start codon of the structural gene to a centre portion of the gene, and the 3' end is considered herein to define a region substantially between the centre portion of the gene and the terminating codon of the structural gene. It, is clear, therefore, that oligonucleotides or probes may hybridize to the 5' end or the 3' end or to a region common to both the 5' and the 3' ends, the present invention extends to all such probes.

In one embodiment, the nucleic acid sequence encoding a F3'5'H or various functional derivatives thereof is used to reduce the level of an endogenous a F3'5'H (e.g. via co-suppression or antisense-mediated suppression) or other post-transcriptional gene silencing (PTGS) processes including RNAi or alternatively the nucleic acid sequence encoding this enzyme or various derivatives or parts thereof is used in the sense or antisense orientation to reduce the level of a F3'5'H. The use of sense strands, double or partially single stranded such as constructs with hairpin loops is particularly useful in inducing a PTGS response. In a further alternative, ribozymes, minizymes or DNAzymes could be used to inactivate target nucleic acid sequences.

Still a further embodiment encompasses post-transcriptional inhibition to reduce translation into polypeptide material. Still yet another embodiment involves specifically inducing or removing methylation.

Reference herein to the altering of a F3'5'H activity relates to an elevation or reduction in activity of up to 30% or more preferably of 30-50%, or even more preferably 50-75% or still more preferably 75% or greater above or below the normal endogenous or existing levels of activity. Such elevation or reduction may be referred to as modulation of a F3'5'H enzyme activity. Generally, modulation is at the level of, transcription or translation of F3'5'H genetic sequences.

The nucleic acids of the present invention may be a ribonucleic acid or deoxyribonucleic acids, single or double stranded and linear or covalently closed circular molecules. Preferably, the nucleic acid molecule is cDNA. The present invention also extends to other nucleic acid molecules which hybridize under low, preferably under medium and most preferably under high stringency conditions with the nucleic acid molecules of the present invention and in particular to the sequence of nucleotides set forth in SEQ ID NO:9 or SEQ ID NO:11 or SEQ ID NO:13 or SEQ ID NO:15 or SEQ ID NO:17 or SEQ ID NO:31 or SEQ ID NO:26 or a part or region thereof. In its most preferred embodiment, the present invention extends to a nucleic acid molecule having a nucleotide sequence set forth in SEQ ID NO:9 or SEQ ID NO:11 or SEQ ID NO:13 or SEQ ID NO:15 or SEQ ID NO:17 or SEQ ID NO:31 or SEQ ID NO:26 or to a molecule having at least 40%, more preferably at least 45%, even more preferably at least 55%, still more preferably at least 65%-70%, and yet even more preferably greater than 85% similarity at the level of nucleotide or amino acid sequence to at least one or more regions of the sequence set forth in SEQ ID NO:9 or SEQ ID NO:11 or SEQ ID NO:13 or SEQ ID NO:15 or SEQ ID NO:17 or SEQ ID NO:31 or SEQ ID NO:26 and wherein the nucleic acid encodes or is complementary to a sequence which encodes an enzyme having a F3'5'H activity. It should be noted, however, that nucleotide or amino acid sequences may have similarities below the above given percentages and yet still encode a F3'5'H activity and such molecules may still be considered in the scope of the present invention where they have regions of sequence conservation. The present invention further extends to nucleic acid molecules in the form of oligonucleotide primers or probes capable of hybridizing to a portion of the nucleic acid molecules contemplated above, and in particular those set forth in SEQ ID NO:9 or SEQ ID NO:11 or SEQ ID NO:13 or SEQ ID NO:15 or SEQ ID NO:17 or SEQ ID NO:31 or SEQ ID NO:26, under low, preferably under medium and most preferably under high stringency-conditions. Preferably the portion corresponds to the 5' or the 3' end of the gene. For convenience the 5' end is considered herein to define a region substantially between the start codon of the structural genetic sequence to a centre portion of the gene, and the 3' end is considered herein to define a region substantially between the centre portion of the gene and the terminating codon of the structural genetic sequence. It is clear, therefore, that oligonucleotides or probes nay hybridize to the 5' end or the 3' end or to a region common to both the 5' and the 3' ends. The present invention extends to all such probes.

The term gone is used in its broadest sense and includes cDNA corresponding to the exons of a gene. Accordingly, reference herein to a gene is to be taken to include:

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term gene is also used to describe synthetic or fusion molecules encoding all or part of an expression product. In particular embodiments, the term nucleic acid molecule and gene may be used interchangeably.

The nucleic acid or its complementary form may encode the full-length enzyme or a part or derivative thereof. By "derivative" is meant any single or multiple amino acid substitutions, deletions, and/or additions relative to the naturally occurring enzyme and which retains a F3'5'H activity. In this regard, the nucleic acid includes the naturally occurring nucleotide sequence encoding a F3'5'H or may contain single or multiple nucleotide substitutions, deletions and/or additions to said naturally occurring sequence. The nucleic acid of the present invention or its complementary form may also encode a "part" of the F3'5'H, whether active or inactive, and such a nucleic acid molecule may be useful as an oligonucleotide probe, primer for polymerase chain reactions or in various mutagenic techniques, or for the generation of antisense molecules.

Reference herein to a "part" of a nucleic acid molecule, nucleotide sequence or amino acid sequence, preferably relates to a molecule which contains at least about 10 contiguous nucleotides or five contiguous amino acids, as appropriate.

Amino acid insertional derivatives of the F3'5'H of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Typical substitutions are those made in accordance with Table 3.

TABLE 3

Suitable residues for amino acid substitutions

| Original residue | Exemplary substitutions |
| --- | --- |
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where the F3'5'H is derivatized by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, *J. Am. Chem. Soc.* 85: 2149, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989, supra).

Other examples of recombinant or synthetic mutants and derivatives of the F3'5'H enzyme of the present invention include single or multiple substitutions, deletions and/or additions of any molecule associated with the enzyme such as carbohydrates, lipids and/or proteins or polypeptides.

The terms "analogs" and "derivatives" also extend to any functional chemical equivalent of a F3'5'H and also to any amino acid derivative described above. For convenience, reference to F3'5'H herein includes reference to any functional mutant, derivative, part, fragment, homolog or analog thereof.

The present invention is exemplified using nucleic acid sequences derived from pansy, *salvia, sollya* or lavender or *kennedia* since this represents die most convenient and preferred source of material to date. However, one skilled in the art will immediately appreciate that similar sequences can be isolated from any number of sources such as other plants or certain microorganisms. All such nucleic acid sequences encoding directly or indirectly a F3'5'H are encompassed by the present invention regardless of their source. Examples of other suitable sources of genes encoding F3'5'H include, but are not limited to *Vitis* spp., *Babiana stricta*, *Pinus* spp., *Picea* spp., *Larix* spp., *Phaseolus* spp., *Vaccinium* spp., *Cyclamen* spp., *Iris* spp., *Pelargonium* spp., Lipadeae, *Geranium* spp., *Pisum* spp., *Lathyrus* spp., *Clitoria* spp., *Catharanthus* spp., *Malva* spp., *Mucana* spp., *Vicia* spp., *Saintpaulia* spp., *Lagerstroemia* spp., *bouchina* spp., *Plumbago* spp., *Hypocalyptus* spp., *Rhododendron* spp., *Linum* spp., *Macroptilium* spp., *Hibiscus* spp., *Hydrangea* spp., *Cymbidium* spp., *Millettia* spp., *Hedysarum* spp., *Lespedeza* spp., *Asparagus* spp. *Antigonon* spp., *Freesia* spp., *Brunella* spp., *Clarkia* spp., etc.

In accordance with the present invention, a nucleic acid sequence encoding a F3'5'H may be introduced into and expressed in a transgenic plant in either orientation thereby providing a means either to convert suitable substrates, if synthesized in the plant cell; ultimately into DHM, or alternatively to inhibit such conversion of metabolites by reducing or eliminating endogenous or existing F3'5'H activity. The production of these 3',5'-hydroxylated substrates will subsequently be converted to delphinidin-based pigments that will modify petal color and may contribute to the production of a bluer color. Expression of the nucleic acid sequence in the plant may be constitutive, inducible or developmental and may also be tissue-specific. The word "expression" is used in its broadest sense to include production of RNA or of both RNA and protein. It also extends to partial expression of a nucleic acid molecule.

According to this aspect of the present invention, there is provided a method for producing a transgenic flowering plant capable of synthesizing a F3'5'H, said method comprising stably transforming a cell of a suitable plant with a nucleic acid sequence which comprises a sequence of nucleotides encoding said F3'5'H under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous F3'5'H at elevated levels relative to the amount expressed in a comparable non-transgenic plant.

Another aspect of the present invention contemplates a method for producing a transgenic plant with reduced indigenous or existing flavonoid 3',5'-hydroxylase activity, said method comprising stably transforming a cell of a suitable plant with a nucleic acid molecule which comprises a sequence of nucleotides encoding or complementary to a sequence encoding a F3'5'H activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing F3'5'H activity, said method comprising altering the F3'5'H gene through modification of the indigenous sequences via homologous recombination from an appropriately altered F3'5'H gene or derivative or part thereof introduced into the plant cell, and regenerating the genetically modified plant from the cell.

As used herein an "indigenous" enzyme is one, which is native to or naturally expressed in a particular cell. A "non-indigenous" enzyme is an enzyme not native to the cell but expressed through the introduction of genetic material into a plant cell, for example, through a transgene. An "endogenous" enzyme is an enzyme produced by a cell but which may or may not be indigenous to that cell.

In a preferred embodiment, the present invention contemplates a method for producing a transgenic flowering plant exhibiting altered floral or inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence.

Alternatively, said method may comprise stably transforming a cell of a suitable plant with a nucleic acid sequence of the present invention or its complementary sequence, regenerating a transgenic plant from the cell and growing said transgenic plant or a time and under conditions sufficient to alter the level of activity of the indigenous or existing F3'5'H. Preferably the altered level would be less than the indigenous or existing level of F3'5'H activity in a comparable non-transgenic plant. Without wishing to limit the present invention, one theory of mode of action is that reduction of the indigenous F3'5'H activity requires the expression of the introduced nucleic acid sequence or its complementary sequence. However, expression of the introduced genetic sequence or its complement may not be required to achieve the desired effect: namely, a flowering plant exhibiting altered floral or inflorescence properties.

In a related embodiment, the present invention contemplates a method for producing a flowering plant exhibiting altered floral or inflorescence properties, said method comprising alteration of the flavonoid 3',5'-hydroxylase gene through modification of the indigenous sequences via homologous recombination from an appropriately altered F3'5'H gene or derivative or part thereof introduced into the plant cell, and regenerating the genetically modified plant from the cell.

Preferably, the altered floral or inflorescence includes the production of different shades of blue or purple or red flowers or other colors, depending on the genotype and physiological conditions of the recipient plant.

Accordingly, the present invention extends to a method for producing a transgenic plant capable of expressing a recombinant gene encoding a F3'5'H or part thereof or which caries a nucleic acid sequence which is substantially complementary to all or a part of a mRNA molecule encoding the F3'5'H, said method comprising stably transforming a cell of a suitable plant with the isolated nucleic acid molecule comprising a sequence of nucleotides encoding, or complementary to a sequence encoding, a F3'5'H, where necessary under conditions permitting the eventual expression of said isolated nucleic acid molecule, and regenerating a transgenic plant from the cell. By suitable plant is meant a plant capable of producing DHK and possessing the appropriate physiological properties required for the development of the color desired.

One skilled in the art will immediately recognise the variations applicable to the methods of the present invention, such as increasing or decreasing the expression of the enzyme naturally present in a target plant leading to differing shades of colors such as different shades of blue, purple or red.

The present invention, therefore, extends to all transgenic plants or parts or cells therefrom of transgenic plants or progeny of the transgenic plants containing all or part of the nucleic acid sequences of the present invention, or antisense forms thereof and/or any homologs or related forms thereof and, in particular, those transgenic plants which exhibit altered floral or inflorescence properties. The transgenic plants may contain an introduced nucleic acid molecule comprising a nucleotide sequence encoding or complementary to a sequence encoding a F3'5'H. Generally, the nucleic acid would be stably introduced into the plant genome, although the present invention also extends to the introduction of a F3'5'H nucleotide sequence within an autonomously-replicating nucleic acid sequence such as a DNA or RNA virus capable of replicating within the plant cell. The invention also extends to seeds from such transgenic plants. Such seeds, especially if colored, are useful as proprietary tags for plants. Any and all methods for introducing genetic material into plant cells including but not limited to *Agrobacterium*-mediated transformation, biolistic particle bombardment etc. are encompassed by the present invention.

Another aspect of the present invention contemplates the use of the extracts from transgenic plants or plant parts or cells therefrom of transgenic plants or progeny of the transgenic plants containing all or part of the nucleic acid sequences of the present invention and, in particular, the extracts from those transgenic plants when used as a flavouring or food additive or health product or beverage or juice or coloring.

Plant parts contemplated by the present invention includes, but is not limited to flowers, fruits, vegetables, nuts, roots, stems, leaves or seeds.

The extracts of the present invention may be derived from the plants or plant part or cells therefrom in a number of different ways including but not limited to chemical extraction or heat extraction or filtration or squeezing or pulverization.

The plant, plant part or cells therefrom or extract can be utilized in any number of different ways such as for the production of a flavouring (e.g. a food essence), a food additive (e.g. a stabilizer, a colorant) a health product (e.g. an antioxidant, a tablet) a beverage (e.g. wine, spirit, tea) or a juice (e.g. fruit juice) or coloring (e.g. food coloring, fabric coloring, dye, paint, tint).

A further aspect of the present invention is directed to recombinant forms of F3'5'H. The recombinant forms of the enzyme will provide a source of material for research, for example, more active enzymes and may be useful in developing in vitro systems for production of colored compounds.

Still a further aspect of the present invention contemplates the use of the genetic sequences described herein in the manufacture of a genetic construct capable of expressing a F3'5'H or down-regulating an indigenous F3'5'H enzyme in a plant.

The term genetic construct has been used interchangeably throughout the specification and alims with the terms "fusion molecule", "recombinant molecule", "recombinant nucleotide sequence". A genetic construct may include a single nucleic acid molecule comprising a nucleotide sequence encoding a single protein or may contain multiple open reading frames encoding 2 or more proteins. It may also contain a promoter operably linked to 1 or more of the open reading frames.

Another aspect of the present invention is directed to a prokaryotic or eukaryotic organism carrying a genetic sequence encoding a F3'5'H extrachromasomally in plasmid form.

The present invention further extends to a recombinant polypeptide comprising a sequence of amino acids substantially as set forth in SEQ ID NO:10 or SEQ ID NO:12 or SEQ ID NO:14 or SEQ ID NO:16 or SEQ ID NO:18 or SEQ ID NO:32 or SEQ ID NO:27 or an amino acid sequence having at least about 50% similarity to SEQ ID NO:10 or SEQ ID NO:12 or SEQ ID NO: 14 or SEQ ID NO:16 or SEQ ID NO:18 or SEQ ID NO:32 or SEQ ID NO:27 or a derivative of said polypeptide.

A "recombinant polypeptide" means a polypeptide encoded by a nucleotide sequence introduced into a cell directly or indirectly by human intervention or into a parent or other relative or precursor of the cell. A recombinant polypeptide may also be made using cell-free, in vitro transcription systems. The term "recombinant polypeptide" includes an isolated polypeptide or when present in a cell or cell preparation. It may also be in a plant or parts of a plant regenerated from a cell which produces said polypeptide.

A "polypeptide" includes a peptide or protein and is encompassed by the term "enzyme".

The recombinant polypeptide may also be a fusion molecule comprising two or more heterologous amino acid sequences.

The present invention is further described by the following non-limiting Examples.

Example 1

General Methods

In general, the methods followed were as described in Sambrook et al. (1989, supra) or Sambrook and Russell, Molecular Cloning: A Laboratory Manual $3^{rd}$ edition, Cold Spring Harbor Laboratories, Cold Spring Harbor, N.Y., USA, 2001 or Plant Molecular Biology Manual ($2^{nd}$ edition), Gelvin and Schilperoot (ads), Kluwer Academic Publisher, The Netherlands, 1994 or Plant Molecular Biology Labfax, Croy (ed), Bios scientific Publishers, Oxford, UK, 1993.

The cloning vectors pBluescript and PCR script were obtained from Stratagene, USA pCR7 2.1 was obtained from Invitrogen, USA.

E. coli Transformation

The *Escherichia coli* strains used were:

DH5α supE44, Δ (lacZYA-ArgF)U169, (ø80lacZΔM15), hsdR17 ($r_k^-$, $m_k^+$).

recA1, endA1, gyrA96, thi-1, relA1, deoR (Hanahan, *J. Mol. Biol.* 166: 557, 1983)

XL1-Blue supE44, hsdR17($r_k^-$, $m_k^+$), recA1, endA1, gyrA96, thi-1, relA1, lac$^-$, [F'proAB, lac1$^q$, lacZΔM15, Tn10(tet$^R$)] (Bullock et al., *Biotechniques* 5: 376, 1987).

BL21-CodonPlus-RIL Strain ompT hsdS(Rb– mB–) dcm+ Tet$^r$ gal endA Hte [argU ileY leuW Cam$^r$]

M15 *E. coli* is derived from *E. coli* K12 and has the phenotype Nal$^S$, Str$^S$, Rif$^S$, Thi$^-$, Ara$^+$, Gal$^+$, Mtl$^-$, F$^-$, RecA$^+$, Uvr$^+$, Lon$^+$.

Transformation of the *E. coli* strains was performed according to the method of Inoue et al., (*Gene* 96: 23-28, 1990).

*Agrobacterium tumefaciens* Strains and Transformations

The disarmed *Agrobacterium tumefaciens* strain used was AGL0 (Lazo et at. *Bio/technology* 9: 963-967, 1991).

Plasmid DNA was introduced into the *Agrobacterium tumefaciens* strain AGL0 by adding 5 µg of plasmid DNA to 100 µL of competent AGL0 cells prepared by inoculating a 50 mL LB culture (Sambrook et al., 1989, supra) and incubation for 16 hours with shaking at 28° C. The cells were then pelleted and resuspended in 0.5 mL of 85% (v/v) 100 mM CaCl$_2$/15% (v/v) glycerol. The DNA-*Agrobacterium* mixture was frozen by incubation in liquid N$_2$ for 2 minutes and then allowed to thaw by incubation at 37° C. for 5 minutes. The DNA/bacterial mix was then placed on ice for a further 10 minutes. The cells were then mixed with 1 mL of LB (Sambrook et al., 1989 supra) media and incubated with long for 16 hours at 28° C. Cells of *A. tumefaciens* carrying the plasmid were selected on LB agar plates containing appropriate antibiotics such as 50 µg/mL tetracycline or 100 µg/mL gentamycin. The confirmation of the plasmid in *A. tumefaciens* was done by restriction endonuclease mapping of DNA isolated from the antibiotic-resistant transformants.

DNA Ligations

DNA ligations were carried out using the Amersham Ligation Kit or Promega Ligation Kit according to procedures recommended by the manufacturer.

Isolation and Purification of DNA Fragments

Fragments were generally isolated on a 1% (w/v) agarose gel and purified using the QIAEX II Gel Extraction kit (Qiagen) or Bresaclean Kit (Bresatec, Australia) following procedures recommended by the manufacturer.

Repair of Overhanging Ends after Restriction Endonuclease Digestion

Overhanging 5' ends were repaired using DNA polymerase (Klenow fragment) according to standard protocols (Sambrook et al., 1989 supra). Overhanging 3' ends were repaired using T4 DNA polymerase according to standard protocols (Sambrook et al., 1989 supra).

Removal of Phosphoryl Groups from Nucleic Acids

Shrimp alkaline phosphatase (SAP) (USB) was typically used to remove phosphoryl groups from cloning vectors to prevent re-circularization according to the manufacturer's recommendations.

Polymerase Chain Reaction (PCR)

Unless otherwise specified, PCR conditions using plasmid DNA as template included using 2 ng of plasmid DNA, 100 ng of each primer, 2 µL 10 mM dNTP mix, 5 µL 10×Taq DNA polymerase buffer, 0.5 µL Taq DNA Polymerase in a total volume of 50 µL. Cycling conditions comprised an initial denaturation step of 5 minutes at 94° C., followed by 35 cycles of 94° C. for 20 sec, 50° C. for 30 sec and 72° C. for 1 minute with a final treatment at 72° C. for 10 minutes before storage at 4° C.

PCRs were performed in a Perkin Elmer GeneAmp PCR System 9600.

$^{32}$P-Labelling of DNA Probes

DNA fragments (50 to 100 ng) were radioactively labelled with 50 µCi of [α-$^{32}$P]-dCTP using a Gigaprime kit (Geneworks). Unincorporated [α-$^{32}$P]-dCTP was removed by chromatography on Sephadex G-50 (Fine) columns or Microbiospin P-30 Tris chromatography columns (BioRad).

Plasmid Isolation

Single colonies were analyzed for inserts by inoculating LB broth (Sambrook et al., 1989, supra) with appropriate antibiotic selection (e.g. 100 µg/mL ampicillin or 10 to 50 µL/mL tetracycline etc.) and incubating the liquid culture at 37° C. (for *E. coli*) or 29° C. (for *A. tumefaciens*) for ~16 hours with shaking. Plasmid DNA was purified using the alkali-lysis procedure (Sambrook et al., 1989, supra) or using The WizardPlus SV minipreps DNA purification system (Promega) or Qiagen Plasmid Mini Kit (Qiagen). Once the presence of an insert had been determined, larger amounts of plasmid DNA were prepared from 50 mL overnight cultures using the alkali-lysis procedure (Sambrook et al., 1989, supra) or QIAfilter Plasmid Midi kit (Qiagen) and following conditions recommended by the manufacturer.

DNA Sequence Analysis

DNA sequencing was performed using the PRISM (trademark) Ready Reaction Dye Primer Cycle Sequencing Kits from Applied Biosystems. The protocols supplied by the manufacturer were followed. The cycle sequencing reactions were performed using a Perkin Elmer PCR machine (GeneAmp PCR System 9600). Sequencing runs were generally performed by the Australian Genome Research Facility at The Walter and Eliza Hall Institute of Medical Research (Melbourne, Australia) or in-house on an automated 373A DNA sequencer (Applied Biosystems).

Sequences were analysed using a MacVector™ application (version 6.5.3) (Oxford Molecular Ltd., Oxford, England).

Homology searches against Genbank, SWISS-PROT and EMBL databases were performed using the FASTA and TFASTA programs (Pearson and Lipman, Proc. Natl. Acad. Sci. USA 85(8): 2444-2448, 1988) or BLAST programs (Altschul et al., *J. Mol. Biol.* 275(3): 403-410, 1990). Percentage sequence similarities were obtained using LALIGN program (Huang and Miller, *Adv. Appl. Math.* 12: 373-381, 1991) or ClustalW program (Thompson et al., *Nucleic Acids Research* 22: 4673-4680, 1994) within the MacVector™ application (Oxford Molecular Ltd., England) using default settings.

Multiple sequence alignments were produced using ClustalW (Thompson et al., 1994, supra) using default settings.

Example 2

Plant Transformations

*Petunia hybrida* Transformations (Sw63×Skr4)

As described in Holton et al. (1993a supra) by any other method well known in the art.

*Rosa hybrida* Transformations

As described in U.S. patent application Ser. No. 542,841 (PCT/US91/04412) or Robinson and Firoozabady (*Scientia Horticulturae,* 55: 83-99, 1993). Rout et al. (*Scientia Horticulturae,* 81: 201-238, 1999) or Marchant et al. (*Molecular Breeding* 4: 187-194, 1998) or by any other method well known in the art.

Cuttings of *Rosa hybrida* were generally obtained from Van Wyk and Son Flower Supply, Victoria.

*Dianthus caryophyllus* Transformations

International Patent Application No. PCT/US92/02612 (carnation transformation). As described in International Patent Application No. PCT/AU96/00296 (Violet carnation), Lu et al. (*Bio/Technology* 9: 864-868, 1991), Robinson and Firoozabady (1993, supra) or by any other method well known in the art.

Cuttings of *Dianthus caryophyllus* cv. Kortina Chanel or Monte Lisa were obtained from Van Wyk and Son Flower Supply, Victoria.

Example 3

Transgenic Analysis

Color Coding

The Royal Horticultural Society's Color Chart (Kew, UK) was used to provide a description of observed color. They provide an alternative means by which to describe the color phenotypes observed. The designated numbers, however, should be taken only as a guide to the perceived colors and should not be regarded as limiting the possible colors which may be obtained.

Chromatographic Analysis

Thin Layer Chromatography (TLC) and High Performance Liquid Chromatography (HPLC) analysis was performed generally as described in Brugliera et al. (*Plant J.* 5, 81-92, 1994).

Extraction of Anthocyanidins

Prior to HPLC analysis, the anthocyanin and flavonol molecules present in petal and stamen extracts were acid hydrolysed to remove glycosyl moieties from the anthocyanidin or flavonol core. Anthocyanidin and flavonol standards were used to help identify the compounds present in the floral extracts.

Anthocyanidins in the reaction mixture were analysed by HPLC via gradient elution using gradient conditions of 50% B to 60% B over 10 minutes, then 60% B for 10 minutes and finally 60% B to 100% B over 5 minutes where solvent A consisted of TFA: $H_2O$ (5:995) and solvent B consisted of acetonitrile: TFA: $H_2O$ (500:5:495). An Asahi Pac ODP-50 cartridge column (250 mm×4.6 mm ID) was used for the reversed phase chromatographic separations. The flow rate was 1 mL/min and the temperature was 40° C. The detection of the anthocyanidin compounds was carried out using a Shimadzu SPD-M6A three dimensional detector at 400-650 nm.

The anthocyanidin peaks were identified by reference to known standards, viz delphinidin or delphinidin-based molecules, petunidin, malvidin, cyanidin and peonidin.

States of Flower Development

*Petunia*

*Petunia hybrida* cv. Skr4×Sw63 flowers were harvested at developmental stages defined as follows:

Stage 1: Unpigmented, closed bud.
Stage 2: Pigmented, closed bud.
Stage 3: Pigmented bud with emerging corolla
Stage 4: Pigmented, opened flower with anther intact (pre-dehiscence)
Stage 5: Fully opened flower with all anthers dehisced.

For TLC or HPLC analysis, petals were collected from stage 4 flowers at the stage of maximum pigment accumulation.

For Northern blot analysis, petals were collected from stages 2 to 3 flowers at the stage of maximal expression of flavonoid pathway genes.

Carnation.

*Dianthus caryophyllus* flowers were harvested at developmental stages defined as follows:

Stage 1: Closed bud, petals not visible.
Stage 2: Flower buds opening: tips of petals visible.
Stage 3: Tips of nearly all petals exposed. "Paint-brush stage".
Stage 4: Outer petals at 45° angle to stem.
Stage 5: Flower fully open.

For TLC or HPLC analysis, petals were collected from stage 4 flowers at the stage of maximum pigment accumulation.

For Northern blot analysis, petals were collected from stage 3 flowers at the stage of maximal expression of flavonoid pathway genes.

Rose

Stages of *Rosa hybrida* flower development were defined as follows:

Stage 1: Unpigmented, tightly closed bud.
Stage 2: Pigmented, tightly closed bud
Stage 3: Pigmented, closed bud; sepals just beginning to open.
Stage 4: Flower bud beginning to open; petals heavily pigmented; sepals have separated.
Stage 5: Sepals completely unfolded; some curling. Petals are heavily pigmented and unfolding.

For TLC or HPLC analysis, petals were collected from stage 4 flowers at the stage of maximum pigment accumulation.

For Northern blot analysis, petals were collected from stage 3 to 4 flowers at the stage of maximal expression of flavonoid pathway genes (Tanaka et al., *Plant Cell Physiol.*, 36(6): 1023-1031, 1995).

Anthocyanin/Flavonol Measurements by Spectrophotometric Measurements

Approximately 200 mg of fresh petal tissue was added to 2 mL of methanol/1% (v/v) HCl and incubated for ~16 hours at 4° C. A 1 in 20 dilution (e.g. 50 µL made to 1000 µL) was then made and the absorbance at 350 nm and 530 nm was recorded.

The approximate flavonols and anthocyanin amounts (nmoles/gram) were then calculated according to the following formulae:

Anthocyanin Content $$\frac{(A_{530}/34{,}000) \times \text{volume of extraction buffer(mL)} \times \text{dilution factor} \times 10^6}{\text{mass of petal tissue (grams)}}$$

Flavonol Content $$\frac{(A_{350}/14{,}300) \times \text{volume of extraction buffer(mL)} \times \text{dilution factor} \times 10^6}{\text{mass of petal tissue (grams)}}$$

Northern/RNA Blot Analyst

Transcription of a transferred gene was monitored by isolating RNA and estimating the quantity and size of the expected transcript. Northern blot analysis was used to monitor the steady-state level of particular transcripts in petals. A transcript was determined to be intact or full-length based on the estimated size expected from the gene used. In general when cDNAs were used as coding sequences the size of the transcript expected would be the size of the cDNA plus any 5' untranslated component of the fused promoter fragment plus any 3' untranslated sequence from the fused terminator fragment. In some cases where a cDNA region contained a putative polyadenylation site and the terminator region contained a putative polyadenylation site, 2 transcripts would be detected. One would be of a size consistent with polyadenylation occurring just downstream from the polyadenylation site within the cDNA sequence. The second transcript would be larger and consistent with the transcript being polyadenylated after the polyadenylation site within the terminator fragment.

Total RNA was isolated from petals or leaves using a Plant RNAeasy kit (QIAGEN) following procedures recommended by the manufacturer. For rose samples 1% (w/v) PVP was added to the extraction buffer.

RNA samples (5 µg) were electrophoresed through 2.2 M formaldehyde/1.2% w/v agarose gels using running buffer containing 40 mM morpholinopropanesulphonic acid (pH 7.0), 5 mM sodium acetate, 0.1 mM EDTA (H 8.0). The RNA was stained with ethidium bromide and visualised under UV-light. The ribosomal RNA was generally used as a guide in confirming that the RNA had not been degraded by intra- or extra-cellular ribonucleases. The RNA was transferred to Hybond-N membrane filters (Amersham) and treated as described by the manufacturer.

Control samples were included on RNA gels as a measure of the integrity of the radiolabelled probe and as guides to expected transcript sizes. Controls for petHf1 and petHf2 genes included RNA isolated from *petunia* OGB petals (stages 3 to 4) or from flowers of transgenic carnations shown previously to accumulate petHf1 transcripts. Controls for other F3'5'H genes generally included RNA isolated from petals of the same species from which the F3'5'H sequence had been isolated.

RNA blots were probed with $^{32}$P-labelled fragments. Prehybridization (1 hour at 42° C.) and hybridization (16 hours at 42° C.) of the membrane filters were cared out in 50% v/v formamide, 1 M NaCl, 1% w/v SDS, 10% w/v dextran sulphate. The membrane filters were generally washed in 2×SSC, 1% w/v SDS at 65° C. for between 1 to 2 hours and then 0.2×SSC, 1% w/v SDS at 65° C. for between 0.5 to 1 hour. Membrane filters were generally exposed to Kodak XAR film with an intensifying screen at −70° C. for 16 to 72 hours.

Example 4

Introduction of Chimeric *Petunia* F3'5'H Genes into Rose

As described in the introduction, the pattern of hydroxylation of the B-ring of the anthocyanidin molecule plays a key role in determining petal color. The production of the dihydroflavonol DHM, leads to the production of the purple/blue delphinidin-based pigments in plants such as petunia. The absence of the F3'5'H activity has been correlated with the absence of blue flowers in many plant species such as *Rosa, Gerbera, Antirrhinum, Dianthus* and *Dendranthema*.

Based on success in producing delphinidin-based pigments in a mutant *petunia* line (Holton et al., 1993a, supra and International Patent Application No. PCT/AU92/00334), in tobacco flowers (International Patent Application No. PCT/AU92/00334) and in carnation flowers (International Patent Application No. PCT/AU96/00296), similar chimeric *petunia* F3'5'H genes were also introduced into roses in order to produce novel delphinidin-based pigments and modify flower color.

Preparation of Chimeric *Petunia* F3'5'H Gene Constructs

A summary of promoter, terminator and coding fragments used in the preparation of constructs and the respective abbreviations is listed in Table 4.

TABLE 4

Abbreviations used in construct preparations

| ABBREVIATION | DESCRIPTION |
|---|---|
| AmCHS 5' | 1.2 kb promoter fragment from the *Antirrhinum majus* chalcone synthase (CHS) gene (Sommer and Saedler, Mol Gen. Gent., 202: 429-434, 1986) |
| CaMV 35S | ~0.2 kb incorporating BglII fragment containing the promoter region from the Cauliflower Mosaic Virus 35S (CaMV 35S) gene - (Franck et at., Cell 21: 285-294, 1980, Guilley et al., Cell, 30: 763-773, 1982) |
| 35S 5' | promoter fragment from CaMV 35S gene (Franck et al., 1980, supra) with an ~60 bp 5' untranslated leader sequence from the petunia chlorophyll a/b binding protein gene (Cab 22 gene) (Harpster et al., MGG, 212: 182-190, 1988) |

TABLE 4-continued

Abbreviations used in construct preparations

| ABBREVIATION | DESCRIPTION |
| --- | --- |
| chrysCHS 5' | promoter region from a CHS gene from chrysanthemum (SEQ ID NO: 30) |
| eCaMV 35S | enhanced CaMV 35S promoter as described in Mitsuhara et al., Plant Cell Physiol. 37: 49-59, 1996 |
| GUS | β-glucuronidase (GUS) coding sequence (Jefferson, et al., EMBO J. 6: 3901-3907, 1987) |
| Mac | Hybrid promoter consisting of the promoter from the mannopine synthase (mas) gene and a CaMV 35S enhancer region (Comai et al., Plant Mol. Biol 15: 373-381, 1990) |
| mas/35S | Hybrid promoter consisting of a promoter region from CaMV 35S gene with enhancer elements from a promoter fragment of mannopine synthase (mas) gene of *Agrobacterium tumefaciens* (Janssen and Gardner, Plant Molecular Biology. 14: 61-72, 1989) |
| mas 5' | Promoter region from the mas of *A. tumefaciens* |
| mas 3' | Terminator region from the mas gene of *A. tumefaciens* |
| nos 5' | Promoter region from the nopaline synthase (nos) gene of *A. tumefaciens* (Depicker et al., J Mol. and Appl. Genetics 1: 561-573, 1982) |
| nos 3' | Terminator region from the nos gene of *A. tumefaciens* (Depicker et al., 1982, supra) |
| nptII | Kanamycin-resistance gene (encodes neomycin phosphotransferase which deactivates aminoglycoside antibiotics such as kanamycin, neomycin and G418) |
| ocs 3' | ~1.6 kb terminator fragment from octopine synthase gene of *A. tumefaciens* (described in Janssen and Gardner, 1989, supra) |
| petD8 5' | ~3.2 kb promoter region from a phospholipid transfer protein gene (D8) of *Petunia hybrida* (Holton, Isolation and characterization of petal specific genes from *Petunia hybrida*. PhD thesis, University of Melbourne, Australia, 1992) (SEQ ID NO: 24) |
| petD8 3' | ~0.7 kb terminator region from a phospholipid transfer protein gene (D8) of *Petunia hybrida* cv. OGB (Holton, 1992, supra) |
| long petFLS 5' | ~4.0 kb fragment containing the promoter region from a flavonol synthase (FLS) gene of *P. hybrida* |
| short petFLS 5' | ~2.2 kb fragment containing the promoter region from FLS gene of *P. hybrida* |
| petFLS 3' | ~0.95 kb fragment containing the terminator region from FLS gene of *P. hybrida* |
| petHf1 | Petunia F3'5'H Hf1 cDNA clone (Holton et al., 1993a, supra) (SEQ ID NO: 1) |
| petHf2 | Petunia F3'5'H Hf2 cDNA clone (Holton et al., 1993a, supra) (SEQ ID NO: 3) |
| petRT 5' | Promoter region of an anthocyanidin-3-glucoside rhamnosyltransferase (3RT) gene from *P. hybrida* (Brugliera, Characterization of floral specific genes isolated from *Petunia hybrida*. RMIT, Australia. PhD thesis, 1994) |
| petRT 3' | Terminator region of a 3RT gene from *P. hybrida* (Brugliera, 1994, supra) |
| RoseCHS 5' | ~2.8 kb fragment containing the promoter region from a CHS gene of *Rosa hybrida* (SEQ ID: 5) |
| SuRB | Chlorsulfuron-resistance gene (encodes Acetolactate Synthase) with its own terminator from *Nicotiana tabacum* (Lee et al., EMBO J. 7: 1241-1248, 1988) |

In order to produce delphinidin or delphinidin-based molecules in rose petals, a number of binary vector constructs were prepared utilising the *petunia* F3'5'H cDNA fragments and various promoter and terminator fragments. The chimeric *petunia* F3'5'H genes had proved successful in carnation and *petunia* leading to detectable intact F3'5'H transcripts (as detected by Northern blot analysis) and to the production of delphinidin or delphinidin-based molecules pigments. Table 5 summarises the list of binary vector constructs containing *petunia* F3'5'H cDNA fragments.

TABLE 5

Summary of chimaeric petunia F3'5'H gene expression cassettes contained in binary vector constructs used in the transformation of roses (see Table 4 for an explanation of abbreviations).

| PLASMID | F3'5'H GENE | SELECTABLE MARKER GENE |
| --- | --- | --- |
| pCGP1452 | AmCHS 5':petHf1:petD8 3' | 35S 5':SuRB |
| pCGP1453 | Mac:petHf1:mas 3' | 35S 5':SuRB |

TABLE 5-continued

Summary of chimaeric petunia F3'5'H gene expression cassettes contained in binary vector constructs used in the transformation of roses (see Table 4 for an explanation of abbreviations).

| PLASMID | F3'5'H GENE | SELECTABLE MARKER GENE |
|---|---|---|
| pCGP1457 | petD8 5':petHfl:petD8 3' | 35S 5':SuRB |
| pCGP1461 | short petFLS 5':petHfl:petFLS 3' | 35S 5':SuRB |
| pCGP1616 | petRT 5':petHfl:nos 3' | 35S 5':SuRB |
| pCGP1638 | CaMV 35S:petHfl:ocs 3' | 35S 5':SuRB |
| pCGP1623 | mas 35S:petHfl:ocs 3' | 35S 5':SuRB |
| pCGP1860 | Rose CHS 5':petHfl:nos 3' | 35S 5':SuRB |
| pCGP2123 | CaMV 35S:petHf2:ocs 3' | 35S 5':SuRB |

The Isolation of Petunia F3'5'H cDNA Clones (petHf1 and petHf2)

The isolation and characterisation of cDNA clones of *petunia* F3'5'H (petHf1 and petHf2 contained in pCGP602 (FIG. 2) and pCGP175 (FIG. 3) respectively) (SEQ ID NO:1 and SEQ ID NO:3, respectively) have been described in International Patent Application No. PCT/AU92/00334 and Holton et al. (1993a, supra).

The plasmid pCGP601 (FIG. 2), pCGP602 (FIG. 2), pCGP176 (FIG. 2) contain homologs of the *petunia* petHf1 F3'5'H cDNA clone. The plasmid pCGP601 contains a *petunia* F3'5'H petHf1 homolog that includes 52 bp of 5' untranslated sequence. The plasmid pCGP602 contains a *petunia* F3'5'H petHf1 homolog that includes 125 bp of 5' untranslated sequence (SEQ ID NO:1). The plasmid pCGP176 (described in Holton et al., 1993a supra) contains a *petunia* F3'5'H petHf1 homolog that includes 27 bp of 5' untranslated sequence and a further ~127 bp of 3' untranslated sequence over the petunia F3'5'H petHf1 cDNA clone in pCGP602.

Construction of pCGP1303 (petHf1 in pUC19 Backbone).

Figure 4:
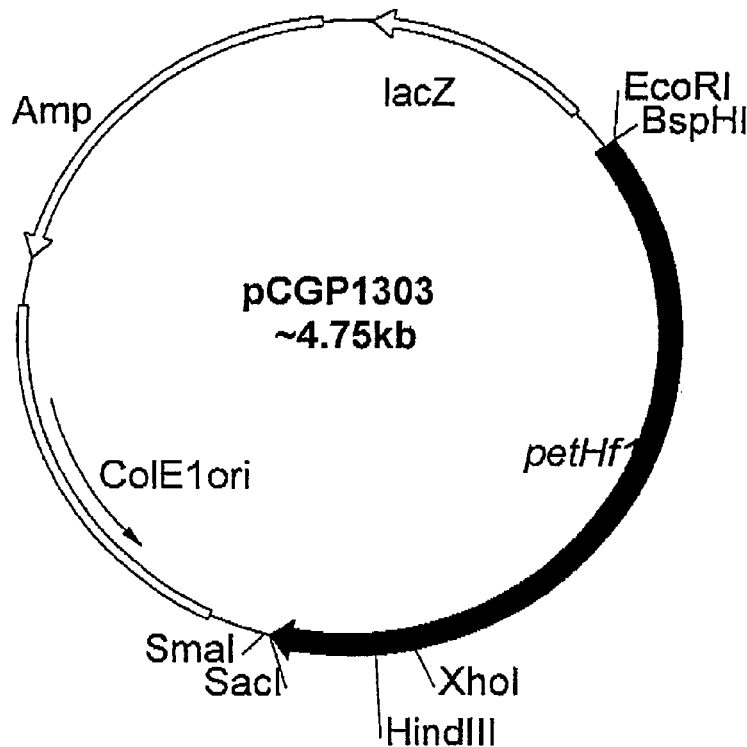
FIG. 4 is a diagrammatic representation of the plasmid pCGP1303 containing a subclone of the *petunia* F3'5'H petHf1 cDNA clone from pCGP601. The construction of pCGP1303 is described in Example 4. Selected restriction endonuclease sites are marked. Refer to Table 2 and Table 4 for a description of the abbreviations.

The *petunia* F3'5'H cDNA clone contained in the plasmid pCGP601 (described above) (FIG. 2) included 52 bp of 5' untranslated sequence and 141 bp of 3' untranslated sequence including 16 bp of the poly A tail. The plasmid pCGP601 (FIG. 2) was firstly linearized by digestion with the restriction endonuclease BspHI. The ends were repaired and the *petunia* F3'5'H petHf1 cDNA clone was released upon digestion with the restriction endonuclease FspI. The BspHI recognition sequence encompasses the putative translation initiating codon and the FspI recognition sequence commences 2 bp downstream from the stop codon. The 1.6 kb fragment containing the *petunia* F3'5'H petHf1 cDNA clone was purified and ligated with repaired EcoRI ends of pUC19 (New England Biolabs). Correct insertion of the fragment was established by restriction endonuclease analysis of DNA isolated from ampicillin-resistant transformants. The resulting plasmid was designated as pCGP1303 (FIG. 4).

Construction of pCGP27 (Short petHf1 in pBluescript Backbone)

The plasmid pCGP176 (Holton et al., 1993a, supra) (FIG. 2) was digested with the restriction endonuclease SpeI and EcoRI. The ends were then repaired and allowed to religate. The resulting plasmid was designated as pCGP627 and contained the identical cDNA clone as in pCGP176 except that the restriction endonuclease sites PstI, BamHI and SmaI were removed from the multi-cloning site of the pBluescript vector at the 5' end of the cDNA clone.

The Binary Vector pCGP1452 (AmCHS 5': petHf1: petD8 3').

The plasmid pCGP1452 (FIG. 5) contains a chimeric *petunia* F3'5'H (petHf1) gene under the control of a promoter fragment from the *Antirrhinum majus* chalcone synthase gene (CHS) (Sommer and Saedler, 1986, supra) with a terminator fragment from the *petunia* phospholipid transfer protein (PLTP) gene (petD8 3') (Holton, 1992, supra). The chimeric *petunia* F3'5'H cassette is in a tandem orientation with respect to the 35S 5': SuRB gene of the binary vector, pWTT2132 (DNA Plant Technologies, USA=DNAP) (FIG. 6).

Intermediates in the Preparation of the Binary pCGP1452

The Binary Vector pWTT2132

The binary vector plasmid pWTT2132 (DNAP) (FIG. 6) contains a chimeric gene comprised of a 35S 5' promoter sequence (Franck et al., 1980, supra), ligated with the coding region and terminator sequence for acetolactate synthase (ALS) gene from the SuRB locus of tobacco (Lee et al., 1988, supra). An ~60 bp 5' untranslated leader sequence from the *petunia* chlorophyll a/b binding protein gene (Cab 22 gene) (Harpster et al., MGG, 212: 182-190, 1988) is included between the 35S 5' promoter fragment and the SuRB sequence.

Construction of pCGP725 (AmCHS 5': petHf1: petD8 3' in pBluescript)

A chimeric *petunia* F3'5'H gene under the control *Antirrhinum majus* CHS (AmCHS 5') promoter with a *petunia* PLTP terminator (petD8 3') was constructed by cloning the 1.6 kb BclI/FspI *petunia* F3'5'H (petHf1) fragment from pCGP602 (Holton et al., 1993a, supra) (FIG. 2) between a 1.2 kb *Antirrhinum majus* CHS gene fragment 5' to the site of translation initiation (Sommer and Saedler, 1986, supra) and a 0.7 kb SmaI/XhoI PLTP fragment (petD8 3') from pCGP13ΔBam (Holton, 1992, supra), 3' to the deduced stop codon. The resulting plasmid in a pBluescript II KS (Stratagene, USA) backbone vector was designated pCGP725 (FIG. 7).

Construction of pCGP485 and pCGP1452 (AmCHS 5': petHf1: petD8 3' Binary Vectors)

Figure 5:
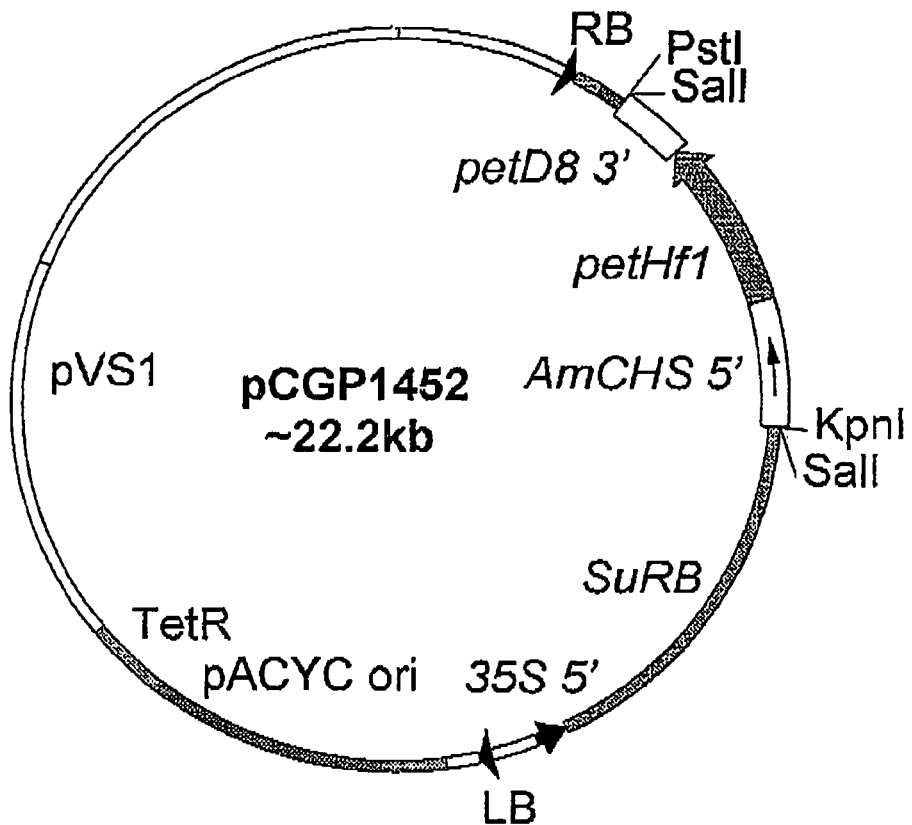
FIG. 5 is a diagrammatic representation of the binary plasmid pCGP1452. The AmCHS 5': petHf1: petD8 3' gene from pCGP485 was cloned into the binary vector pWTT2132 (DNAP) in a tandem orientation with the chimaeric SuRB gene. The construction of pCGP1452 is described in Example 4. Selected restriction endonuclease sites are marked. Refer to Table 2 and Table 4 for a description of the abbreviations.

The chimeric F3'5'H gene from pCGP725 (FIG. 7) was cloned into the binary vector pCGN1547 containing an nptII selectable marker gene cassette (McBride and Summerfelt *Plant Molecular Biology* 14: 269-276, 1990) to create pCGP485. A 3.5 kb fragment containing the AmCHS 5'; petHf1: petD8 3' cassette was released upon digestion of pCGP485 with the restriction endonuclease PstI. The overhanging ends were repaired and the purified 3.5 kb fragment was ligated with SmaI ends of the binary vector, pWTT2132 (DNAP). Correct insertion of the fragment in a tandem orientation with respect to the 35S 5': SuRB selectable marker gene cassette was established by restriction endonuclease analysis of plasmid DNA isolated from tetracycline-resistant transformants. The plasmid was designated as pCGP1452 (FIG. 5).

Plant Transformation with pCGP1452

The T-DNA contained in the binary vector plasmid pCGP1452 (FIG. 5) was introduced into rose via *Agrobacterium*-mediated transformation.

The Binary Vector pCGP1453 (Mac: petHf1: mas 3')

The plasmid pCGP1453 (FIG. 8) contains a chimeric *petunia* F3'5'H (petHf1) gene under the control of a Mac promoter (Comai et al., 1990, supra) with a terminator fragment from the mannopine synthase gene of *Agrobacterium* (mas 3'). The chimeric *petunia* F3'5'H cassette is in a tandem orientation with respect to the 35S 5': SuRB selectable marker gene cassette of the binary vector, pWTT2132 (DNAP) (FIG. 6).

A 3.9 kb fragment containing the Mac: petHf1: mas 3' gene was released from the plasmid pCGP628 (described in International Patent Application No. PCT/AU94/00265) upon digestion with the restriction endonuclease PstI. The overhanging ends were repaired and the purified fragment was ligated with SmaI ends of pWTT2132 (DNAP). Correct insertion of the Mac: petHf1: mas 3' gene in a tandem orientation with respect to the 35S 5': SuRB selectable marker gene cassette was established by restriction endonuclease analysis of plasmid DNA isolated from tetracycline-resistant transformants. The plasmid was designated as pCGP1453 (FIG. 8).

Plant Transformation with pCGP1453

The T-DNA contained in the binary vector plasmid pCGP1453 (FIG. 8) was introduced into rose via *Agrobacterium*-mediated transformation.

The Binary Vector pCGP1457 (petD8 5': petHf1: pet D8 3')

The plasmid pCGP1457 (FIG. 9) contains a chimeric *petunia* F3'5'H (petHf1) gene under the control of a promoter fragment from the *petunia* PLTP gene (petD8 5') with a terminator fragment from the *petunia* PLTP gene (petD8 3'). The chimeric *petunia* F3'5'H cassette is in a tandem orientation with respect to the 35S 5': SuRB gene of the binary vector, pWTT2132 (DNAP) (FIG. 6).

Intermediates in the Preparation of the Binary Vector pCGP1457

Isolation of Petunia D8 Genomic Clone

Preparation of *P. hybrida* cv. OGB (Old Glory Blue) Genomic Library in λ2001

A genomic DNA library was constructed from *Petunia hybrida* cv. OGB DNA in the vector λ2001 (Karn et al., *Gene* 32: 217-224, 1984) using a Sau3A partial digestion of the genomic DNA as described in Holton, 1992 (supra). Screening of the OGB genomic library for the *petunia* D8 gene was as described in Holton, 1992. supra.

Isolation of D8 Genomic Clone OGB2.6

PCR was performed in order to find a non-mutant genomic clone representing D8. Oligo #2 (5' to 3' GTTCTCGAG-GAAAGATAATACAAT) (SEQ ID NO:6) and Oligo #4 (5' to 3' CAAGATCGTAGGACTGCATG) (SEQ ID NO:7) were used to amplify D8 gene fragments, across the intron region, using 4 μL of phage suspension from the clones isolated from the primary screening of the OGB genomic library. The reactions were carried out in a total volume of 50 μl containing 1× Amplification buffer (Cetus), 0.2 mM dNTP mix, <1 μg of template DNA, 50 pmoles of each primer and 0.25 μL of Taq polymerase (5 units/μL-Cetus). The reaction mixtures were overlaid with 30 μL of mineral oil and temperature cycled using a Gene Machine (Innovonics). The reactions were cycled 30 times using the following conditions: 94° C. for 1 minute, 55° C. for 50 seconds, 72° C. for 2 minutes. One quarter of each PCR reaction was run on an agarose gel using TAE running buffer.

Three clones, λOGB-2.4, λOGB-2.5, and λOGB-2.6, gave fragments of approximately 1 kb whereas the mutant clone, λOGB-3.2 (described in Holton, 1992, supra), had produced a product of 1.25 kb. The λOGB-2.6 clone was chosen for further analysis.

pCGP382

The genomic clone, λOGB-2.6, contained a single 3.9 kb XbaI fragment that hybridized with the D8 cDNA. This XbaI fragment was isolated and purified and ligated with the XbaI ends of pBluescriptII KS—(Stratagene, USA). Restriction mapping of this clone revealed an internal PstI site 350 bp from the 3' end. However, the "mutant" genomic clone in pCGP13, had an internal PstI near the putative initiating "ATG" of the coding region (approximately 1.5 kb from its 3' end). The difference in the position of the PstI site in both clones suggested that the λOGB-2.6 XbaI fragment did not contain the whole genomic sequence of D8. A Southern blot was performed on PstI digested λOGB-2.6 DNA, and a fragment of 2.7 kb was found to hybridize with the D8 cDNA. Restriction endonuclease mapping confirmed that this fragment contained the 3' coding region and flanking sequences.

In order to obtain a fragment containing the whole D8 genomic sequence, a number of cloning steps were undertaken. The λOGB-2.6 PstI fragment of 2.7 kb was purified and ligated with PstI ends of pBluescriptII KS—(Stratagene, USA). The resultant clone was digested with XbaI to remove the 350 bp PstI/XbaI fragment. This fragment was replaced by the 3.9 kb XbaI fragment from λOGB-2.6 to produce the plasmid pCGP382.

A 3.2 kb fragment containing the promoter region from the D8 2.6 gene in pCGP382 was released upon digestion with the restriction endonucleases HindIII and NcoI. The fragment was purified and ligated with the 4.8 kb NcoI/HindIII fragment of pJB1 (Bodean, Molecular and genetic regulation of Bronze-2 and other maize anthocyanin genes. Dissertation, Stanford University, USA, 1994) to produce pCGP1101 containing a petD85': GUS: nos 3' cassette.

A 1.6 kb *petunia* F3'5'H petHf1 fragment was released from the plasmid pCGP602 (Holton et al., 1993a, supra) (SEQ ID NO:1) (FIG. 2) upon digestion with the restriction endonucleases BspHI and BamHI. The fragment was purified and ligated with the 6.2 kb NcoI/BamHI fragment of pCGP1101 to produce pCGP1102 containing a petD8 5': petHf1: nos 3' expression cassette.

A 0.75 kb BamHI petD8 3' fragment (Holton, 1992, supra) was purified from the plasmid pCGP13ΔBamHI and ligated with BamHI/BglII ends of pCGP1102 to produce the plasmid pCGP1107 containing a petD8 5': petHf1: petD8 3' expression cassette.

The plasmid pCGP1107 was linearised upon digestion with the restriction endonuclease XbaI. The overhanging ends were repaired and then the 5.3 kb fragment containing the petD8 5': petHf1: petD8 3' expression cassette was released upon digestion with the restriction endonuclease PstI. The fragment was purified and ligated with SmaI/PstI ends of the binary vector pWTT2132 (DNAP) (FIG. 6). Correct insertion of the petD8 5': petHf1: petD8 3' gene in a tandem orientation with respect to the 35S 5': SuRB selectable marker gene cassette was established by restriction endonuclease analysis of plasmid DNA isolated from tetracycline-resistant transformants. The plasmid was designated as pCGP147 (FIG. 9).

Plant Transformation with pCGP1457

The T-DNA contained in the binary vector plasmid pCGP1457 (FIG. 9) was introduced into rose via *Agrobacterium*-mediated transformation.

The Binary Vector pCGP1461 (Short petFLS 5': petHf1: pet FLS 3')

The plasmid pCGP1461 (FIG. 10) contains a chimeric pea F3'5'H (petHf1) gene under the control of a promoter fragment from the *petunia* flavonol synthase (FLS) gene (short petFLS 5') with a terminator fragment from the *petunia* FLS gene (petFLS 3'). The chimeric *petunia* F3'5'H gene is in a tandem orientation with respect to the 35S 5': SuRB gene of the binary vector, pWTT2132 (FIG. 6).

Intermediates in the Preparation of the Binary Vector pCGP1461

Isolation of *Petunia* FLS Gene

Preparation of *P. hybrida* cv. Th7 Genomic Library

A *P. hybrida* cv. Th7 genomic library was prepared according to Sambrook et al. (1989, supra) using a Sau3A partial digestion of the genomic DNA. The partially digested DNA was cloned into EMBL-3 lambda vector (Stratagene, USA).

The Th7 genomic DNA library was screened with $^{32}$P-labelled fragments of a *petunia* FLS cDNA clone (Holton et al., *Plant J.* 4: 1003-1010, 1993b) using high stringency conditions.

Two genomic clones (FLS2 and FLS3) were chosen for further analysis and found to contain sequences upstream of the putative initiating methionine of the *petunia* FLS coding region with FLS2 containing a longer promoter region than FLS3.

pCGP486

A 6 kb fragment was released upon digestion of the genomic clone FLS2 with the restriction endonuclease XhoI. The fragment containing the short *petunia* FLS gene was purified and ligated with XhoI ends of pBluescript SK (Stratagene, USA). Correct insertion of the fragment was established by restriction endonuclease analysis of DNA isolated from ampicillin-resistant transformants. The resulting plasmid was designated as pCGP486.

pCGP487

A 9 kb fragment was released upon digestion of the genomic clone FLS3 with the restriction endonuclease XhoI. The fragment containing the *petunia* FLS gene was purified and ligated with XhoI ends of pBluescript SK (Stratagene, USA). Correct insertion of the fragment was established by restriction endonuclease analysis of DNA isolated from ampicillin-resistant transformants. The resulting plasmid was designated as pCGP487.

pCGP717

A 2.2 kb *petunia* FLS promoter fragment upstream from the putative translational initiation site was released from the plasmid pCGP487 upon digestion with the restriction endonucleases XhoI and PstI. The fragment generated was purified and ligated with XhoI/PstI ends of pBluescript II KS+ (Stratagene, USA). Correct insertion of the fragment was established by restriction endonuclease analysis of DNA isolated from ampicillin-resistant transformants. The resulting plasmid was designated as pCGP717.

pCGP716

A 0.95 kb *petunia* FLS terminator fragment downstream from the putative translational stop site was released from the plasmid pCGP487 upon digestion with the restriction endonucleases HindIII and SacI. The fragment generated was purified and ligated with HindIII/SacI ends of pBluescript II KS+ (Stratagene, USA). Correct insertion of the fragment was established by restriction endonuclease analysis of DNA isolated from ampicillin-resistant transformants. The resulting plasmid was designated as pCGP716.

Construction of pCGP493 (Short petFLS 5': petFLS 3' Expression Cassette)

A 1.8 kb fragment containing the short *petunia* FLS promoter fragment was amplified by PCR using the plasmid pCGP717 as template and the T3 primer (Stratagene, USA) and an FLS-Nco primer (5' AAA ATC GAT ACC ATG GTC TTT TTT TCT TTG TCT ATA C 3') (SEQ ID. NO:19). The PCR product was digested with the restriction endonucleases XhoI and ClaI and the purified fragment was ligated with XhoI/ClaI ends of pCGP716. Correct insertion of the fragment was established by restriction endonuclease analysis of DNA isolated from ampicillin-resistant transformants. The resulting plasmid was designated as pCGP493.

Construction of pCGP497 (Short petFLS 5': petHf1: petFLS3' Expression Cassette)

The *petunia* F3'5'H (petHf1) cDNA clone was released from the plasmid pCGP627 (described above) upon digestion with the restriction endonucleases BspHI and FspI. The BspHI recognition sequence encompasses the putative translation initiating codon and the FspI recognition sequence commences 2 bp downstream from the stop codon. The *petunia* F3'5'H petHf1 fragment generated was purified and ligated with ClaI (repaired ends)/NcoI ends of the plasmid pCGP493. Correct insertion of the fragment was established by restriction endonuclease analysis of DNA isolated from ampicillin-resistant transformants. The resulting plasmid was designated as pCGP497.

Construction of pCGP1461 (Short petFLS 5': petHf1: petFLS3' Binary Vector)

The plasmid pCGP497 was linearised upon digestion with the restriction endonuclease SacI. The overhanging ends were repaired and a 4.35 kb fragment containing the short petFLS 5': petHf1: petFLS3' gene expression cassette was released upon digestion with the restriction endonuclease KpnI. The fragment generated was purified and ligated with PstI (ends repaired)/KpnI ends of the binary vector pWTT2132 (DNAP) (FIG. 6). Correct insertion of the fragment in a tandem orientation with respect to the 35S 5': SuRB selectable marker gene cassette of pWTT2132 was established by restriction endonuclease analysis of plasmid DNA isolated from tetracycline-resistant transformants. The resulting plasmid was designated as pCGP1461 (FIG. 10).

Plant Transformation with pCGP1461

The T-DNA contained in the binary vector plasmid pCGP1461 (FIG. 10) was introduced into rose via *Agrobacterium*-mediated transformation.

The Binary Vector pCGP1616 (petRT 5': petHf1: nos 3')

The plasmid pCGP1616 (FIG. 11) contains a chimeric *petunia* F3'5'H (petHf1) gene under the control of a promoter fragment from the *P. hybrida* 3RT gene (petRT 5') (Brugliera, 1994, supra) with a terminator fragment from the nopaline synthase gene (nos 3') of *Agrobacterium* (Depicker, et al., 1982, supra). The chimeric *petunia* F3'5'H cassette is in a tandem orientation with respect to the 35S 5': SuRB gene of the binary vector, pWTT2132 (DNAP) (FIG. 6).

Intermediates in the Preparation of the Binary Vector pCGP1616

Isolation of Petunia 3RT Gene

*P. hybrida* cv. Th7 Genomic DNA Library Construction in EMBL3

A *Petunia hybrida* cv. Th7 genomic library was prepared according to Sambrook et al. 1989, supra using a Sau3A partial digestion of the genomic DNA. The partially digested DNA was cloned into EMBL-3 lambda vector (Stratagene, USA). Screening of the Th7 genomic library for the *petunia* 3RT gene was as described in Brugliera, 1994, supra.

A 3 kb fragment containing the petRT 5': petHf1: nos 3' cassette was released from the plasmid pCGP846 (described in Brugliera, 1994, supra) upon digestion with the restriction endonucleases PstI and BamHI. The purified fragment was ligated with PstI/BamHI ends of pWTT2132 (DNAP) (FIG.

6). Correct insertion of the fragment in a tandem orientation with respect to the 35S 5': SuRB selectable marker gene cassette was established by restriction endonuclease analysis of plasmid DNA isolated from tetracycline-resistant transformants. The plasmid was designated as pCGP1616 (FIG. 11).

Plant Transformation with pCGP1616

The T-DNA contained in the binary vector plasmid pCGP1616 (FIG. 11) was introduced into rose via *Agrobacterium*-mediated transformation.

The Binary Vector pCGP1623 (mas/35S: petHf1: ocs 3')

The plasmid pCGP1623 (FIG. 12) contains a chimeric *petunia* F3'5'H (petHf1) gene under the control of the expression cassette contained in pKIWI101 (Janssen and Gardner, 1989, supra) consisting of a promoter fragment from the cauliflower mosaic virus 35S gene (35S 5') with an enhancing sequence from the promoter of the mannopine synthase gene (mas) of *Agrobacterium* and a terminator fragment from the octopine synthase gene of *Agrobacterium* (ocs 3'). The chimeric *petunia* F3'5'H cassette is in a tandem orientation with respect to the 35S 5': SuRB gene of the binary vector, pWTT2132 (DNAP) (FIG. 6).

Intermediates in the Preparation of the Binary Vector pCGP1623

The ~1.6 kb fragment of the *petunia* F3'5'H petHf1 cDNA clone contained in the plasmid pCGP1303 (FIG. 4) was released upon digestion with the restriction endonucleases BspHI and SmaI. The *petunia* F3'5'H petHf1 fragment was purified and ligated with a ~5.9 kb NcoI/EcoRI (repaired ends) fragment of pKIWI101 (Janssen and Gardner, 1989, supra) to produce the plasmid pCGP1619.

A partial digest of the plasmid pCGP1619 with the restriction endonuclease XhoI released a 4.9 kb fragment containing the mas/35S: petHf1: ocs 3' expression cassette. The fragment was purified and ligated with SalI ends of pWTT2132 (DNAP) (FIG. 6), Correct insertion of the fragment in a tandem orientation with respect to the 35S 5': SuRB selectable marker gene cassette was established by restriction endonuclease analysis of plasmid DNA isolated from tetracycline-resistant transformants. The plasmid was designated as pCGP1623 (FIG. 12).

Plant Transformation with pCGP1623

The T-DNA contained in the binary vector plasmid pCGP1623 (FIG. 12) was introduced into rose via *Agrobacterium*-mediated transformation.

The Binary Vector pCGP1638 (35S 5': petHf1: ocs 3')

The plasmid pCGP1638 (FIG. 13) contains a chimeric *petunia* F3'5'H (petHf1) gene under the control of a CaMV 35S promoter (35S 5') with an octopine synthase terminator (ocs 3'). A ~60 bp 5' untranslated leader sequence from the *petunia* chlorophyll a/b binding protein gene (Cab 22 gene) (Harpster et al., 1988, supra) is included between the CaMV 35S promoter fragment and the *petunia* F3'5'H petHf1 cDNA clone. The chimeric *petunia* F3'5'H cassette is in a tandem orientation with respect to the 35S 5': SuRB selectable marker gene cassette of the binary vector, pWTT2132 (FIG. 6).

Intermediates in the Preparation of the Binary Vector pCGP1638

Construction of pCGP1273

The plasmid pCGP1273 was constructed by subcloning a ~3 kb HindIII/HpaI fragment containing 35S 5': GUS: ocs 3' gene from the binary vector pJJ3499 (Jones et al., *Transgenic Research*, 1: 285-297, 1992) with the HindIII/SmaI ends of the plasmid pBluescript KS II (+) (Stratagene, USA).

Construction of pCGP1634

A ~3 kb HindIII/BamHI fragment containing the 35S 5': GUS: ocs 3' gene from pCGP1273 was then isolated and ligated with the HindIII/BamHI ends of the cloning vector pUC19 (New England Biolabs) to, create the plasmid pCGP1634.

Construction of pCGP1636

The GUS fragment from the plasmid pCGP1634 was removed by digesting pCGP1634 with the restriction endonucleases NcoI and XbaI and purifying the ~3.7 kb fragment containing the 35S 5' promoter fragment, the ocs 3' terminator fragment and the pUC19 vector backbone.

The *petunia* F3'5'H petHf1 cDNA clone was released from pCGP1303 (FIG. 4) upon digestion with the restriction endonucleases BspHI and XbaI. The resulting ~1.6 kb fragment was purified and ligated with the ~3.7 kb NcoI/XbaI fragment from pCGP1634. Correct insertion of the *petunia* F3'5'H petHf1 fragment was established by restriction endonuclease analysis of plasmid DNA isolated from ampicillin-resistant transformants. The resulting plasmid containing a 35S5': petHf1: ocs 3' gene was designated pCGP1636.

Construction of pCGP1638

The 35S 5': petHf1; ocs 3' gene from the plasmid pCGP1636 was released upon digestion of pCGP1636 with the restriction endonucleases PstI and EcoRI. The ends were repaired and the ~2.6 kb fragment was purified and ligated with the Sam ends of the binary vector, pWTT2132 (DNAP). Correct insertion of the 35S 5': petHf1: ocs 3' gene in a tandem orientation with respect to the 35S 5': SuRB selectable marker gene cassette was established by restriction endonuclease analysis of plasmid DNA isolated from tetracycline-resistant transformants. The plasmid was designated as pCGP1638 (FIG. 13).

Plant Transformation with pCGP1638

The T-DNA contained in the binary vector plasmid pCGP1638 (FIG. 13) was introduced into rose via *Agrobacterium*-mediated transformation.

The Binary Vector pCGP1860 (RoseCHS 5': petHf1: nos 3')

The plasmid pCGP1860 (FIG. 14) contains a chimeric *petunia* F3'5'H (petHf1) gene under the control of a promoter fragment from the chalcone synthase gene of *Rosa hybrida* (RoseCHS 5') with a terminator fragment from the nopaline synthase gene of *Agrobacterium* (nos 3'). The chimeric *petunia* F3'5'H cassette is in a tandem orientation with respect to the 35S 5': SuRB selectable marker gene cassette of the binary vector, pWTT2132 (DNAP) (FIG. 6).

Intermediates in the Preparation of the Binary Vector pCGP1860

Isolation of Rose CHS Promoter

A rose genomic DNA library was prepared from genomic DNA isolated from young leaves of *Rosa hybrida* cv. Kardinal.

The Kardinal genomic DNA library was screened with $^{32}$P-labelled fragment of rose CHS cDNA clone contained in the plasmid pCGP634. The rose CHS cDNA clone was isolated by screening of a petal cDNA library prepared from RNA isolated from petals of *Rosa hybrida* cv Kardinal (Tanaka et al., 1995, supra) using a *petunia* CHS cDNA fragment as probe (clone 1F11 contained in pCGP701, described in Brugliera et al., 1994, supra). Conditions are as described in Tanaka et al., 1995 (supra).

A rose genomic clone (roseCHS20λ) was chosen for further analysis and found to contain ~6.4 kb of sequence upstream of the putative initiating methionine of the rose CHS coding region.

An ~6.4 kb fragment upstream from the translational initiation site was cloned into pBluescript KS (−) (Stratagene) and the plaid was designated as pCGP1114.

The plasmid pCGP1114 was digested with the restriction endonucleases HindIII and EcoRV to release a 2.7-3.0 kb fragment which was purified and ligated with the HindIII/SmaI ends of pUC19 (Now England Biolabs). Correct insertion of the rose CHS promoter fragment was established by restriction endonuclease analysis of DNA isolated from ampicillin-resistant transformants. The resulting plasmid was designated as pCGP1116. The DNA sequence of the rose CHS promoter fragment was determined using pCGP1116 as template (SEQ ID NO:5).

Construction of pCGP197 (RoseCHS 5': GUS: nos 3' in a pUC18 Backbone)

An ~3.0 kb fragment containing the rose chalcone synthase promoter (RoseCHS 5') was released from the plasmid pCGP1116 upon digestion with the restriction endonucleases HindIII and Asp718. The fragment was purified and ligated with a HindII/Asp718 fragment from pJ18 (Bodeau, 1994, supra) containing the vector backbone, β-glucoronidase (GUS) and nos 3' fragments. Correct insertion of the rose CHS promoter fragment upstream of the GUS coding sequence was established by restriction endonuclease analysis of DNA isolated from ampicillin-resistant transformants. The resulting plasmid was designated as pCGP197.

Construction of pCGP200 (RoseCHS 5': petHf1: nos 3' in pUC18 Backbone)

A 1.8 kb fragment containing the *petunia* F3'5'H (petHf1) fragment was released from the plasmid pCGP1303 (described above) (FIG. 4) upon digestion with the restriction endonucleases BspHI and SacI. The *petunia* F3'5'H petHf1 fragment was purified and ligated with NcoI/SacI ends of pCGP197. Correct insertion of the *petunia* F3'5'H petHf1 fragment between the rose CHS promoter and nos 3' fragments was established by restriction endonuclease analysis of DNA isolated from ampicillin-resistant transformants. The resulting plasmid was designated as pCGP200.

Construction of pCGP1860 (RoseCHS 5': petHf1: nos 3' in a Binary Vector)

An ~4.9 kb fragment containing the RoseCHS 5': petHf1: nos 3' cassette was released from the plasmid pCGP200 upon digestion with the restriction endonuclease BglII. The fragment was purified and ligated with BamHI ends of the binary vector, pWTT2132 (DNAP) (FIG. 6). Correct insertion of the fragment in a tandem orientation with respect to the 35S 5': SuRB selectable marker gene cassette of pWTT2132 was established by restriction endonuclease analysis of plasmid DNA isolated from tetracycline-resistant transformants. The resulting plasmid was designated as pCGP1860 (FIG. 13).

Plant Transformation with pCGP1860

The T-DNA contained in the binary vector plasmid pCGP1860 (FIG. 14) was introduced into rose via *Agrobacterium*-mediated transformation.

The Binary Vector pCGP2123 (CaMV35S: petHf2: ocs 3')

The plasmid pCGP2123 (FIG. 15) contains a chimeric *petunia* F3'5'H (petHf2) gene under the control of a CaMV35S promoter with a terminator fragment from the octopine synthase gene of *Agrobacterium* (ocs 3'). The chimeric *petunia* F3'5'H cassette is in a tandem orientation with respect to the 35S 5': SuRB selectable marker gene cassette of the binary vector, pCGP1988 (FIG. 16).

Intermediates in the Preparation of the Binary Vector pCGP2123

Construction of pCGP1988 (a Derivative of the Binary Vector, pWTT2132)

The binary vector pCGP1988 (FIG. 16) is based on binary vector pWTT2132 (DNAP) (FIG. 6) but contains the multi-cloning site from pNEB193 (New England Biolabs). The plasmid pNEB193 was firstly linearized by digestion with the restriction endonuclease EcoRI. The overhang ends were repaired and the multi-cloning fragment was released upon digestion with the restriction endonuclease PstI. The fragment was purified and ligated with SalI (ends repaired)/PstI ends of the binary vector pWTT12132 (DNAP). Correct insertion of the multi-cloning fragment into pWTT2132 was established by restriction endonuclease analysis of plasmid DNA isolated from tetracycline-resistant transformants. The resulting plasmid was designated as pCGP1988 (FIG. 16).

Construction of pCGP2000 (CaMV 35S Promoter Fragment in pBluescript)

The plasmid pCGP2000 was an intermediate plasmid containing a cauliflower mosaic virus (CaMV) 35S promoter fragment in a pBluescript SK (Stratagene, USA) backbone. The CaMV 35S promoter fragment from pKIWI101 (Janssen and Gardner, 1989, supra) was released upon digestion with the restriction endonucleases XbaI and PstI. The ~0.35 kb fragment generated was purified and ligated with XbaI/PstI ends of the vector pBluescript SK. Correct insertion of the fragment was established by restriction endonuclease analysis of plasmid DNA isolated from ampicillin-resistant transformants. The plasmid was designated as pCGP2000.

Construction of pCGP2105 (CaMV 35S 5' and ocs 3' Fragments in pBluescript)

The plasmid pCGP2105 (FIG. 17) contained a CaMV 35S promoter fragment along with a terminator fragment from the octopine synthase gene of *Agrobacterium* (ocs 3') both from pKIWI101 (Janssen and Gardner, 1989, supra).

The ocs 3' fragment from pKIWI101 (Janssen and Gardner, 1989, supra) was isolated by firstly digesting the plasmid pKIWI101 with the restriction endonuclease EcoRI, followed by repair of the overhanging ends, and finally by digestion with the restriction endonuclease XhoI to release a 1.6 kb fragment. This fragment was then ligated with HincII/XhoI ends of pCGP2000. Correct insertion of the fragment was established by restriction endonuclease analysis of plasmid DNA isolated from ampicillin-resistant transformants. The plasmid was designated pCGP2105 (FIG. 17).

Construction of pCGP2109 (CaMV 35S: petHf2: ocs 3'Gene in pBluescript)

The plasmid pCGP2109 contained the CaMV 35S: petHf2: ocs 3' expression gene cassette in a pBluescript backbone.

The 1.8 kb *petunia* F3'5'H petHf2 cDNA clone was released from pCGP175 (Holton et al., 1993a, supra) upon digestion with the restriction endonucleases XbaI and SspI. The overhanging ends were repaired and the purified fragment was ligated with PstI (ends repaired)/EcoRV ends of pCGP2105 (described above) (FIG. 17). Correct insertion of the fragment was established by restriction endonuclease analysis of plasmid DNA isolated from ampicillin-resistant transformants. The plasmid was designated pCGP2109.

Construction of pCGP2123 (CaMV 35S: petHf2: ocs 3' Binary Vector)

The CaMV 35S: petHf2: ocs 3' cassette was released from pCGP2109 upon digestion with the restriction endonucleases Asp718 and XbaI. The overhanging ends were repaired and the resultant ~3.7 kb fragment containing the CaMV 35S: petHf2: ocs 3' gene was purified and ligated with repaired ends of Asp718 of the binary vector, pCGP1988 (FIG. 16). Correct insertion of the CaMV 35S: petHf2: ocs 3' gene in a tandem orientation with respect to the 35S5': SuRB selectable marker gene cassette was established by restriction endonuclease analysis of plasmid DNA isolated from tetracycline-resistant transformants. The plasmid was designated as pCGP2123 (FIG. 15).

Plant Transformation will pCGP2123

The T-DNA contained in the binary vector plasmid pCGP2123 (FIG. 15) was introduced into rose via *Agrobacterium*-mediated transformation.

Example 5

Analysis of Transgenic Roses

The transgenic roses produced in the experiments described in Example 4 were grown to flowering. Flowers were collected and the colors of the petals were coded using the Royal Horticultural Society Colour Charts (RHSCC). The anthocyanins were extracted and the anthocyanidins (specifically the presence of delphinidin or delphinidin-based molecules) analysed by TLC and/or HPLC analysis. Total RNA was also isolated from petal tissue and Northern blot analysis was used to detect transcripts of *petunia* F3'5'H transgenes, endogenous rose CHS gene and SuRB transgene. The results of the transgenic analysis are summarised in Table 6.

Although over 250 transgenic Kardinal roses were produced (Table 6) none produced flowers with a change in color. TLC and/or HPLC analysis failed to detect accumulation of delphinidin or delphinidin-based molecules pigments confirming the absence of efficient F3'5'H activity. Subsequent Northern analysis on total RNA isolated from petal tissue of these transgenic roses revealed either no detectable intact *petunia* F3'5'H (petHf1 or petHf2) transcripts, or in some cases (see footnotes), degraded transcripts. Hybridization of the same membranes with the selectable marker gene (SuRB) or with an endogenous rose CHS cDNA probe revealed discrete hybridizing transcripts indicating that the total RNA isolated was not degraded. The detection of the SuRB transgene transcripts confirmed that the roses were transgenic.

TABLE 6

Results of transgenic analysis of rose petals transformed with the T-DNA from various *petunia* F3'5'H (petHf1 or petHf2) gene expression cassettes.

| PLASMID | F3'5'H GENE | EVENTS | DEL | RNA |
|---------|-------------|--------|-----|-----|
| pCGP1452 | AmCHS 5':petHf1:petD8 3' | 34 | 0/28 | 0/34[1] |
| pCGP1453 | Mac:petHf1:mas 3' | 16 | 0/14 | 0/13[2] |
| pCGP1457 | petD8 5':petHf1:petD8 3' | 11 | 0/11 | 0/11 |
| pCGP1461 | short petFLS 5':petHf1:petFLS 3' | 11 | 0/11 | 0/11 |
| pCGP1616 | petRT 5':petHf1:nos 3' | 4 | 0/4 | 0/4 |
| pCGP1623 | mas/35S:petHf1:ocs 3' | 27 | 0/20 | 0/12[3] |
| pCGP1638 | CaMV 35S:petHf1:ocs 3' | 22 | 0/14 | 0/14 |
| pCGP1860 | RoseCHS 5':petHf1:nos 3' | 15 | 0/13 | 0/13 |
| pCGP2123 | CaMV 35S:petHf2:ocs 3' | 40 | 0/26 | 0/10 |

EVENTS = number of independent transgenic events produced
DEL = number of transgenic events in which delphinidin or delphinidin-based molecules was detected (by TLC or HPLC) in petals over the total number of events analyzed
RNA = number of transgenic events in which intact F3'5'H (petHf1 or petHf2) transcripts were detected by Northern blot analysis in total RNA isolated from rose petals over the total number of events analyzed
[1] = Degraded transcripts were detected in 5 of the 34 analyzed
[2] = Degraded transcripts were detected in 8 of the 13 analyzed
[3] = Degraded transcripts were detected in 8 of the 12 analyzed The fact that no intact *petunia* F3'5'H (petHf1 or petHf2) transcripts were ever detected in transgenic rose petals transformed with the T-DNAs described (Table 6) suggested a number of possibilities:

1. that the RNA isolated was degraded. This was not the case as the RNA had been stained by ethidium bromide and visualised under UV-light. The intact visible ribosomal RNA bands were used as an indicator of the quality of the RNA isolated. Furthermore the detection of full-length transcripts of the endogenous rose CHS and SuRB transgenes confirmed that the RNA preparation was not degraded.

2. that there was no initiation of transcription of the chimeric F3'5'H genes evaluated. This was a possibility with some of the expression cassettes analysed, as no F3'5'H transcripts were detected by Northern analysis. However all of the *petunia* F3'5'H expression cassettes had proven to be functional (ie. result in an intact transcript and result in the production of delphinidin-based pigments) in other plants such as carnation and petunia.

3. that the *petunia* F3'5'H petHf1 and petHf2 mRNAs were unstable in roses. This was also a possibility as degraded *petunia* F3'5'H transcripts were detected by Northern analysis in total RNA isolated from petals of some events. However the *petunia* petHf1 and petHf2 mRNAs had boon proven to be stable in other plants such as carnation and petunia. Such instability could be due to aberrant translation leading to mRNA turnover, some feature of the sequence inherently unstable in rose cells, some other factor or factors.

There was a need therefore to find suitable promoter fragments that would efficiently drive expression of genes in rose petals and find suitable F3'5'H sequences that would result in intact transcripts accumulating in rose petals leading to functional F3'5'H activity and to the production of delphinidin-based pigments.

Example 6

Evaluation of Promoters in Roses

Development of GUS Gene Expression Cassettes.

The evaluation of the promoter and terminator fragments was performed using the (GUS reporter gene. Therefore, a number of promoters were linked to the β-glucuronidase reporter gene (GUS) (Jefferson et al., 1987, supra) and introduced into roses in an attempt to identify expression cassettes that lead to effective initiation of transcription in rose flowers.

A summary of the promoters and terminator agents evaluated is given in Table 7.

TABLE 7

List of chimaeric GUS gene expression cassettes evaluated in roses

| PLASMID | GUS EXPRESSION CASSETTE | SELECTABLE MARKER GENE | BACKBONE VECTOR |
|---------|-------------------------|------------------------|-----------------|
| pCGP1307 | petD8 5':GUS:petD8 3' | mas 5':nptII:mas 3' | pCGN1548 |
| pCGP1506 | long petFLS 5':GUS:petFLS 3' | nos 5':nptII:nos 3' | pBIN19 |
| pCGP1626 | chrysCHS 5':GUS:petRT 3' | 35S 5':SuRB | pWTT2132 |
| pCGP1641 | petRT 5':GUS:petRT 3' | 35S 5':SuRB | pWTT2132 |
| pCGP1861 | RoseCHS 5':GUS:nos 3' | 35S 5':SuRB | pWTT2132 |
| pCGP1953 | AmCHS 5':GUS:petD8 3' | 35S 5':SuRB | pWTT2132 |
| pWTT2084 | 35S 5':GUS:ocs 3' | 35S 5':SuRB | pWTT2132 |

The Binary Vector pCGP1307 (petD8 5': GUS: petD8 3')

The plasmid pCGP1307 (FIG. 18) contains a chimeric GUS gene under the control of a promoter and terminator fragment from the *petunia* PLTP gene (petD8 5' and petD8 3', respectively). The chimeric GUS reporter gene cassette is in a tandem orientation with respect to the mas 5': nptII: mas 3' selectable marker gene cassette of the binary vector pCGN1548 (McBride and Summerfelt, 1990, supra).

Intermediates in the Preparation of the Binary Vector pCGP1307

The nos 3' fragment from pCGP1101 (see Example 4) was replaced with the 0.75 kb petD8 3' fragment (Holton, 1992, supra) to produce the plasmid pCGP1106 containing a petD8 5': GUS: petD8 3' expression cassette.

The 5.3 kb fragment containing the petD8 5': GUS: petD8 3' expression cassette was released from the plasmid pCGP1106 upon digestion with the restriction endonucleases HindIII and PstI. The fragment was purified and ligated with HindIII/PstI ends of the binary vector, pCGN1548 (McBride and Summerfelt, 1990, supra). Correct insertion of the fragment was established by restriction endonuclease analysis of DNA isolated from gentamycin-resistant transformants. The resulting plasmid was designated as pCGP1307 (FIG. 18).

Plant Transformation with pCGP1307

The T-DNA contained in the binary vector plasmid pCGP1307 (FIG. 18) was introduced into rose via *Agrobacterium*-mediated transformation.

The Binary Vector pCGP1506 (Long petFLS 5': GUS: petFLS 3')

The plasmid pCGP1506 (FIG. 19) contains a chimeric GUS gene under the control of promoter and terminator fragments from the *petunia* flavonol synthase gene (petFLS 5' and petFLS 3', respectively). The chimeric GUS reporter gene cassette is in a tandem orientation with respect to the nos 5': nptII: nos 3' selectable marker gene cassette of the binary vector pBIN19 (Bevan, *Nucleic Acids Res* 12: 8711-8721, 1984).

Intermediates in the Preparation of the Binary Vector pCGP1506

A 4 kb long *petunia* FLS promoter fragment upstream from the putative translational initiation site was released from the plasmid pCGP486 (described in Example 4) upon digestion with the restriction endonucleases XhoI and PstI. The fragment generated was purified and ligated with XhoI/PstI ends of pBluescript II KS+ (Stratagene, USA). Correct insertion of the fragment was established by restriction endonuclease analysis of DNA isolated from ampicillin-resistant transformants. The resulting plasmid was designated as pCGP715.

Construction of pCGP494 (Long petFLS 5': petFLS3' Expression Cassette)

A 4.0 kb fragment containing the long *petunia* FLS promoter fragment was amplified by PCR using the plasmid pCGP715 as template and the T3 primer (Stratagene, USA) and an FLS-Nco primer (5' AAA ATC GAT ACC ATG GTC TTT TTT TCT TTG TCT ATA C 3') (SEQ ID NO:19). The PCR product was digested with the restriction endonucleases XhoI and ClaI and the purified fragment was ligated with XhoI/ClaI ends of pCGP716 (described in Example 4). Correct insertion of the fragment was established by restriction endonuclease analysis of DNA isolated from ampicillin-resistant transformants. The resulting plasmid was designated as pCGP494.

Construction of pCGP496 (Long petFLS 5': GUS: petFLS3' Expression Cassette)

The GUS coding sequence from the plasmid pjB1 (Bodeau, 1994, supra) was released upon digestion with the restriction endonucleases NcoI and SmaI. The GUS fragment generated was purified and ligated with ClaI (repaired ends)/NcoI ends of the plasmid pCGP494. Correct insertion of the fragment was established by restriction endonuclease analysis of DNA isolated from ampicillin-resistant transformants. The resulting plasmid was designated as pCGP496.

Construction of pCGP1506 (Long petFLS 5': GUS: petFLS3' Binary Vector)

The plasmid pCGP496 was firstly linearised upon digestion with the restriction endonuclease XhoI. The overhanging ends were partially repaired (using only dTTP and dCTP in the reparation reaction) and a 6.7 kb fragment containing the long petFLS 5': GUS: petFLS3' gene expression cassette was released upon digestion with the restriction endonuclease SacI. The fragment generated was purified and ligated with BamHI (partially repaired ends using dGTP and dATP in the reparation reaction)/SacI ends of the binary vector pBIN19. Correct insertion of the fragment in a tandem orientation with respect to the nos 5': nptII: nos 3' selectable marker gene cassette was established by restriction endonuclease analysis of plasmid DNA isolated from kanamycin-resistant transformants. The resulting plasmid was designated as pCGP1506 (FIG. 19).

Plant Transformation with pCGP1506

The T-DNA contained in the binary vector plasmid pCGP1506 (FIG. 19) was introduced into rose via *Agrobacterium*-mediated transformation.

The Binary Vector pCGP1626 (chrysCHS 5': GUS: petRT 3')

The plasmid pCGP1626 (FIG. 20) contains a chimeric GUS gene under the control of promoter fragment from the chalcone synthase gene of chrysanthemum (chrysCHS 5') and a terminator fragment from the 3RT gene of *petunia* (petRT 3') (Brugliera, 1994, supra). The chimeric GUS reporter gene cassette is in a tandem orientation with respect to the 35S 5': SuRB selectable marker gene cassette of the binary vector pWTT2132 (DNAP) (FIG. 6).

Intermediates in the Preparation of the Binary Vector pCGP1626

Isolation of Chrysanthemum CHS Promoter

A chrysanthemum genomic DNA library was prepared from genomic DNA isolated from young leaf material of the chrysanthemum cv Hero.

The chrysanthemum genomic DNA library was screened with $^{32}$P-labelled fragments of a chrysanthemum CHS cDNA clone (SEQ ID NO:28) (contained in the plasmid pCGP856) using high stringency conditions. The plasmid pCGP856 contains a 1.5 kb cDNA clone of CHS isolated from a petal cDNA library prepared from RNA isolated from the chrysanthemum cv. Dark Pink Pom Pom.

A genomic clone (CHS5) was chosen for further analysis and found to contain ~3 kb of sequence upstream of the putative initiating methionine of the chrysanthemum CHS coding region.

A 4 kb fragment was released upon digestion of the genomic clone CHS5 with the restriction endonuclease HindIII. The fragment containing the chrysanthemum CHS promoter was purified and ligated with HindIII ends of pBluescript SK (Stratagene, USA). Correct insertion of the fragment was established by restriction endonuclease analysis of DNA isolated from ampicillin-resistant transformants. The resulting plasmid was designated as pCGP1316.

A 2.6 kb chrysanthemum CHS promoter fragment upstream from the putative translational initiation site was amplified by PCR using pCGP1316 as template and primers "chrysanCHSATG" (5'-GTTAAGGAAGCCATGGGTGT-3') (SEQ ID NO:8) and the M13 reverse primer (Stratagene, USA). Primer "chrysanCHSATG" incorporated an NcoI restriction endonuclease recognition sequence at the putative translation initiation point for ease of cloning. The PCR fragment was purified and ligated with EcoRV (dT-tailed) ends of pBluescript KS (Holton and Graham, *Nuc. Acids Res.* 19: 1156, 1990). Correct insertion of the fragment was established by restriction endonuclease analysis of DNA isolated from ampicillin-resistant transformants. The resulting plasmid was designated as pCGP1620. The nucleotide sequence of the chrysanthemum CHS promoter fragment contained in pCGP1620 is represented as SEQ ID NO:30.

Construction of pCGP1622 (chrysCHS 5': GUS: nos 3' pUC Backbone)

A ~2.5 kb fragment containing the chrysanthemum CHS promoter was released from the plasmid pCGP1620 upon digestion with the restriction endonucleases NcoI and PstI. The fragment was purified and ligated with a 4.8 kb NcoI/PstI fragment of pjB1 (Bodeau, 1994, supra) containing the backbone vector with the GUS and nos 3' fragments. Correct insertion of the fragment was established by restriction endonuclease analysis of DNA isolated from ampicillin-resistant transformants. The resulting plasmid was designated as pCGP1622.

Construction of pCGP1626 (chrysCHS 5': GUS: nos 3' in Binary Vector)

A ~4.6 kb fragment containing the chrysCHS 5': GUS: nos 3' cassette was released from the plasmid pCGP1622 upon digestion with the restriction endonucleases PstI and BglII. The fragment was purified and ligated with PstI/BamHI ends of the binary vector pWTT2132 (DNAP) (FIG. 6). Correct insertion of the cassette in a tandem orientation with respect to the 35S 5': SuRB selectable marker gene cassette was established by restriction endonuclease analysis of DNA isolated from tetracycline-resistant transformants. The resulting plasmid was designated as pCGP1626 (FIG. 20).

Plant Transformation with pCGP1626

The T-DNA contained in the binary vector plasmid pCGP1626 (FIG. 20) was introduced into rose via *Agrobacterium*-mediated transformation.

The Binary Vector pCGP1641 (petRT 5': GUS: petRT 3')

The plasmid pCGP1641 (FIG. 21) contains a chimeric GUS gene under the control of a *petunia* 3RT promoter (petRT 5') covering 1.1 kb upstream from the putative 3RT translation initiation codon with a *petunia* 3RT terminator (petRT 3') covering 2.5 kb downstream from the 3RT stop codon. The chimeric GUS cassette is in a tandem orientation with respect to the 35S 5': SuRB selectable marker gene cassette of the binary vector, pWTT2132 (DNAP) (FIG. 6).

Intermediates in the Preparation of the Binary Vector pCGP1641

Isolation of Petunia 3RT Gene

The isolation of the *petunia* 3RT gene corresponding to the Rt locus of *P. hybrida* has been described in Brugliera, 1994, supra.

Construction of pCGP1625 (CaMV 35S: GUS: petRT 3' Cassette)

The intermediate plasmid pCGP1625 contains a CaMV 35S: GUS: petRT 3' cassette in a pUC backbone. The 2.5 kb fragment containing a petRT terminator sequences was released from the plasmid pCGP1610 (described in Brugliera 1994, supra) upon digestion with the restriction endonucleases BamHI and SacI. The fragment was purified and ligated with the BglII/SacI 4.9 kb fragment of pJB1 (Bodeau, 1994, supra) containing the vector backbone and the CaMV 35S promoter and GUS fragments. Correct insertion of the *petunia* 3RT terminator fragment downstream of the GUS fragment was established by restriction endonuclease analysis of DNA isolated from ampicillin-resistant transformants. The resulting plasmid was designated as pCGP1625.

Construction of pCGP1628 (petRT 5': GUS: petRT 3' Cassette)

A 1.1 kb petRT promoter fragment was released from the plasmid pCGP1611 (described in Brugliera, 1994, supra) upon digestion with the restriction endonucleases NcoI and PstI. The purified fragment was ligated with NcoI/PstI ends of the 7 kb fragment of pCGP1625 containing the vector backbone and the GUS and petRT 3' fragments. Correct insertion of the petRT promoter fragment upstream of the GUS fragment was established by restriction endonuclease analysis of DNA isolated from ampicillin-resistant transformants. The resulting plasmid was designated as pCGP1628.

Construction of pCGP1641, (petRT5': GUS: petRT 3'Binary Vector)

A 5.4 kb fragment containing the petRT 5': GUS: petRT 3' cassette was released from pCGP1628 upon digestion with the restriction endonuclease PstI. The fragment was purified and ligated with PstI ends of the binary vector pWTT2132 (DNAP) (FIG. 6). Correct insertion of the fragment in a tandem orientation with respect to the 35S 5': SuRB selectable marker gene cassette was established by restriction endonuclease analysis of plasmid DNA isolated from tetracycline-resistant transformants. The resulting plasmid was designated as pCGP1641 (FIG. 21).

Plant Transformation with pCGP1641

The T-DNA contained in the binary vector plasmid pCGP1641 (FIG. 21) was introduced into rose via *Agrobacterium*-mediated transformation.

The Binary Vector pCGP1861 (RoseCHS 5': GUS: nos 3')

The plasmid pCGP1861 (FIG. 22) contains a chimeric GUS gene under the control of a promoter fragment from the CHS gene of *R. hybrida* (RoseCHS 5') with a terminator fragment from the nos gene of *Agrobacterium* (nos 3'). The chimeric GUS reporter gene cassette is in a tandem orientation with respect to the 35S 5': SuRB selectable marker gene cassette of the binary vector, pWTT2132 (FIG. 6).

An ~5 kb fragment containing the RoseCHS 5': GUS: nos 3' cassette was released from pCGP197 (described in Example 4) upon digestion with the restriction endonuclease BglII. The fragment was purified and ligated with BamHI ends of the binary vector, pWTT2132 (DNAP). Correct insertion of the fragment in a tandem orientation with respect to the 35S 5': SuRB selectable marker gene cassette was established by restriction endonuclease analysis of plasmid DNA isolated from tetracycline-resistant transformants. The resulting plasmid was designated as pCGP1861 (FIG. 22).

Plant Transformation with pCGP1861

The T-DNA contained in the binary vector plasmid pCGP1861 (FIG. 22) was introduced into rose via *Agrobacterium*-medicated transformation.

The Binary Vector pCGP1953 (AmCHS 5': GUS: petD8 3')

The plasmid pCGP1953 (FIG. 23) contains a chimeric GUS gene under the control of a promoter fragment from the CHS gene of *Antirrhinum majus* (AmCHS 5') with a *petunia* PLTP terminator (petD8 3'). The chimeric GUS reporter gene cassette is in a tandem orientation with respect to the 35S 5': SuRB selectable marker gene cassette of the binary vector, pWTT2132 (DNAP) (FIG. 6).

Intermediates in the Preparation of the Binary Vector pCGP1953

The plasmid pJB1 (Bodeau, 1994, supra) was linearised with the restriction endonuclease NcoI. The overhanging ends were repaired and the 1.8 kb GUS fragment was released upon digestion with BamHI. The GUS fragment was purified and was ligated with the 5 kb XbaI (ends repaired)/BamHI fragment of pCGP726 containing the pBluescript backbone vector and the AmCHS 5' and petD8 3' fragments (described in Example 4). Correct insertion of the GUS fragment between the AmCHS 5' and petD8 3' fragments was established by restriction endonuclease analysis of plasmid DNA isolated from ampicillin-resistant transformants. The plasmid was designated as pCGP1952.

A 3.8 kb fragment containing the AmCHS 5': GUS: petD8 3' expression cassette was released from the plasmid pCGP1952 upon digestion with the restriction endonucleases EagI and PstI. The overhanging ends were repaired and the purified fragment was ligated with the repaired ends of an Asp718 digested pWTT2132 binary vector (FIG. 6). Correct insertion of the fragment in a tandem orientation with respect to the 35S 5': SuRB selectable marker gene cassette was established by restriction endonuclease analysis of plasmid DNA isolated from tetracycline-resistant transformants. The plasmid was designated as pCGP1953 (FIG. 23).

Plant Transformation with pCGP1953

The T-DNA contained in the binary vector plasmid pCGP1953 (FIG. 23) was introduced into rose via *Agrobacterium*-mediated transformation.

The Binary Vector pWTT2084 (35S 5': GUS: ocs 3')

The plasmid pWTT2084 (DNAP) (FIG. 24) contains a chimeric GUS gene under the control of a CaMV 35S promoter (35S 5') with an octopine synthase terminator (ocs 3'). An ~60 bp 5' untranslated leader sequence from the *petunia* chlorophyll a/b binding protein gene (Cab 22 gene) (Harpster et al., 1988, supra) is included between the CaMV 35S promoter fragment and the GUS clone. The chimeric GUS cassette is in a tandem orientation with respect to the 35S 5': SuRB selectable marker gene cassette of the binary vector, pWTT2084.

Plant Transformation with pWTT2084

The T-DNA contained in the binary vector plasmid pWTT2084 (FIG. 24) was introduced into rose via *Agrobacterium*-mediated transformation.

Transgenic Analysis of Roses Transformed with GUS Expression Cassettes

Northern blot analysis was performed on total RNA isolated from petals of developmental stages 3 to 4 of transgenic Kardinal roses transformed with the T-DNA of various GUS expression cassettes. There was either no accumulating transcript or an intact full-length transcript of the expected size of ~1.8 kb as detected by Northern blot hybridisation. The relative levels of GUS transcripts accumulating in the rose petals were recorded (see Table 8).

TABLE 8

Summary of Northern analysis on transgenic Kardinal rose flowers (open bud stage) containing GUS constructs.

| PLASMID | GUS REPORTER GENE | SELECTABLE MARKER GENE | GUS TRANSCRIPT LEVELS |
| --- | --- | --- | --- |
| pCGP1307 | petD8 5':GUS:petD8 3' | mas 5':nptII:mas 3' | — |
| pCGP1506 | petFLS 5':GUS:petFLS 3' | nos 5':nptII:nos 3' | — |
| pCGP1626 | chrysCHS 5':GUS:petRT 3' | 35S 5':SuRB | ++ to +++ |
| pCGP1641 | petRT 5':GUS:petRT 3' | 35S 5':SuRB | — |
| pCGP1861 | RoseCHS 5':GUS:nos 3' | 35S 5':SuRB | ++++ |
| pCGP1953 | AmCHS 5':GUS:petD8 3' | 35S 5':SuRS | — |
| pWTT2084 | 35S 5':GUS:ocs 3' | 35S 5':SuRB | +++++ |

—= no transcripts detected
+ to +++++ = relative levels (low to high) of full-length GUS transcript detected by Northern blot analysis Based on the above results (Table 8), the CaMV 35S (35S 5') and rose CHS (RoseCHS 5') promoters appear to drive relatively high levels of transcription in rose petals. The chrysanthemum CHS promoter (chrysCHS 5') appears to also lead to high transcript levels but not as high as those obtained using CaMV 35S or rose CRS promoters. Surprisingly, antirrhinum (snapdragon) CHS (AmCHS 5'), *petunia* 3RT (petRT 5'), *petunia* FLS (petFLS 5') and *petunia* PLTP-(petD8 5') promoters did not appear to function in rose petals as no GUS transcripts were detected with expression cassettes incorporating these promoters. However, these same promoters fused to petHf1 and/or -GUS genes had previously been proven to function well in carnation and *petunia* leading to relatively high full-length transcript levels and for petHf1 genes, the production of delphinidin or delphinidin-based molecules pigments. The result obtained with the antirrhinum CHS promoter (AmCHS 5') fused with the GUS gene was more surprising as promoter regions from homologous genes from two other species (rose and chrysanthemum) appeared to function relatively well in roses. The antirrhinum CHS promoter had also been successfully used in conjunction with *petunia* F3'5'H (petHf1) to produce the novel violet-colored carnations Florigene Moondust (see International Patent Application No. PCT/AU96/00296).

The evaluation of promoter and terminator fragments fused with the GUS gene also provided further evidence to suggest that the *petunia* F3'5'H petHf1 and petHf2 sequences were unstable in roses as constructs containing the *petunia* F3'5'H sequences ligated to the CaMV 35S, -rose CHS and chrysanthemum CHS promoters (which do function in rose) did not result in intact *petunia* F3'5'H petHf1 or petHf2 transcripts in roses (see Table 6).

Example 7

Isolation of F3'5'H Sequences from Species Other than Petunia

Since the *petunia* F3'5'H sequences had already been proven to function in various plants such as carnation, *petunia* and tobacco and ultimately resulted in the production of delphinidin-based pigments, it was reasonable to assume that these sequences would also prove functional in roses. There was an assumption that the enzyme activity may vary depending on the background of the species, indeed between cultivars of a given species, that the *petunia* F3'5'H was introduced into. However, there was no expectation that full-length recombinant *petunia* F3'5'H mRNA would not accumulate. Analysis of the *petunia* F3'5'H nucleotide sequences (petHf1 and petHf2) did not reveal any sequences which might lead to instability and subsequent degradation (Johnson et al., *In A look beyond transcription*, ASPP, USA, Bailey-Serres and Gallie, eds, 1998), intron: exon splice junctions (Brendel et al., *In A look beyond transcription*, ASPP, USA. Bailey-Serres and Gallie, eds, 1998), or any autocatalytic or degradation trigger sequences reported in the scientific literature to date (*In A look beyond transcription*, ASPP, USA, Bailey-Serres and Gallie, eds, 1998). The surprising result suggested that there were factors specific to rose that resulted in *petunia* F3'5'H sequences being unstable.

Since it was not obvious why the *petunia* F3'5'H sequences were unstable in roses but stable in carnation, *petunia* or tobacco, a number of F3'5'H sequences were isolated across a range of families in an attempt to determine whether any F3'5'H sequence would be stable in rose and then identify any F3'5'H sequences that would lead to the synthesis of stable F3'5'H transcripts and F3'5'H activity and ultimately the production of delphinidin-based pigments in roses leading to a change in flower color.

Construction of Petal cDNA Libraries

Petal cDNA libraries were prepared from RNA isolated from petals from bud to opened flower stages from various species of plants described in Table 9, *Rosa hybrida* is classified in the family Rosaciae, Order Rosales, Subclass Rosidae and so species that produced delphinidin-based pigments and so contained a functional F3'5'H and belonged to the Subclass Rosidae were selected. *Petunia hybrida* is classified in the Family Solanaceae, Order Solanales, Subclass Asteridae and so species from the Subclass Asteridae that produced delphinidin-based pigments were also selected.

TABLE 9

List of flowers from which total RNA was isolated for the preparation of petal cDNA libraries. Information obtained from National Center for Biotechnology Information (NCBI) website under Taxonomy browser (TaxBrowser) as of August 2003.

| FLOWER | SPECIES | FAMILY | ORDER | SUBCLASS |
|---|---|---|---|---|
| gentian | *Gentiana* spp. | Gentianaceae | Gentianales | Asteridae |
| lavender | *Lavandula* spp. | Lamiaceae | Lamiales | Asteridae |
| salvia | *Salvia* spp. | Lamiaceae | Lamiales | Asteridae |
| sollya | *Sollya* spp. | Pittosporaceae | Apiales | Asteridae |
| kennedia | *Kennedia* spp. | Fabaceae | Fabales | Rosidae |
| butterfly pea | *Clitoria ternatea* | Fabaceae | Fabales | Rosidae |
| pansy | *Viola* spp. | Violaceae | Malpighiales | Rosidae |

Unless otherwise described, total RNA was isolated from the petal tissue of purple/blue flowers using the method of Turpen and Griffith (BioTechniques 4: 11-15, 1986). Poly (A)+ RNA was selected from the total RNA, using oligotex-dT™ (Qiagen) or by three cycles of oligo-dT cellulose chromatography (Aviv and Leder, *Proc. Natl. Acad. Sci. USA* 69: 1408, 1972).

In general a λZAPII/Gigapack II Cloning kit (Stratagene, USA) (Short et al., *Nucl. Acids Res.* 16: 7583-7600, 1988) was used to construct directional petal cDNA libraries in λZAPII using around 5 μg of poly(A)+ RNA isolated from petal as template. The total number of recombinants obtained was generally in the order of $1 \times 10^5$ to $1 \times 10^6$.

After transfecting XL1-Blue MRF' cells, the packaged cDNA mixtures were plated at around 50,000 pfu per 15 cm diameter plate. The plates were incubated at 37° C. for 8 hours, and the phage were eluted in 100 mM NaCl, 8 mM $MgSO_4$, 50 mM Tris-HCl pH 8.0, 0.01% (w/v) gelatin (Phage Storage Buffer (PSB)) (Sambrook et al., 1989, supra). Chloroform was added and the phages stored at 4° C. as amplified libraries.

In general around 100,000 pfu of the amplified libraries were plated onto NZY plates (Sambrook et al., 1989, supra) at a density of around 10,000 pfu per 15 cm plate after transfecting XL1-Blue MRF' cells, and incubated at 37° C. for 8 hours. After incubation at 4° C. overnight, duplicate lifts were taken onto Colony/Plaque Screen™ filters (DuPont) and treated as recommended by the manufacturer.

Plasmid Isolation

Helper phage R408 (Stratagene, USA) was used to excise pBluescript phagemids containing cDNA inserts from amplified λZAPII or λZAP cDNA libraries using methods described by the manufacturer.

Screening of Petal cDNA Libraries

Prior to hybridization, duplicate plaque lifts were washed in prewashing solution (50 mM Tris-HCl pH7.5, 1 M NaCl, 1 mM EDTA, 0.1% (w/v) sarcosine) at 65° C. for 30 minutes; followed by washing in 0.4 M sodium hydroxide at 65° C. for, 30 minutes; then washed in a solution of 0.2 M Tris-HCl pH 8.0, 0.1×SSC, 0.1% (w/v) SDS at 65° C. for 30 minutes and finally rinsed in 2×SSC, 1.0% (w/v) SDS.

The membrane lifts from the petal cDNA libraries were hybridized with $^{32}$P-labelled fragments of a 1.6 kb BspHI/FspI fragment from pCGP602 (FIG. 2) (SEQ ID NO: 1) containing the *petunia* F3'5'H petHf1 cDNA clone (Holton et al., 1993a, supra).

Hybridization conditions included a prehybridization step in 10% v/v formamide, 1 M NaCl, 10% w/v dextran sulphate, 1% w/v SDS at 42° C. for at least 1 hour. The $^{32}$P-labelled fragments (each at $1 \times 10^6$ cpm/mL) were then added to the hybridization solution and hybridization was continued at 42° C. for a further 16 hours. The filters were then washed in 2×SSC, 1% w/v SDS at 42° C. for 2×1 hour and exposed to Kodak XAR film with an intensifying screen at −70° C. for 16 hours.

Strongly hybridizing plaques were picked into PSB (Sambrook at al., 1989, supra) and rescreened to isolate purified plaques, using the plating and hybridization conditions as described for the initial screening of the cDNA library. The plasmids contained in the λZAPII or λZAP bacteriophage vectors were rescued and sequence data was generated from the 3' and 5' ends of the cDNA inserts. New F3'5'H cDNA clones were identified based on sequence similarity to the *petunia* F3'5'H petHf1 cDNA clone.

The cDNA clones isolated were given plasmid designation numbers as described in Table 10.

TABLE 10

Plasmid numbers and SEQ ID NO. of F3'5'H cDNA clones isolated from various species

| SPECIES | CLONE | PLASMID NUMBER | FIG. NUMBER | SEQ ID NO. |
|---|---|---|---|---|
| *Viola* spp. | BP#18 | pCGP1959 | 25 | 9 |
| *Viola* spp. | BP#40 | pCGP1961 | 26 | 11 |
| *Salvia* spp. | Sal#2 | pCGP1995 | 31 | 13 |
| *Salvia* spp. | Sal#47 | pCGP1999 | 32 | 15 |
| *Sollya* spp. | Soll#5 | pCGP2110 | 37 | 17 |
| *Kennedia* spp. | Kenn#31 | pCGP2231 | 40 | 26 |
| *Clitoria ternatea* | BpeaHF2 | pBHF2F4 | 43 | 20 |
| *Gentiana triflora* | Gen#48 | pG48 | 47 | 22 |
| *Lavandula nil* | LBG | pLHF8 | 51 | 31 |

Viola (Pansy) F3'5'H Constructs

Isolation of F3'5'H cDNA Clones from Petals of *Viola* spp. (Pansy)

Total RNA and poly (A)$^+$ RNA was isolated from petals of young buds of *Viola* spp. cultivar black pansy as described above. A petal cDNA library was constructed using λZAPII/ Gigapack II Cloning kit (Stratagene, USA) and screened as described above. Two full-length pansy F3'5'H cDNA clones (BP#18 (SEQ ID NO:9) in pCGP1959 (FIG. 25) and BP#40 (SEQ ID NO:11) in pCGP1961 (FIG. 26)) were identified by sequence similarity to the *petunia* F3'5'H petHf1 cDNA clone (SEQ D NO:1). The BP#18 and BP#40 shared 82% identity at the nucleotide level. Comparison of the nucleotide sequence of pansy F3'5'H clones (BP#18 and BP#40) with that of the *petunia* P3'5'H revealed around 60% identity to the *petunia* F3'5'H petHf1 clone and 62% identity to the *petunia* F3'5'H petHf2 clone.

The Binary Vectors, pCGP1972 and pCGP1973 (AmCHS 5': BP#18 or BP#40: petD8 3')

The plasmids pCGP1972 (FIG. 27) and pCGP1973 (FIG. 28) contain the pansy F3'5'H cDNA clone (BP#18 and BP#40, respectively) between an *A. majus* (snapdragon) CHS promoter fragment (Am CHS 5') and a *petunia* PLTP terminator fragment (petD8 3'). The chimeric F3'5'H genes are in tandem with respect to the 35S 5': SuRB selectable marker gene cassette of the binary vector, pWTT2132 (DNAP) (FIG. 6).

The *petunia* F3'5'H (petHf1) cDNA clone in pCGP725 (described in Example 4) (FIG. 7) was removed by initially digesting pCGP725 with the restriction endonuclease BamHI. The ends were repaired and the linearised plasmid was further digested with the restriction endonuclease XbaI. The ~4.9 kb fragment containing the vector with the AmCHS 5' and petD8 3' fragments was purified and ligated with the ~1.6 kb KpnI (ends repaired)/XbaI fragment containing the pansy F3'5'H BP#18 or BP#40 cDNA clone from pCGP1959 or pCGP1961, respectively to produce pCGP1970 and pCGP1971, respectively. The AmCHS 5': pansy F3'5'H: petD8 3' cassette was then isolated from pCGP1970 or pCGP1971 by firstly digesting with the restriction endonuclease NotI. The ends of the linearised plasmid were repaired and then the chimeric F3'5'H genes were released upon digestion with the restriction endonuclease EcoRV. The purified fragments were then ligated with Asp718 (repaired ends) of the binary vector pWTT2132 (DNAP). Correct insertion of the fragment was established by restriction endonuclease analysis of plasmid DNA isolated from tetracycline-resistant transformants. The resulting plasmids were designated pCGP1972 (FIG. 27) and pCGP1973 (FIG. 28), respectively.

Carnation and Petunia Transformation with pCGP1972 and 1973

The T-DNAs contained in the binary vector plasmids pCGP1972 (FIG. 27) and pCGP1973 (FIG. 28) were introduced separately into *Dianthus caryoplhyllus* cultivars Kortina Chanel and Monte Lisa and *Petunia hybrid* cv. Skr4x Sw63 via *Agrobacterium*-mediated transformation.

The Binary Vectors, pCGP1967 and pCGP1969 (CaMV 35S: pansy F3'5'H: ocs 3')

The binary vectors pCGP1967 (FIG. 29) and pCGP1969 (FIG. 30) contain chimeric CaMV 35S: pansy F3'5'H: ocs 3' genes in tandem with respect to the 35S 5': SuRB selectable marker gene cassette of the binary vector, pWTT2132 (DNAP) (FIG. 6).

Intermediates in the Preparation of the Binary Vectors pCGP1967 and pCGP1969

The plasmids pCGP1959 (FIG. 25) and pCGP1961 (FIG. 26) were firstly linearized upon digestion with the restriction endonuclease KpnI. The overhanging KpnI ends were repaired and the pansy F3'5'H cDNA clones, BP#18 and BP#40, were released upon digestion with the restriction endonuclease PstI. The ~1.6 kb fragments generated were ligated with an ~5.9 kb EcoRI (repaired ends)/PstI fragment of pKIWI101 (Janssen and Gardner, 1989, supra). Correct insertion of each fragment was established by restriction endonuclease analysis of plasmid DNA isolated from ampicillin-resistant transformants. The resulting plasmids were designated pCGP1965 and pCGP1966, respectively.

The plasmids pCGP1965 and pCGP1966 were firstly partially digested with the restriction endonuclease XhoI. The resulting fragments were further digested with the restriction endonuclease XbaI. The overhanging ends were repaired and the 3.6 kb fragments containing the CaMV 35S: pansy F3'5'H: ocs 3' chimeric genes were isolated and ligated with Asp718 repaired ends of pWTT2132 (FIG. 6). Correct insertion of each fragment was established by restriction endonuclease analysis of plasmid DNA isolated from tetracycline-resistant transformants. The resulting plasmids were designated pCGP1967 (FIG. 29) and pCGP1969 (FIG. 30), respectively.

Rose Transformation with pCGP1967 and pCGP1969

The T-DNAs contained in the binary vector plasmids pCGP1967 (FIG. 29) and pCGP1969 (FIG. 31) were introduced separately into *Rosa hybrida* cv. Kardinal and Soft Promise via *Agrobacterium*-mediated transformation. The T-DNA contained in the binary vector plasmids pCGP1969 (FIG. 31) was also introduced into *Rosa hybrida* cu. Pamela and Medeo via *Agrobacterium*-mediated transformation,

Salvia F3'5'H Constructs

Isolation of a F3'5'H cDNA Clone from Petals of *Salvia* spp.

Total RNA and poly (A)$^+$ RNA was isolated from young petal buds of *Salvia* spp. (bought from a nursery) as described above. A petal cDNA library was constructed using λZAPII/ Gigapack II Clog kit (Stratagene, USA). Two full-length *salvia* F3'5'H cDNA clones (Sal#2 (SEQ ID NO:13) in pCGP1995 (FIG. 31) and Sal#47 (SEQ ID NO:15) in pCGP1999 (FIG. 32)) were identified by sequence similarity with the *petunia* F3'5'H petHf1 cDNA clone. The Sal#2 and Sal#47 shared 95% identity at the nucleotide level Comparison of the nucleotide sequence of *salvia* F3'5'H clones (Sal#2 and Sal#47) with that of the *petunia* F3'5'H revealed around 57% identity to the *petunia* F3'5'H petHf1 clone (SEQ ID NO:1) and 58% identity to the *petunia* F3'5'H petHf2 clone (SEQ ID NO:3).

The Binary Vectors, pCGP2121 and pCGP2122

(AmCHS 5': *Salvia* F3'5'H #2 or #47: petD8 3')

The plasmids pCGP2121 (FIG. 33) and pCGP2122 (FIG. 34) contain the *salvia* F3'5'H cDNA clones (Sal#2 and Sal#47, respectively) between a snapdragon CHS promoter fragment (AmCHS 5') and a *petunia* PLTP terminator fragment (petD8 3') in tandem with the 35S 5': SuRB selectable marker gene cassette of the binary vector pWTT2132 (DNAP) (FIG. 6).

The *petunia* F3'5'H (petHf1) cDNA clone in pCGP725 (described in Example 4) (FIG. 7) was removed by initially digesting pCGP725 with the restriction endonuclease BamHI. The ends were repaired and the linearised plasmid was further digested with the restriction endonuclease XbaI.

The ~4.9 kb fragment containing the vector with the AmCHS 5' and petD8 3' fragments was purified and ligated with the ~1.6 kb XhoI/BamHI (ends repaired) fragment from pCGP 1995 (FIG. 31) containing the salvia F3'4'H #2 or XhoI/EcoRI (ends repaired) fragment from pCGP1999 (FIG. 32) containing the salvia F3'5'H #47, respectively to produce pCGP2116 and pCGP2117, respectively.

The AmCHS 5': salvia F3'5'H: petD8 3' cassette was isolated from pCGP2116 or pCGP2117 by firstly digesting with the restriction endonuclease NotI. The ends of the linearized plasmid were repaired and then the chimeric F3'5'H gene cassettes were released upon digestion with the restriction endonuclease EcoRV. The ~3.6 kb purified fragments were then ligated with Asp718 repaired ends of the binary vector pCGP1988 (FIG. 16) (described in Example 4). Correct insertion of each fragment was established by restriction endonuclease analysis of plasmid DNA isolated from tetracycline-resistant transformants. The resulting plasmids were designated pCGP2121 (FIG. 33) and pCGP2122 (FIG. 34), respectively.

Carnation and Petunia Transformation with pCGP2121 and pCGP2122

The T-DNAs contained in the binary vector plasmids pCGP2121 (FIG. 33) and pCGP2122 (FIG. 34) were introduced separately into *Dianthus caryoplhyllus* cultivars Kortina Chanel and Monte Lisa and *Petunia hybrida* cv. Skr4×Sw63 via *Agrobacterium*-mediated transformation.

The Binary Vectors, pCGP2120 and pCGP2119 (CaMV 35S: Salvia F3'5'H: ocs 3')

The binary vectors pCGP2120 (FIG. 35) and pCGP2119 (FIG. 36) contain chimeric CaMV 35S: salvia F3'5'H: ocs 3' gene cassettes in tandem with the 35S 5'. SuRB selectable marker gene cassette of the binary vector pCGP1988 (FIG. 16).

Intermediates in the Preparation of the Binary Vectors pCGP2120 and pCGP2119

The plasmids pCGP1995 (FIG. 31) and pCGP1999 (FIG. 32) were firstly linearized upon digestion with the restriction endonuclease XhoI. The overhanging XhoI ends were repaired and then the salvia F3'5'H cDNA clones Sal#2 or Sal#47 were released upon digestion with the restriction endonuclease EcoRI. In the case of pCGP1995 a partial digest with EcoRI was undertaken. The ~1.7 kb fragments were ligated with the ClaI (repaired ends)/EcoRI ends of pCGP2105 (FIG. 17). Correct insertion of each fragment was established by restriction endonuclease analysis of plasmid DNA isolated from ampicillin-resistant transformants. The resulting plasmids were designated pCGP2112 and pCGP2111, respectively.

The plasmids pCGP2112 and pCGP2111 were digested with the restriction endonucleases XhoI and XbaI. The resulting overhanging ends were repaired and ~3.6 kb fragments containing the CaMV 35S: *salvia* F3'5'H: ocs 3' chimeric genes were isolated and ligated with Asp718 repaired ends of the binary vector, pCGP1988 (described in Example 4). Correct insertion of each fragment was established by restriction endonuclease analysis of plasmid DNA isolated from tetracycline-resistant transformants. The resulting plasmids were designated pCGP2120 (FIG. 35) and pCGP2119 (FIG. 36), respectively, Rose Transformation with pCGP2120 and pCGP2119

The T-DNAs contained in the binary vector plasmids pCGP2120 (FIG. 35) and pCGP2119 (FIG. 36) were introduced separately into *Rosa hybrida* cv. Kardinal via *Agrobacterium*-mediated transformation.

*Sollya* F3'5'H Constructs

Isolation of a F3'5'H cDNA Clone from Petals of *Sollya* spp.

Total RNA and poly (A)+ RNA was isolated from young petal buds of *Sollya* spp. (bought from a nursery) as described above. A petal cDNA library was constructed using λZAPII/Gigapack II Cloning kit (Stratagene, USA). One full-length *Sollya* F3'5'H cDNA clone (Soll#S5 (SEQ ID NO:17) in pCGP2110 (FIG. 37)) was identified by sequence similarity to the *petunia* F3'5'H petHf1 cDNA clone. Comparison of the nucleotide sequence of the *sollya* F3'5'H clone with that of the *petunia* F3'5'H revealed around 48% identity to the *petunia* F3'5'H petHf1 clone (SEQ ID NO:1) and 52% identity to the *petunia* F3'5'H petHf2 clone (SEQ ID NO:3).

The Binary Vector pCGP2130 (AmCHS 5': *Sollya* F3'5'H: petD8 3')

The plasmid pCGP2130 (FIG. 38) contains the *sollya* F3'5'H Soll#5 cDNA clone between a snapdragon CHS promoter fragment (AmCHS 5') and a *petunia* PLTP terminator fragment (petD8 3') in a tandem orientation with respect to the 35S 5': SuRB selectable marker gene cassette of the binary vector pCGP1988 (FIG. 16).

The *petunia* F3'5'H (petHf1) cDNA clone in pCGP725 (described in Example 4) (FIG. 7) was removed by initially digesting pCGP725 with the restriction endonucleases XbaI and BamHI. The ends were repaired the ~4.9 kb fragment containing the vector with the AmCHS 5' and petD8 3' fragments was purified and ligated with the repaired ends of the ~1.6 kb Asp718/PstI fragment from pCGP2110 containing the *sollya* F3'5'H cDNA clone to produce pCGP2128. Correct insertion of the *sollya* F3'5'H fragment in tandem with the AmCHS 5' and petD8 3' fragments was confirmed by restriction endonuclease mapping.

The AmCHS 5': *sollya* F3'5'H: petD8 3' gene cassette was then isolated from pCGP2128 by firstly digesting with the restriction endonuclease NotI. The ends of the linearized plasmid were repaired and then the chimeric F3'5'H gene was released upon digestion with the restriction endonuclease EcoRV. The ~3.5 kb purified fragment was then ligated with Asp718 (repaired ends) of the binary vector pCGP 1988 (described in Example 4) (FIG. 16). Correct insertion of the fragment was established by restriction endonuclease analysis of plasmid DNA isolated from tetracycline-resistant transformants. The resulting plasmid was designated pCGP2130 (FIG. 38).

Carnation and Petunia Transformation with pCGP2130

The T-DTA contained in the binary vector plasmid pCGP2130 (FIG. 38) was introduced into *Dianthus caryoplhyllus* cultivars Kortina Chanel and Monte Lisa and *Petunia hybrida* cv. Skr4×Sw63 via *Agrobacterium*-mediated transformation.

The Binary Vector pCGP2131 (CaMV35S: *sollya* F3'5'H: ocs 3')

The binary vector pCGP2131 (FIG. 39) contains a chimeric CaMV 35S: *sollya* F3'5'H: ocs 3' gene in tandem with the 35S 5': SuRB selectable marker gene cassette of the binary vector pCGP1988 (FIG. 16).

Intermediates in the Preparation of the Binary Vector pCGP2131

The plasmid pCGP2110 was firstly linearized upon digestion with the restriction endonuclease Asp718. The overhanging ends were repaired and then the *sollya* F3'5'H cDNA clone was released upon digestion with the restriction endonuclease PstI. The ~1.7 kb fragment was ligated with the EcoRV/PstI ends of pCGP2105 (FIG. 17). Correct insertion of the fragment was established by restriction endonuclease analysis of plasmid DNA isolated from ampicillin-resistant transformants. The resulting plasmid was designated pCGP2129.

A 3.6 kb fragment containing the CaMV 35S: *sollya* F3'5'H: ocs 3' chimeric gene was released upon digestion with the restriction endonucleases Asp718 and XbaI The overhanging ends were repaired and the purified fragment was ligated with of Asp718 repaired ends of the binary vector, pCGP1988 (FIG. 16). Correct insertion of the fragment was established by restriction endonuclease analysis of plasmid DNA isolated from tetracycline-resistant transformants. The resulting plasmid was designated pCGP2131 (FIG. 39).

Rose Transformation with pCGP2131

The T-DNA contained in the binary vector plasmid pCGP2131 (FIG. 39) was introduced into *Rosa hybrida* cv. Kardinal via *Agrobacterium*-mediated transformation.

*Kennedia* F3'5'H Constructs

Isolation of a F3'5'H cDNA Clone from Petals of *Kennedia* spp.

Total RNA and poly (A)+ RNA was isolated from young petal buds of *Kennedia* spp. (bought from a nursery) as described above. A petal cDNA library was constructed using λZAPII/Gigapack II Cloning kit (Stratagene, USA). One full-length *kennedia* F3'5'H cDNA clone (Kenn#31 in pCGP2231 (FIG. 40)) (SEQ ID NO:26) was identified by sequence similarity to the *petunia* F3'5'H petHf1 cDNA clone. Comparison of the nucleotide sequence of the *kennedia* F3'5'H clone with that of the *petunia* F3'5'H revealed around 64% identity to the *petunia* F3'5'H petHf1 clone (SEQ ID NO:1) and 60% identity to the *petunia* F3'5'H petHf2 clone (SEQ ID NO:3).

The Binary Vector pCGP2256 (AmCHS 5': *kennedia* F3'5'H: petD8 3')

The plasmid pCGP2256 (FIG. 41) contains the *kennedia* F3'5'H (Kenn#31) cDNA clone between a snapdragon CHS promoter fragment (AmCHS 5') and a *petunia* PLTP terminator fragment (petD8 3') in tandem with the 35S5'. SuRB selectable marker gene cassette of the binary vector pCGP1988 (FIG. 16).

The *petunia* F3'5'H (petHf1) cDNA clone in pCGP725 (described in Example 4) (FIG. 7) was removed by initially digesting pCGP725 with the restriction endonucleases XbaI and BamHI. The ends were repaired the ~4.9 kb fragment containing the vector with the AmCHS 5' and petD8 3' fragments was purified and ligated with the repaired ends of the ~1.8 kb XhoI/BamHI fragment from pCGP2231 containing the *kennedia* F3'5'H cDNA clone to produce pCGP2242. Correct insertion of the *kennedia* F3'5'H fragment in tandem with the AmCHS 5' and petD8 3' fragments was confirmed by restriction endonuclease mapping.

The AmCHS 5': *kennedia* F3'5'H: petD8 3' cassette was then isolated from pCGP2242 by digesting with the restriction endonucleases NotI and EcoRI. The ends were repaired and the ~3.7 kb purified fragment was then ligated with Asp718 repaired ends of the binary vector pCGP1988 (described in Example 4) (FIG. 16). Correct insertion of the fragment was established by restriction endonuclease analysis of plasmid DNA isolated from tetracycline-resistant transformants. The resulting plasmid was designated pCGP2256 (FIG. 41).

*Petunia* Transformation with pCGP2256

The T-DNA contained in the binary vector plasmid pCGP2256 (FIG. 41) was introduced into *Petunia hybrida* cv. Skr4×Sw63 via *Agrobacterium*-mediated transformation.

The Binary Vector pCGP2252 (CaMV 35S: *kennedia* F3'5'H: ocs 3')

The binary vector pCGP2252 (FIG. 42) contains a chimeric CaMV 35S: *kennedia* F3'5'H: ocs 3' gene in tandem with the 35S 5'. SuRB selectable marker cassette of the binary vector pCGP1988 (FIG. 16).

Intermediates in the Preparation of the Binary Vector pCGP2252

The plasmid pCGP2231 was firstly linearized upon digestion with the restriction endonuclease XhoI. The overhanging ends were repaired and then the *kennedia* F3'5'H cDNA clone was released upon digestion with the restriction endonuclease PstI. The ~1.7 kb fragment was ligated with the ClaI (repaired ends)/PstI ends of pCGP2105 (FIG. 17). Correct insertion of the fragment was established by restriction endonuclease analysis of plasmid DNA isolated from ampicillin-resistant transformants. The resulting plasmid was designated pCGP2236.

A 3.6 kb fragment containing the CaMV 35S: *kennedia* F3'5'H: ocs 3' chimeric gene cassette was released from the plasmid pCGP2236 upon digestion with the restriction endonucleases XhoI and NotI. The overhanging ends were repaired and the purified fragment was ligated with Asp718 repaired ends of the binary vector, pCGP1988 (FIG. 16). Correct insertion of the fragment was established by restriction endonuclease analysis of plasmid DNA isolated from tetracycline-resistant transformants. The resulting plasmid was designated pCGP2252 (FIG. 42).

Rose Transformation with pCGP2252

The T-DNA contained in the binary vector plasmid pCGP2252 (FIG. 42) was introduced into *Rosa hybrida* cv. Kardinal via *Agrobacterium*-mediated transformation.

Butterfly Pea F3'5'H Constructs

Isolation of a F3'5'H cDNA Clone from Petals of *Clitoria ternatea* (Butterfly Pea)

Construction of Butterfly Pea Petal cDNA Library

A blue variety of *Clitoria ternatea* (butterfly pea the seeds were kindly provided by Osaka Botanical Garden) was grown in a field in Osaka. Total RNA was isolated from fresh and pigmented petals at a pre-anthesis stage as described above. PolyA+ RNA was prepared using Oligotex (Takara) according to the manufacturer's recommendation. A petal cDNA library of butterfly pea was constructed from the polyA+ RNA using a directional λZAP-cDNA synthesis kit (Stratagene, USA) following the manufacturers protocols.

Screen of Butterfly Pea cDNA Library for a F3'5'H cDNA Clone

The butterfly pea petal cDNA library was screened with DIG-labelled *petunia* F3'5'H petHf1 cDNA clone as described previously (Tanaka et al., *Plant Cell Physiol.* 37: 711-716, 1996). Two cDNA clones that showed high sequence similarity to the *petunia* F3'5'H petHf1 were identified. The plasmid containing the longest cDNA clone was designated pBHF2 and the cDNA clone was sequenced. Alignment between the deduced amino acid sequences of the butterfly pea F3'5'H clone and the *petunia* F3'5'H petHf1 clone (SEQ ID NO:2) revealed that the butterfly pea F3'5'H cDNA (contained in pBHF2) did not represent a full-length cDNA and lacked first 2 bases of the putative initiation codon. These two bases along with a BamHI restriction endonuclease recognition site were added to the cDNA clone using PCR and a synthetic primer, 5'-GGGATCCAACAATGTTC-CTTCTAAGAGAAAT-3' [SEQ ID NO:25] as described previously (Yonekura-Sakakibara et al., *Plant Cell Physiol.* 41: 495-502, 2000). The resultant fragment was digested with the restriction endonucleases BamHI and PstI and the subsequent DNA fragment of about 200 bp was recovered. The DNA fragment was ligated with a 3.3 kb fragment of BamHI/EcoRI digested pBHF2 to yield pBHF2F (FIG. 43). The DNA sequence was confirmed to exclude errors made during PCR (SEQ ID NO:20).

Comparison of the nucleotide sequence of butterfly pea F3'5'H clone (SEQ ID NO:20) with that of the *petunia* F3'5'H revealed around 59% identity to the *petunia* F3'5'H petHf1 clone (SEQ ID NO:1) and 62% identity to the *petunia* F3'5' petHf2 clone (SEQ ID NO:3).

The Binary Vector pCGP2135 (AmCHS 5': Butterfly Pea F3'5'H: petD8 3')

The plasmid pCGP2135 (FIG. 44) contains the butterfly pea F3'5'H cDNA clone between a snapdragon CHS promoter fragment (AmCHS 5') and a *petunia* PLTP terminator fragment (petD8 3') in tandem with the 35S 5': SuRB selectable marker gene cassette of the binary vector pCGP1988 (FIG. 16).

The *petunia* F3'5'H (petHf1) cDNA clone in pCGP725 (described in Example 4) (FIG. 7) was removed by initially digesting pCGP725 with the restriction endonucleases XbaI and BamHI. The ends were repaired the ~4.9 kb fragment containing the vector with the AmCHS 5' and petD8 3' fragments was purified and ligated with the repaired ends of the ~1.6 kb XhoI/BamHI fragment from pBHF2F (FIG. 43) containing the butterfly pea F3'5'H cDNA clone to produce pCGP2133. Correct insertion of the butterfly pea F3'5'H fragment in tandem with the AmCHS 5' and petD8 3' fragments was confirmed by restriction endonuclease mapping.

The AmCHS 5': butterfly pea F3'5'H: petD8 3' cassette was then isolated from pCGP2133 by firstly digesting with the restriction endonuclease NotI. The ends of the linearised plasmid were repaired and then the chimeric F3'5'H gene was released upon digestion with the restriction endonuclease EcoRV. The ~3.6 kb purified fragment was then ligated with Asp718 repaired ends of the binary vector pCGP1988 (described in Example 4) (FIG. 16). Correct insertion of the fragment was established by restriction endonuclease analysis of plasmid DNA isolated from tetracycline-resistant transformants. The resulting plasmid was designated pCGP2135 (FIG. 44).

Carnation and *Petunia* Transformation with pCGP2135

The T-DNA contained in the binary vector plasmid pCGP2135 FIG. 44) was introduced into *Dianthus caryoplhyllus* cultivars Kortina Chanel and Monte Lisa and *Petunia hybrida* cv. Skr4×Sw63 via *Agrobacterium*-mediated transformation.

The Binary Vector pBEBF5 (eCaMV 35S: Butterfly Pea F3'5'H: nos 3')

The binary vector, pBE2113-GUS contains a GUS coding region between an enhanced CaMV 35S promoter and nos terminator in a pBI121 binary vector (Mitsuhara et al., 1996, supra). The plasmid pBE2113-GUS was digested with the restriction endonuclease SacI. The overhang ends were repaired and then ligated with a SalI linker to yield pBE2113-GUSs. The 1.8 kb BamHI-XhoI fragment from pBHF2F was ligated with BamHI-SalI digested pBE2113-GUSs to create pBEBF5 (FIG. 45).

Rose Transformation with pBEBF5

The T-DNA contained in the binary vector plasmid pBEBF5 (FIG. 45) was introduced into *Rosa hybrida* cultivar Lavande via *Agrobacterium*-mediated transformation.

The Binary Vector pCGP2134 (CaMV 35S: Butterfly Pea F3'5'H: ocs 3')

The binary vector pCGP2134 (FIG. 46) contains a chimeric CaMV 35S: butterfly pea F3'5'H: ocs 3' gene cassette in a tandem orientation with the 35S 5': SuRB selectable marker gene cassette of the binary vector pCGP1988 (FIG. 16).

Intermediates in the Preparation of the Binary Vector pCGP2134

The butterfly pea F3'5'H cDNA clone was released upon digestion of the plasmid pBHF2F (FIG. 43) with the restriction endonucleases XhoI and BamHI. The overhanging ends were repaired and the ~1.7 kb fragment was ligated with the PstI (repaired ends)/EcoRV ends of pCGP2105 (described in Example 4) (FIG. 17). Correct insertion of the fragment was established by restriction endonuclease analysis of plasmid DNA isolated from ampicillin-resistant transformants. The resulting plasmid was designated pCGP2132.

An ~3.6 kb fragment containing the CaMV 35S: butterfly pea F3'5'H: ocs 3' chimeric gene cassette was released upon digestion with the restriction endonucleases XhoI and XbaI. The overhanging ends were repaired and the purified fragment was ligated with Asp718 repaired ends of the binary vector, pCGP1988 (described in Example 4) (FIG. 16). Correct insertion of the fragment was established by restriction endonuclease analysis of plasmid DNA isolated from tetracycline-resistant transformants. The resulting plasmid was designated pCGP2134 (FIG. 46).

Rose Transformation with pCGP2134

The T-DNA contained in the binary vector plasmid pCGP2134 (FIG. 46) was introduced into *Rosa hybrida* cv. Kardinal via *Agrobacterium*-mediated transformation.

Gentia F3'5'H Contructs

Isolation of a F3'5'H cDNA Clone from Petals of *Gentiana triflora* (Gentian).

Construction and Screening of a Gentian Petal cDNA Library

The isolation of a gentian cDNA encoding F3'5'H has been described previously (Tanaka et al., 1996, supra) and is contained within the plasmid pG48 (FIG. 47). Comparison of the nucleotide sequence of the gentia F3'5'H clone (Gen#48) (SEQ ID NO:22) contained in the plasmid pG48 (FIG. 47) with that of the *petunia* F3'5'H revealed around 61% identity to the *petunia* F3'5'H petHf1 clone (SEQ ID NO:1) and 64% identity to the *petunia* F3'5'H petHf2 clone (SEQ ID NO:3).

The Binary Vector pCGP1498 (AmCHS 5': Gentia F3'5'H: petD8 3')

The plasmid pCGP1498 (FIG. 48) contains the gentia F3'5'H (Gen#48) cDNA clone between a snapdragon CHS promoter fragment (AmCHS 5') and a *petunia* PLTP terminator fragment (petD8 3') in tandem with the 35S 5': SuRB selectable marker gene cassette of the binary vector pWTT2132 (FIG. 6).

The *petunia* F3'5'H (petHf1) cDNA clone in pCGP725 (described in Example 4) FIG. 7) was removed by initially digesting pCGP725 with the restriction endonucleases XbaI and BamHI. The ends were repaired the ~4.9 kb fragment containing the vector with the AmCHS 5' and petD8 3' fragments was purified and ligated with the repaired ends of the ~1.7 kb XhoI/BamHI fragment from pG48 (FIG. 47) containing the gentia F3'5'H cDNA clone to produce pCGP1496. Correct insertion of the gentia F3'5'H fragment in tandem with the AmCHS 5' and petD8 3' fragments was confirmed by restriction endonuclease mapping.

The AmCHS 5': gentia F3'5'H: petD8 3' cassette was then isolated from pCGP1496 by firstly digesting with the restriction endonuclease NotI. The overhanging ends of the linearised plasmid were repaired and then the chimeric F3'5'H gene was released upon digestion with the restriction endonuclease EcoRV. The ~3.6 kb purified fragment was then ligated with Asp718 repaired ends of the binary vector pWTT2132 (FIG. 6). Correct insertion of the fragment was established by restriction endonuclease analysis of plasmid DNA isolated from tetracycline-resistant transformants. The resulting plasmid was designated pCGP1498 (FIG. 48).

Carnation and *Petunia* Transformation with pCGP498

The T-DNA contained in the binary vector plasmid pCGP1498 (FIG. 48) was introduced into *Dianthus caryophyllus* cultivars Kortina Chanel and Monte Lisa and *Petunia hybrida* cv. Skr4×Sw63 via *Agrobacterium*-mediated transformation.

The Binary Vector pBEGHF48 (eCaMV 35S: Gentia F3'5'H: nos 3')

The gentia F3'5'H cDNA clone was released by digestion of the plasmid pG48 with the restriction endonucleases BamHI and XhoI. The resulting ~1.7 kb DNA fragment was isolated and ligated with BamHI/SalI digested pBE22113-GUSs (Mitsuhara et al., 1996, supra) to create pBEGHF48 FIG. 49).

Rose Transformation with pBEGHF48

The T-DNA contained in the binary vector plasmid pBEGHF48 (FIG. 49) was introduced into *Rosa hybrida* cv. Lavande via *Agrobacterium*-mediated transformation.

The Binary Vector pCGP1982 (CaMV 35S: Gentia F3'5'H: ocs 3')

The binary vector pCGP1982 (FIG. 50) contains a chimeric CaMV 35S: gentia F3'5'H: ocs 3' gene cassette in tandem with the 35S 5': SuRB selectable marker gene cassette of the binary vector pWTT2132 (FIG. 6).

Intermediates in the Preparation of the Binary Vector pCGP1982

The plasmid pG48 (FIG. 47) was linearised upon digestion with the restriction endonuclease Asp718. The overhanging ends were repaired and then the gentia F3'5'H cDNA clone (Gen#48) was released upon digestion with the restriction endonuclease BamHI. The ~1.7 kb fragment was ligated with the 5.95 kb EcoRI (repaired ends)/BamHI fragment of pKIWI101 (Janssen and Gardner, 1989, supra). Correct insertion of the fragment was established by restriction endonuclease analysis of plasmid DNA isolated from ampicillin-resistant transformants. The resulting plasmid was designated pCGP1981.

An ~3.6 kb fragment containing the CaMV 35S: gentia F3'5'H: ocs 3' chimeric gene cassette was released upon digestion of the plasmid pCGP1981 with the restriction endonucleases XhoI and XbaI The overhanging ends were repaired and the purified fragment was ligated with repaired ends of Asp718 digested binary vector, pWTT2132. Correct insertion of the fragment was established by restriction endonuclease analysis of plasmid DNA isolated from tetracycline-resistant transformants. The resulting plasmid was designated pCGP1982 (FIG. 50).

Rose Transformation with pCGP1982

The T-DNA contained in the binary vector plasmid pCGP1982 (FIG. 50) was introduced into *Rosa hybrida* cv. Kardinal via *Agrobacterium*-mediated transformation.

Lavender F3'5'H Constructs

Isolation of a F3'5'H cDNA Clone from Petals of *Lavandula nil* (Lavender)

Construction of Lavender Petal cDNA Library

Cut flowers of a violet variety of *Lavandula nil* were purchased from a florist. Total RNA was isolated from fresh and pigmented petals as described above. PolyA+ RNA was prepared using Oligotex (Takara) according to the manufacture's recommendations. A petal cDNA library of lavender was constructed from the polyA+ RNA using a directional λZAP-cDNA synthesis kit (Stratagene, USA) following the manufacturer's protocols.

Screening of Lavender cDNA Library for a F3'5'H cDNA Clone

The lavender petal cDNA library was screened with DIG labelled *petunia* F3'5'H petHf1 cDNA clone as described previously (Tanaka et al. 1996, supra). One cDNA clone (LBG) that showed high similarity to *petunia* F3'5'H petHf1 was identified and the plasmid was designated pLHF8 (FIG. 51). The nucleotide sequence of the lavender F3'5'H (LBG) cDNA clone was designated as SEQ ID NO: 31.

Comparison of the nucleotide sequence of lavender F3'5'H clone with that of the *petunia* F3'5'H cDNA clones revealed around 59% identity to the *petunia* F3'5'H petHf1 clone (SEQ ID NO:1) and 60% identity to the *petunia* petHf2 clone (SEQ ID NO:3).

The Binary Vector pBELF8 (eCaMV 35S: Lavender F3'5'H: nos 3')

The plasmid of pLHF8 (FIG. 51) was digested with the restriction endonucleases BamHI and XhoI to release a DNA fragment of approximately 1.8 kb. The ~1.8 kb purified fragment from pLHF8 was then ligated with the BamHI-SalI digested ends of the plasmid pBE2113-GUSs (described above) to create pBELF8 (FIG. 52).

Rose Transformation with pBELF8

The T-DNA contained in the binary vector plasmid pBELF8 (FIG. 52) was introduced into *Rosa hybrida* cultivar Lavande via *Agrobacterium*-mediated transformation.

Example 8

Analysis of Transgenic Carnation, *Petunia* and Rose

The transgenic plants produced in the experiments described in Example 7 were grown to flowering. Flowers were collected and the colors of the petals were coded using the Royal Horticultural Society Colour Charts (RHSCC). The anthocyanins were extracted and the anthocyanidins analysed by spectrophotometric, TLC and/or HPLC analysis. Total RNA was also isolated from petal tissue of the appropriate stages of flower development and Northern blot analysis was used to detect transcripts of F3'5'H transgenes. The results of the transgenic analysis are summarised in Tables 11, 12 and 13.

Carnation

The F3'5'H genes described in Example 7 were evaluated for their ability to lead to the production of delphinidin-based pigments in carnation petals. Two carnation cultivars, Kortina Chanel (KC) and Monte Lisa (ML), were used in the transformation experiments. The carnation cultivar Kortina Chanel produces pink colored flowers that normally accumulate cyanidin-based anthocyanins. This cultivar therefore contains a carnation F3'H and DFR activity that an introduced F3'5'H would need to compete with for substrate. The carnation cultivar Monte Lisa produces brick red colored flowers that normally accumulate pelargonidin-based anthocyanins. This cultivar is thought to lack fully functional F3'H activity and contain a DFR that is capable of acting on DHK and thus an introduced F3'5'H would only be required to compete with the endogenous DFR for substrate.

TABLE 11

Results of transgenic analysis of petals from carnations transformed with T-DNAs containing F3'5'H gene expression cassettes (AmCHS 5':F3'5'H:petD8 3').

| F3'5'H | pCGP | cv. | #tg | TLC+ | HPLC+ | Highest % del | Av. % del | Northern+ |
|---|---|---|---|---|---|---|---|---|
| Salvia#2 | 2121 | KC | 22 | 2/16 | 3/4 | 12.5% | 7% | nd |
|  |  | ML | 21 | 17/18 | 9/9 | 76% | 57% | 14/15 |
| Salvia#47 | 2122 | KC | 23 | 6/12 | 8/8 | 29% | 12% | nd |
|  |  | ML | 25 | 21/22 | 17/17 | 88% | 56% | 12/14 |
| Sollya | 2130 | KC | 30 | 22/27 | 17/17 | 35% | 11% | nd |
|  |  | ML | 23 | 14/15 | 14/14 | 76% | 49% | 13/14 |
| Butterfly pea | 2135 | KC | 22 | 0/16 | 0/1 | nd | nd | nd |
|  |  | ML | 24 | 19/20 | 13/13 | 23% | 10% | 14/14 |
| Gentian | 1498 | KC | 22 | 0/14 | nd | nd | nd | 7/8 |
|  |  | ML | 2 | 2/2 | 1/1 | nd | nd | 1/2 |
| pansy BP#18 | 1972 | KC | 26 | 18/20 | 12/12 | 14% | 9% | 19/19 |
|  |  | ML | 21 | 15/16 | 8/8 | 80% | 66% | 14/16 |
| pansy BP#40 | 1973 | KC | 26 | 11/15 | 7/8 | 18% | 8% | 13/17 |
|  |  | ML | 33 | 19/22 | 20/20 | 72% | 52% | 12/15 |
| petunia petHf1 | 1452 | KC | 104 | 41/64 | nd | 3.5% | 1.3% | 15/17 |
|  |  | ML | 48 | 39/41 | 26/26 | 75% | 30% | 12/13 |
| petunia petHf2 | 1524 | ML | 27 | 18/19 | 17/17 | 81% | 41% | 12/14 |

F3'5'H = F3'5'H sequence contained on the T-DNA
pCGP = plasmid pCGP number of the binary vector used in the transformation experiment
cv. = cultivar
KC = carnation cultivar Kortina Chanel (cyanidin line)
ML = carnation cultivar Monte Lisa (pelargonidin line)
tg = total number of transgenics produced
TLC+ = number of individual events in which delphinidin or delphinidin-based molecules was detected in petals (as determined by TLC) over the total number of individual events analyzed
HPLC+ = number of individual events in which delphinidin or delphinidin-based molecules was detected in petals (as determined by HPLC) over the total number of individual events analyzed
Highest % del = Highest % delphinidin or delphinidin-based molecules detected in the petals for the population of transgenic event
Av % del = average % delphinidin or delphinidin-based molecules detected in the petals for the population of transgenic events
Northern = number of individual events in which the specific intact F3'5H transcripts were detected by Northern blot analysis in total RNA isolated from petals over the total number of events analyzed
nd = not done The results suggest that all of the F3'5'H sequences evaluated (*petunia* petHf1, *petunia* petHf2, *Salvia* Sal#2, *Salvia* Sal#47, *Sollya* Sol#5, Butterfly pea BpeaHF2, pansy BP#18, pansy BP#40 and Gentian Gen#48) were stable in carnation and resulted in the production of novel delphinidin-based pigments in carnation flowers. Intact transcripts of each F3'5'H were detected by Northern blot analysis in total RNA isolated from petals of the transgenic carnations.

*Petunia*

Figure 1A:
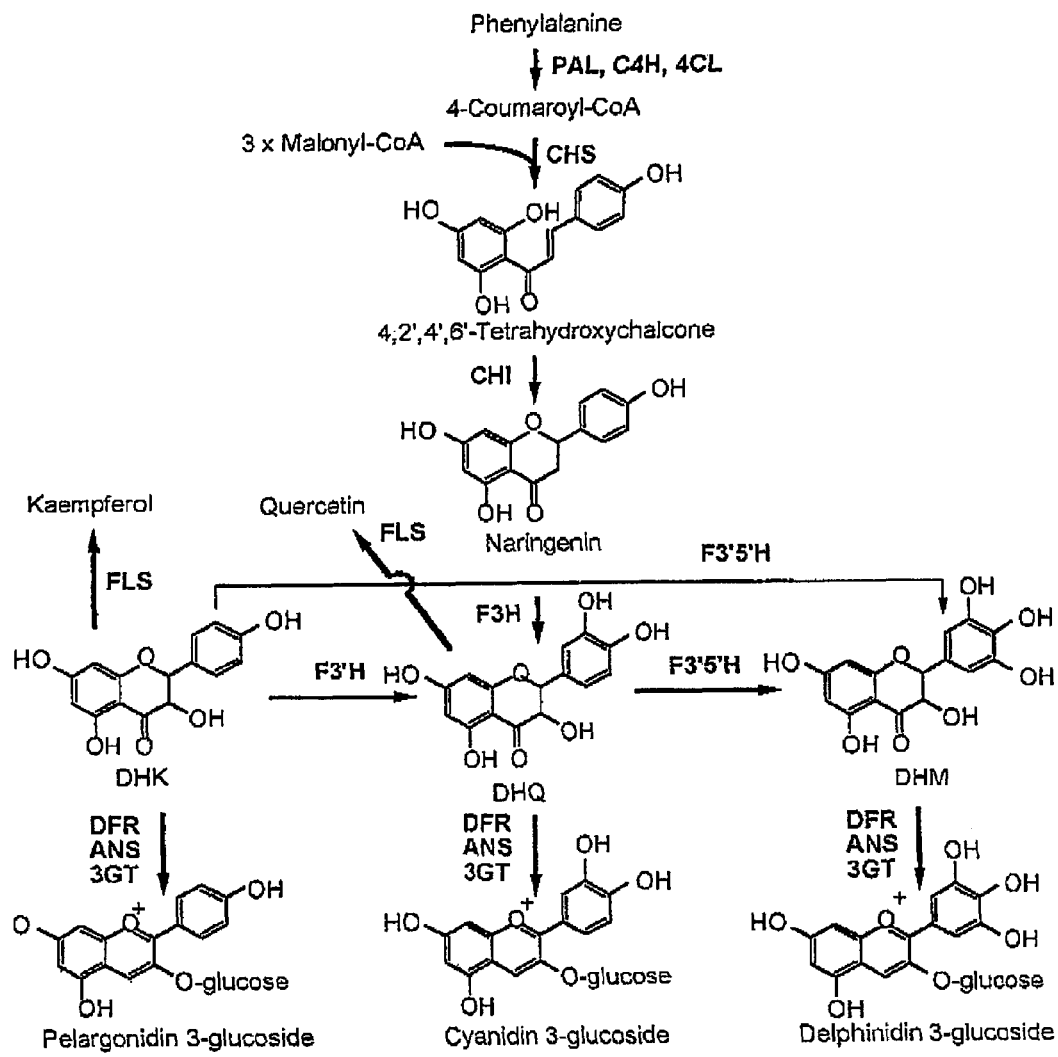
FIGS. 1A and 1B are schematic representations of the biosynthesis pathway for the flavonoid pigments.
Figure 1B:
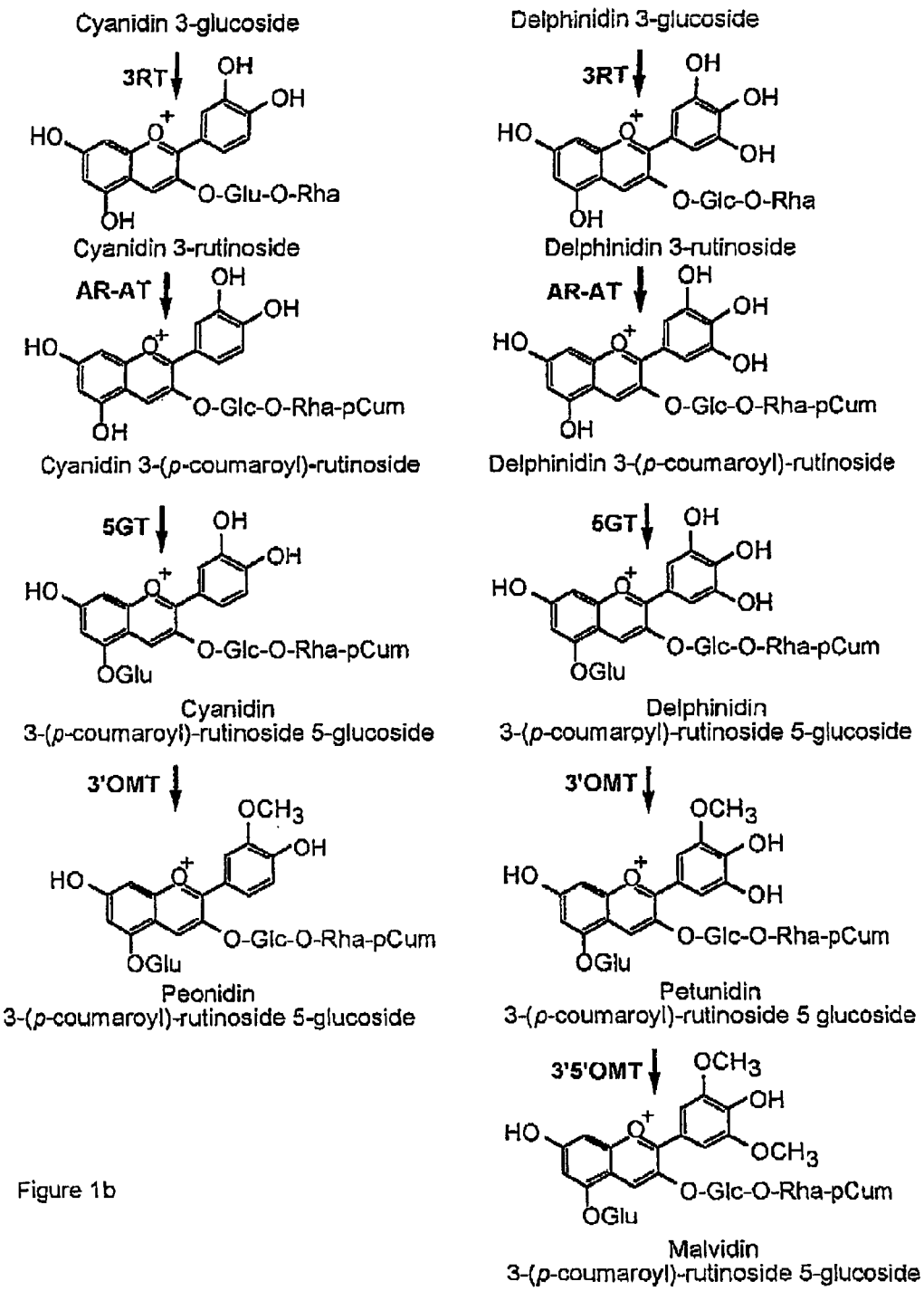

The F3'5'H genes described in Example 7 were evaluated for their ability to lead to the production of delphinidin-based pigments in *petunia* petals. The *P. hybrida* F1 hybrid Skr4× SW63 which is homozygous recessive for Hf1 and Hf2, was used in the transformation experiments. Although Skr4× SW63 is homozygous recessive for Hf1 and Hf2, these mutations do not completely block production of the endogenous F3'5'H (see U.S. Pat. No. 5,349,125) and low levels of malvidin are produced to give the petal limb a pale lilac color. Malvidin is the methylated derivative of the 3'5'-hydroxylated pigment, delphinidin or delphinidin-based molecules (FIGS. 1A and 1B). Spectrophotometric analysis was used as a measure of total anthocyanins accumulating in petals from the transgenic *petunia* flowers. The increased level of anthocyanins and/or the color change detected was used as a guide to the efficacy of the F3'5'H gene under evaluation.

TABLE 12

Results of transgenic analysis of petals from *P. hybrida* cv Skr4 × SW63 plants transformed with T-DNAs containing F3'5'H gene expression cassettes (AmCHS 5':F3'5'H:petD8 3').

| F3'5'H | pCGP | #tg | TLC+ | Col | ↑ A/c | Best | Av. | Northern+ | Best color |
|---|---|---|---|---|---|---|---|---|---|
| control | na | na | na | na | na | 144-250 |  | 0 | 75C |
| Gentian#48 | 1498 | 22 | 3/5 | 18/20 | nd |  |  | 6/6 | 72B/78A |
| Butterfly pea | 2135 | 24 | 18/20 | 22/24 | 23/24 | 4427 | 2397 | nd | 74A/78A |
| *Kennedia* | 2256 | 24 | 22/24 | 22/24 | 22/24 | 4212 | 2592 | nd | 74A/78A |
| *Salvia*#2 | 2121 | 24 | 21/24 | 21/24 | 21/24 | 2471 | 1730 | nd | 78A |

TABLE 12-continued

Results of transgenic analysis of petals from *P. hybrida* cv Skr4 × SW63 plants
transformed with T-DNAs containing F3'5'H gene expression cassettes
(AmCHS 5':F3'5'H:petD8 3').

| F3'5'H | pCGP | #tg | TLC+ | Col | ↑ A/c | Best | Av. | Northern+ | Best color |
|---|---|---|---|---|---|---|---|---|---|
| Salvia#47 | 2122 | 19 | 17/19 | 16/19 | 16/19 | 2634 | 1755 | nd | 78A/80A |
| Sollya#5 | 2130 | 22 | 14/16 | 13/16 | 13/16 | 3446 | 1565 | nd | 78A |
| pansy BP#18 | 1972 | 22 | nd | 20/22 | nd | nd | nd | 9/9 | 74A/B |
| pansy BP#40 | 1973 | 19 | 8/8 | 18/19 | 18/20 | 2583 | 1556 | nd | 74/78A |
| petunia petHf1 | 484 | 16 | nd | 9/16 | 8/15 | 2683 | 1250 | nd | 74A/B |
| petunia petHf2 | 1524 | 20 | nd | 18/20 | 8/8 | 4578 | 2357 | 8/8 | 74A/B |

F3'5'H = F3'5'H sequence contained on the T-DNA
pCGP = plasmid pCGP number of the binary vector used in the transformation experiment
tg = total number of transgenics produced
TLC+ = number of individual events in which malvidin was detected in the flowers (at a level above the Skr4 × Sw63 background) (as determined by TLC) over the total number of individual events analyzed
Col = number of individual events that produced flowers with an altered flower color compared to the control over the total number examined
↑ A/c = number of individual events that had an increased level of anthocyanins in petals as measured by spectrophotometric analysis of crude extracts over the number of individual events analyzed (in μmoles/g)
Best = highest anthocyanin amount as measured by spectrophotometric analysis of crude extracts from a flower of an individual event (in μmoles/g)
Av = the average amount of anthocyanin detected as measured by spectrophotometric analysis of crude extracts from a flower in the population of transgenic flowers analysed (in μmoles/g)
Northern = number of individual events in which the specific intact F3'5H transcripts were detected by Northern blot analysis in total RNA isolated from petals over the total number of events analyzed
Best color = most dramatic color change recorded for the transgenic population
nd = not done
na = not applicable Introduction of the F3'5'H gene expression cassettes into Skr4×SW63 led to a dramatic flower color change from pale lilac to purple with a dramatic increase in the production of malvidin in the petals.

The results suggest that all of the F3'5'H sequences tested (*petunia* petHf1, *petunia*, petHf2, *Salvia* Sal#2, *Salvia* Sal#47, *Sollya* Sol#5, Butterfly pea BpeaHF2, pansy BP#18, pansy BP#40, Gentian Gen#48, *Kennedia* Kenn#31) were stable in *petunia* petals and resulted in the complementation of the Hf1 or Hf2 mutation in the Skr4×SW63 *petunia* line leading to dramatically increased levels of malvidin cumulation with a concomitant color change Rose The F3'5'H genes described in Example 7 were evaluated for their ability to lead to the production of delphinidin-based pigments in rose petals. A selection of three rose cultivars, Kardinal (Kard), Soft Promise (SP) or Lavande (Lav) were used in transformation experiments. The rose cultivar Kardinal produces red colored flowers that normally accumulate cyanidin-based anthocyanins. This cultivar therefore contains rose F3'H and DFR activities that the introduced F3'5'H would need to compete with for substrate. The rose cultivar Lavande produces light pink colored flows that normally accumulate cyanidin-based anthocyanins. This cultivar therefore contains functional rose F3'H and DFR activities that the introduced F3'5'H would need to compete with for substrate. The rose cultivar Soft Promise produces apricot colored flowers that normally accumulate pelargonidin. This cultivar is thought to lack a fully functional rose F3'5'H activity and contain a DFR that is capable of acting on DHK and thus the introduced F3'5'H would only be required to compete with the endogenous rose DFR for substrate.

TABLE 13

Results of transgenic analysis of petals from roses transformed with T-DNAs
containing F3'5'H gene expression cassettes
(CaMV 35S:F3'5'H:ocs 3').

| F3'5'H | plasmid | Cult | #tg | TLC+ | HPLC+ | Highest % del | Av. % del | Northern+ |
|---|---|---|---|---|---|---|---|---|
| Salvia2 | pCGP2120 | Kard | 30 | 18/20 | 21/21 | 12% | 5% | 18/18 |
| Salvia47 | pCGP2119 | Kard | 22 | 11/16 | 9/9 | 7.1% | 2% | 12/15 |
| Sollya | pCGP2131 | Kard | 27 | 0/23 | 2/2 | 1% | 0.5% | 6/6 |
| Butterfly pea | pCGP2134 | Kard | 29 | 0/15 | nd | na | na | 0/9 |
| | pBEBF5 | Lav | 25 | nd | 0/25 | 0% | 0% | nd |
| Gentian | PCGP1482 | Kard | 27 | 0/23 | nd | na | na | 0/23 |
| | pBEGHF48 | Lav | 23 | nd | 0/23 | 0% | 0% | 0/23 |
| pansy | PCGP1967 | Kard | 56 | 30/33 | 33/34 | 58% | 12% | 21/21 |

TABLE 13-continued

Results of transgenic analysis of petals from roses transformed with T-DNAs containing F3'5'H gene expression cassettes (CaMV 35S:F3'5'H:ocs 3').

| F3'5'H | plasmid | Cult | #tg | TLC+ | HPLC+ | Highest % del | Av. % del | Northern+ |
|---|---|---|---|---|---|---|---|---|
| BP18 |  | SP | 36 | 21/24 | 18/18 | 65% | 35% | 16/21 |
| pansy | pCGP1969 | Kard | 22 | 15/15 | 15/15 | 24% | 9% | 16/16 |
| BP40 |  | SP | 37 | 17/17 | 16/17 | 80% | 54% | 11/13 |
| *Petunia* | pCGP1638 | Kard | 22 | 0/21 | nd | na | na | 0/16 |
| petHf1 | pCGP1392 | Lav | 34 | nd | 0/34 | 0% | 0% | nd |
| *Petunia* petHf2 | PCGP2123 | Kard | 41 | 0/26 | nd | na | na | 0/10 |
| Lavender | pBELF8 | Lav | 28 | nd | 4/28 | 4% | 3.5% | nd |

F3'5'H = the F3'5'H sequence contained on the T-DNA
plasmid = the plasmid number of the binary vector used in the transformation experiment
Cult = *Rosa hybrida* cultivar
Kard = Kardinal
SP = Soft Promise
Lav = Lavande
tg = # of independent transgenic events produced
TLC+ = number of individual events that accumulated detectable delphinidin or delphinidin-based molecules (as determined by TLC) in the petals over the number of individual events analyzed
HPLC+ = number of individual events that accumulated detectable delphinidin or delphinidin-based molecules (as determined by HPLC) in the petals over the number of individual events analyzed
Northern = number of individual events in which the specific intact F3'5H transcripts were detected by Northern blot analysis in total RNA isolated from petals over the total number of events analyzed
nd = not done The results suggest surprisingly that not all of the F3'5'H sequences assessed (*petunia* petHf1, *petunia* petHf2, *Salvia* Sal#2, *Salvia* Sal#47, *Sollya* Sol#5, Butterfly pea BpeaHF2, pansy BP#18, pansy BP#40, Gentian Gen#48, *Kennedia* Kenn#31 and Lavender LBG) were functional in rose. In fact transcripts of the introduced F3'5'H sequences isolated from *Clitoria ternatea* (butterfly pea), *Gentiana triflora*, (gentian) and *Petunia hybrida* (petunia) failed to accumulate in rose petals. Only full-length F3'5'H transcripts from pansy, *salvia, kennedia, sollya* and lavender accumulated in rose petals. However although *Kennedia* F3'5'H transcripts did accumulate in rose petals, there was either no accumulation of the enzyme or the enzyme produced was either not functional or was unable to compete with the endogenous rose F3'H and DFR enzymes to allow for the production of delphinidin or delphinidin-based molecules pigments. Of the F3'5'H sequences evaluated, only the F3'5'H sequences derived from cDNA clones from *Salvia* spp. (Sal#2 and Sal#47), *Viola* spp. (BP#18 and BP#40), *Sollya* spp. (Soll#5) and *Lavandula nil* (LBG) resulted in the production of delphinidin or delphinidin-based molecules based pigments in rose petals. Based on the relative percentages of delphinidin or delphinidin-based molecules produced in rose petals, the F3'5'H sequences from pansy (BP#18 and BP#40) were revealed to be the most effective of those assessed at producing delphinidin or delphinidin-based molecules in rose petals.

Introduction of *Viola* spp. F3'5'H Sequence into *Rosa hybrida* cv. Medeo and Pamela As described in the introduction, copigmentation with other flavonoids, further modification of the anthocyanidin molecule and the pH of the vacuole impact on the color produced by anthocyanins. Therefore, selection of rose cultivars with relatively high levels of flavonols and relatively high vacuolar pH would result in bluer flower colors upon production of delphinidin or delphinidin-based molecules pigments.

The rose cultivar Medeo generally produces cream-colored to pale apricot flowers (RHSCC 158C to 159A). HPLC analysis of the anthocyanidins and flavonols accumulating in Medeo rose petals revealed that the petals accumulate high levels of flavonols (2.32 mg/g kaempferol, 0.03 mg/g quercetin) and very low levels of anthocyanins (0.004 mg/g cyanidin, 0.004 mg/g pelargonidin). The estimated vacuolar pH of Medeo petals is around 4.6.

The rose cultivar Pamela produces white to very pale pink colored flowers. It similarly accumulates low levels of anthocyanin and relatively high levels of flavonols.

The T-DNA contained in the construct pCGP1969 (FIG. 30) incorporating the pansy F3'5'H clone, BP#40, was also introduced into the rose cultivars Medeo and Pamela resulting in the production of over 90% delphinidin or delphinidin-based molecules in these roses and leading to a dramatic color change and novel colored flowers. The most dramatic color change in transgenic Medeo flowers was to a purple/violet color of RHSCC 70b, 70c, 80c, 186b. The most dramatic color change in transgenic Pamela flowers was to a purple/violet color of RHSCC 71c, 60c, 71a, 80b.

In conclusion, two unexpected findings were revealed when gene sequences that had been proven to lead to functionality in *petunia* and carnation were introduced into roses.

First, the *petunia* F3'5'H petHf1 (and petHf2) sequences that had resulted in novel color production in carnation and also proven to lead to synthesis of a functional enzyme in *petunia* did not lead to full-length (or intact) transcript accumulation (as detectable by Northern blot analysis) in rose petals. In fact, there was either no accumulation of full-length or intact transcript or the transcripts that were detected were degraded and were seen as low MW (or fast migrating) smears on RNA blots indicating the presence of low MW heterologous hybridizing RNA. Therefore in order to find a F3'5'H sequence that would accumulate in rose and load to a functional enzyme, a number of F3'5'H sequences were isolated. Again it was not obvious which sequence would lead to an active enzyme in rose petals. All of the F3'5'H sequences isolated were tested for functionality in carnation and/or *petunia* and all led to accumulation of intact transcripts and production of a functional F3'5'H activity. However only F3'5'H sequences from pansy (BP#18 and BP#40), *salvia* (Sal#2 and Sal#47), *sollya* (Soll#5), *kennedia* (Kenn#31) and lavender (LBG) resulted in accumulation of intact full-length transcripts and only those from pansy (BP#18 and BP#40), *salvia* (Sal#2 and Sal#47), *sollya* (Soll#5) and lavender (LBG) resulted in production of a functional enzyme in rose as measured by the synthesis of delphinidin or delphinidin-based molecules.

Secondly that it was not obvious which promoters would be effective in rose. Promoter cassettes that had been tested and proven to be functional in carnation and *petunia* flowers did not lead to accumulation of detectable transcripts in rose petals. Of the promoters tested in rose, only CaMV 35S, RoseCHS 5', ChrysCHS 5', mas 5' and nos 5' promoters led to intact and detectable GUS or nptII or SuRB transcript accumulation in rose petals.

Table 14 shows a summary of the results obtained when assessing F3'5'H sequences from various species in *petunia*, carnation and rose.

TABLE 14

Summary of effectiveness of the F3'5'H sequences in *petunia*, carnation and rose

| F3'5'H | Petunia | | Carnation | | Rose | |
|---|---|---|---|---|---|---|
| | Mal | RNA | Del | RNA | Del | RNA |
| *Kennedia* (Kenn#31) | + | nd | nd | nd | − | + |
| Gentian (Gen#48) | + | + | + | + | − | − |
| *Salvia* (Sal#2) | + | nd | + | + | + | + |
| *Salvia* (Sal#47) | + | nd | + | + | + | + |
| *Sollya* (Sol#5) | + | nd | + | + | + | + |
| Butterfly pea (BpeaHF2) | + | nd | + | + | − | − |
| Pansy (BP#18) | + | + | + | + | + | + |
| Pansy (BP#40) | + | nd | + | + | + | + |
| *Petunia* (petHf1) | + | + | + | + | − | − |
| *Petunia* (petHf2) | + | + | + | + | − | − |
| Lavender (LBG) | nd | nd | nd | nd | nd | + | nd = not done
Mal = malvidin detected in petals as analysed by TLC
Del = delphinidin or delphinidin-based molecules detected in petals as analysed by TLC or HPLC
+ = yes
− = no Example 9

Use of Pansy F3'5'H Sequences in Species other than Rose

Gerbera

From the examples above, it was clear that the pansy F3'5'H sequences, BP18 and BP#40, resulted in functional F3'5'H activity and lead to the production of high levels of delphinidin or delphinidin-based molecules in roses and carnations.

The T-DNA from binary construct pCGP1969 (described in Example 8) (FIG. 30) containing the chimeric CaMV 35S: pansy BP#40 F3'5'H: ocs 3' gene expression cassette was introduced into the gerbera cultivar Boogie via *Agrobacterium*-mediated transformation, to test the functionality of the pansy F3'5'H sequence in gerbera.

Of six events produced to date, one (#23407) has produced flowers with a dramatic color change (RHSCC 70c) compared to the control flower color (RHSCC 38a, 38c).

The color change of the petals of the transgenic gerbera has been correlated with the presence of delphinidin or delphinidin-based molecules as detected by TLC Other Species In order to produce delphinidin or delphinidin-based molecules pigments in plants that do not normally produce delphinidin-based pigments and does not contain a flavonoid 3'5'-hydroxylase constructs containing a F3'5'H gene (such as but not limited to a chimaeric *Viola* spp. and/or *Salvia* spp. and/or *Sollya* spp. and/or *Lavandula* spp. and/or *Kennedia* spp. F3'5'H gene) are introduced into a species that does not normally produce delphinidin-based pigments. Such plants may include but are not limited to carnation, chrysanthemum, gerbera, orchids, *Euphorbia, Begonia* and apple.

Example 10

Characteristics of F3'5'H Sequences Evaluated in *Petunia*, Carnation and Rose

Gene regulation in eukaryotes is, in simple terms, facilitated by a number of factors which interact with a range of sequences proximal and distal to a nucleotide sequence coding for a given polypeptide. Engineering expression cassettes for introduction into plants for the generation of one or more traits is based on an understanding of gene regulation in eukaryotes in general and, in selected cases, plants in particular. The essential elements include a series of transcriptional regulation sequences typically, but not exclusively, located upstream or 5' to the point of transcription initiation. Such elements are typically described as enhancers and promoters, the latter being proximal to the point of transcription initiation. Immediately downstream from, or 3' to, the initiation of transcription point is a variable region of transcribed DNA which is denoted as the 5' untranslated region (5'utr) which plays a role in transcript stability and translational efficiency. Such sequences, when engineered into expression cassettes, are frequently chimeric and may be derived from sequences naturally occurring adjacent to the coding sequence and/or adjacent to a given promoter sequence. The coding sequence (sometimes disrupted by introns) lies 3' to the 5'utr followed by a 3'utr important to transcript (mRNA) stability and translational efficiency. Sequences 3' to the end of the coding region and 3' to the 3'utr itself are denoted as terminator sequences. All these elements make up an expression cassette. In making direct comparisons between promoters or other elements it is important to maintain uniformity in the remaining elements of an expression cassette. Hence, when comparing the efficacy of various F3'5'H sequences it was possible to confine the sequences leading to instability and the subsequent autodegradation of engineered mRNA and resultant absence of tri-hydroxylated products (delphinidin or delphinidin-based molecules derivatives) to the region coding for the F3'5'H and not to other elements in the expression cassette such as 5'utr and/or 3'utr sequences for example.

In an attempt to identify motifs or similarities between the F3'5'H sequences that resulted in full-length transcripts being detected in total RNA isolated from rose flowers, and ultimately delphinidin or delphinidin-based molecules production, comparisons across a range of parameters were performed. These included sequence identities at nucleic acid and amino acid levels, sequence alignments, taxonomic classifications, % of A or T nucleotides present in the sequence, % of codons with an A or T in the third position etc.

Taxonomic Classification

The taxonomy of each species from which the F3'5'H sequences were isolated was examined (Table 15). There appeared to be no obvious link between the subclass classification and whether the F3'5'H sequence resulted in an intact transcript and subsequent delphinidin or delphinidin-based molecules production in roses.

TABLE 15

Taxonomic classifications of the species that F3'5'H sequences were isolated from and whether the use of the sequences resulted in intact transcript in rose petals that were detectable by RNA blot analysis.

| Flower | Species | Family | Order | Subclass | Intact transcript | Delphinidin in rose petals |
|---|---|---|---|---|---|---|
| gentian | Gentiana triflora | Gentianaceae | Gentianales | Asteridae | NO | NO |
| lavender | Lavandula nil | Lamiaceae | Lamiales | Asteridae | YES | YES |
| salvia | Salvia spp. | Lamiaceae | Lamiales | Asteridae | YES | YES |
| sollya | Sollya spp. | Pittosporaceae | Apiales | Asteridae | YES | YES |
| petunia | Petunia hybrida | Solanaceae | Solanales | Asteridae | NO | NO |
| kennedia | Kennedia spp. | Fabaceae | Fabales | Rosidae | YES | NO |
| butterfly pea | Clitoria ternatea | Fabaceae | Fabales | Rosidae | NO | NO |
| pansy | Viola spp. | Violaceae | Malpighiales | Rosidae | YES | YES |
| rose | Rosa hybrida | Rosaciae | Rosales | Rosidae | na | na |

Intact transcript = full-length F3'5'H mRNA detected by Northern blot analysis in total RNA isolated from petals from transgenic roses

Comparison of F3'5'H Nucleotide Sequences

The nucleotide sequence identities between each of the F3'5'H sequences evaluated were determined using the ClustalW program (Thompson et al., 1994, supra) within the MacVector™ version 6.5.3 application program (Oxford Molecular Ltd., England) (Table 16). There were no obvious differences between the F3'5'H sequences that resulted in the detection of intact full-length transcripts in RNA isolated from rose petals and those that didn't.

Comparison of F3'5'H Translated Nucleotide Sequences

The translated nucleotide sequence identities and similarities between each of the F3'5'H sequences evaluated were also determined using the ClustalW program (Thompson et al., 1994, supra) within the MacVector™ version 6.5.3 application program (Oxford Molecular Ltd., England) (Table 17). There were no obvious differences between the F3'5'H sequences that resulted in the detection of intact full-length transcripts in RNA isolated from rose petals and those that didn't.

TABLE 16

Percentage of nucleic acid sequence identity between the nucleotide sequences of the F3'5'H isolated from various species. F3'5'H sequences that resulted in intact transcripts being detected in RNA isolated from rose petals are underlined and in italics.

| | BP18 | BP40 | Lav | Sal47 | Sal2 | Soll | Kenn | Bpea | Gent | PetHf1 | PetHf2 |
|---|---|---|---|---|---|---|---|---|---|---|---|
| BP18 | 100 | 82 | 60 | 61 | 62 | 51 | 60 | 62 | 62 | 59 | 62 |
| BP40 | | 100 | 60 | 57 | 58 | 50 | 59 | 62 | 58 | 60 | 62 |
| Lav | | | 100 | 68 | 68 | 48 | 57 | 57 | 58 | 59 | 60 |
| Sal47 | | | | 100 | 95 | 48 | 56 | 57 | 59 | 57 | 58 |
| Sal2 | | | | | 100 | 49 | 57 | 58 | 60 | 57 | 59 |
| Soll | | | | | | 100 | 48 | 50 | 50 | 48 | 51 |
| Kenn | | | | | | | 100 | 70 | 56 | 64 | 60 |
| Bpea | | | | | | | | 100 | 59 | 59 | 62 |
| Gent | | | | | | | | | 100 | 61 | 64 |
| PetHf1 | | | | | | | | | | 100 | 84 |
| PetHf2 | | | | | | | | | | | 100 |

TABLE 17

Percentage of the amino acid sequence identity and similarity (in brackets) between F3'5'H sequences isolated from various species. F3'5'H sequences that resulted in intact transcripts being detected in RNA isolated from rose petals are underlined and in italics.

| | BP18 | BP40 | Lav | Sal47 | Sal2 | Soll | Kenn | Bpea | Gent | PetHf1 | PetHf2 |
|---|---|---|---|---|---|---|---|---|---|---|---|
| BP18 | 100 | 91 (94) | 65 (77) | 65 (76) | 65 (76) | 44 (63) | 69 (83) | 64 (75) | 69 (80) | 74 (85) | 74 (85) |
| BP40 | | 100 | 67 (89) | 66 (77) | 66 (77) | 46 (64) | 69 (82) | 64 (75) | 68 (79) | 74 (85) | 75 (86) |
| Lav | | | 100 | 75 (86) | 75 (86) | 45 (63) | 63 (79) | 59 (74) | 66 (80) | 68 (82) | 69 (83) |
| Sal47 | | | | 100 | 98 | 45 (65) | 64 (78) | 60 (72) | 64 (76) | 68 (79) | 69 (81) |

TABLE 17-continued

Percentage of the amino acid sequence identity and similarity (in brackets) between F3'5'H sequences isolated from various species. F3'5'H sequences that resulted in intact transcripts being detected in RNA isolated from rose petals are underlined and in italics.

| | BP18 | BP40 | Lav | Sal47 | Sal2 | Soll | Kenn | Bpea | Gent | PetHf1 | PetHf2 |
|---|---|---|---|---|---|---|---|---|---|---|---|
| *Sal2* | | | | | 100 | 45 (65) | 64 (78) | 60 (72) | 63 (75) | 68 (79) | 69 (81) |
| *Soll* | | | | | | 100 | 46 (66) | 41 (61) | 44 (62) | 46 (67) | 46 (66) |
| *Kenn* | | | | | | | 100 | 72 (80) | 65 (75) | 71 (83) | 72 (83) |
| Bpea | | | | | | | | 100 | 69 (81) | 65 (75) | 65 (74) |
| Gent | | | | | | | | | 100 | 73 (82) | 73 (82) |
| PetHf1 | | | | | | | | | | 100 | 93 (95) |
| PetHf2 | | | | | | | | | | | 100 |

Percentage of Nucleotides A or T in the F3'5'H DNA Sequences

There is some evidence to suggest that the choice of codons influences the rate of translation and mRNA degradation. Certain codons are used less frequently than others are and this may be related to the abundance of isoaccepting tRNAs. Transfer RNAs corresponding to rare codons are less abundant in *E. coli* and yeast than tRNAs corresponding to preferred codons (van Hoof and Green, *Plant Molecular Biology*, 35: 383-387, 1997). Examples of altering codon usage and making a gene more "plant-like" are the bacterial B.t. toxin gene (reviewed in Diehn et al., *Genet Engin*, 18: 83-99, 1996) and the jellyfish gfp gene (Haseloff et al., *Proc. Natl. Acad. Sci USA*, 94: 2122-2127, 1997). However as commented in van Hoof and Green, (1997) (supra), the effect of eliminating the rare codons in the B.t. genes increased the GC content, thereby eliminating AU-rich sequences that may be responsible for improper recognition of introns and polyadenylation sites as well as removing instability determinants. Alteration of codon usage in the jellyfish gfp gene also resulted in removal of a cryptic intron (Haseloff et al., 1996, supra). Studies examining the effect of codon usage and instability elements have generally been limited to differences between genes isolated from species in different kingdoms ie. bacterial versus yeast versus animal versus plant. Within the plant kingdom, differences have been observed between the dicotyledons and the monocotyledons. Studies on transgenic plants have suggested that promoter fragments used to drive gene expression in dicotyledonous plants are not as effective when used in monocotyledonous plants (see Galun and Breiman, Transgenic Plants, Imperial College Press, London, England, 1997). Differences in the methylation and ultimate expression of a DFR transgene in *Petunia hybrida* (dicot) were detected when a maize (monocot) DFR cDNA was compared with a gerbera (dicot) DFR cDNA (Elomaa et al., *Molecular, and General Genetics*, 248: 649-656, 1995). The conclusion was that the gerbera DFR cDNA had a higher AT content (lower CC content) and was more, "compatible" with the genomic organization of *petunia* preventing it being recognised as a foreign gene and hence silenced by methylation. (Rose along with carnation and *petunia* are dicotyledons and the F3'5'H genes tested were all isolated from dicotyledonous plants.) These points serve to illustrate that degradation and stability mechanisms are not understood in detail and differences appear between plants and other kingdoms and within the plant kingdom.

The content of A and T was examined in the F3'5'H cDNAs evaluated along with that of four flavonoid pathway genes (F3'H, DFR, CHS, FLS) that had been isolated from rose (Table 18). The third position of each codon (within the open reading frame) was also examined and the percentage of codons with an A or a T in the third position was calculated (able 18).

TABLE 18

Summary of the percentage amount of A or T dinucleotides in the F3'5'H sequences isolated and whether the F3'5'H resulted in full-length transcripts being detected in rose petals by Northern blot analysis.

| F3'5'H seq | % AT | % A or T in 3rd | RNA | Delphinidin |
|---|---|---|---|---|
| Viola BP#18 | 50 | 40 | YES | YES |
| Viola BP#40 | 51 | 35 | YES | YES |
| Salvia#2 | 48 | 33 | YES | YES |
| Salvia#47 | 48 | 34 | YES | YES |
| Sollya#5 | 54 | 54 | YES | YES |
| LavenderLBG | 50 | 37 | YES* | YES |
| Kennedia#31 | 54 | 47 | YES | NO |
| petunia petHf1 | 61 | 66 | NO | NO |
| petunia petHf2 | 59 | 65 | NO | NO |
| Gentian#48 | 57 | 57 | NO | NO |
| Butterfly pea#HF2 | 57 | 53 | NO | NO |
| rose F3'H | 47 | 34 | ** | na |
| rose CHS | 52 | 42 | ** | na |
| rose DFR | 53 | 46 | ** | na |
| rose FLS | 56 | 43 | ** | na |

% AT = % of nucleotides that are A or T in the nucleic acid sequence
% A or T in $3^{rd}$ = the percentage of codons that have an A or T in the third position
RNA = whether a full-length mRNA transcript was detected by Northern blot analysis in total RNA isolated from rose petals
Del = whether any delphinidin or delphinidin-based molecules was detected by TLC or HPLC in rose petals
YES* = although Northern blot analysis of transgenic roses transformed with the lavender F3'5'H expression cassettes was not performed, it can be assumed that full-length transcript was produced since delphinidin or delphinidin-based molecules was detected in the rose petals.
rose F3'H (described in International Patent Application No. PCT/AU97/00124)
rose DFR (Tanaka et al., 1995, supra)
rose FLS (GenBank accession number AB038247)
rose CHS (GenBank accession number AB038246)

The AT content of the four rose sequences (above) encoding flavonoid pathway enzymes had an AT content of between 47 and 56%. In general the AT content of the F3'5'H sequences that resulted in intact transcripts in rose petals was between 48 and 54%. However the F3'5'H sequences that did not result in intact transcripts accumulating in rose petals generally had a higher AT content of between 57 and 61%. Hence the AT content of the introduced F3'5'H genes into rose may be a factor in whether an intact transcript accumulates in rose petals and so leads to production of F3'5'H and delphinidin or delphinidin-based molecules.

The nucleotide base at the third position of each codon of the four rose sequences encoding flavonoid pathway enzymes was generally an A or a T in 34 to 46% of the codons. In general F3'5'H sequences that resulted in intact transcripts in rose petals contained an A or a T in the third position of each codon in 33 to 54% of the codons. Howevvr the F3'5'H sequences that did not result in intact transcripts accumulating in rose petals generally contained an A or a T in the third position of each codon in 53 to 66% of the codons. So the percentage of codons with an A or a T in the third position of the introduced F3'5'H genes into rose may also be a factor in whether an intact transcript is accumulates in rose petals and so leads to production of F3'5'H and delphinidin or delphinidin-based molecules.

It may be that by altering the overall content of the nucleotides A and/or T in any F3'5'H DNA sequence that does not result in an intact transcript in rose such as but nor limited to the *Petunia hybrida* petHf1, *Petunia hybrida* petHf2, *Clitora ternatea* (butterfly pea) BpeaHF2 or *Gentiana triflora* (gentian) Gen#48, to a level more consistent with that found in rose genes, intact transcripts will accumulate and result in the efficient translation of F3'5'H transcripts and so to delphinidin or delphinidin-based molecules accumulation in rose petals. One way of altering the AT content of the DNA sequence without altering the amino acid sequence is to target the degeneracy of the third position of each codon.

Those skilled in the at will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said stops or features.

BIBLIOGRAPHY

*A look beyond transcription, ASPP*, USA, Bailey-Serres and Gallie, eds. 1998
Altschul et al., *J. Mol. Biol.* 215(3): 403-410, 1990.
Altschul et al., *Nucl. Acids Res.* 25: 3389-3402, 1997.
Ausubel et al., "Current Protocols in Molecular Biology" John Wiley & Sons Inc, 1994-1998, Chapter 15.
Aviv and Leder, *Proc. Natl. Acad. Sci. USA* 69: 1408, 1972.
Bevan, *Nucleic Acids Res* 12: 8711-8721, 1984.
Bonner and Laskey, *Eur. J. Biochem.* 46: 83, 1974.
Bodeau, Molecular and genetic regulation of Bronze-2 and other maize anthocyanin genes. Dissertation, Stanford University, USA, 1994
Brendel et al., In *A look beyond transcription, ASPP*, USA, Bailey-Serres and Gallie, eds, 1998.
Brouillard and Dangles, In: *The Flavonoids—Advance in Research since 1986*. Harborne, J. B. (ed), Chapman and Hall, London, UK, 1-22, 1993.
Brugliera et al., *Plant J.* 5: 81-92, 1994.
Brugliera, Characterization of floral specific genes isolated from *Petunia hybrida*. RMIT, Australia. PhD thesis, 1994.
Bullock et al., *Biotechniques* 5: 376, 1987.
Comai et al., *Plant Mol. Biol.* 15: 373-381, 1990.
Depicker et al., *J Mol. and Appl. Genetics I:* 561-573, 1982.
Diehn et al., *Genet Engin*, 18: 83-99, 1996
Elomaa et al., *Molecular and General Genetics*, 248: 649-656, 1995
Franck et al., *Cell* 21: 285-294, 1980.
Galun and Breiman, Transgenic Plants, Imperial College Press, London, England, 1997
Guilley et al., *Cell* 30: 763-773. 1982,
Hanahan, *J. Mol. Biol.* 166: 557, 1983.
Harpster et al., *MGG* 212: 182-190, 1988.
Haseloff et al., *Proc. Natl. Acad. Sci USA*, 94: 2122-2127, 1997
Holton and Cornish, *Plant Cell* 7: 1071-1083, 1995.
Holton and Graham, *Nuc. Acids Res.* 19: 1156, 1990.
Holton et al., *Nature* 366: 276279, 1993a.
Holton et al., *Plant J.* 4: 1003-1010, 1993b
Holton, Isolation and characterization of petal specific genes from *Petunia hybrida*. PhD thesis, University of Melbourne, Australia, 1992
Huang and Miller, *Adv. Appl. Math.* 12: 373-381, 1991.
Inoue et al., *Gene* 96: 23-28, 1990.
Janssen and Gardner, *Plant Molecular Biology*, 14: 61-72, 1989
Jefferson, et al., *EMBO J.* 6: 3901-3907, 1987.
Johnson et al., In *A look beyond transcription, ASPP*, USA, Bailey-Serres and Gallie, eds, 1998.
Karn et al., *Gene* 32: 217-224, 1984.
Lazo et al., *Bio/Technology* 9: 963-967, 1991.
Lee et al., *EMBO J.* 7: 1241-1248, 1988.
Lu et al., *Bio/Technology* 9: 864-868, 1991.
Merchant et al., *Molecular Breeding* 4: 187-194, 1998.
Marmur and Doty, *J. Mol. Biol.* 5: 109, 1962.
McBride and Summerfelt, *Plant Molecular Biology* 14: 269-276, 1990.
Merrfield, *J. Am. Chem. Soc.* 85: 2149, 1964.
Mitsuhara et al., *Plant Cell Physiol.* 37: 49-59, 1996.
Mol et al., *Trends Plant Sci.* 3: 212-217, 1998.
Pearson and Lipman, *Proc. Natl. Acad. Sci.* USA 85(8): 2444-2448, 1988.
Plant Molecular Biology Labfax, Croy (ed), Bios scientific Publishers, Oxford, UK, 1993.
Plant Molecular Biology Manual ($2^{nd}$ edition), Gelvin and Schilperoot (eds), Kluwer Academic Publisher, The Netherlands, 1994.
Robinson and Firoozabady, *Scientia Horticulturae* 55: 93-99, 1993.
Rout et al., *Scientia Horticulturae* 81: 201-238, 1999.
Sambrook et al., Molecular Cloning: A Laboratory Manual, Cold Spring Harbor Laboratories, Cold Spring Harbor, N.Y., USA, 1989.
Sambrook and Russell, Molecular Cloning: A Laboratory Manual $3^{rd}$ edition, Cold Spring Harbor Laboratories, Cold Spring Harbor, N.Y., USA, 2001
Seitz and Hinderer, Anthocyanins. In: *Cell Culture and Somatic Cell Genetics of Plants*. Constabel, F. and Vasil, I. K. (eds.), Academic Press, New York, USA, 5: 49-76, 1988.
Short et al., *Nucl. Acids Res.* 16: 7583-7600, 1988.
Sommer and Saedler, *Mol Gen. Gent.*, 202: 429-434, 1986.
Strack and Wray, In: *The Flavonoids—Advances in Research since 1986*. Harborne, J. B. (ed), Chapman and Hall, London, UK, 1-22, 1993.
Tanaka et al., *Plant Cell Physiol.* 36: 1023-1031, 1995.
Tanaka et al., *Plant Cell Physiol.* 37: 711-716, 1996.
Thompson et al., *Nucleic Acids Research* 22: 4673-4680, 1994.
Turpen and Griffith, *Bio Techniques* 4: 11-15, 1986.
van Hoof and Green, *Plant Molecular Biology*, 35: 383-387, 1997
Winkel-Shirley, *Plant Physiol.* 126: 485-493, 2001a.
Winkel-Shirley, *Plant Physiol.* 127: 1399-1404, 2001b.
Yonekura-Sakakibara et al., *Plant Cell Physiol.* 41: 495-502, 2000.

The claims defining the invention are as follows:

1. An isolated nucleic acid molecule comprising a sequence of nucleotides encoding a flavonoid 3',5' hydroxylase (F3'5'H), said nucleotide sequence selected from the group consisting of:
   (i) a nucleotide sequence encoding the amino acid sequence as set forth in SEQ ID NO: 12;
   (ii) a nucleotide sequence encoding an amino acid sequence having at least 95% identity to the amino acid sequence as set forth in SEQ ID NO: 12;
   (iii) the nucleotide sequence as set forth in SEQ ID NO: 11; and
   (iv) a nucleotide sequence capable of hybridizing to the complementary sequence of the nucleotide sequence as set forth in SEQ ID NO: 11 under high stringency conditions which comprise hybridization at 42° C. in 50% v/v formamide, 1M NaCl, 1% w/v SDS, and 10% w/v dextran sulphate, and washings at 65° C. first in 2×SSC, 1% w/v SDS and subsequently in 0.2×SSC, 1% w/v SDS.

2. The isolated nucleic acid molecule of claim 1 operably linked to a promoter.

3. The isolated nucleic acid molecule of claim 2 wherein the promoter is the CaMV 35S promoter.

4. A genetic construct comprising the nucleic acid molecule of any one of claims 1 to 3.

5. A genetically modified plant or progeny thereof comprising the nucleic acid molecule of claim 1 which is heterologous to said plant and said progeny thereof, wherein expression of said nucleic acid molecule results in an altered flower color in said plant and said progeny thereof.

6. The genetically modified plant of claim 5 wherein said nucleic acid molecule is operably linked to the CaMV 35S promoter.

7. The genetically modified plant according to claim 5 or claim 6, wherein the plant is a rose or a progeny thereof, and wherein said rose progeny comprises said nucleic acid molecule.

* * * * *

UNITED STATES PATENT AND TRADEMARK OFFICE
CERTIFICATE OF CORRECTION

PATENT NO.      : 7,612,257 B2                                    Page 1 of 1
APPLICATION NO. : 10/526133
DATED           : November 3, 2009
INVENTOR(S)     : Brugliera et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this

Nineteenth Day of October, 2010

David J. Kappos
*Director of the United States Patent and Trademark Office*

SEQUENCE LISTING

<160> NUMBER OF SEQ ID NOS: 32

<210> SEQ ID NO 1
<211> LENGTH: 1812
<212> TYPE: DNA
<213> ORGANISM: petunia

<400> SEQUENCE: 1

| | | | | | | |
|---|---|---|---|---|---|---|
| ctttctacta | gctacttcgt | tatatatatg | taaaattgtg | actttgaaaa | tcatttaaat | 60 |
| tatcataagg | ttcattttat | cttgatcaaa | atatttactt | cggccatata | cgttttcctt | 120 |
| tagtcatgat | gctacttact | gagcttggtg | cagcaacttc | aatctttcta | atagcacaca | 180 |
| taatcatttc | aactcttatt | tcaaaaacta | ccggccggca | tctaccgccg | gggccaagag | 240 |
| ggtggccggt | gatcggagca | cttccacttt | taggagccat | gccacatgtt | tccttagcta | 300 |
| aaatggcaaa | aaaatatgga | gcaatcatgt | atctcaaagt | tggaacatgt | ggcatggcag | 360 |
| ttgcttctac | ccctgatgct | gctaaagcat | tcttgaaaac | acttgatatc | aacttctcca | 420 |
| atcgtccacc | taatgcaggt | gccactcact | tagcttataa | tgctcaagac | atggtttttg | 480 |
| cacattatgg | accacgatgg | aagttgctaa | ggaaattaag | caacttgcat | atgctagggg | 540 |
| gaaaagcctt | agagaattgg | gcaaatgttc | gtgccaatga | gctagggcac | atgctaaaat | 600 |
| caatgtccga | tatgagtcga | gagggccaga | gggttgtggt | ggcggagatg | ttgacatttg | 660 |
| ccatggccaa | tatgatcgga | caagtgatgc | taagcaaaag | agtatttgta | gataaaggtg | 720 |
| ttgaggtaaa | tgaatttaag | gacatggttg | tagagttaat | gacaatagca | gggtatttca | 780 |
| acattggtga | ttttattcct | tgtttagctt | ggatggattt | acaagggata | gaaaaacgaa | 840 |
| tgaaacgttt | acataagaag | tttgatgctt | tattgacaaa | gatgtttgat | gaacacaaag | 900 |
| caactaccta | tgaacgtaag | gggaaaccag | attttcttga | tgttgttatg | gaaaatgggg | 960 |
| acaattctga | aggagaaaga | ctcagtacaa | ccaacatcaa | agcacttttg | ctgaatttgt | 1020 |
| tcacagctgg | tacggacact | tcttctagtg | caatagaatg | ggcacttgca | gaaatgatga | 1080 |
| agaaccctgc | cattttgaaa | aaagcacaag | cagaaatgga | tcaagtcatt | ggaagaaata | 1140 |
| ggcgtttact | cgaatccgat | atcccaaatc | tcccttacct | ccgagcaatt | tgcaaagaaa | 1200 |
| catttcgaaa | acaccttct | acaccattaa | atcttcctag | gatctcgaac | gaaccatgca | 1260 |
| tagtcgatgg | ttattacata | ccaaaaaaca | ctaggcttag | tgttaacata | tgggcaattg | 1320 |
| gaagagatcc | ccaagtttgg | gaaaatccac | tagagtttaa | tcccgaaaga | ttcttgagtg | 1380 |
| gaagaaactc | caagattgat | cctcgaggga | acgattttga | attgatacca | tttggtgctg | 1440 |
| gacgaagaat | ttgtgcagga | acaagaatgg | gaattgtaat | ggtggaatat | atattaggaa | 1500 |
| ctttggttca | ttcatttgat | tggaaattac | caagtgaagt | tattgagttg | aatatggaag | 1560 |
| aagcttttgg | cttagctttg | cagaaagctg | tccctcttga | agctatggtt | actccaaggt | 1620 |
| tacaattgga | tgtttatgta | ccatagctat | agatgtgtat | tgtgctataa | ttgcgcatgt | 1680 |
| tgttggttgt | agcatgagat | attaaaagga | gtacatgaag | cgcattgcat | gagtttaact | 1740 |
| tgtagctcct | taatatttta | ggtattttc | aattaataag | ttcttgttgg | ttgggtaaaa | 1800 |
| aaaaaaaaaa | aa | | | | | 1812 |

<210> SEQ ID NO 2
<211> LENGTH: 506
<212> TYPE: PRT
<213> ORGANISM: petunia

<400> SEQUENCE: 2

```
Met Met Leu Leu Thr Glu Leu Gly Ala Ala Thr Ser Ile Phe Leu Ile
1               5                   10                  15

Ala His Ile Ile Ile Ser Thr Leu Ile Ser Lys Thr Thr Gly Arg His
                20                  25                  30

Leu Pro Pro Gly Pro Arg Gly Trp Pro Val Ile Gly Ala Leu Pro Leu
            35                  40                  45

Leu Gly Ala Met Pro His Val Ser Leu Ala Lys Met Ala Lys Lys Tyr
        50                  55                  60

Gly Ala Ile Met Tyr Leu Lys Val Gly Thr Cys Gly Met Ala Val Ala
65                  70                  75                  80

Ser Thr Pro Asp Ala Ala Lys Ala Phe Leu Lys Thr Leu Asp Ile Asn
                85                  90                  95

Phe Ser Asn Arg Pro Pro Asn Ala Gly Ala Thr His Leu Ala Tyr Asn
            100                 105                 110

Ala Gln Asp Met Val Phe Ala His Tyr Gly Pro Arg Trp Lys Leu Leu
        115                 120                 125

Arg Lys Leu Ser Asn Leu His Met Leu Gly Gly Lys Ala Leu Glu Asn
            130                 135                 140

Trp Ala Asn Val Arg Ala Asn Glu Leu Gly His Met Leu Lys Ser Met
145                 150                 155                 160

Ser Asp Met Ser Arg Glu Gly Gln Arg Val Val Ala Glu Met Leu
                165                 170                 175

Thr Phe Ala Met Ala Asn Met Ile Gly Gln Val Met Leu Ser Lys Arg
            180                 185                 190

Val Phe Val Asp Lys Gly Val Glu Val Asn Glu Phe Lys Asp Met Val
        195                 200                 205

Val Glu Leu Met Thr Ile Ala Gly Tyr Phe Asn Ile Gly Asp Phe Ile
    210                 215                 220

Pro Cys Leu Ala Trp Met Asp Leu Gln Gly Ile Glu Lys Arg Met Lys
225                 230                 235                 240

Arg Leu His Lys Lys Phe Asp Ala Leu Leu Thr Lys Met Phe Asp Glu
                245                 250                 255

His Lys Ala Thr Thr Tyr Glu Arg Lys Gly Lys Pro Asp Phe Leu Asp
            260                 265                 270

Val Val Met Glu Asn Gly Asp Asn Ser Glu Gly Glu Arg Leu Ser Thr
        275                 280                 285

Thr Asn Ile Lys Ala Leu Leu Leu Asn Leu Phe Thr Ala Gly Thr Asp
    290                 295                 300

Thr Ser Ser Ser Ala Ile Glu Trp Ala Leu Ala Glu Met Met Lys Asn
305                 310                 315                 320

Pro Ala Ile Leu Lys Lys Ala Gln Ala Glu Met Asp Gln Val Ile Gly
                325                 330                 335

Arg Asn Arg Arg Leu Leu Glu Ser Asp Ile Pro Asn Leu Pro Tyr Leu
            340                 345                 350

Arg Ala Ile Cys Lys Glu Thr Phe Arg Lys His Pro Ser Thr Pro Leu
        355                 360                 365

Asn Leu Pro Arg Ile Ser Asn Glu Pro Cys Ile Val Asp Gly Tyr Tyr
    370                 375                 380

Ile Pro Lys Asn Thr Arg Leu Ser Val Asn Ile Trp Ala Ile Gly Arg
385                 390                 395                 400

Asp Pro Gln Val Trp Glu Asn Pro Leu Glu Phe Asn Pro Glu Arg Phe
```

405                 410                 415
Leu Ser Gly Arg Asn Ser Lys Ile Asp Pro Arg Gly Asn Asp Phe Glu
            420                 425                 430
Leu Ile Pro Phe Gly Ala Gly Arg Arg Ile Cys Ala Gly Thr Arg Met
        435                 440                 445
Gly Ile Val Met Val Glu Tyr Ile Leu Gly Thr Leu Val His Ser Phe
    450                 455                 460
Asp Trp Lys Leu Pro Ser Glu Val Ile Glu Leu Asn Met Glu Glu Ala
465                 470                 475                 480
Phe Gly Leu Ala Leu Gln Lys Ala Val Pro Leu Glu Ala Met Val Thr
                485                 490                 495
Pro Arg Leu Gln Leu Asp Val Tyr Val Pro
            500                 505

<210> SEQ ID NO 3
<211> LENGTH: 1756
<212> TYPE: DNA
<213> ORGANISM: petunia

<400> SEQUENCE: 3
ttgaatccag ctctatctgg ctttagacaa tggtgctact tagtgagctt gctgcagcaa        60
ccttaatctt tctaacaaca catatcttca tttcaactct tctttctata actaacggcc       120
ggcgtctccc gccagggcca agagggtggc cggtgatcgg agcacttcca cttttaggag       180
ccatgccaca tgtttcctta gctaaaatgg caaaaaaata tggagcaatc atgtatctca       240
aagttggaac gtgtggcatg gtagttgctt ctacccctga tgctgctaaa gcgttcttga       300
aaacacttga tctcaacttc tccaatcgtc cacctaatgc aggtgccacc cacttagcct       360
atggtgctca agacatggtt tttgcacatt atggaccaag atggaagttg ctaaggaaat       420
taagcaactt acatatgcta ggggggaaag ccttagaaaa ttgggcaaat gttcgtgcca       480
atgagctagg acacatgcta aaatcgatgt ttgatatgag cagagaaggg gagagagttg       540
tggtggcgga gatgttgaca tttgccatgc gaatatgatc ggacaggtg atacttagca       600
aaagagtatt tgtaaataaa ggtgttgagg taatgaatt taaggacatg gtggtagagt       660
taatgacaac agcagggtat tttaacattg gtgattttat tccttgttta gcttggatgg       720
atttacaagg gatagaaaaa ggaatgaaac gtttacataa gaagtttgat gctttattga       780
caaagatgtt tgatgaacac aaagcaacta gctatgaacg taaggggaaa ccagattttc       840
ttgattgtgt tatggaaaat agggacaatt ctgaaggaga aaggctcagt acaaccaaca       900
tcaaagcact cttgctgaat tgttcacag ctggtacaga cacttcttct agtgcaatag       960
aatgggcact tgcagagatg atgaagaacc ctgccatttt aaagaaagca caaggagaaa      1020
tggatcaagt cattggaaac aataggcgtc tgctcgaatc ggatatccca aatctcccgt      1080
acctccgagc aatttgcaaa gaaacatttc gaaagcaccc ttctacacca ttaaatctcc      1140
ctaggatctc gaacgaacca tgcattgtcg atggttatta cataccaaaa aacactaggc      1200
ttagtgttaa catatgggca attggaagag atcccgaagt tgggagaaac ccactagagt      1260
tttatcctga aaggttcttg agtggaagaa actcgaagat tgatcctcga gggaacgact      1320
tgaattgat accatttggt gctggacgaa gaatttgtgc agggacaaga atgggaatcg      1380
taatggtgga atatatatta ggaactttgg tccattcatt tgattggaaa ttaccaagtg      1440
aagttattga gctaaatatg gaagaagctt tggattagc tttgcagaaa gctgtccctc      1500
ttgaagctat ggttactcca aggctgccta ttgatgttta tgcacctta gcttgaaaca      1560

```
tgcctttacg ttggtttcag ttttgggtag tataatgttg tggtgtttgg ctatagaaat    1620
attaataaat gctagtatct tgaaggcgcg tgcagggga gggggttgtc ttagatagta     1680
gtaatatgtt agccttcctt ttatttcttg tgattgtgag aatcttgata tgttttcttg    1740
gaaaaaaaaa aaaaaa                                                     1756

<210> SEQ ID NO 4
<211> LENGTH: 508
<212> TYPE: PRT
<213> ORGANISM: petunia

<400> SEQUENCE: 4

Met Val Leu Leu Ser Glu Leu Ala Ala Thr Leu Ile Phe Leu Thr
1               5                   10                  15

Thr His Ile Phe Ile Ser Thr Leu Leu Ser Ile Thr Asn Gly Arg Arg
                20                  25                  30

Leu Pro Pro Gly Pro Arg Gly Trp Pro Val Ile Gly Ala Leu Pro Leu
            35                  40                  45

Leu Gly Ala Met Pro His Val Ser Leu Ala Lys Met Ala Lys Lys Tyr
50                  55                  60

Gly Ala Ile Met Tyr Leu Lys Val Gly Thr Cys Gly Met Val Val Ala
65                  70                  75                  80

Ser Thr Pro Asp Ala Ala Lys Ala Phe Leu Lys Thr Leu Asp Leu Asn
                85                  90                  95

Phe Ser Asn Arg Pro Pro Asn Ala Gly Ala Thr His Leu Ala Tyr Gly
            100                 105                 110

Ala Gln Asp Met Val Phe Ala His Tyr Gly Pro Arg Trp Lys Leu Leu
        115                 120                 125

Arg Lys Leu Ser Asn Leu His Met Leu Gly Gly Lys Ala Leu Glu Asn
130                 135                 140

Trp Ala Asn Val Arg Ala Asn Glu Leu Gly His Met Leu Lys Ser Met
145                 150                 155                 160

Phe Asp Met Ser Arg Glu Gly Glu Arg Val Val Val Ala Glu Met Leu
                165                 170                 175

Thr Phe Ala Met Ala Asn Met Ile Gly Gln Val Ile Leu Ser Lys Arg
            180                 185                 190

Val Phe Val Asn Lys Gly Val Glu Val Asn Glu Phe Lys Asp Met Val
        195                 200                 205

Val Glu Leu Met Thr Thr Ala Gly Tyr Phe Asn Ile Gly Asp Phe Ile
210                 215                 220

Pro Cys Leu Ala Trp Met Asp Leu Gln Gly Ile Glu Lys Gly Met Lys
225                 230                 235                 240

Arg Leu His Lys Lys Phe Asp Ala Leu Leu Thr Lys Met Phe Asp Glu
                245                 250                 255

His Lys Ala Thr Ser Tyr Glu Arg Lys Gly Lys Pro Asp Phe Leu Asp
            260                 265                 270

Cys Val Met Glu Asn Arg Asp Asn Ser Glu Gly Glu Arg Leu Ser Thr
        275                 280                 285

Thr Asn Ile Lys Ala Leu Leu Leu Asn Leu Phe Thr Ala Gly Thr Asp
290                 295                 300

Thr Ser Ser Ser Ala Ile Glu Trp Ala Leu Ala Glu Met Met Lys Asn
305                 310                 315                 320

Pro Ala Ile Leu Lys Lys Ala Gln Gly Glu Met Asp Gln Val Ile Gly
                325                 330                 335
```

```
Asn Asn Arg Arg Leu Leu Glu Ser Asp Ile Pro Asn Leu Pro Tyr Leu
            340                 345                 350

Arg Ala Ile Cys Lys Glu Thr Phe Arg Lys His Pro Ser Thr Pro Leu
            355                 360                 365

Asn Leu Pro Arg Ile Ser Asn Glu Pro Cys Ile Val Asp Gly Tyr Tyr
            370                 375                 380

Ile Pro Lys Asn Thr Arg Leu Ser Val Asn Ile Trp Ala Ile Gly Arg
385                 390                 395                 400

Asp Pro Glu Val Trp Glu Asn Pro Leu Glu Phe Tyr Pro Glu Arg Phe
            405                 410                 415

Leu Ser Gly Arg Asn Ser Lys Ile Asp Pro Arg Gly Asn Asp Phe Glu
            420                 425                 430

Leu Ile Pro Phe Gly Ala Gly Arg Arg Ile Cys Ala Gly Thr Arg Met
            435                 440                 445

Gly Ile Val Met Val Glu Tyr Ile Leu Gly Thr Leu Val His Ser Phe
            450                 455                 460

Asp Trp Lys Leu Pro Ser Glu Val Ile Glu Leu Asn Met Glu Glu Ala
465                 470                 475                 480

Phe Gly Leu Ala Leu Gln Lys Ala Val Pro Leu Glu Ala Met Val Thr
            485                 490                 495

Pro Arg Leu Pro Ile Asp Val Tyr Ala Pro Leu Ala
            500                 505

<210> SEQ ID NO 5
<211> LENGTH: 2934
<212> TYPE: DNA
<213> ORGANISM: rosa

<400> SEQUENCE: 5
aagcttcagc aagagttgaa gaaataggga cagagccatc catgtgcttt gatgaatctg      60
atgggataca aaatgtgaaa gattcacttg ctgatttatc cagaatttct tcatatagtg     120
aggagaatgt tgaaagatct aatgatgagc actctgttaa actagacgga attcatgtgc     180
agcacgagtg tcatgagggc agtgaagaag acaaacctga tggtaagagc ggtgagaatg     240
cagttgatct ggctaatcat ggcatggctc gaactgattt ttgtcagata acagaagaga     300
ttgagaatgg agtagtcatc actgagatga gcaacattgc caaccctgat aaaactgata     360
ttccaaacgg ggtgcctcaa aatgagactg atgatggatt taataacact caggatgatg     420
ctaatacaaa ggaagtgaca gaagagaatt ctgacagacg tgcgaaggaa gtgacagaag     480
agaattctga caaagatgtt ttgaagaata tccttgaatt ctcacgtgct tcttctgtgg     540
tggattttga aattccagtg ttggatgtga aatttacttc tcttgaaagt tgcagtgcca     600
cttgttctct tgcagccctt ttgtctgaat cgccggaatc aatgactgaa gcaccttgtg     660
tgaggcaaat tgatgatgtg ccccgggttg gtgaggagtc tagcttgatt ttggtggaag     720
atcgggagcc ggttggtcct actcctgatg gtaattttc  tgtggatatg gattactata     780
gtgtagcaga accttttgagc acatgggatg cgaatctgca gtgtgaaaca tcaaatagcc     840
atgagacttt tgctgcaagt ctcatttgat agcttctgtg ttaataactt gttagtctg      900
tacataaatt tgtctagaca agaattggtc gtgtactatc gtgtgttttt gccgtgcttt     960
agtactcatg aaccaattca gagaaaactg gctgcatatt tgaggagtc  tctgaattct    1020
tcaatgctca actggtatgc atgtaggtgg catatcactt cagggattct tctattcttt    1080
aactttacgc atcttgacat tttgtatata acaaaatcag gtctattggg tgaaagtaat    1140
```

```
tggctagaat ggaaagctct acggttttac cgcaggtcaa ttttcatagc tccacaagtg   1200
aattgaaaat gctcataggc tttatgtttg tcctccacct ctggcgacga tgtttgttgg   1260
ggagttaact caaacctacc accaaactcg aacccatctt ccataattta taatacaaat   1320
ttgcgatcat ttgttcatcc aattattgtg acactcggct accacccaaa atatcggtca   1380
cagacccaaa cgtattgtca caacaaatcg tgtctctcgc attaaacaca gctagaaaga   1440
agagttgaac ccacaattcg agcacccact acctatgtac gaagtcatga gttcgagtca   1500
ccataggggt agaagtgaaa tcatttgatc atctttaaag aaataaaagg aagagttgaa   1560
cccacaattg gctcttgtcc caaaagaaac taatagttca gtgcaccgac gtgtatttgc   1620
accgacataa atggattgtt agattatatt aaatacactc ttaggttatt aataaaaata   1680
ttaattataa atatcaaaag ttgagatcat cttataaatg ttgggtcagt tacaccgtcg   1740
gtgcatagaa taatttccaa actatataat agccttcatt ttctgattta gctcatggga   1800
catgattgct ataaataatt gtactcgtag aggcatactt gtgtcttttt atacagttgt   1860
actgaagctc agaaaagttt atgaaggtga gaactgagaa gggcaaggca tttggtagtt   1920
gaggtatatg agagcatgaa ccccatgcat tgcagctacc acctctcttt tttccttctt   1980
cccatacaaa taaaaccaac tcttctcacc taagtctatc atctttattt atggcagctc   2040
ttgcttaatt agctcatcta tattatatta tttatctata atatgtgtca ctctgtctac   2100
ctaccagccc aaaataaaac tgataatagt caatttgatg atattttttg ttttttgttt   2160
tgttttgtct ttttttgtatt gattttttta aaattaaaat gacttcattt tttgtttttg   2220 ttttttttc tatttttttt tatagaaaaa ttggcaaact ttcattatct gttattgatg   2280
acaattaagc cattaaaacc tataattaat tatctttcaa ttcgagtaaa tttaaaacgg   2340
tgtaaaatta aaatatgatc gtattcttaa atgaataaaa ctcacttaat aatagtaata   2400
cttgaatcac atctacgaac atagattctt ttcatccagt ctaaccatgt ttgaatatat   2460
agagtttgat tatggttatg tctttgtcca cattttggtt tgtaaataaa tgtgcaacgg   2520
aggtatggta ctgttgctct atcaaattca gtttgaatt aaaagaaaaa aaaaagacg   2580 atattttgtg cgctttgttt ggtaggtaaa acgagagaac aaacgcattc caaatcatgc   2640
ggattttgat cggcaacaca caccacaaaa aaccgtacac gatgcacgtg ccatttgccg   2700
ggggtttcta acaaggtaat tgggcaggca cgtgatcccc cagctaccca cctctcgctt   2760
cccttctcaa actccttttc catgtatata taaccccct tttctcagac cattatattc   2820
taacattttt gctttgctat tgtaacgcaa caaaaactgc tcattccatc cttgttcctc   2880
cccattttga tcttctctcg acccttctcc gagatgggta ccgagctcga attc         2934
```

<210> SEQ ID NO 6
<211> LENGTH: 24
<212> TYPE: DNA
<213> ORGANISM: petunia

<400> SEQUENCE: 6
gttctcgagg aaagataata caat                                           24

<210> SEQ ID NO 7
<211> LENGTH: 20
<212> TYPE: DNA
<213> ORGANISM: petunia

<400> SEQUENCE: 7

```
caagatcgta ggactgcatg                                                  20

<210> SEQ ID NO 8
<211> LENGTH: 20
<212> TYPE: DNA
<213> ORGANISM: chrysanthemum

<400> SEQUENCE: 8
gttaaggaag ccatgggtgt                                                  20

<210> SEQ ID NO 9
<211> LENGTH: 1648
<212> TYPE: DNA
<213> ORGANISM: viola

<400> SEQUENCE: 9
agccaatatg gcaattccag tcactgacct tgctgtcgcg gttatccttt tcttgatcac      60
tcgcttccta gttcgttctc ttttcaagaa accaaccgga ccgctcccgc cgggtccttc     120
aggctggccc ttggtgggcg cgctccctct cctaggcgcc atgcctcacg tcacactagc     180
caacctcgct aaaaaatacg gtccgatcat gtacctaaaa atgggcacgt gcgacatggt     240
ggtcgcgtcc actcccgact cggctcgagc cttcctcaaa accctagacc tcaacttctc     300
cgaccgcccg cccaacgccg cgccacccca tttggcgtac ggcgcgcagg acttggtctt     360
cgcgaagtac ggtccaaggt ggaagaccct aagaaaattg agcaacctcc acatgctagg     420
cgggaaggcg ctggacgatt gggctcacgt gagggctaac gagctaggcc acatgcttaa     480
cgccatgtgc gaggcgagcc ggtgcggaga gcccgtggtg ctggccgaga tgctcacgta     540
cgccatggcc aacatgatcg gtcaagtgat actgagtcgg cgcgtgttcg tcaccaaagg     600
gacagagtcg aacgagttca agatatggt ggtcgagttg atgacttccg cggggtattt     660
caacattggt gacttcatac cgtcgattgc ttggatggat ttgcaaggga tcgagcgagg     720
gatgaagaaa ttgcacacga aattcgatgt tttgttgacg aagatgatga aggagcacag     780
agcgacgagt catgagcgcg aagggaaatc ggatttcctc gacgtcctct tggaagaatg     840
cgagaataca aatggcgaga agcttaatgt taccaacgtc aaagctgtcc tcttgaactt     900
attcacggcg gtacggaca catcttcaag cataatcgaa tgggcgttaa ccgaaatgat     960
gaagaatccg acgatcttaa aaaagaccca agaagagatg gatcgagtca tcggtcgcga    1020
tcggagattg ctcgaatccg acgttttcgaa actcccgtat ttacaagcca tagcgaaaga    1080
aacatatcgt aaacacccat cgacacctct aaacctgccg aggattgcga tccaagcatg    1140
tgaagttgat ggctactaca tccccaaaga cacgaggctt agcgtcaaca tttgggcgat    1200
cggtcgggac ccaagtgttt gggagaatcc atcggagttc tcgcctgaaa gattcttgtc    1260
tgaggagaat gggaagatca gtccaggcgg gaatgatttt gagctgattc cgtttggagc    1320
agggaggaga atttgtgctg gacaaggat gggaatggtc cttgtaagtt atattttggg    1380
cactttggtc cattcttttg attggaaatt accaaatggg gtcagtgaga ttaacatgga    1440
tgagagtttt gggcttgcgt tgcaaaaggc cgtgcctctc tcggctacgg tcagtccacg    1500
attggcccca agcgcgtacg ttatatgagc tgatgggctg ggcctgagcc caaacatatt    1560
gggtgtgttt tatctgtaat ttttaatatt ataaagttcg taattttgta tttatggtta    1620
attatgagtt aaaaaaaaaa aaaaaaaa                                        1648

<210> SEQ ID NO 10
<211> LENGTH: 506
```

<212> TYPE: PRT
<213> ORGANISM: viola

<400> SEQUENCE: 10

```
Met Ala Ile Pro Val Thr Asp Leu Ala Val Ala Val Ile Leu Phe Leu
1               5                   10                  15

Ile Thr Arg Phe Leu Val Arg Ser Leu Phe Lys Lys Pro Thr Gly Pro
            20                  25                  30

Leu Pro Pro Gly Pro Ser Gly Trp Pro Leu Val Gly Ala Leu Pro Leu
        35                  40                  45

Leu Gly Ala Met Pro His Val Thr Leu Ala Asn Leu Ala Lys Lys Tyr
    50                  55                  60

Gly Pro Ile Met Tyr Leu Lys Met Gly Thr Cys Asp Met Val Val Ala
65                  70                  75                  80

Ser Thr Pro Asp Ser Ala Arg Ala Phe Leu Lys Thr Leu Asp Leu Asn
                85                  90                  95

Phe Ser Asp Arg Pro Pro Asn Ala Gly Ala Thr His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
    130                 135                 140

Trp Ala His Val Arg Ala Asn Glu Leu Gly His Met Leu Asn Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
    210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Met Lys Glu
                245                 250                 255

His Arg Ala Thr Ser His Glu Arg Glu Gly Lys Ser Asp Phe Leu Asp
            260                 265                 270

Val Leu Leu Glu Glu Cys Glu Asn Thr Asn Gly Glu Lys Leu Asn Val
        275                 280                 285

Thr Asn Val Lys Ala Val Leu Leu Asn Leu Phe Thr Ala Gly Thr Asp
    290                 295                 300

Thr Ser Ser Ser Ile Ile Glu Trp Ala Leu Thr Glu Met Met Lys Asn
305                 310                 315                 320

Pro Thr Ile Leu Lys Lys Thr Gln Glu Glu Met Asp Arg Val Ile Gly
                325                 330                 335

Arg Asp Arg Arg Leu Leu Glu Ser Asp Val Ser Lys Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
    370                 375                 380

Ile Pro Lys Asp Thr Arg Leu Ser Val Asn Ile Trp Ala Ile Gly Arg
385                 390                 395                 400
```

```
Asp Pro Ser Val Trp Glu Asn Pro Ser Glu Phe Ser Pro Glu Arg Phe
            405                 410                 415

Leu Ser Glu Glu Asn Gly Lys Ile Ser Pro Gly Gly Asn Asp Phe Glu
            420                 425                 430

Leu Ile Pro Phe Gly Ala Gly Arg Arg Ile Cys Ala Gly Thr Arg Met
            435                 440                 445

Gly Met Val Leu Val Ser Tyr Ile Leu Gly Thr Leu Val His Ser Phe
            450                 455                 460

Asp Trp Lys Leu Pro Asn Gly Val Ser Glu Ile Asn Met Asp Glu Ser
465                 470                 475                 480

Phe Gly Leu Ala Leu Gln Lys Ala Val Pro Leu Ser Ala Thr Val Ser
            485                 490                 495

Pro Arg Leu Ala Pro Ser Ala Tyr Val Ile
            500                 505

<210> SEQ ID NO 11
<211> LENGTH: 1782
<212> TYPE: DNA
<213> ORGANISM: viola
<220> FEATURE:
<221> NAME/KEY: misc_feature
<222> LOCATION: (307)..(307)
<223> OTHER INFORMATION: n = any nucleotide

<400> SEQUENCE: 11
bgacaacatg gcaattctag tcaccgactt cgttgtcgcg gctataattt tcttgatcac      60
tcggttctta gttcgttctc ttttcaagaa accaacccga ccgctccccc cgggtcctct     120
cggttggccc ttggtgggcg ccctccctct cctaggcgcc atgcctcacg tcgcactagc     180
caaactcgct aagaagtatg gtccgatcat gcacctaaaa atgggcacgt gcgacatggt     240
ggtcgcgtcc accccgagt cggctcgagc cttcctcaaa acgctagacc tcaacttctc     300
caaccgncca cccaacgcgg gcgcatccca cctagcgtac ggcgcgcagg acttagtctt     360
cgccaagtac ggtccgaggt ggaagacttt aagaaaattg agcaacctcc acatgctagg     420
cgggaaggcg ttggatgatt gggcaaatgt gagggtcacc gagctaggcc acatgcttaa     480
agccatgtgc gaggcgagcc ggtgcgggga gcccgtggtg ctggccgaga tgctcacgta     540
cgccatggcg aacatgatcg gtcaagtgat actcagccgg cgcgtgttcg tgaccaaagg     600
gaccgagtct aacgagttca agacatggt ggtcgagttg atgacgtccg ccgggtactt     660
caacatcggt gacttcatac cctcgatcgc ttggatggat ttgcaaggga tcgagcgagg     720
gatgaagaag ctgcacacga gtttgatgt gttattgacg aagatggtga aggagcatag     780
agcgacgagt catgagcgca aagggaaggc agatttcctc gacgttctct ggaagaatg     840 cgacaataca aatggggaga agcttagtat taccaatatc aaagctgtcc ttttgaatct     900
attcacggcg gcacggaca catcttcgag cataatcgaa tgggcgttaa cggagatgat     960
caagaatccg acgatcttaa aaaaggcgca agaggagatg gatcgagtca tcggtcgtga    1020
tcggaggctg ctcgaatcgg acatatcgag cctcccgtac ctacaagcca ttgctaaaga    1080
aacgtatcgc aaacacccgt cgacgcctct caacttgccg aggattgcga tccaagcatg    1140
tgaagttgat ggctactaca tccctaagga cgcgaggctt agcgtgaaca tttgggcgat    1200
cggtcgggac ccgaatgttt gggagaatcc gttggagttc ttgccggaaa gattcttgtc    1260
tgaagagaat gggaagatca atccggtgg gaatgatttt aagctgattc cgtttggagc    1320
cgggaggaga atttgtgcgg ggacaaggat gggaatggtc cttgtaagtt atattttggg    1380
```

```
cactttggtc cattcttttg attggaaatt accaaatggt gtcgctgagc ttaatatgga      1440
tgaaagtttt gggcttgcat tgcaaaaggc cgtgccgctc tcggccttgg tcagcccacg      1500
gttggcctca aacccgtacg caacctgagc taatgggctg ggcctagttt tgtgggccct      1560
aatttagaga cttttgtgtt ttaaggtgtg tactttatta attgggtgct taaatgtgtg      1620
ttttaatttg tatttatggt taattatgac tttattgtat aattatttat ttttcccttc      1680 tgggtattttt atccatttaa ttttcttca gaattatgat catagttatc agaataaaat      1740
tgaaaataat gaatcggaaa aaaaaaaaa aaaaaaaaa aa                           1782
```

<210> SEQ ID NO 12
<211> LENGTH: 506
<212> TYPE: PRT
<213> ORGANISM: viola

<400> SEQUENCE: 12

```
Met Ala Ile Leu Val Thr Asp Phe Val Val Ala Ile Ile Phe Leu
1               5                   10                  15

Ile Thr Arg Phe Leu Val Arg Ser Leu Phe Lys Lys Pro Thr Arg Pro
            20                  25                  30

Leu Pro Pro Gly Pro Leu Gly Trp Pro Leu Val Gly Ala Leu Pro Leu
        35                  40                  45

Leu Gly Ala Met Pro His Val Ala Leu Ala Lys Leu Ala Lys Lys Tyr
    50                  55                  60

Gly Pro Ile Met His Leu Lys Met Gly Thr Cys Asp Met Val Val Ala
65                  70                  75                  80

Ser Thr Pro Glu Ser Ala Arg Ala Phe Leu Lys Thr Leu Asp Leu Asn
                85                  90                  95

Phe Ser Asn Arg Pro Pro Asn Ala Gly Ala Ser His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
    130                 135                 140

Trp Ala Asn Val Arg Val Thr Glu Leu Gly His Met Leu Lys Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
    210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Val Lys Glu
                245                 250                 255

His Arg Ala Thr Ser His Glu Arg Lys Gly Lys Ala Asp Phe Leu Asp
            260                 265                 270

Val Leu Leu Glu Glu Cys Asp Asn Thr Asn Gly Glu Lys Leu Ser Ile
        275                 280                 285

Thr Asn Ile Lys Ala Val Leu Leu Asn Leu Phe Thr Ala Gly Thr Asp
    290                 295                 300
```

```
Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
            325                 330                 335

Arg Asp Arg Arg Leu Leu Glu Ser Asp Ile Ser Ser Leu Pro Tyr Leu
                340                 345                 350

Gln Ala Ile Ala Lys Glu Thr Tyr Arg Lys His Pro Ser Thr Pro Leu
            355                 360                 365

Asn Leu Pro Arg Ile Ala Ile Gln Ala Cys Glu Val Asp Gly Tyr Tyr
370                 375                 380

Ile Pro Lys Asp Ala Arg Leu Ser Val Asn Ile Trp Ala Ile Gly Arg
385                 390                 395                 400

Asp Pro Asn Val Trp Glu Asn Pro Leu Glu Phe Leu Pro Glu Arg Phe
                405                 410                 415

Leu Ser Glu Glu Asn Gly Lys Ile Asn Pro Gly Gly Asn Asp Phe Lys
                420                 425                 430

Leu Ile Pro Phe Gly Ala Gly Arg Arg Ile Cys Ala Gly Thr Arg Met
            435                 440                 445

Gly Met Val Leu Val Ser Tyr Ile Leu Gly Thr Leu Val His Ser Phe
450                 455                 460

Asp Trp Lys Leu Pro Asn Gly Val Ala Glu Leu Asn Met Asp Glu Ser
465                 470                 475                 480

Phe Gly Leu Ala Leu Gln Lys Ala Val Pro Leu Ser Ala Leu Val Ser
                485                 490                 495

Pro Arg Leu Ala Ser Asn Pro Tyr Ala Thr
                500                 505

<210> SEQ ID NO 13
<211> LENGTH: 1659
<212> TYPE: DNA
<213> ORGANISM: salvia

<400> SEQUENCE: 13
catggaagcc caagaaaata tgttgttgat tgctagggca cttgttgtag catccttact      60
ctacattttg atccgtatgt ttatctcaaa attgagcacc accggccacc ctctgccccc     120
ggggccgagg ggcttttcta gtggtgggct ccttcccttg ctgggcgaca tgccacatgt     180
cgccctagca aaatggccaa aacttacggg cccgatcatg tacttgaaaa tgggcacagt     240
cggcatggtc gtggcgtcca cgccagacgc ggcgcgggcg ttcctaaaaa cccacgacgc     300
taatttctcg aaccggccgg tcaacgcggg tgccaccatc ctggcataca atgcccagga     360
catggtgttt gccccgtacg gccccaagtg agagactgct ggaagctga gcagtctcca     420 catgctgggg agcaaggccc tggaggagtg ggctgacgtc cggacctcgg aggtggggca     480
catgctggcg gcgatgcacg aggccagccg cctgggcgag gccgtggggt tgccggagat     540
gctggtgtac gcgacggcga acatgatcgg gcaggtgata ttgagccgga gattttcgt      600 gacgaaaggg aaggagatga atgaattcaa ggaaatggtg gtggagctca tgaccacagc     660
tggctatttc aacattggtg atttcattcc atggcttgct tggatggatt tgcaggggat     720
tgagagaggg atgaagaaac tgcacaagaa gtgggaccgc ttgatcggta agatgctgga     780
tgatcgattg aaatcaacct acaaacgcaa cgacaagcca gatcttcttg attctctctt     840
ggcaaatcat gatgatgaga gtaaggatga tgatgaggat tgcaagctca ccaccaccaa     900
tattaaagcc cttttactga atttatttac tgcagggaca gacacatcgt cgagcataat     960
```

-continued

```
agaatgggca ttagcggaga tgatcaagaa tccaagcatc caaaaaaggg ctcaccaaga    1020
gatggacaga gtcatcggga gagagcggcg tttgctcgaa tccgacatcc caaatctgcc    1080
atacctcaaa gccatatgca aagaggcata ccgaaaacac ccttccacgc cactaaacct    1140
gcctcggatc tccacggatg catgcgtcgt cgatggctac cacatcccca agaacacgag    1200
gttgagcgtc aacatctggg ccataggccg agatcccgac gtttgggaga atccccttga    1260
cttcaaccct gacaggttta tgtcagggtt gcaggggatt gagcccggag ggaatcactt    1320
cgagctcatt cccttttgggg cggggcgcag gatctgcgcc ggcagcagaa tggggattgt    1380
aatagtggag tatttgctgg cgacactcgt gcactctttc gaatgggatt tgccggccgg    1440
ctcagcggag atggacatgg aggaggtgtt cgggctggcc ttgcagaaag ctgtaccact    1500
tgctgctagg ctcactccta ggttgccttc acattgctat gcacctcctt ctatttaatt    1560
tgcatattta catatgttgt gttacattga gcctttgcat atgttgtatc caacctatct    1620
tataacttgt gcatgaaatt gaaaaaaaaa aaaaaaaa                            1659
```

<210> SEQ ID NO 14
<211> LENGTH: 520
<212> TYPE: PRT
<213> ORGANISM: salvia

<400> SEQUENCE: 14

```
Gly Thr Ser Met Glu Ala Gln Glu Asn Met Leu Leu Ile Ala Arg Ala
1               5                   10                  15

Leu Val Val Ala Ser Leu Leu Tyr Ile Leu Arg Met Phe Ile Ser
            20                  25                  30

Lys Leu Ser Thr Thr Gly His Pro Leu Pro Pro Gly Pro Arg Gly Phe
        35                  40                  45

Leu Val Val Gly Ser Leu Pro Leu Leu Gly Asp Met Pro His Val Ala
    50                  55                  60

Leu Ala Lys Met Ala Lys Thr Tyr Gly Pro Ile Met Tyr Leu Lys Met
65                  70                  75                  80

Gly Thr Val Gly Met Val Val Ala Ser Thr Pro Asp Ala Ala Arg Ala
                85                  90                  95

Phe Leu Lys Thr His Asp Ala Asn Phe Ser Asn Arg Pro Val Asn Ala
            100                 105                 110

Gly Ala Thr Ile Leu Ala Tyr Asn Ala Gln Asp Met Val Phe Ala Pro
        115                 120                 125

Tyr Gly Pro Lys Trp Arg Leu Leu Arg Lys Leu Ser Ser Leu His Met
    130                 135                 140

Leu Gly Ser Lys Ala Leu Glu Glu Trp Ala Asp Val Arg Thr Ser Glu
145                 150                 155                 160

Val Gly His Met Leu Ala Ala Met His Glu Ala Ser Arg Leu Gly Glu
                165                 170                 175

Ala Val Gly Leu Pro Glu Met Leu Val Tyr Ala Thr Ala Asn Met Ile
            180                 185                 190

Gly Gln Val Ile Leu Ser Arg Arg Val Phe Val Thr Lys Gly Lys Glu
        195                 200                 205

Met Asn Glu Phe Lys Glu Met Val Val Glu Leu Met Thr Thr Ala Gly
    210                 215                 220

Tyr Phe Asn Ile Gly Asp Phe Ile Pro Trp Leu Ala Trp Met Asp Leu
225                 230                 235                 240

Gln Gly Ile Glu Arg Gly Met Lys Lys Leu His Lys Lys Trp Asp Arg
```

245                 250                 255
Leu Ile Gly Lys Met Leu Asp Asp Arg Leu Lys Ser Thr Tyr Lys Arg
            260                 265                 270

Asn Asp Lys Pro Asp Leu Leu Asp Ser Leu Leu Ala Asn His Asp Asp
        275                 280                 285

Glu Ser Lys Asp Asp Asp Glu Asp Cys Lys Leu Thr Thr Thr Asn Ile
    290                 295                 300

Lys Ala Leu Leu Leu Asn Leu Phe Thr Ala Gly Thr Asp Thr Ser Ser
305                 310                 315                 320

Ser Ile Ile Glu Trp Ala Leu Ala Glu Met Ile Lys Asn Pro Ser Ile
                325                 330                 335

Gln Lys Arg Ala His Gln Glu Met Asp Arg Val Ile Gly Arg Glu Arg
            340                 345                 350

Arg Leu Leu Glu Ser Asp Ile Pro Asn Leu Pro Tyr Leu Lys Ala Ile
        355                 360                 365

Cys Lys Glu Ala Tyr Arg Lys His Pro Ser Thr Pro Leu Asn Leu Pro
    370                 375                 380

Arg Ile Ser Thr Asp Ala Cys Val Val Asp Gly Tyr His Ile Pro Lys
385                 390                 395                 400

Asn Thr Arg Leu Ser Val Asn Ile Trp Ala Ile Gly Arg Asp Pro Asp
                405                 410                 415

Val Trp Glu Asn Pro Leu Asp Phe Asn Pro Asp Arg Phe Met Ser Gly
            420                 425                 430

Leu Gln Gly Ile Glu Pro Gly Gly Asn His Phe Glu Leu Ile Pro Phe
        435                 440                 445

Gly Ala Gly Arg Arg Ile Cys Ala Gly Ser Arg Met Gly Ile Val Ile
    450                 455                 460

Val Glu Tyr Leu Leu Ala Thr Leu Val His Ser Phe Glu Trp Asp Leu
465                 470                 475                 480

Pro Ala Gly Ser Ala Glu Met Asp Met Glu Glu Val Phe Gly Leu Ala
                485                 490                 495

Leu Gln Lys Ala Val Pro Leu Ala Ala Arg Leu Thr Pro Arg Leu Pro
            500                 505                 510

Ser His Cys Tyr Ala Pro Pro Ser
        515                 520

<210> SEQ ID NO 15
<211> LENGTH: 1617
<212> TYPE: DNA
<213> ORGANISM: salvia

<400> SEQUENCE: 15
agatagtaag catggaagcc caagaaaata tgttgttgat tgctagggca cttgttgtag    60
catccttact ctacattttg atccgtatgt ttatctcaaa attgagcacc cccgccacc   120 ctctgccccc ggggccgagg ggcttccag tggtgggctc ccttcccttg ctgggcgaca   180
tgccacatgt tgccctagca aaatggcca aacttatgg cccgatcatg tacttgaaaa   240
tgggcacagt cggcatggtc gtggcgtcca cgccagacgc ggcgcgggcg ttcctaaaaa   300
cccaggacgc taatttctct aaccggccgg tcaacgcggg tgccaccatc ctggcataca   360
atgcccagga catggtgttt gccccgtacg gccccaagtg gagattgctg aggaagctga   420
gcagtctcca catgctgggg agcaaggcc tggaggagtg gccgacgtc cggacctcgg   480 aggtggggca catgctggcg gcgatgcacg aggccagccg cctggacgag gccgtggggt   540

```
tgccggagat gctggtgtac gcgacggcga acatgatcgg gaaggtgata ttgagccgga      600
gagttttcgt gacgaaaggg aaggagatga atgagttcaa ggaaatggtg gtggagctca      660
tgaccacagc tggctatttc aacattggtg atttcattcc atggcttgct tggatggatt      720
tgcaggggat tgagagaggg atgaagaaac tgcacaagaa gtgggaccgc ttgatcggta      780
agatgctgga tgatcgattg aaatcaacct acaaacgcaa cgacaagcca gatcttcttg      840
attctctctt ggcaaatcat gatgatgaga gtaaggatga tgatgaggat tgcaagctca      900
ccaccaccaa tattaaagcc ttttactga atttatttac tgcagggaca gacacatcgt       960
cgagcataat agaatgggca ctagcggaga tgatcaagaa tccaagcatc caaaaaaggg     1020
ctcaccaaga gatggacaga gtcatcggga gagagcggcg tttgctcgaa tccgacatcc     1080
caaatctgcc atacctcaaa gccatatgca agaggcata ccgaaaacac ccttccacgc      1140
cactaaacct gcctcggatc tccacggatg catgcgtcgt cgatggctac acatccccca     1200
agaacacgag gttgagcgtc aacatctggg ccataggccg agatcccgac gtttgggaga     1260
atccccttga cttcaaccct gacaggttta tgtcagggtt gcaggggatt gagcccggag     1320
ggaatcactt cgagctcatt ccctttgggg cggggcgcag gatctgcgcc ggcagcagaa     1380
tggggattgt aatagtggag tatttgctgg cgacactcgt gcactctttc gaatgggatt     1440
tgccagccgg ctcagcggag atggacatgg aggaggtgtt cgggctggcc ttgcagaaag     1500
ctgtaccact gctgctaggc tcactcccta ggttgccttc acattgctat gcacctcctt     1560
ctatttaatt tgcatattta tatatgttgt gttacattga aaaaaaaaaa aaaaaaa       1617

<210> SEQ ID NO 16
<211> LENGTH: 518
<212> TYPE: PRT
<213> ORGANISM: salvia

<400> SEQUENCE: 16

Met Glu Ala Gln Glu Asn Met Leu Leu Ile Ala Arg Ala Leu Val Val
1               5                  10                  15

Ala Ser Leu Leu Tyr Ile Leu Ile Arg Met Phe Ile Ser Lys Leu Ser
            20                  25                  30

Thr Pro Gly His Pro Leu Pro Pro Gly Pro Arg Gly Phe Pro Val Val
        35                  40                  45

Gly Ser Leu Pro Leu Leu Gly Asp Met Pro His Val Ala Leu Ala Lys
    50                  55                  60

Met Ala Lys Thr Tyr Gly Pro Ile Met Tyr Leu Lys Met Gly Thr Val
65                  70                  75                  80

Gly Met Val Val Ala Ser Thr Pro Asp Ala Ala Arg Ala Phe Leu Lys
                85                  90                  95

Thr Gln Asp Ala Asn Phe Ser Asn Arg Pro Val Asn Ala Gly Ala Thr
            100                 105                 110

Ile Leu Ala Tyr Asn Ala Gln Asp Met Val Phe Ala Pro Tyr Gly Pro
        115                 120                 125

Lys Trp Arg Leu Leu Arg Lys Leu Ser Ser Leu His Met Leu Gly Ser
    130                 135                 140

Lys Ala Leu Glu Glu Trp Ala Asp Val Arg Thr Ser Glu Val Gly His
145                 150                 155                 160

Met Leu Ala Ala Met His Glu Ala Ser Arg Leu Asp Glu Ala Val Gly
                165                 170                 175

Leu Pro Glu Met Leu Val Tyr Ala Thr Ala Asn Met Ile Gly Lys Val
            180                 185                 190
```

```
Ile Leu Ser Arg Arg Val Phe Val Thr Lys Gly Lys Glu Met Asn Glu
            195                 200                 205

Phe Lys Glu Met Val Val Glu Leu Met Thr Thr Ala Gly Tyr Phe Asn
        210                 215                 220

Ile Gly Asp Phe Ile Pro Trp Leu Ala Trp Met Asp Leu Gln Gly Ile
225                 230                 235                 240

Glu Arg Gly Met Lys Lys Leu His Lys Lys Trp Asp Arg Leu Ile Gly
                245                 250                 255

Lys Met Leu Asp Asp Arg Leu Lys Ser Thr Tyr Lys Arg Asn Asp Lys
            260                 265                 270

Pro Asp Leu Leu Asp Ser Leu Leu Ala Asn His Asp Asp Glu Ser Lys
        275                 280                 285

Asp Asp Asp Glu Asp Cys Lys Leu Thr Thr Thr Asn Ile Lys Ala Leu
290                 295                 300

Leu Leu Asn Leu Phe Thr Ala Gly Thr Asp Thr Ser Ser Ser Ile Ile
305                 310                 315                 320

Glu Trp Ala Leu Ala Glu Met Ile Lys Asn Pro Ser Ile Gln Lys Arg
                325                 330                 335

Ala His Gln Glu Met Asp Arg Val Ile Gly Arg Glu Arg Arg Leu Leu
            340                 345                 350

Glu Ser Asp Ile Pro Asn Leu Pro Tyr Leu Lys Ala Ile Cys Lys Glu
        355                 360                 365

Ala Tyr Arg Lys His Pro Ser Thr Pro Leu Asn Leu Pro Arg Ile Ser
        370                 375                 380

Thr Asp Ala Cys Val Val Asp Gly Tyr His Ile Pro Lys Asn Thr Arg
385                 390                 395                 400

Leu Ser Val Asn Ile Trp Ala Ile Gly Arg Asp Pro Asp Val Trp Glu
                405                 410                 415

Asn Pro Leu Asp Phe Asn Pro Asp Arg Phe Met Ser Gly Leu Gln Gly
            420                 425                 430

Ile Glu Pro Gly Gly Asn His Phe Glu Leu Ile Pro Phe Gly Ala Gly
        435                 440                 445

Arg Arg Ile Cys Ala Gly Ser Arg Met Gly Ile Val Ile Val Glu Tyr
        450                 455                 460

Leu Leu Ala Thr Leu Val His Ser Phe Glu Trp Asp Leu Pro Ala Gly
465                 470                 475                 480

Ser Ala Glu Met Asp Met Glu Glu Val Phe Gly Leu Ala Leu Gln Lys
                485                 490                 495

Ala Val Pro Leu Ala Ala Arg Leu Thr Pro Arg Leu Pro Ser His Cys
            500                 505                 510

Tyr Ala Pro Pro Ser Ile
        515

<210> SEQ ID NO 17
<211> LENGTH: 1730
<212> TYPE: DNA
<213> ORGANISM: sollya
<220> FEATURE:
<221> NAME/KEY: misc_feature
<222> LOCATION: (1372)..(1372)
<223> OTHER INFORMATION: n = any nucleotide

<400> SEQUENCE: 17
gatggctact accttagaat tcattctatg cttcaccatt actgcacttc ctttctata       60 ttgcatactt aacatgcgca tcctccttaa ccgtcacccg aggtcactcc caccaggtcc     120
```

-continued

```
aagaccatgg cctattgtag gaaacctccc acaccttggc accaagccac accactccat      180
agctgccatg gctcggaaat acggtcccct cctgcacctc cgcatgggca tcgtgcacgt      240
ggtggttgcc gcctctgctg atgtggcggc acagttcttg aagaatgatg ccaacttctc      300
tagccggcca ccgaattctg gtgctaagca tatggcttat aactatcacg acatggtgtt      360
tgcaccctac ggtccaaggt ggcgcatgtt gaggaaaatt tgtgccctcc atatattctc      420
cgctaaggct ctcgatgatt ttcatcgcgt gcgtgaggag gaggttgcca tactcgcgag      480
gacccctagc acacgcaggc caaaagccgg tgaatttgggg cagttgttct ctacgtgtaa      540
tgctaatgcg ctatcagtgc tgatgctagg caggaggttg ttcagcacag aagttgattc      600
aaaagcatat gatttcaaac aaatggtggt ggagctgatg actctagccg gtgagtttaa      660
cgtcagtgat tcatcccac ccctcgagtg gctagacttg caaggcgtgg cagcgaaaat      720
gaagaacgtg cacaatcgat tcgatgcgtt tctgaatgta attttggagg agcataagct      780
gaaacttaat aatagtggac atggggaaca aaaacatatg gacttgttga gtacgttgat      840
tttgcttaag gatgatgctg atagtgaggg aggaaaactc actgatactg aaatcaaagc      900
gctgcttttg aatttgtttt ctgctgggac ggacacttca tccagcacaa tagaatgggt      960
tatagctgag cttatacgca atcctaaaat cttagcccaa gcccaaagag agttggactt     1020
ggtggttggt ccaaatagac ttgtaacgga tttggaccct aaacaattaa cctacctaca     1080
agccatcgtc aaagaaacct ttcggctaca tcctgctacc ccactttcac ttccacggat     1140
cgcaaccgaa agctgtgaaa tcaacgggtt ttacattcca aagggctcaa cacttctcgt     1200
taacatatgg gccataggcc gtgatccaaa cacttgggct gaaccattgg tattccgacc     1260
tgaacgattc ttatcggatg gtgaaagtcc taatgttgat gttaaaggac gtaatttga     1320
attgatacca tttggggcgg ggcgaagaat ttgtgctggg atgaactttg gnctacgcat     1380
ggtccagtta gttactgcaa cgttaattca tgcatttaac tgggagttgc cagaagggga     1440
attgccagaa aatatgaata tggaggaaga ctatgggatt agcttgcaac ggacagtgcc     1500
attagttgtt catccaaagc ccagactaga ccatgaagtt tatcagtccc atggagttgt     1560
aaactgagta cattcatgaa ctgacccaga agctgtcaga tgtcgtctta tattgcctta     1620
tgtagtgcga ccccttgtgtg ttttttatgt attgttttgt acaaggttga agcccgtgcg     1680
gcgcatggac aattttataa gttaatttta ataaaaaaaa aaaaaaaaa                  1730
```

<210> SEQ ID NO 18
<211> LENGTH: 521
<212> TYPE: PRT
<213> ORGANISM: sollya

<400> SEQUENCE: 18

```
Met Ala Thr Thr Leu Glu Phe Ile Leu Cys Phe Thr Ile Thr Ala Leu
1               5                   10                  15

Pro Phe Leu Tyr Cys Ile Leu Asn Met Arg Ile Leu Leu Asn Arg His
                20                  25                  30

Pro Arg Ser Leu Pro Pro Gly Pro Arg Pro Trp Pro Ile Val Gly Asn
            35                  40                  45

Leu Pro His Leu Gly Thr Lys Pro His His Ser Ile Ala Ala Met Ala
        50                  55                  60

Arg Lys Tyr Gly Pro Leu Leu His Leu Arg Met Gly Ile Val His Val
65                  70                  75                  80

Val Val Ala Ala Ser Ala Asp Val Ala Ala Gln Phe Leu Lys Asn Asp
```

-continued

```
                85                  90                  95
Ala Asn Phe Ser Ser Arg Pro Pro Asn Ser Gly Ala Lys His Met Ala
            100                 105                 110
Tyr Asn Tyr His Asp Met Val Phe Ala Pro Tyr Gly Pro Arg Trp Arg
            115                 120                 125
Met Leu Arg Lys Ile Cys Ala Leu His Ile Phe Ser Ala Lys Ala Leu
            130                 135                 140
Asp Asp Phe His Arg Val Arg Glu Glu Val Ala Ile Leu Ala Arg
145                 150                 155                 160
Thr Leu Ala His Ala Gly Gln Lys Pro Val Asn Leu Gly Gln Leu Phe
            165                 170                 175
Ser Thr Cys Asn Ala Asn Ala Leu Ser Val Leu Met Leu Gly Arg Arg
            180                 185                 190
Leu Phe Ser Thr Glu Val Asp Ser Lys Ala Tyr Asp Phe Lys Gln Met
            195                 200                 205
Val Val Glu Leu Met Thr Leu Ala Gly Glu Phe Asn Val Ser Asp Phe
            210                 215                 220
Ile Pro Pro Leu Glu Trp Leu Asp Leu Gln Gly Val Ala Ala Lys Met
225                 230                 235                 240
Lys Asn Val His Asn Arg Phe Asp Ala Phe Leu Asn Val Ile Leu Glu
            245                 250                 255
Glu His Lys Leu Lys Leu Asn Asn Ser Gly His Gly Glu Gln Lys His
            260                 265                 270
Met Asp Leu Leu Ser Thr Leu Ile Leu Leu Lys Asp Ala Asp Ser
            275                 280                 285
Glu Gly Gly Lys Leu Thr Asp Thr Glu Ile Lys Ala Leu Leu Leu Asn
            290                 295                 300
Leu Phe Ser Ala Gly Thr Asp Thr Ser Ser Ser Thr Ile Glu Trp Val
305                 310                 315                 320
Ile Ala Glu Leu Ile Arg Asn Pro Lys Ile Leu Ala Gln Ala Gln Arg
            325                 330                 335
Glu Leu Asp Leu Val Val Gly Pro Asn Arg Leu Val Thr Asp Leu Asp
            340                 345                 350
Leu Lys Gln Leu Thr Tyr Leu Gln Ala Ile Val Lys Glu Thr Phe Arg
            355                 360                 365
Leu His Pro Ala Thr Pro Leu Ser Leu Pro Arg Ile Ala Thr Glu Ser
            370                 375                 380
Cys Glu Ile Asn Gly Phe Tyr Ile Pro Lys Gly Ser Thr Leu Leu Val
385                 390                 395                 400
Asn Ile Trp Ala Ile Gly Arg Asp Pro Asn Thr Trp Ala Glu Pro Leu
            405                 410                 415
Val Phe Arg Pro Glu Arg Phe Leu Ser Asp Gly Glu Ser Pro Asn Val
            420                 425                 430
Asp Val Lys Gly Arg Asn Phe Glu Leu Ile Pro Phe Gly Ala Gly Arg
            435                 440                 445
Arg Ile Cys Ala Gly Met Asn Phe Gly Leu Arg Met Val Gln Leu Val
            450                 455                 460
Thr Ala Thr Leu Ile His Ala Phe Asn Trp Glu Leu Pro Glu Gly Glu
465                 470                 475                 480
Leu Pro Glu Asn Met Asn Met Glu Glu Asp Tyr Gly Ile Ser Leu Gln
            485                 490                 495
Arg Thr Val Pro Leu Val Val His Pro Lys Pro Arg Leu Asp His Glu
            500                 505                 510
```

Val Tyr Gln Ser His Gly Val Val Asn
        515                 520

<210> SEQ ID NO 19
<211> LENGTH: 37
<212> TYPE: DNA
<213> ORGANISM: petunia

<400> SEQUENCE: 19
aaaatcgata ccatggtctt tttttctttg tctatac                              37

<210> SEQ ID NO 20
<211> LENGTH: 1748
<212> TYPE: DNA
<213> ORGANISM: clitoria

<400> SEQUENCE: 20
ggatccaaca atgttccttc taagagaaat tggggtatca attttgatct tcatgatcac      60
ccatcttgtg attcgtttag ttctgaaaga aaggaacaa cggaaacttc caccagggcc     120
aaaaggttgg ccaattgtgg gtgcactgcc tctaatggga agcatgcccc atgtcacact    180
ctcagaaatg gctaaaaaat atggacctgt tatgtacctt aaaatgggca caacaacat    240
ggctgtagca tctactccct ctgcagctcg tgcattcctc aaaacccttg accttaactt    300
ctccaatcgc cccccaaatg ctgggcaac tcacttagct tatgatgccc aggacatggt    360
gtttgctgat tacggatcta ggtggaagtt gcttagaaaa ctaagcaact tacacatgct    420
tggaggaaag gctcttgaag aatggtcaca agttagagag attgagatgg gcacatgct    480
tcgtgcaatg tacgattgta gtggtggcgg tgacggcaac aacgcaatg atggcaacaa    540
gaaaaagggt actcgtcatg agcctattgt ggtggctgaa atgttaacat acgcgatggc    600
caacatgata ggtcaagtga tcttgagccg tcgtgtattc gagacaaagg gttcggaatc    660
gaacgagttt aaggacatgg tggttcagct catgaccgtt gctggctact ttaacattgg    720
tgattttatt cccttttggg ctcgcttcga cctccaaggc atcgagcgtg gcatgaaaac    780
tttgcataac aagttcgatg ttttgttgac gacaatgatt catgagcatg tggcttctgc    840
tcataaacga aagggtaaac ctgatttctt ggatgttctc atggctcatc ataccaacga    900
gtctcatgaa ctgtcgctca ccaacatcaa agcactcctc ttaaatctat ttactgcagg    960
cacagataca tcatcaagta tcatagagtg ggcactagca gagatgttga taaacccaaa   1020
aatcatgaag aaagtgcatg aggaaatgga caaagtgata ggcaaggata gaaggctaaa   1080
agaatccgac atagaaaatc tcccttactt gcaggcaatt tgcaaagaga catatagaaa   1140
gcacccatca acgccactca acttgcctag aatctcatcc caagcatgcc aagtgaatgg   1200
ctactacatc ccaaagaaca ctaggcttag tgtcaacatc tgggccattg gaagagaccc   1260
taatgtgtgg gagaacccct tggagttcaa tccagagagg tttatgggtg ccaataagac   1320
tattgatcca cgtgggaatg attttgagct cattccattt ggtgctggga aaggatttg   1380
tgctgggaca aggatgggga ttgtgttggt tcaatacatt tgggcactt tggtacattc   1440
ctttgattgg aagttaccaa atggtgttgt ggagttgaac atggaagaga cttttggcct   1500
tgctttgcag aaaagatac cactttctgc tttgattacc cctaggttgc ccccaactgc   1560
ttacaatgtt attaattcct aatttgatct tagtactatg gtaagttata accaaataag   1620
taattactgt ttgtattaat gtttctgaat tccgagtgtc tttctttgtt gtatgggaaa   1680
tctgtaccca ccacctggga ttaatgtttt aattaatttt catatgttta aaaaaaaaa   1740

```
aaaaaaaa                                                            1748

<210> SEQ ID NO 21
<211> LENGTH: 525
<212> TYPE: PRT
<213> ORGANISM: clitoria

<400> SEQUENCE: 21

Met Phe Leu Leu Arg Glu Ile Gly Val Ser Ile Leu Ile Phe Met Ile
 1               5                  10                  15

Thr His Leu Val Ile Arg Leu Val Leu Lys Glu Lys Glu Gln Arg Lys
            20                  25                  30

Leu Pro Pro Gly Pro Lys Gly Trp Pro Ile Val Gly Ala Leu Pro Leu
        35                  40                  45

Met Gly Ser Met Pro His Val Thr Leu Ser Glu Met Ala Lys Lys Tyr
    50                  55                  60

Gly Pro Val Met Tyr Leu Lys Met Gly Thr Asn Asn Met Ala Val Ala
65                  70                  75                  80

Ser Thr Pro Ser Ala Ala Arg Ala Phe Leu Lys Thr Leu Asp Leu Asn
                85                  90                  95

Phe Ser Asn Arg Pro Pro Asn Ala Gly Ala Thr His Leu Ala Tyr Asp
            100                 105                 110

Ala Gln Asp Met Val Phe Ala Asp Tyr Gly Ser Arg Trp Lys Leu Leu
        115                 120                 125

Arg Lys Leu Ser Asn Leu His Met Leu Gly Gly Lys Ala Leu Glu Glu
    130                 135                 140

Trp Ser Gln Val Arg Glu Ile Glu Met Gly His Met Leu Arg Ala Met
145                 150                 155                 160

Tyr Asp Cys Ser Gly Gly Asp Gly Asn Asn Asp Asn Asp Gly Asn
                165                 170                 175

Lys Lys Lys Gly Thr Arg His Glu Pro Ile Val Val Ala Glu Met Leu
            180                 185                 190

Thr Tyr Ala Met Ala Asn Met Ile Gly Pro Ser Asp Leu Glu Pro Ser
        195                 200                 205

Cys Ile Pro Arg Gln Arg Val Arg Asn Arg Thr Ser Leu Arg Thr Trp
    210                 215                 220

Trp Phe Lys Leu Met Thr Val Ala Gly Tyr Phe Asn Ile Gly Asp Phe
225                 230                 235                 240

Phe Pro Phe Leu Ala Arg Arg Arg Gln Gly Ile Glu Arg Gly Met
                245                 250                 255

Lys Thr Leu His Asn Lys Lys Asp Asp Leu Leu Thr Thr Met Ile His
            260                 265                 270

Glu His Val Ala Ser Ala His Lys Arg Lys Gly Lys Pro Pro Phe Leu
        275                 280                 285

Asp Val Leu Met Ala His His Thr Asn Glu Ser His Glu Leu Ser Leu
    290                 295                 300

Thr Asn Ile Lys Ala Leu Leu Leu Asn Leu Phe Thr Ala Gly Thr Asp
305                 310                 315                 320

Thr Ser Ser Ser Ile Ile Glu Trp Ala Leu Ala Glu Met Leu Ile Asn
                325                 330                 335

Pro Lys Ile Met Lys Lys Val His Glu Glu Met Asp Lys Val Ile Gly
            340                 345                 350

Lys Asp Arg Arg Leu Lys Glu Ser Asp Ile Glu Asn Leu Pro Tyr Leu
        355                 360                 365
```

| Gln | Ala | Ile | Cys | Lys | Glu | Thr | Tyr | Arg | Lys | His | Pro | Ser | Thr | Pro | Leu |
|---|---|---|---|---|---|---|---|---|---|---|---|---|---|---|---|
| | | | 370 | | | | 375 | | | | | 380 | | | |

Asn Leu Pro Arg Ile Ser Ser Gln Ala Cys Gln Val Asn Gly Tyr Tyr
385                        390                    395                        400

Ile Pro Lys Asn Thr Arg Leu Ser Val Asn Ile Trp Ala Ile Gly Arg
                      405                    410                        415

Asp Pro Asn Val Trp Glu Asn Pro Leu Glu Phe Asn Pro Glu Arg Phe
              420                    425                    430

Met Gly Ala Asn Lys Thr Ile Asp Pro Arg Gly Asn Asp Phe Glu Leu
            435                    440                    445

Ile Pro Phe Gly Ala Gly Arg Arg Ile Cys Ala Gly Thr Arg Met Gly
450                        455                    460

Ile Val Leu Val Gln Tyr Ile Leu Gly Thr Leu Val His Ser Phe Asp
465                        470                    475                    480

Trp Lys Leu Pro Asn Gly Val Val Glu Leu Asn Met Glu Glu Thr Phe
              485                    490                    495

Gly Leu Ala Leu Gln Lys Lys Ile Pro Leu Ser Ala Leu Ile Thr Pro
            500                    505                    510

Arg Leu Pro Pro Thr Ala Tyr Asn Val Ile Asn Ser Ser
            515                    520                    525

<210> SEQ ID NO 22
<211> LENGTH: 1684
<212> TYPE: DNA
<213> ORGANISM: gentiana

<400> SEQUENCE: 22

```
tacaaatgtc acccatttac accaccctca cattacacct tgctacagct cttttctct      60
tctttcatgt ccagaaactt gttcactacc tccacggcaa agccaccggc caccgctgcc    120
gccgccttcc acagggccc accggatggc caatcctagg tgcccttcct cttttgggca    180
acatgccaca tgttactttt gctaacatgg cgaaaaaata tggctcggta atgtacctaa    240
aagtcggtag ccatggctta gcaatagcgt cgacaccgga cgctgctaaa gcgttcctca    300
aaccctcga tttaaatttc tcgaaccggc caccaaatgc cggagctacc catttagcct    360
ataacgctca agatatggtt tttgcacatt atggtcctaa atggaaattg ttacgtaaac    420
tcagtaactt acacatgcta ggtggcaaag ccttggaaaa ttgggctgat gttagaaaaa    480
cagagcttgg ttatatgctt aaagccatgt ttgaatcgag tcaaaacaat gagccggtga    540
tgatttcgga gatgctaacg tacgccatgg cgaacatgtt aagccaagtt atacttagcc    600
gtcgcgtatt caataaaaaa ggcgcgaaat caaacgagtt taaagatatg gtggtcgaat    660
taatgacgag tgccgggtat tcaatatag gtgatttat accatcaatt ggttggatgg    720
atttgcaagg gattgaaggt ggaatgaaaa gattgcacaa aaagttcgac gttttgttga    780
ctcgattatt ggatgatcat aaaagaacga gtcaggagcg taaacaaaag cccgattttc    840
ttgattttgt gattgcaaat ggcgataatt ctgatggtga aaggctcaac ccgacaaca    900
tcaaggctct tttattgaac ttgtttactg ctggtacgga tacatcatca agcatcattg    960
agtgggcact agcagaactg ctaaagaatc ggacactcct cacccgagcc aggacgaaa   1020
tggatcgggt aatcgggcga gaccgccgtc ttcttgaatc agacatcccc aacttaccat   1080
atcttcaagc aatctgcaaa gaaacattcg taaacacccc ttcaacacca ttaaaccttc   1140
caaggaattg catcagaggc catgtggatg taaatgggta ctacattccg aaagggactc   1200
```

```
ggctcaacgt caacatatgg gcgattggaa gagacccatc ggtttggggg gataacccga    1260
acgagttcga cccggagagg tttttgtatg ggaggaatgc taagattgat ccacgaggaa    1320
accattttga attgatccca tttggtgctg gacgaagaat ttgtgcagga acaagaatgg    1380
ggatattgct tgttgagtat attttgggga cattggtgca tagttttgat tggaaactgg    1440
gattttctga ggatgagctt aatatggatg agacatttgg gcttgctctg cagaaagctg    1500
tgcctttagc ggccatggtt attccacgcc ttcctcttca tgtttatgct ccttaattca    1560
gagatttaat ttcatgcttt gttttattaa tcattttctt aatatgaatt gatggaggtt    1620
atctagttat gaaaaataat aatggaggat ttgtttatca tcatgcaaaa aaaaaaaaaa    1680
aaaa                                                                 1684
```

<210> SEQ ID NO 23
<211> LENGTH: 516
<212> TYPE: PRT
<213> ORGANISM: gentiana

<400> SEQUENCE: 23

```
Met Ser Pro Ile Tyr Thr Thr Leu Thr Leu His Leu Ala Thr Ala Leu
1               5                   10                  15

Phe Leu Phe Phe His Val Gln Lys Leu Val His Tyr Leu His Gly Lys
            20                  25                  30

Ala Thr Gly His Arg Cys Arg Arg Leu Pro Pro Gly Pro Thr Gly Trp
        35                  40                  45

Pro Ile Leu Gly Ala Leu Pro Leu Leu Gly Asn Met Pro His Val Thr
    50                  55                  60

Phe Ala Asn Met Ala Lys Lys Tyr Gly Ser Val Met Tyr Leu Lys Val
65                  70                  75                  80

Gly Ser His Gly Leu Ala Ile Ala Ser Thr Pro Asp Ala Ala Lys Ala
                85                  90                  95

Phe Leu Lys Thr Leu Asp Leu Asn Phe Ser Asn Arg Pro Pro Asn Ala
            100                 105                 110

Gly Ala Thr His Leu Ala Tyr Asn Ala Gln Asp Met Val Phe Ala His
        115                 120                 125

Tyr Gly Pro Lys Trp Lys Leu Leu Arg Lys Leu Ser Asn Leu His Met
    130                 135                 140

Leu Gly Gly Lys Ala Leu Glu Asn Trp Ala Asp Val Arg Lys Thr Glu
145                 150                 155                 160

Leu Gly Tyr Met Leu Lys Ala Met Phe Glu Ser Ser Gln Asn Asn Glu
                165                 170                 175

Pro Val Met Ile Ser Glu Met Leu Thr Tyr Ala Met Ala Asn Met Leu
            180                 185                 190

Ser Gln Val Ile Leu Ser Arg Arg Val Phe Asn Lys Lys Gly Ala Lys
        195                 200                 205

Ser Asn Glu Phe Lys Asp Met Val Val Glu Leu Met Thr Ser Ala Gly
    210                 215                 220

Tyr Phe Asn Ile Gly Asp Phe Ile Pro Ser Ile Gly Trp Met Asp Leu
225                 230                 235                 240

Gln Gly Ile Glu Gly Gly Met Lys Arg Leu His Lys Lys Phe Asp Val
                245                 250                 255

Leu Leu Thr Arg Leu Leu Asp Asp His Lys Arg Thr Ser Gln Glu Arg
            260                 265                 270

Lys Gln Lys Pro Asp Phe Leu Asp Phe Val Ile Ala Asn Gly Asp Asn
        275                 280                 285
```

```
Ser Asp Gly Glu Arg Leu Asn Thr Asp Asn Ile Lys Ala Leu Leu Leu
    290                 295                 300

Asn Leu Phe Thr Ala Gly Thr Asp Thr Ser Ser Ile Ile Glu Trp
305                 310                 315                 320

Ala Leu Ala Glu Leu Leu Lys Asn Arg Thr Leu Leu Thr Arg Ala Gln
                325                 330                 335

Asp Glu Met Asp Arg Val Ile Gly Arg Asp Arg Leu Leu Glu Ser
                340                 345                 350

Asp Ile Pro Asn Leu Pro Tyr Leu Gln Ala Ile Cys Lys Glu Thr Phe
            355                 360                 365

Arg Lys His Pro Ser Thr Pro Leu Asn Leu Pro Arg Asn Cys Ile Arg
    370                 375                 380

Gly His Val Asp Val Asn Gly Tyr Tyr Ile Pro Lys Gly Thr Arg Leu
385                 390                 395                 400

Asn Val Asn Ile Trp Ala Ile Gly Arg Asp Pro Ser Val Trp Gly Asp
                405                 410                 415

Asn Pro Asn Glu Phe Asp Pro Glu Arg Phe Leu Tyr Gly Arg Asn Ala
                420                 425                 430

Lys Ile Asp Pro Arg Gly Asn His Phe Glu Leu Ile Pro Phe Gly Ala
            435                 440                 445

Gly Arg Arg Ile Cys Ala Gly Thr Arg Met Gly Ile Leu Leu Val Glu
    450                 455                 460

Tyr Ile Leu Gly Thr Leu Val His Ser Phe Asp Trp Lys Leu Gly Phe
465                 470                 475                 480

Ser Glu Asp Glu Leu Asn Met Asp Glu Thr Phe Gly Leu Ala Leu Gln
                485                 490                 495

Lys Ala Val Pro Leu Ala Ala Met Val Ile Pro Arg Leu Pro Leu His
                500                 505                 510

Val Tyr Ala Pro
        515

<210> SEQ ID NO 24
<211> LENGTH: 3731
<212> TYPE: DNA
<213> ORGANISM: petunia

<400> SEQUENCE: 24
tctagatatg catttggtc gacgaactca caaatttgta ccaaacatgt aatttttttt        60 ttcttttta cccttttaaa cattacaatt gaataagtag tacaacaaca tacccagttt      120
tattttacag gtgggacctg gggagggtga aatgtacgca caccttacca ccaccaaggt      180
ggagaggcag tttccggtag agcctcggct gaagaaaata tttcgagaac acgtttgaaa      240
aataggacag aaagaacaca ctataaaata ataaaactaa agcatataca tattaaacat      300
atagtagcag taggtataaa ggcactgact acgacagaaa taatctatat ataggagaga      360
agacactcat ccattatcta cccttctact ttaatcattg acctccaagc tttcctatct      420
agggtcatgt cctcggtgat ctagatctgg gccatgtctt atctaatcac ctcggtccag      480
ttcttcttag gtctacctct acctctccgt agacctaaca ctgcgaacct ctcacacctc      540
ctaaccgagc atctggactt ctcctctttta cgtatctgaa ccatctcaat cttgtctctc      600
gcatcttttc tgccactgga gatacgtcca ccttgtctca agtgatctca ttcataatct      660
tgcccctcct agtattccca acatccatc tgagcattct taattctgcc acaccaaacc      720
ttctaaatgt gtgagttctt gactggcaaa cactcagccc catacaatat agctggtata      780
```

```
acgaccatgt ataatataat gaagctaatt aaaatcatta attactactt gtacatatgg      840
cacggaaaag aagttcattg aacaataatg gatataaaaa ttgcggtcaa cacattggtg      900
agggaaatat ttttatcagc acaccaacat ttccaaacat caataaagca atgaagatgg      960
atagatcaag gtgtcctttt tcatcttatt aggaaaataa aatttgaaga tgcaaatcca     1020
aggacgatca tgcattctaa attaatagtt aatgattcta attttcattt atttaaattt     1080
tgatttttgc ggcttcaaat tcatatttga ttttcaacca cataaatatt taattatgac     1140
ttgtgttagg caacaaatac caaaagtctt actactttct tttggagatt gacctttcta     1200
tatctccttc ccaatttgat cgatcgagct ctcgtaatct attgctactg tgtcttttt     1260
gttctggcta gcgaagacag aatattctac gtaaactcta tgtcaagtca aaccgtgcca     1320
cataaaataa aatgtaggga atatagatca attagtgtct aagtgtacaa ctatatatat     1380
gttatctaag aatagattag attacaaaaa tgtatttacc attgattgat cactactttt     1440
cagcgaatta gtcaagaggt cagggttatt tataaaacat gcataatgta tacatatcat     1500
gccgtggcca ttgtacaatt atgttataaa aggtatacat taaatataac ttgtatttat     1560
tttttataca tgtcagcaat gtttgaaagt gtgaagttcc ctggttctta taattcaatc     1620
ttctgataat gttttaacc ggccagaaca cagcattaac tccattaatc ataccaatta     1680
tgaccatgga atcagattct agtaacaaca tacccggcta tattctacaa gtggggcctg     1740
aggagggtaa ggtatacgta aaccatacac ttaaggtaga gaaattattt ctgaaagatc     1800
ctagactcac acgtttcgaa aaataggttt aaaaaatact tacataaaaa aaaaataata     1860
aaataaagat acagataaag ataaacagag taaacaaaac aacaatggta atatacagac     1920
aaaaagcaag ataaaaatag tatatggaag aaaaatacaa atgcttatat gacagaagtc     1980
gctcgactac cttcaaacgt tctactctaa tccttgacct ccatacactc ctatctaagg     2040
ttatgtcctc gattatccga aagattgaat cttgaatcaa attctatata tacaagaatt     2100
atttaactcc tgtattacaa gttcttatat ttcatcgaac aaccactttt ggttcatcaa     2160
gaatagtgca atatagataa aattatctct aaatactttg gacgagggat tatcatttaa     2220
atgtaataag aaaaatgtcg atggtattgg aagtgcaaac aaagtcccac atcggtagtt     2280
gaaaagtttg gaatccaacg tataaggtgt atgtatctct taatggtgta agacatttta     2340
tgaaaactgt gttggcttag ccaaaagcga acaatatcac tccatttcaa gaatatcttg     2400
gttgttttag tccagcaact ggtatcagag caaatggttt agcaaaatga gtatgttgtg     2460
tagtgattgc gtggggcatg acttagccct taccctttgac ttggagaggg cccggttaat     2520
gtctttgctc atctacagcc agtttattac ctttccatgt agctttaaag acgcacacag     2580
aggtattcgg ttgatgtggg tgacacacaa taaatctcca aataaaccca atagtggtga     2640
ttggtcatgt gaaacttagt tcgagggga gattgttgag agtgtgaaca aaaagtccta     2700
catatagatg aaaagtttag gagcctattt ataaggtata tggatctctt aataatgtgg     2760
gggtttatag gaatttagat tttacttata tcgtttataa attgattaga tacgggacca     2820
tccagcttcc taaaatgtag gcacgttcca tgcttcaatg ttccatctga tttgtaggct     2880
ataaaggtag aatacgttta agaaagttta aatttacgt aataatccaa aagtgaaatg     2940
tgtttatttta ttggttatac tctaattggt gtttatgtga tctaattttc gtccggatca     3000
gtctccaaag attagccaca aatacatatg tgttcataaa atgttacact tgggaactaa     3060
ctttataggt agctcgatct attagtaatg gtaaaacttc accgtgttat ttgcagcaag     3120
```

```
ccaataaatg cacgatatat gattatacat aaattttat catttgatca tcatggttaa    3180
tacttcaacc gtcccaaaat agatggttag ttttcacttt tttttatcaa aataaatgtt    3240
aatttagaat atcaatgaaa ttactttttt ttttaaccaa tattgtcctt gctattgaaa    3300
aggtagaata tgataattta ttcttttaca tataacaatg aaataaataa gaataattag    3360
gtaaaatata tgtatagtag atacatgttt ttctcaatgg gcataaaaat gtgaaattca    3420
attataacgg gataaggggt atatttctca gctcactcta atacaatttg gtgtaaatac    3480
cgaatgcgag tatttaacct gagtttggta attatgtacc atcagaaatc gcatcgaatg    3540
taactcaaaa atagtacaaa caaattccct cactgctcca ttggccatta atttaggtcc    3600
aattttcact ctataaaagc ccataggatc tctctagctt ttgtactcaa cactcaggca    3660
aaaccattag caatatcgtc cactacttcc tccgactatt ctctccattg tattatcttt    3720
cctcttaaac a                                                         3731
```

<210> SEQ ID NO 25
<211> LENGTH: 31
<212> TYPE: DNA
<213> ORGANISM: clitoria

<400> SEQUENCE: 25

```
gggatccaac aatgttcctt ctaagagaaa t                                     31
```

<210> SEQ ID NO 26
<211> LENGTH: 1831
<212> TYPE: DNA
<213> ORGANISM: kennedia

<400> SEQUENCE: 26

```
cccctgaata tcctcactaa agggaacaaa agctggagct ccaccgcggt ggcggccgct      60
ctagaactag tggatccccc gggctgcagg aattttttaa atattaaaga ttttgataaa     120
atttaaaatc ttagtacggc atggccaact tagatcactt gttccttctc aaagaaattg     180
ctatgtccat tttgatcttc ttgatcactc acctcaccat tcattcactc ttcacaaaacc    240 gtcacaaaaa gcttccacca gggcctagag gctggccaat cgtaggtgcc ctccctgtct     300
tgggaagcat gcctcatgtc accctctcta gaatggccaa aaagtatgga cccgtcatgt     360
acctcaagat gggcaccaaa aacatggttg tggcctctac tcccgctgca gctcgtgcat     420
tcctcaaaac ccttgatcaa aacttctcca accgccctcc aaatgctggt gcaactcact     480
tagcttatga ttcacaggac atggtgtttg cccactatgg ctctaggtgg aggttgctta     540
ggaaactgag caacttgcac atgctgggtg gaaaggctct tgatgattgg gcacatgttc     600
gggagaaaga gatgaggtac atgcttggtt caatgtatga ttgtagcaaa aggggtgagg     660
ctgtggtggt ggctgagatg ttgacatatg ctatggccaa tatgattggt caagtgatat     720
tgagccgtcg tgtgttcgag tcaaagggtt cggaatcaaa cgagttcaag acatggttg    780 ttgagctcat gaccgttgcc gggtacttca acattggaga ttttgtgcct tttcttgcgt     840
ggtttgactt gcaaggcata gagcgtgaga tgaaggcctt gcataagaag tttgatgcgt     900
tgttgacaag gatgattgag gagcatgtgg cttctagatg tcacaaaggt aaaggaaact     960
atgatttcct agacgttgtc atggatcatt ctagcgaaag cagtgatgga gagagactca    1020
cactcaccaa tgtcaaggca ctgctcttga atcttttcac agcaggcact gatacatctt    1080
cgagtgtgat agagtgggca ctagcggaga tgttgaaaaa tccccacata acaaagagag    1140
ctcatgagga aatggaccaa gtcataggca aggatcgacg cctcaaggaa tctgacctaa    1200
```

-continued

```
ggaaccttcc ttacttgcaa gctatttgca aagaggcatt gagaaagcac ccttcaaccc   1260
cattgaactt gcctagagtc tcatcacaac cgtgccaagt gaatggctat tacatcccca   1320
agaacactag gctgagtgtg aacatatggg ccattggaag agaccccgag gtgtgggaga   1380
acccttgtga gttcaatcct gagaggttta tgagtggaaa aggtgccaaa gttgatccac   1440
atgggaatga ttttgagctg attccgtttg gtgctgggag aagggtgtgt gctgggacaa   1500
ggatggggat tgtgatggtt cagtacatat tgggcacttt ggtgcactca tttgaatgga   1560
agctaccaaa tggggtggtg gagttgaaca tggaagagac ctttgggctt gccttgcaga   1620
aaaaggtgcc actctcggct ttggttagcc ctaggttgca cccaagttct tatattcagt   1680
agagttgggt ttggtttggt tcaccaactc tgttcaaaca ttatgtctag ctatttaaaa   1740
attacaatac atgctttaag gttatgtgac tatatattgc gcaaaccgcg caaataataa   1800
atgtgctttg gatcaaaaaa aaaaaaaaaa a                                  1831
```

<210> SEQ ID NO 27
<211> LENGTH: 513
<212> TYPE: PRT
<213> ORGANISM: kennedia

<400> SEQUENCE: 27

```
Met Ala Asn Leu Asp His Leu Phe Leu Leu Lys Glu Ile Ala Met Ser
1               5                   10                  15

Ile Leu Ile Phe Leu Ile Thr His Leu Thr Ile His Ser Leu Phe Thr
            20                  25                  30

Asn Arg His Lys Lys Leu Pro Pro Gly Pro Arg Gly Trp Pro Ile Val
        35                  40                  45

Gly Ala Leu Pro Val Leu Gly Ser Met Pro His Val Thr Leu Ser Arg
    50                  55                  60

Met Ala Lys Lys Tyr Gly Pro Val Met Tyr Leu Lys Met Gly Thr Lys
65                  70                  75                  80

Asn Met Val Val Ala Ser Thr Pro Ala Ala Arg Ala Phe Leu Lys
                85                  90                  95

Thr Leu Asp Gln Asn Phe Ser Asn Arg Pro Pro Asn Ala Gly Ala Thr
            100                 105                 110

His Leu Ala Tyr Asp Ser Gln Asp Met Val Phe Ala His Tyr Gly Ser
        115                 120                 125

Arg Trp Arg Leu Leu Arg Lys Leu Ser Asn Leu His Met Leu Gly Gly
    130                 135                 140

Lys Ala Leu Asp Asp Trp Ala His Val Arg Glu Lys Glu Met Arg Tyr
145                 150                 155                 160

Met Leu Gly Ser Met Tyr Asp Cys Ser Lys Arg Gly Glu Ala Val Val
                165                 170                 175

Val Ala Glu Met Leu Thr Tyr Ala Met Ala Asn Met Ile Gly Gln Val
            180                 185                 190

Ile Leu Ser Arg Arg Val Phe Glu Ser Lys Gly Ser Glu Ser Asn Glu
        195                 200                 205

Phe Lys Asp Met Val Val Glu Leu Met Thr Val Ala Gly Tyr Phe Asn
    210                 215                 220

Ile Gly Asp Phe Val Pro Phe Leu Ala Trp Phe Asp Leu Gln Gly Ile
225                 230                 235                 240

Glu Arg Glu Met Lys Ala Leu His Lys Lys Phe Asp Ala Leu Leu Thr
                245                 250                 255
```

```
Arg Met Ile Glu Glu His Val Ala Ser Arg Cys His Lys Gly Lys Gly
            260                 265                 270

Asn Tyr Asp Phe Leu Asp Val Met Asp His Ser Ser Glu Ser Ser
        275                 280                 285

Asp Gly Glu Arg Leu Thr Leu Thr Asn Val Lys Ala Leu Leu Leu Asn
        290                 295                 300

Leu Phe Thr Ala Gly Thr Asp Thr Ser Ser Val Ile Glu Trp Ala
305                 310                 315                 320

Leu Ala Glu Met Leu Lys Asn Pro His Ile Thr Lys Arg Ala His Glu
                325                 330                 335

Glu Met Asp Gln Val Ile Gly Lys Asp Arg Arg Leu Lys Glu Ser Asp
            340                 345                 350

Leu Arg Asn Leu Pro Tyr Leu Gln Ala Ile Cys Lys Glu Ala Leu Arg
        355                 360                 365

Lys His Pro Ser Thr Pro Leu Asn Leu Pro Arg Val Ser Ser Gln Pro
    370                 375                 380

Cys Gln Val Asn Gly Tyr Tyr Ile Pro Lys Asn Thr Arg Leu Ser Val
385                 390                 395                 400

Asn Ile Trp Ala Ile Gly Arg Asp Pro Glu Val Trp Glu Asn Pro Cys
                405                 410                 415

Glu Phe Asn Pro Glu Arg Phe Met Ser Gly Lys Gly Ala Lys Val Asp
            420                 425                 430

Pro His Gly Asn Asp Phe Glu Leu Ile Pro Phe Gly Ala Gly Arg Arg
        435                 440                 445

Val Cys Ala Gly Thr Arg Met Gly Ile Val Met Val Gln Tyr Ile Leu
    450                 455                 460

Gly Thr Leu Val His Ser Phe Glu Trp Lys Leu Pro Asn Gly Val Val
465                 470                 475                 480

Glu Leu Asn Met Glu Glu Thr Phe Gly Leu Ala Leu Gln Lys Lys Val
                485                 490                 495

Pro Leu Ser Ala Leu Val Ser Pro Arg Leu His Pro Ser Ser Tyr Ile
        500                 505                 510

Gln

<210> SEQ ID NO 28
<211> LENGTH: 1374
<212> TYPE: DNA
<213> ORGANISM: chrysanthemum

<400> SEQUENCE: 28
gaattccgtt gctgtcgcta cttacaaaga tcatatacat tttcgttcac cgatattaaa     60
caccgatggc ttccttaact gacattgcgg ccattagaga ggctcaacgg gctcaaggtc    120
cagctaccat tctagcgatc ggcactgcaa ctccggctaa ttgtgtatat caagctgatt    180
atcccgatta ctattttcgg atcactaaaa gtgaacacat ggtggatctt aaagagaaat    240
tcaagcgcat gtgcgacaag tctatgataa gaaaacgata catgcacctc acggaggagt    300
atcttaaaga gaacccaaac ctttgtgagt acatggctcc gtccctcgat gctcgccagg    360
atgtggtggt cgttgaggtc ccaaagcttg gaaagaagc cgcaacaaaa gctattaaag    420
aatggggaca accaaaatct aaaatcaccc acctaatctt ctgcaccaca tctggtgtag    480
atatgcccgg ggctgattac caactcacca aactcctcgg cctccgccct cggtcaaac    540
gttttatgat gtaccaacaa gggtgctttg caggtgggac ggttcttcgt ctagcaaaag    600
acctcgcaga aaacaacaag gatgcacgtg tcctagttgt ttgttccgag attactgcag    660
```

```
tcacattccg tggtcctaac gacactcatc ttgattcact cgttggtcaa gctttgtttg    720
gggatggagc tgcggctgtc attgttggtt cagaccctga cttgacaaaa gagcgtccat    780
tgttcgagat gatatctgct gctcaaacta tcttaccaga ctcggaggga gcaatcgatg    840
ggcacttgag ggaagtcggg ctaacatttc atctcctcaa agacgtacct gggttgatct    900
ccaagaacat agagaaggca ttgacacaag ccttttctcc attaggtata agtgactgga    960
actcgatctt ttggatcgct catcctggtg gtccagctat tctggaccaa gttgagctta   1020
agctcggtct caaggaggag aagatgagag ccactagaca cgttcttagt gagtatggaa   1080
acatgtcaag tgcttgtgtt tgttcatta tggatgaaat gaggaagaaa tcggctgagg    1140
aaggtgcagc cacaaccggt gaagggctag attggggtgt tttattcggg ttcggtcctg   1200
gtttgacggt cgaaaccgtg gtcctccaca gcctcccaac cactgtatcg gttgcaaatt   1260
aatttagttg catggttatg gatataagcg tcttttgttg gaacaattaa atttttactg   1320
tttttgtttt ctactaaata aatgtgtgtt tgcaaaaaaa aaaaaaaaaa aaaa          1374
```

<210> SEQ ID NO 29
<211> LENGTH: 398
<212> TYPE: PRT
<213> ORGANISM: chrysanthemum

<400> SEQUENCE: 29

```
Met Ala Ser Leu Thr Asp Ile Ala Ala Ile Arg Glu Ala Gln Arg Ala
1               5                   10                  15

Gln Gly Pro Ala Thr Ile Leu Ala Ile Gly Thr Ala Thr Pro Ala Asn
                20                  25                  30

Cys Val Tyr Gln Ala Asp Tyr Pro Asp Tyr Tyr Phe Arg Ile Thr Lys
            35                  40                  45

Ser Glu His Met Val Asp Leu Lys Glu Lys Phe Lys Arg Met Cys Asp
        50                  55                  60

Lys Ser Met Ile Arg Lys Arg Tyr Met His Leu Thr Glu Glu Tyr Leu
65                  70                  75                  80

Lys Glu Asn Pro Asn Leu Cys Glu Tyr Met Ala Pro Ser Leu Asp Ala
                85                  90                  95

Arg Gln Asp Val Val Val Val Glu Val Pro Lys Leu Gly Lys Glu Ala
            100                 105                 110

Ala Thr Lys Ala Ile Lys Glu Trp Gly Gln Pro Lys Ser Lys Ile Thr
        115                 120                 125

His Leu Ile Phe Cys Thr Thr Ser Gly Val Asp Met Pro Gly Ala Asp
    130                 135                 140

Tyr Gln Leu Thr Lys Leu Leu Gly Leu Arg Pro Ser Val Lys Arg Phe
145                 150                 155                 160

Met Met Tyr Gln Gln Gly Cys Phe Ala Gly Gly Thr Val Leu Arg Leu
                165                 170                 175

Ala Lys Asp Leu Ala Glu Asn Asn Lys Asp Ala Arg Val Leu Val Val
            180                 185                 190

Cys Ser Glu Ile Thr Ala Val Thr Phe Arg Gly Pro Asn Asp Thr His
        195                 200                 205

Leu Asp Ser Leu Val Gly Gln Ala Leu Phe Gly Asp Gly Ala Ala Ala
    210                 215                 220

Val Ile Val Gly Ser Asp Pro Asp Leu Thr Lys Glu Arg Pro Leu Phe
225                 230                 235                 240

Glu Met Ile Ser Ala Ala Gln Thr Ile Leu Pro Asp Ser Glu Gly Ala
```

-continued

```
                    245                 250                 255
Ile Asp Gly His Leu Arg Glu Val Gly Leu Thr Phe His Leu Leu Lys
            260                 265                 270

Asp Val Pro Gly Leu Ile Ser Lys Asn Ile Glu Lys Ala Leu Thr Gln
        275                 280                 285

Ala Phe Ser Pro Leu Gly Ile Ser Asp Trp Asn Ser Ile Phe Trp Ile
    290                 295                 300

Ala His Pro Gly Gly Pro Ala Ile Leu Asp Gln Val Glu Leu Lys Leu
305                 310                 315                 320

Gly Leu Lys Glu Glu Lys Met Arg Ala Thr Arg His Val Leu Ser Glu
                325                 330                 335

Tyr Gly Asn Met Ser Ser Ala Cys Val Leu Phe Ile Met Asp Glu Met
            340                 345                 350

Arg Lys Lys Ser Ala Glu Glu Gly Ala Ala Thr Thr Gly Glu Gly Leu
        355                 360                 365

Asp Trp Gly Val Leu Phe Gly Phe Gly Pro Gly Leu Thr Val Glu Thr
    370                 375                 380

Val Val Leu His Ser Leu Pro Thr Thr Val Ser Val Ala Asn
385                 390                 395
```

<210> SEQ ID NO 30
<211> LENGTH: 2979
<212> TYPE: DNA
<213> ORGANISM: chrysanthemum
<220> FEATURE:
<221> NAME/KEY: misc_feature
<222> LOCATION: (2051)..(2051)
<223> OTHER INFORMATION: n = any nucleotide

<400> SEQUENCE: 30

```
ttttaacgcg cattagcctc actaaaggga caaaagctgg agctccccgc ggtggcggcc      60
gctctgaact agtggatccc ccgggctgca ggaattcgat tggatgactc gaacagctat     120
ggccatgatt acttagtacc acatgtaact gagacttgca atggacaagt acttattatc     180
ctacaaccta acttctttgt tgtgtttaag tccaaaaagt tatgcgtgcg ccagaatcc      240
atcaaaatgt gtagcatttg tttcaacaca tgcccttaa cccgtatagt gttatgagtt      300
ggtactccag acaatacatt aagagatata ttgggtatgc attgttgtgt atcatctccc     360
acacatgctc agttatgtca gtatcacaat cttcctcttc caaacacaat tctaattctc     420
cttccttctc atctctaatc tctaaagtaa catttgacc ttcacactta tgaccatgca      480
tatacttctt atcacgataa aaacatagat tcttagccct ctttcagca tacttttttt      540
tacttaatta ctttctaggt gtaggcatgg tgtttgcaaa ctgttggtt accaactgag       600
ttgtaggcaa agctaaaata tttgaaatat tttttagtag gataagtcac attcctgttt     660
acattccaat tattattgta cttaggagta ggcaacaatg agacacttt ttcttaaca       720
actgctagcc tagcttcttc catcttagcc caacaataga catcatttaa actagttggt     780
ttaaacatgc taaccagcat aactatttcg tcttcaatc caccaatata caaactaata      840
gcatgagatt cactcaattc caccttattc aataaaactt caaagaatc ttggtatacc      900
tgaacagtgc tagtttgcct gacattttc aattccacta taggatcttt aaagactgaa      960
tcaaaccttt tcttgatatg cctttcatac atatcccgag taacaatttc cccatgtctt    1020
tttcataaat tgcttgtttt agttaagggc tttgtcaaac acatgcatag agacaagcct    1080
gatcctaatg aatgaagaac attaacaaaa tcactaaaag aatcaagaac actaacataa    1140
```

```
tcactaattg acaagaataa ccaccaccTt ttcaggtaca ccagaatata ataccactat    1200
acaattccta aggctaagta gggttggatc agttggaaaa cccCttgcct ctcaaccgag    1260
aggtcagggg ttcgatcctc actccctaca aaaggccgga ggtcctttat acctttggta    1320
gagctggaag cagcctctct accttaggta ggggtaaggt tgtctacatc ttaacctccc    1380
ccatacaccg gaaacggtat tgggtaccca taacctgtgg aagacggtat tgggagttac    1440
ttttactttt ttttatacag ttcctaaggc taagcaaagt cgtgacccaa cacgaccttg    1500
ccacatcagc tttatctctc caatgacccg atgacgacca agttgccaca gtcggtgacc    1560
aagttaaaaa aaaagaaaaa aagaaagaa ataagtgtgt gtgtgtgtaa aatcgatcga    1620
agaaatgacc gattgtgtgt ttacatgttg ctcaaccgat cctcgacctc gtctccacaa    1680
tggtgtcgac cgactttaaa gtcggtcctt cccctcgacc gaccgatctc tttcagcccg    1740
ctgtgtctag cctaactaac gtgtgtaaga tttgaaaacg gaatttaat caagaacgat    1800 tttggataag acaaatggtg tagaatgatc agaatttatg tttgtatggt ggttgatcga    1860
agatcaagaa ttgacagtgt accggaaaat gtaacaagat aactgaatta taacataatg    1920
gagttattag ttgtgatcaa atagcatgat gatgctctat tacccattga aatgtactaa    1980
atgtaatgac ttaaccataa tccataagat tgaaagttaa cataatcaaa cacaagaatt    2040
actgaacaag nattgtaact cgaagtgaaa tgataattgg atttgttatt gatcaatgtg    2100
gtttgtcaca aagacttaag agagagcaaa tcatccaaaa actgattacc aaatgaagaa    2160
atgaaaatat ttaaagagaa ttacaaatgg cttgaaaatc ggttatgtgg tttgtttgaa    2220
cttttgaagc tgtcacgtga tataacacat aatatatctt tatctttgtg atgcaccatg    2280
tatgatacaa ctaataagtt gtatcaatat caatttctta aaaactggat atactttttc    2340
ggtaacttat ttaagtccaa tgtattattt agtccctatg aaaagcgtct caatgatatt    2400
tccccaagtc aaatgttaga ttttttattt tatttatttt taaattcagc cataggcaaa    2460
aatattagta agtcagctta tgcgtcccaa atataattgt tatacggctt aaatgatttg    2520
caattactac atttttatgt aatcatatct caatcaacag aattatgaga tgtggttgta    2580
aaggccttct gaaaaattta atcaacagtt acctaatggt agattgatat gaaacaaaaa    2640
cttctggtgt atgcagctgg tcgatgacac tcaaatccgt aaccgaagtg tttaagaatt    2700
atcgtattca cagtcatatc ttacggttaa aactttaaac gaaatcgaac taaactccta    2760
acagatatcg aagctcaatt gtgtaatgtt tttcaatggt ccacaacgtg gcatctatga    2820
ccatcgttcg taaaacttgg gtacgtcata cctaccacac gttccctcta tataagaaac    2880
actcattcac ctaatgtcta ccatcacttg cacttctcta cttacaaaga tcatatacat    2940
tttcgttcac cgatattaaa cacccatggc ttccttaac                          2979
```

<210> SEQ ID NO 31
<211> LENGTH: 1778
<212> TYPE: DNA
<213> ORGANISM: lavendula

<400> SEQUENCE: 31

```
ctagtataaa ttttttaata gtaggcatgc aaaatcaaga atctatcttc gtgatagcta     60
gagagctcac tatagcagcc tcaatctact ttctcatccg ctactttctt tcaagaatca    120
tcaccaccat tacccacggc ggcagccacc gactgccgcc agggccgagg ggctttccga    180
ttgtcggtgc acttcctctc ttgggcgaca tgccacatgt cgcccctagcc aaaatggcca    240 aaacttacgg ccccatcatc tacctaaaag tcggtgcatg gggcatggcc gtcgcgtcaa    300
```

-continued

```
cgcctgcctc cgcccgtgcg tttctcaaaa ccctagacac caacttctct gaccgccctc    360
cgaatgcggg tgccaccata ttagcctaca acgcggaaga tatggtgttc gcccgctatg    420
gcccaaagtg gagattgctc agaaaactga ccaatctcca catgttgggg aatcatgctt    480
tagatgggtg ggcaagtgta aggtcctccg agttgggcta catgctccat gcaaggcacg    540
acgccacccg tcatggcgag cccgtggtgc tgccagagat gctcatgtac gccgtgggga    600
atatgctcgg gcaggtgata ttaagtagac ggattttcga agaaaggg aaggaggtga     660
atgagttgaa agatatggtg gtggagctca tgacttcagc tggatatttc aatattggtg    720
atttcatccc atggcttgct tggatggatt tgcagggat agagagtggg atgaagaaat     780
tgcacaataa gttcgacaag ttgatcggca aaatgattga ggatcatttg aaatcagccc    840
acatacgcaa ggccaagccg atcttcttg attgcctctt ggcaaatcgt gatagctccg     900
atgcggagaa gctcacctca accaacgtca aggccctttt actgaacttg ttcaccgcag    960
ggaccgacac gtcatcaagc ataatagaat gggcattggc cgagatgatc aagaatccaa   1020
ccatcctaaa tagggcccac caagagatgg atagagtcgt tggtagaact cgaaggttgg   1080
tcgaatcgga catcccgaac ctaccctacc tacgagccat atgtaaagaa acatatcgca   1140
agcatccatc cactccccta atctgcccc gaatcgcgtc cgagccttgc gtcgtggacg    1200
ggtattacat acctaaaaac acccggctca gcgttaacat atgggctatc gggagagacc   1260
ccgacgtgtg ggaaaatcct cttgatttca accccgatag atttctatcg gggaagaacg   1320
agcggattga tccccgcggg aaccacttcg agctcatccc gttcggggct gggcggagga   1380
tctgcgccgg ggcccggatg gggatggtgc ttgtggagta tatttaggc acgttggtgc    1440
acgctttcga atgggaactg ccggccgggg ccggggccgg cacggcggag ttgaacatgg   1500
accacgtgtt tgggctggcg ctgcagaaag ctgtgcctct cacggccatg ctcactccta   1560
ggctgccgtc acattgttat gctccttaat ttctgttaca tttatacgtc tcgtatttta   1620
tcttatcgaa ctagtttacc acccatgcat tttgcgttta tgttattata aattctatta   1680
cattattagt ctcgtatttt attttatcga actagtgtac cactcataca ttttgtgttt   1740
atatatacta taaagatcta ttacattaaa aaaaaaaa                           1778
```

<210> SEQ ID NO 32
<211> LENGTH: 520
<212> TYPE: PRT
<213> ORGANISM: lavendula

<400> SEQUENCE: 32

```
Met Gln Asn Gln Glu Ser Ile Phe Val Ile Ala Arg Glu Leu Thr Ile
 1               5                  10                  15

Ala Ala Ser Ile Tyr Phe Leu Ile Arg Tyr Phe Leu Ser Arg Ile Ile
            20                  25                  30

Thr Thr Ile Thr His Gly Gly Ser His Arg Leu Pro Pro Gly Pro Arg
        35                  40                  45

Gly Phe Pro Ile Val Gly Ala Leu Pro Leu Leu Gly Asp Met Pro His
    50                  55                  60

Val Ala Leu Ala Lys Met Ala Lys Thr Tyr Gly Pro Ile Ile Tyr Leu
65                  70                  75                  80

Lys Val Gly Ala Trp Gly Met Ala Val Ala Ser Thr Pro Ala Ser Ala
                85                  90                  95

Arg Ala Phe Leu Lys Thr Leu Asp Thr Asn Phe Ser Asp Arg Pro Pro
            100                 105                 110
```

```
Asn Ala Gly Ala Thr Ile Leu Ala Tyr Asn Ala Glu Asp Met Val Phe
        115                 120                 125
Ala Arg Tyr Gly Pro Lys Trp Arg Leu Leu Arg Lys Leu Thr Asn Leu
    130                 135                 140
His Met Leu Gly Asn His Ala Leu Asp Gly Trp Ala Ser Val Arg Ser
145                 150                 155                 160
Ser Glu Leu Gly Tyr Met Leu His Ala Arg His Asp Ala Thr Arg His
                165                 170                 175
Gly Glu Pro Val Val Leu Pro Glu Met Leu Met Tyr Ala Val Gly Asn
            180                 185                 190
Met Leu Gly Gln Val Ile Leu Ser Arg Arg Ile Phe Glu Lys Lys Gly
        195                 200                 205
Lys Glu Val Asn Glu Leu Lys Asp Met Val Val Glu Leu Met Thr Ser
    210                 215                 220
Ala Gly Tyr Phe Asn Ile Gly Asp Phe Ile Pro Trp Leu Ala Trp Met
225                 230                 235                 240
Asp Leu Gln Gly Ile Glu Ser Gly Met Lys Lys Leu His Asn Lys Phe
                245                 250                 255
Asp Lys Leu Ile Gly Lys Met Ile Glu Asp His Leu Lys Ser Ala His
            260                 265                 270
Ile Arg Lys Ala Lys Pro Asp Leu Leu Asp Cys Leu Leu Ala Asn Arg
        275                 280                 285
Asp Ser Ser Asp Ala Glu Lys Leu Thr Ser Thr Asn Val Lys Ala Leu
    290                 295                 300
Leu Leu Asn Leu Phe Thr Ala Gly Thr Asp Thr Ser Ser Ser Ile Ile
305                 310                 315                 320
Glu Trp Ala Leu Ala Glu Met Ile Lys Asn Pro Thr Ile Leu Asn Arg
                325                 330                 335
Ala His Gln Glu Met Asp Arg Val Val Gly Arg Thr Arg Arg Leu Val
            340                 345                 350
Glu Ser Asp Ile Pro Asn Leu Pro Tyr Leu Arg Ala Ile Cys Lys Glu
        355                 360                 365
Thr Tyr Arg Lys His Pro Ser Thr Pro Leu Asn Leu Pro Arg Ile Ala
    370                 375                 380
Ser Glu Pro Cys Val Val Asp Gly Tyr Tyr Ile Pro Lys Asn Thr Arg
385                 390                 395                 400
Leu Ser Val Asn Ile Trp Ala Ile Gly Arg Asp Pro Asp Val Trp Glu
                405                 410                 415
Asn Pro Leu Asp Phe Asn Pro Asp Arg Phe Leu Ser Gly Lys Asn Glu
            420                 425                 430
Arg Ile Asp Pro Arg Gly Asn His Phe Glu Leu Ile Pro Phe Gly Ala
        435                 440                 445
Gly Arg Arg Ile Cys Ala Gly Ala Arg Met Gly Met Val Leu Val Glu
    450                 455                 460
Tyr Ile Leu Gly Thr Leu Val His Ala Phe Glu Trp Glu Leu Pro Ala
465                 470                 475                 480
Gly Ala Gly Ala Gly Thr Ala Glu Leu Asn Met Asp His Val Phe Gly
                485                 490                 495
Leu Ala Leu Gln Lys Ala Val Pro Leu Thr Ala Met Leu Thr Pro Arg
            500                 505                 510
Leu Pro Ser His Cys Tyr Ala Pro
        515                 520
```